(12) United States Patent
Ebbitt et al.

(10) Patent No.: US 11,160,620 B2
(45) Date of Patent: Nov. 2, 2021

(54) END EFFECTORS AND METHODS FOR DRIVING TOOLS GUIDED BY SURGICAL ROBOTIC SYSTEMS

(71) Applicant: MAKO Surgical Corp., Ft. Lauderdale, FL (US)

(72) Inventors: Peter L. Ebbitt, Boca Raton, FL (US); Oscar Williams, Foster CIty, CA (US); Victor Soto, Doral, FL (US); Hyosig Kang, Weston, FL (US); Xiao H. Gao, Plantation, FL (US); Kana Nishimura, Baden-Baden (DE); Ezra Johnson, Reeds Spring, MO (US)

(73) Assignee: MAKO Surgical Corp., Ft. Lauderdale, FL (US)

( * ) Notice: Subject to any disclaimer, the term of this patent is extended or adjusted under 35 U.S.C. 154(b) by 348 days.

(21) Appl. No.: 16/257,605

(22) Filed: Jan. 25, 2019

(65) Prior Publication Data

US 2019/0231447 A1 Aug. 1, 2019

Related U.S. Application Data

(60) Provisional application No. 62/744,878, filed on Oct. 12, 2018, provisional application No. 62/622,306, filed on Jan. 26, 2018.

(51) Int. Cl.
*A61B 34/30* (2016.01)
*A61B 34/10* (2016.01)
(Continued)

(52) U.S. Cl.
CPC .............. *A61B 34/30* (2016.02); *A61B 34/10* (2016.02); *A61B 34/20* (2016.02); *A61B 34/74* (2016.02);
(Continued)

(58) Field of Classification Search
CPC ...... A61B 2017/00464; A61B 17/1615; A61B 17/1622; A61B 17/1624; A61B 17/1671;
(Continued)

(56) References Cited

U.S. PATENT DOCUMENTS 7,549,998 B2 6/2009 Braun
7,725,162 B2 5/2010 Malackowski et al.
(Continued)

FOREIGN PATENT DOCUMENTS

WO 2014145188 A2 9/2014
WO 2015107099 A1 7/2015
(Continued)

OTHER PUBLICATIONS

International Search Report for Application No. PCT/US2019/015191 dated Jul. 12, 2019, 5 pages.
(Continued)

*Primary Examiner* — Matthew J Lawson
(74) *Attorney, Agent, or Firm* — Howard & Howard Attorneys PLLC

(57) ABSTRACT

End effectors for driving tools at surgical sites along trajectories maintained by surgical robots. A tool has interface and working ends. An end effector has a mount to attach to the surgical robot, and an actuator configured to generate torque. A drive assembly with a geartrain translates rotation from the actuator into rotation of a drive conduit supported about an axis. A rotational lock operatively attached to the drive conduit releasably secures the tool for concurrent rotation about the axis, and an axial lock releasably secures the tool for concurrent translation with the drive conduit along the trajectory maintained by the surgical robot. The axial lock is operable between a release configuration where relative movement between the drive assembly and the tool is permitted along the axis, and a lock configuration where
(Continued)

relative movement between the drive assembly and the tool is restricted along the axis.

41 Claims, 116 Drawing Sheets

(51) Int. Cl.
    *A61B 34/20*     (2016.01)
    *A61B 34/00*     (2016.01)
    *A61F 2/46*     (2006.01)
    *A61B 17/16*     (2006.01)
    *A61B 17/00*     (2006.01)

(52) U.S. Cl.
    CPC ............ *A61F 2/46* (2013.01); *A61B 17/1624* (2013.01); *A61B 17/1671* (2013.01); *A61B 34/76* (2016.02); *A61B 2017/00261* (2013.01); *A61B 2017/00464* (2013.01); *A61B 2017/00477* (2013.01); *A61B 2034/107* (2016.02); *A61B 2034/2051* (2016.02); *A61B 2034/2055* (2016.02); *A61B 2034/305* (2016.02); *A61B 2034/743* (2016.02); *A61B 2034/744* (2016.02); *A61F 2/4603* (2013.01); *A61F 2002/4632* (2013.01); *A61F 2002/4641* (2013.01)

(58) Field of Classification Search
    CPC ................ A61B 17/8875; A61B 34/30; A61B 2034/305; A61F 2002/4632
    See application file for complete search history.

(56) References Cited

U.S. PATENT DOCUMENTS

| | | |
|---|---|---|
| 8,002,798 B2 | 8/2011 | Chin et al. |
| 8,010,180 B2 | 8/2011 | Quaid et al. |
| 8,267,958 B2 | 9/2012 | Braun |
| 9,008,757 B2 | 4/2015 | Wu |
| 9,089,352 B2 | 7/2015 | Jeong |
| 9,119,655 B2 | 9/2015 | Bowling et al. |
| 9,241,771 B2 | 1/2016 | Kostrzewski et al. |
| 9,408,716 B1 | 8/2016 | Reitblat et al. |
| 9,750,510 B2 | 9/2017 | Kostrzewski et al. |
| 9,801,686 B2 | 10/2017 | Lightcap et al. |
| 2009/0024141 A1 | 1/2009 | Stahler et al. |
| 2010/0249497 A1 | 9/2010 | Peine et al. |
| 2011/0295315 A1 | 12/2011 | Jensen et al. |
| 2012/0109172 A1* | 5/2012 | Schmitz .............. A61M 1/0056 606/170 |
| 2012/0116390 A1 | 5/2012 | Madan |
| 2013/0012958 A1 | 1/2013 | Marczyk et al. |
| 2013/0053648 A1 | 2/2013 | Abovitz et al. |
| 2013/0060278 A1* | 3/2013 | Bozung .............. A61B 17/3403 606/205 |
| 2014/0276949 A1* | 9/2014 | Staunton ................ A61B 34/30 606/130 |
| 2015/0133960 A1 | 5/2015 | Lohmeier et al. |
| 2015/0223897 A1 | 8/2015 | Kostrzewski et al. |
| 2015/0305817 A1 | 10/2015 | Kostrzewski |
| 2015/0366624 A1 | 12/2015 | Kostrzewski et al. |
| 2017/0196599 A1* | 7/2017 | Kwon .................... A61B 34/32 |
| 2017/0348061 A1* | 12/2017 | Joshi .................... A61M 5/172 |
| 2018/0042650 A1 | 2/2018 | Gao et al. |

FOREIGN PATENT DOCUMENTS

| | | |
|---|---|---|
| WO | 2015121311 A1 | 8/2015 |
| WO | 2015162256 A1 | 10/2015 |
| WO | 2015193479 A1 | 12/2015 |

OTHER PUBLICATIONS

Partial International Search Report for Application No. PCT/US2019/015191 dated May 7, 2019, 2 pages.
Stryker Spine, "ES2 Spinal System Surgical Technique", Rev. 7, May 2017, 64 pages.
U.S. Appl. No. 62/678,838, filed May 31, 2018.

\* cited by examiner

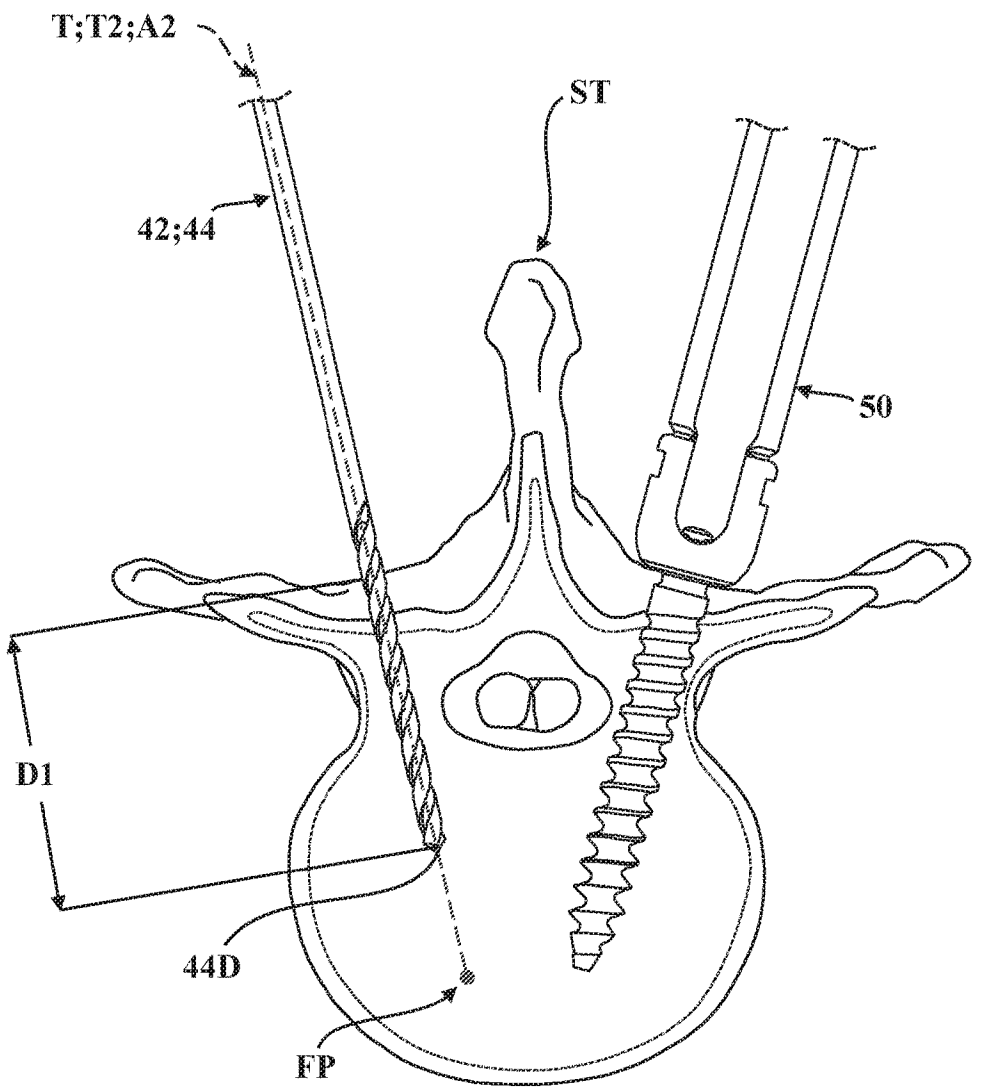

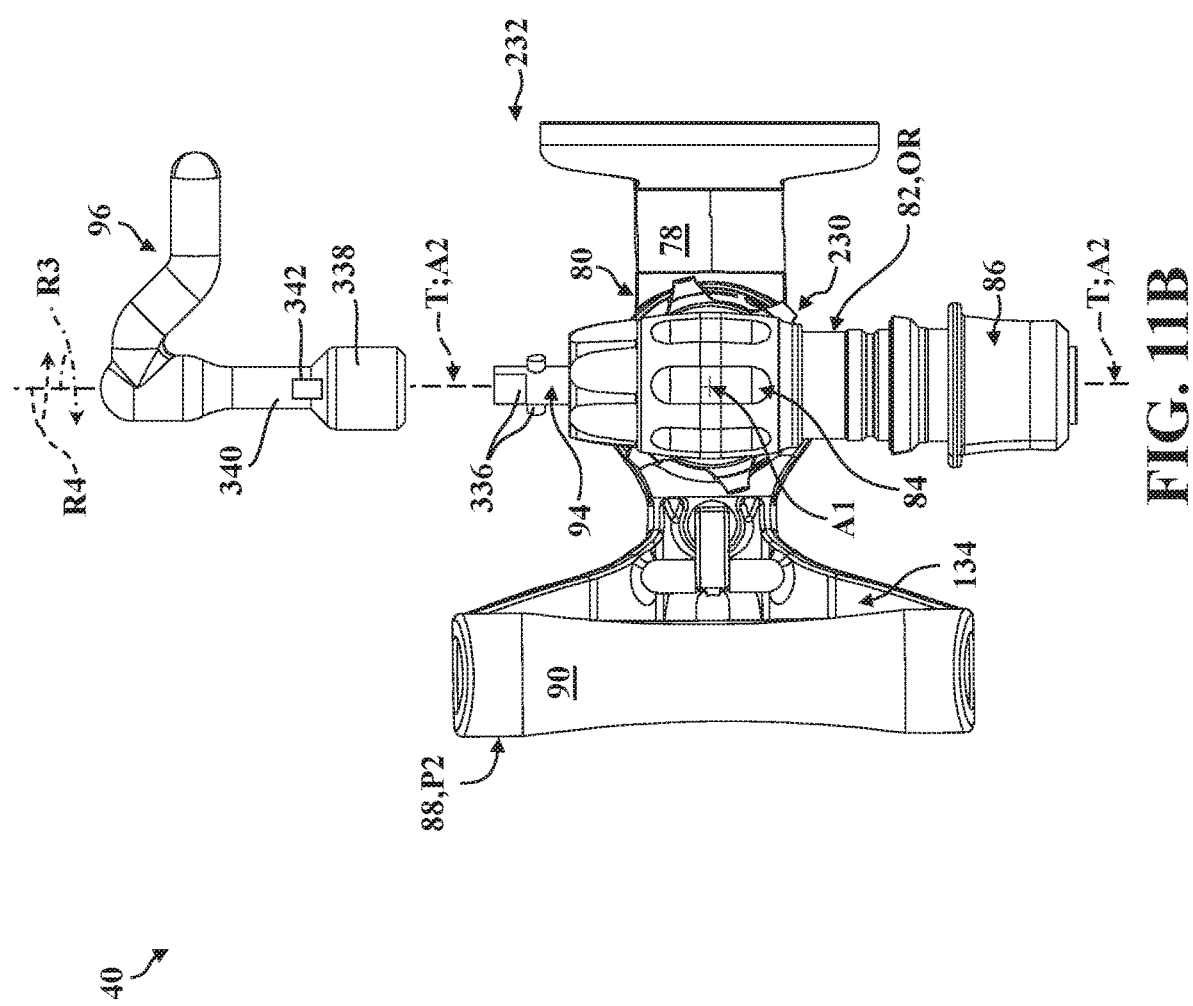

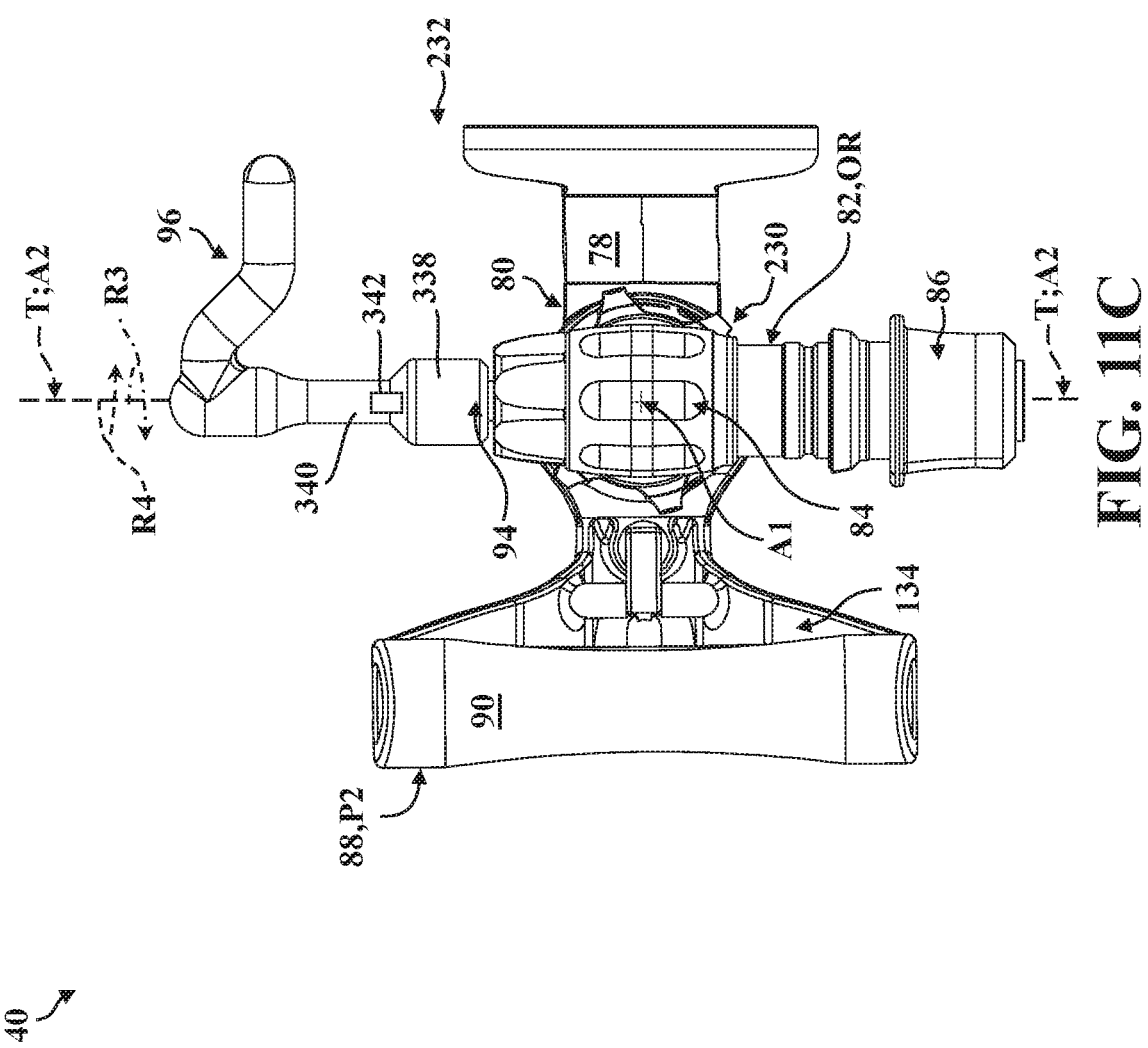

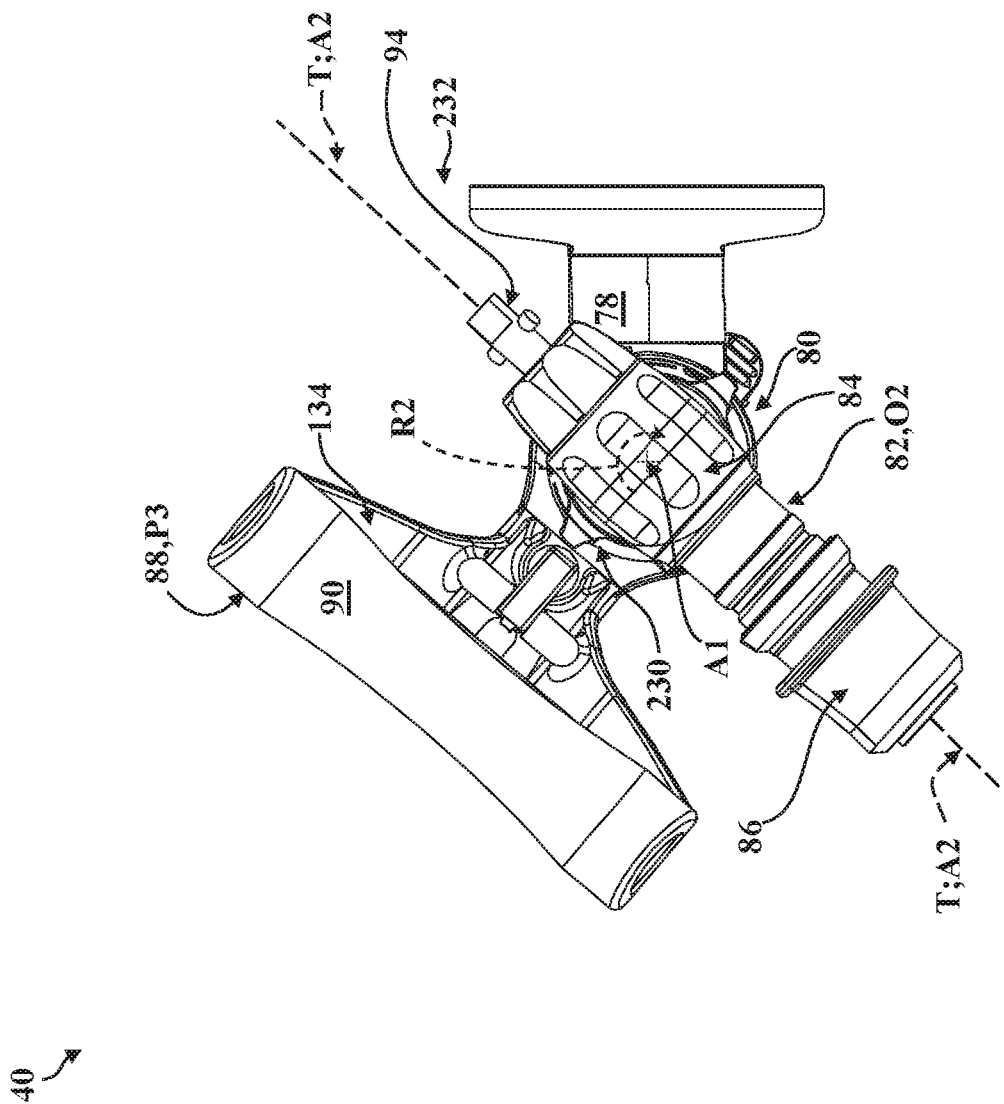

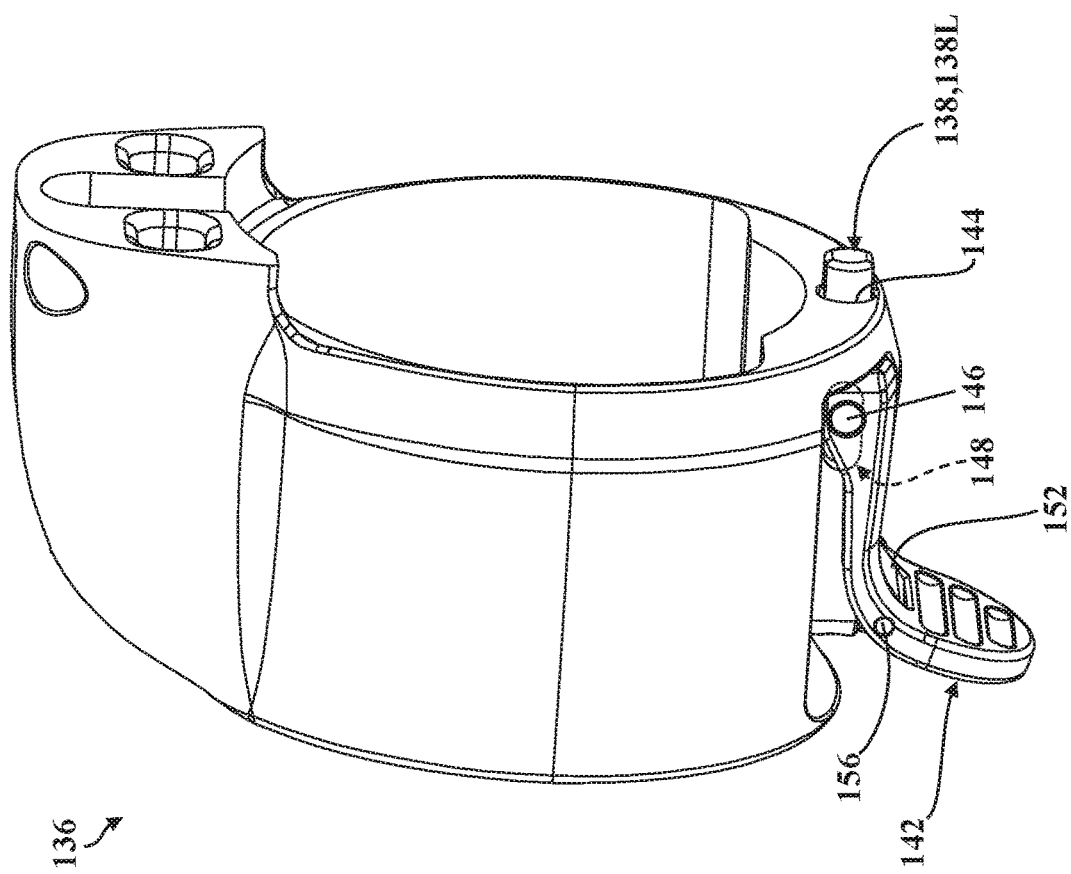

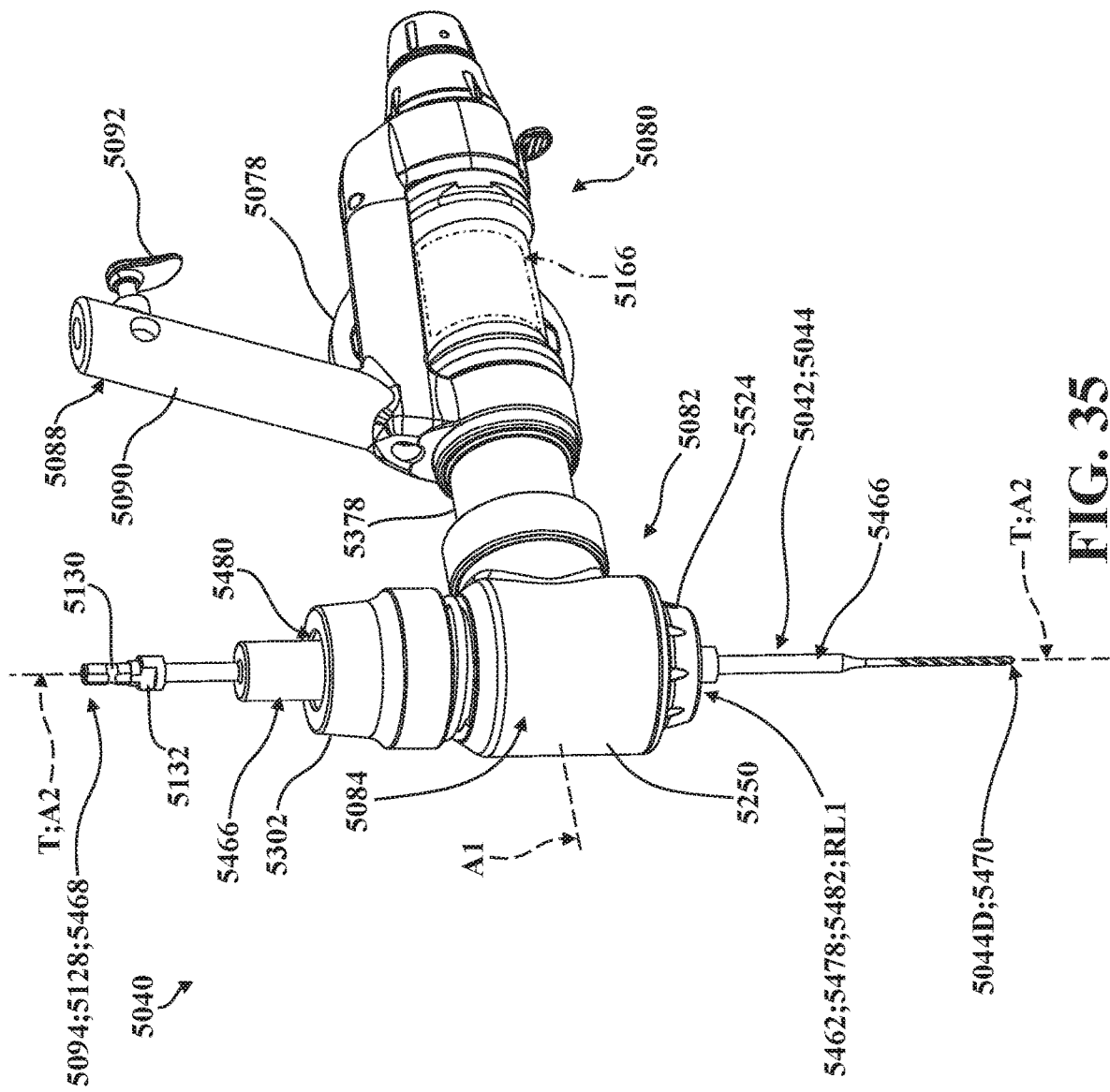

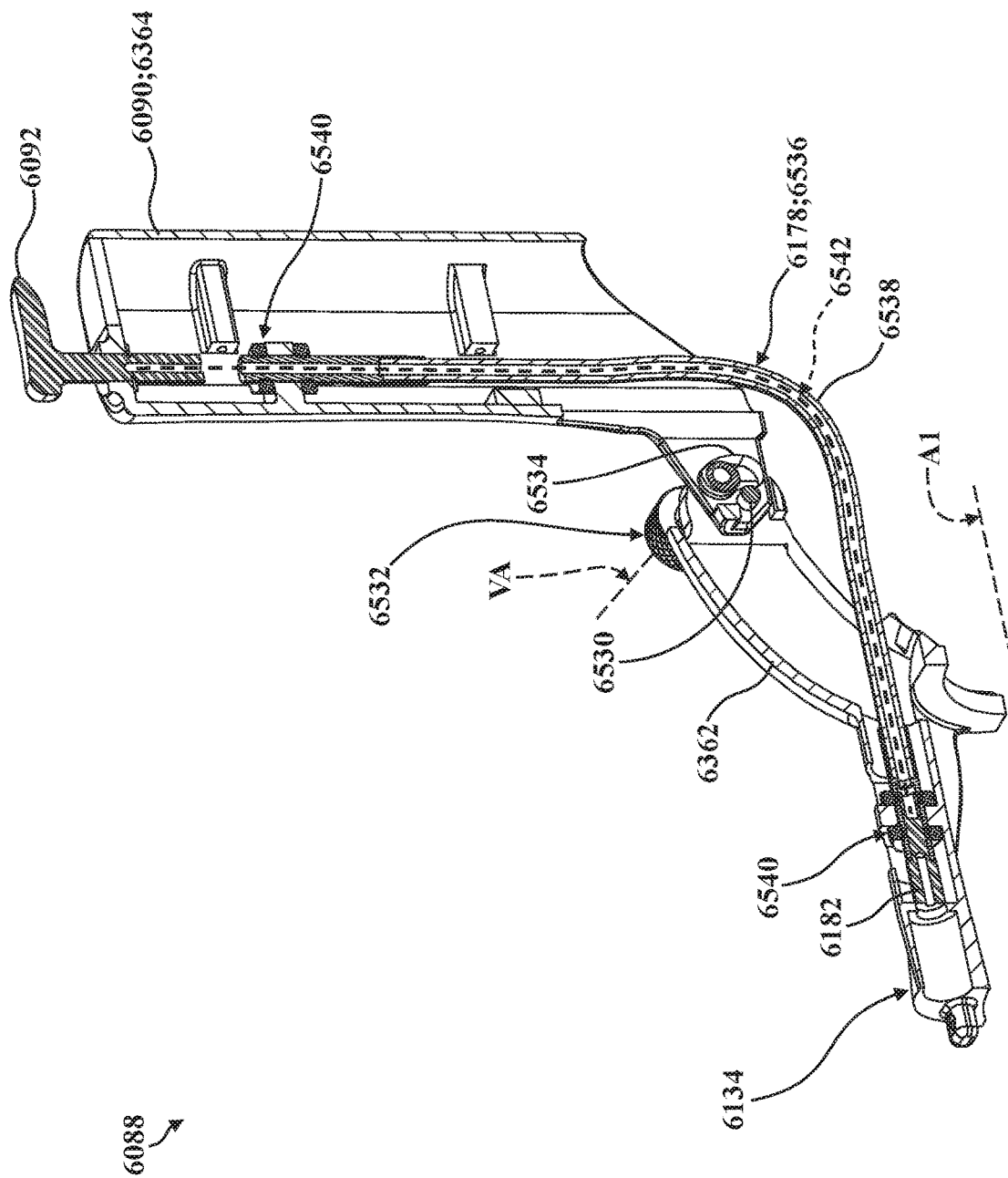

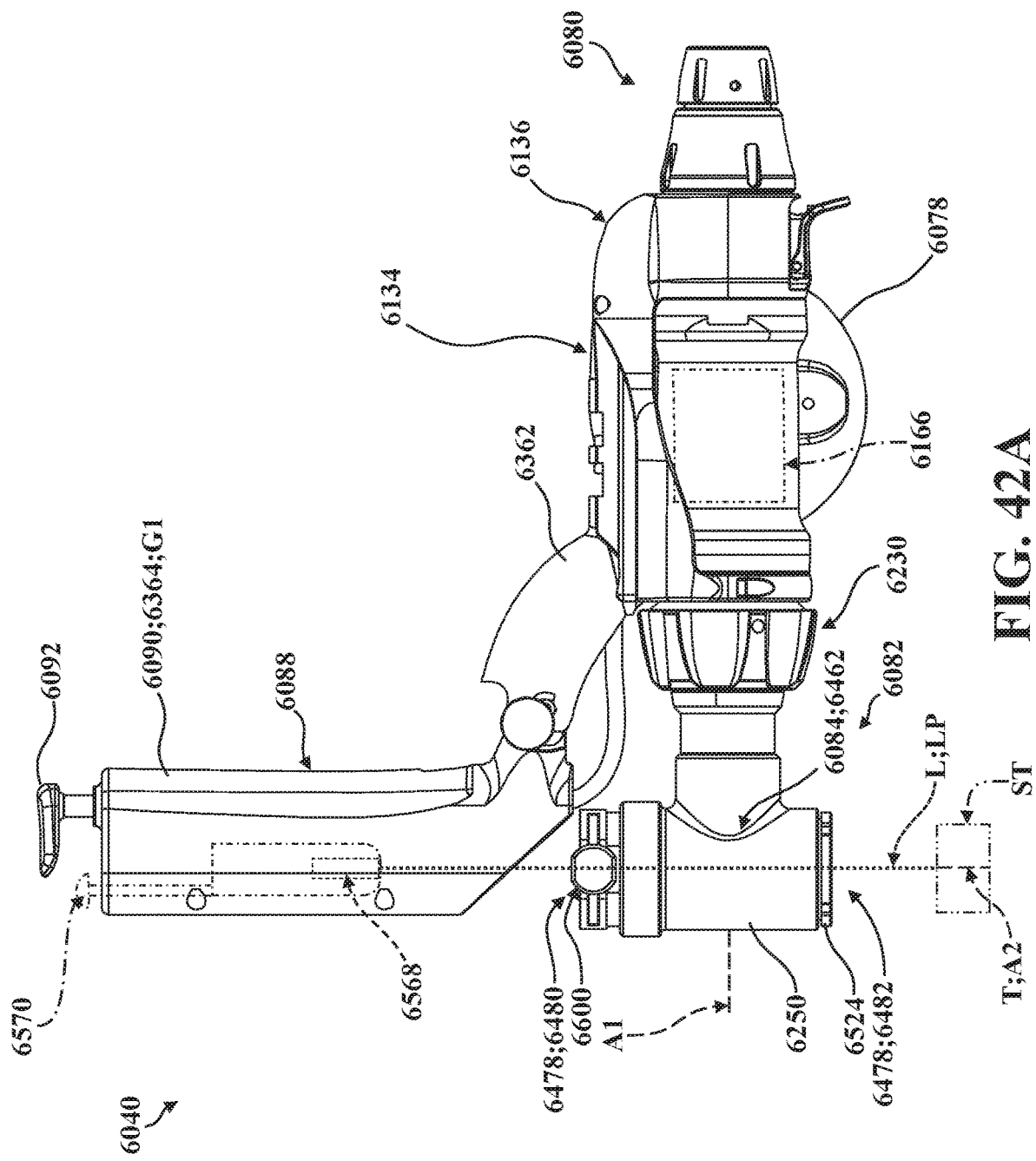

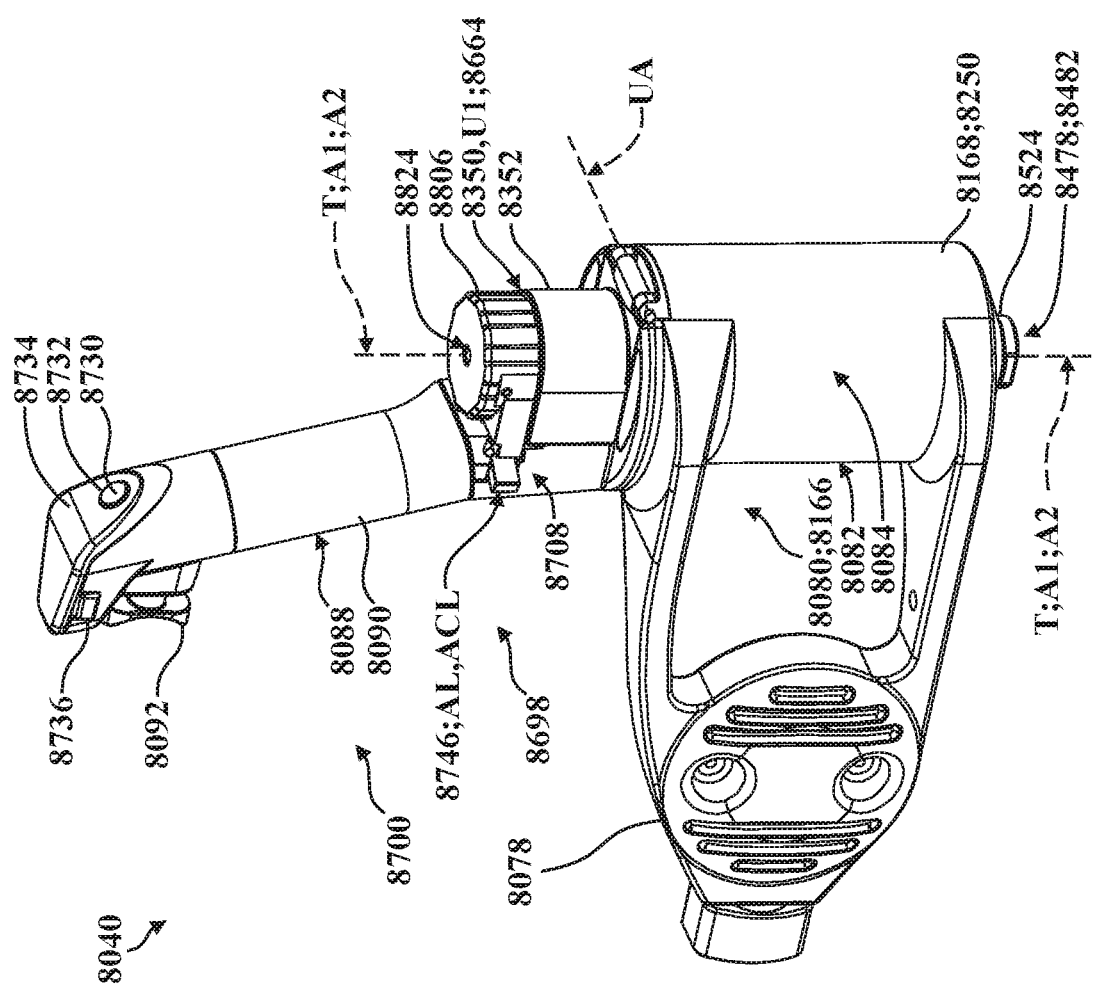

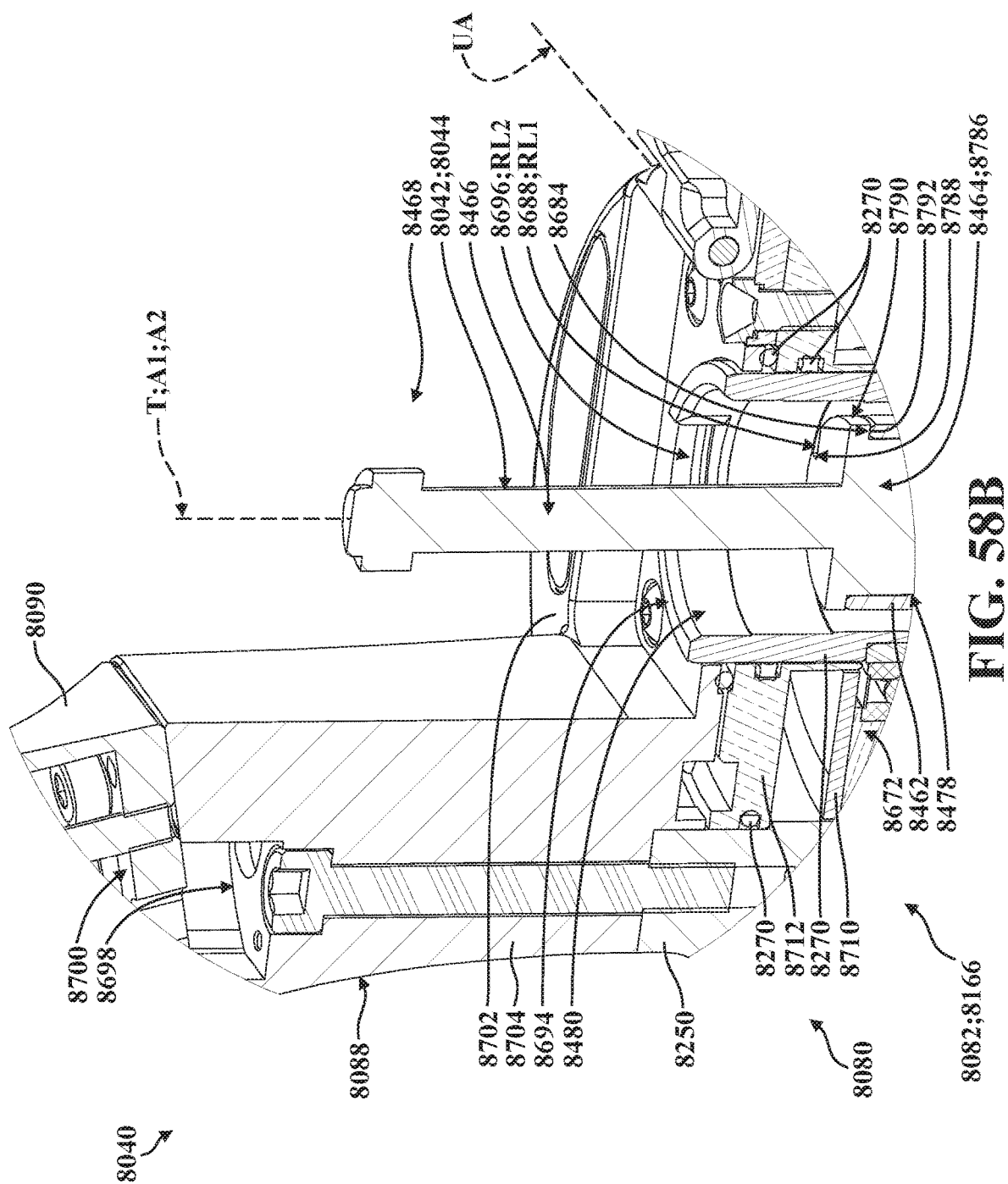

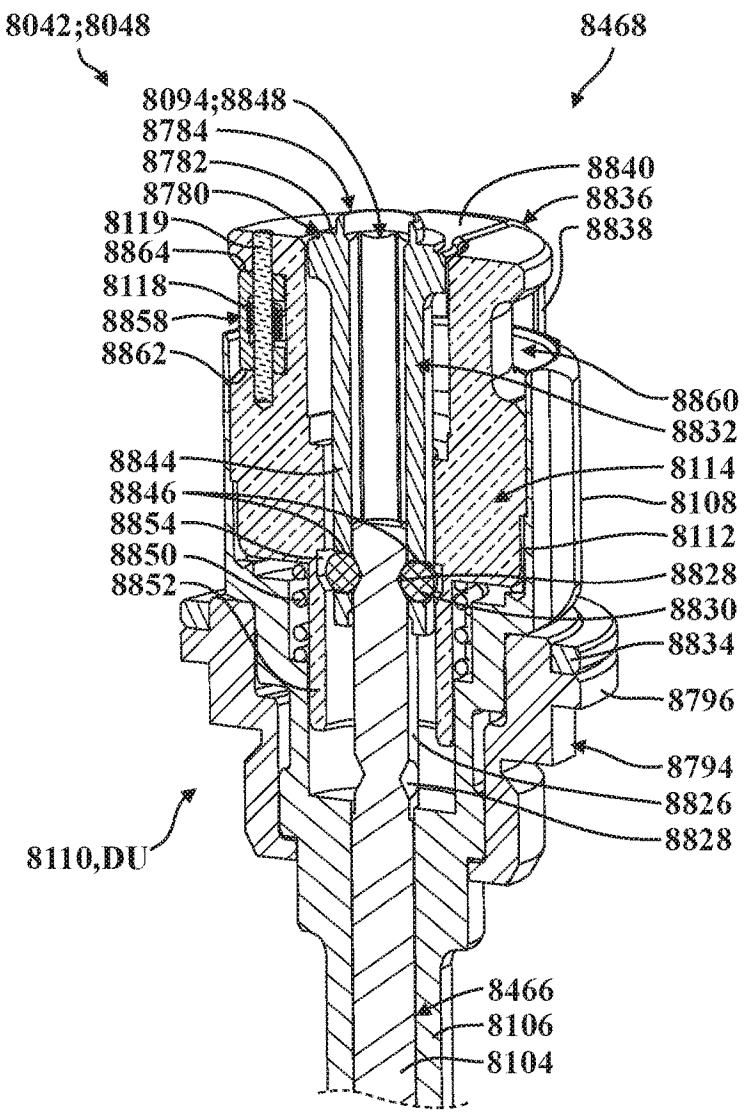

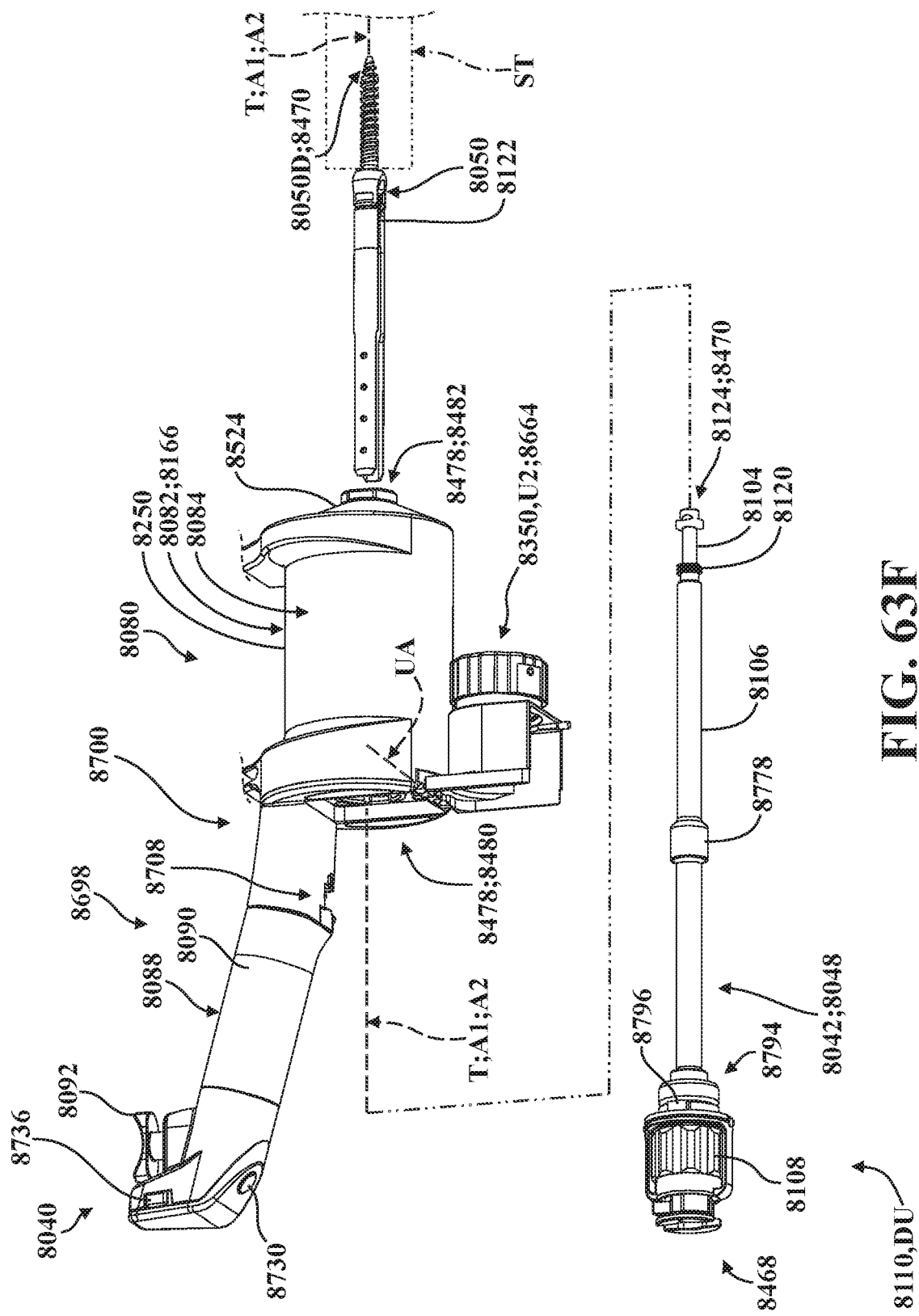

END EFFECTORS AND METHODS FOR DRIVING TOOLS GUIDED BY SURGICAL ROBOTIC SYSTEMS

CROSS-REFERENCE TO RELATED APPLICATIONS

The subject patent application claims priority to and all the benefits of U.S. Provisional Patent Application No. 62/622,306 filed on Jan. 26, 2018, and U.S. Provisional Patent Application No. 62/744,878 filed on Oct. 12, 2018, the disclosures of which are each hereby incorporated by reference in their entirety.

BACKGROUND

Surgical robotic systems are frequently used to assist medical professionals in carrying out various types of surgical procedures. To this end, a surgeon may use a surgical robot to guide, position, move, actuate, or otherwise manipulate various tools, components, prostheses, and the like during a surgery.

It will be appreciated that surgical robots can be used to assist surgeons in performing a number of different types of surgical procedures. By way of illustration, surgical robots are commonly used in procedures involving the correction, stabilization, resection, or replacement of one or more parts of a patient's body, such as to help improve patient mobility, reduce pain, mitigate the risk of subsequent injury or damage, and the like.

By way of illustrative example, in many types of spinal procedures (e.g., a posterior lumbar interbody fusion "PLIF"), robotic systems advantageously help facilitate proper installation of pedicle screws at discrete locations in vertebrae of the patient's spine. The pedicle screws serve as anchors and typically cooperate with additional fixation hardware (e.g., stabilization rods) to restrict movement between anchored vertebrae which, in turn, helps ensure that bone grafts disposed between adjacent vertebrae can successfully fuse together.

When a patient requires surgery that involves placing pedicle screws, pre-operative imaging and/or intra-operative imaging are often utilized by the surgeon to help visualize the patient's anatomy (e.g., vertebrae of the patient's spine). The surgeon typically plans where to place the pedicle screws based on the pre-operative imaging, such as with images captured of the patient's anatomy, 3D models created from the images, and the like. Planning includes determining a desired position and orientation (i.e., pose) of each pedicle screw with respect to the particular vertebra in which it is to be placed, such as by identifying the desired pose in the pre-operative images and/or 3D models. Once set, the plan is transferred to the robotic system for execution.

Typically, the robotic system comprises a surgical robot with a robotic arm that positions a tool guide above the patient and along a desired trajectory that is aligned with the desired orientation of the pedicle screw to be placed. The robotic system also comprises a navigation system to determine a location of the tool guide with respect to the patient's anatomy so that the robotic arm can position the tool guide along the desired trajectory according to the surgeon's plan. In some cases, the navigation system includes tracking devices attached to the surgical robot and to the patient's body so that the robotic system can monitor and respond to movement during the surgical procedure by dynamically moving the tool guide to as needed to maintain the desired trajectory.

In minimally-invasive surgical techniques, once the tool guide has been aligned with the desired trajectory, the surgeon generally positions a cannula through the tool guide, which extends into an incision made in the patient's body adjacent to the vertebra at the surgical site. The surgeon then attaches a drill bit to a hand-held drill, inserts the drill bit into the cannula, and actuates the drill to form a pilot hole for the pedicle screw. The surgeon then removes the drill bit and subsequently drives the pedicle screw into position in the pilot hole with a hand-held driver to install the pedicle screw into the vertebra.

In the types of spinal surgical techniques described above, the robotic arm is somewhat underutilized and plays little to no role in actually drilling the pilot hole or installing the pedicle screw. Moreover, despite the advantages afforded by the surgical system's ability to maintain the trajectory, conventional minimally-invasive techniques often necessitate that the robotic arm be repositioned several times when installing a single pedicle screw. The frequency and extent of this repositioning depends, among other things, on the specific type of surgical technique being utilized, the preferences of the surgeon, as well as the configuration of the pedicle screw, the guide tool, the drill, and the surgical robot itself.

Furthermore, because multiple pedicle screws are usually installed during a single surgery (e.g., a total of four pedicle screws are often employed in a bilateral interbody fusion of two adjacent vertebrae), it may be difficult to efficiently articulate the robotic arm between different trajectories without inconveniencing the surgeon's approach. Moreover, in some circumstances, the surgical robot itself may have to be repositioned relative to the patient's body when the requisite articulation of the robotic arm is impractical to achieve between different trajectories, and/or so as to afford the surgeon with a consistent approach along each trajectory.

Accordingly, there remains a need in the art for addressing one or more of these deficiencies.

SUMMARY

The present disclosure provides an end effector for driving a tool at a surgical site along a trajectory maintained by a surgical robot. The end effector comprises a mount adapted to attach to the surgical robot, a rotary instrument coupled to the mount and comprising an actuator which is configured to generate rotational torque about a first axis. The end effector also comprises a drive assembly with a geartrain to translate rotation from the rotary instrument into rotation about a second axis different from the first axis, and a connector configured to releasably secure the tool for rotation about the second axis. The end effector also comprises a trigger assembly with a grip to support a user's hand, and an input trigger in communication with the rotary instrument. The input trigger is arranged for engagement by the user to drive the rotary instrument and rotate the tool about the second axis. The end effector also comprises a manual interface to communicate with the drive assembly. The manual interface is arranged to receive and translate applied force from the user into rotational torque to rotate the tool about the second axis.

The present disclosure also provides an end effector for driving a tool at a surgical site along different trajectories selectively maintained by a surgical robot. The end effector comprises a mount adapted to attach to the surgical robot, and a rotary instrument coupled to the mount and comprising an actuator configured to generate rotational torque about a first axis. The end effector also comprises a drive assembly with a geartrain to translate rotation from the rotary instrument into rotation about a second axis different from the first axis, and a connector configured to releasably secure the tool for rotation about the second axis. A coupling is operatively attached to the rotary instrument and is configured to releasably secure the drive assembly to the rotary instrument in a plurality of orientations to selectively position the second axis relative to the rotary instrument along different trajectories maintained by the surgical robot.

The present disclosure also provides an end effector for driving a tool at a surgical site along a trajectory maintained by a surgical robot, the tool having an interface end and a working end. The end effector comprises a mount adapted to attach to the surgical robot, and an actuator coupled to the mount and configured to generate rotational torque about a first axis. The end effector also comprises a drive assembly comprises a geartrain to translate rotation from the actuator about the first axis into rotation about a second axis, a drive conduit supported for rotation about the second axis, a first rotational lock operatively attached to the drive conduit to releasably secure the tool for concurrent rotation about the second axis, and an axial lock to releasably secure the tool for concurrent translation with the drive conduit along the trajectory maintained by the surgical robot. The axial lock is operable between a release configuration where relative movement between the drive assembly and the tool is permitted along the second axis, and a lock configuration where relative movement between the drive assembly and the tool is restricted along the second axis.

The present disclosure also provides an end effector for guiding tools relative to a surgical site along a trajectory maintained by a surgical robot, the tools including a first tool and a second tool different from the first tool. The end effector comprises a mount adapted to attach to the surgical robot, and a rotary instrument coupled to the mount and comprising an actuator configured to generate rotational torque about a first axis. The end effector also comprises a drive assembly with a geartrain to translate rotation from the rotary instrument about the first axis into rotation about a second axis, a first rotational lock disposed in rotational communication with the geartrain to releasably secure the first tool for concurrent rotation about the second axis at a first drive ratio, a second rotational lock disposed in communication with the geartrain to releasably secure the second tool for concurrent rotation about the second axis at a second drive ratio different from the first drive ratio, and an axial lock to releasably secure one of the first tool and the second tool for concurrent translation with the drive assembly along the trajectory maintained by the surgical robot. The axial lock is operable between a release configuration where relative movement between the drive assembly and the secured tool is permitted along the second axis, and a lock configuration where relative movement between the drive assembly and the secured tool is restricted along the second axis.

The present disclosure also provides an end effector for driving tools at a surgical site along a trajectory maintained by a surgical robot, the tools including a first tool and a second tool different from the first tool. The end effector comprises a mount adapted to attach to the surgical robot, and a rotary instrument coupled to the mount and comprising an actuator configured to generate rotational torque about a first axis. The end effector also comprises a drive assembly with a geartrain to translate rotation from the rotary instrument into rotation about a second axis different from the first axis, a connector configured to releasably secure one of the first tool and the second tool for rotation about the second axis, and a transmission interposed in rotational communication between the rotary instrument and the connector. The transmission comprises a first gearset, a second gearset, and a shift collar arranged for movement between a first collar position where the shift collar engages the first gearset to translate rotation between the rotary instrument and the connector at a first drive ratio, and a second collar position where the shift collar engages at the second gearset to translate rotation between the rotary instrument and the connector at a second drive ratio different from the first drive ratio.

The present disclosure also provides a method of forming a pilot hole at a surgical site along a trajectory maintained by a surgical robot. The method comprises attaching an end effector to the surgical robot, the end effector supporting an actuator, a drive assembly, a manual interface, and a trigger assembly. The method also comprises attaching a rotary cutting tool to the drive assembly along a second axis, aligning the second axis with the trajectory to position the rotary cutting tool at the surgical site, and engaging the trigger assembly to generate rotational torque with the actuator about a first axis and to translate torque from the actuator about the first axis through the drive assembly to rotate the rotary cutting tool about the second axis. The method also comprises advancing the rotary cutting tool along the trajectory at the surgical site to a first depth, interrupting rotation about the first axis, positioning the trigger assembly to present the manual interface, applying force to the manual interface to rotate the rotary cutting tool about the second axis, and advancing the rotary cutting tool along the trajectory at the surgical site to a second depth greater than the first depth.

The present disclosure also provides a method of installing an anchor at a surgical site along a trajectory maintained by a surgical robot. The method comprises attaching an end effector to the surgical robot, the end effector supporting an actuator, a drive assembly, a manual interface, and a trigger assembly. The method also comprises attaching a tool to the drive assembly along a second axis, attaching the anchor to the tool, aligning the second axis with the trajectory to position the anchor adjacent to the surgical site, and engaging the trigger assembly to generate rotational torque with the actuator about a first axis and to translate torque from the actuator about the first axis through the drive assembly to rotate the tool and the anchor about the second axis. The method also comprises advancing the tool and the anchor along the trajectory at the surgical site to a first depth, interrupting rotation about the first axis, positioning the trigger assembly to present the manual interface, applying force to the manual interface to rotate the tool and the anchor about the second axis, and advancing the anchor along the trajectory at the surgical site to a second depth greater than the first depth.

The present disclosure also provides a method of installing first and the second anchors at a surgical site along respective first and second trajectories maintained by a surgical robot. The method comprises attaching an end effector to the surgical robot, the end effector supporting an actuator, a drive assembly, a manual interface, and a trigger assembly. The method also comprises attaching a tool to the drive assembly along a second axis, attaching the first anchor to the tool, aligning the second axis with the first trajectory to position the first anchor adjacent to the surgical site, and engaging the trigger assembly to generate rotational torque with the actuator about a first axis and to translate torque from the actuator about the first axis through the drive assembly to rotate the tool and the first anchor about the second axis. The method also comprises advancing the tool and the first anchor along the first trajectory at the surgical site to a first depth, interrupting rotation about the first axis, positioning the trigger assembly to present the manual interface, applying force to the manual interface to rotate the tool and the first anchor about the second axis, and advancing the tool and the first anchor along the first trajectory at the surgical site to a second depth greater than the first depth. The method further comprises releasing the first anchor from the tool, attaching the second anchor to the tool, aligning the second axis with the second trajectory to position the second anchor adjacent to the surgical site, engaging the trigger assembly to generate rotational torque with the actuator about the first axis, and translating torque from the actuator about the first axis through the drive assembly to rotate the tool and the second anchor about the second axis. The method further comprises advancing the tool and the second anchor along the second trajectory at the surgical site to a third depth, interrupting rotation about the first axis, positioning the trigger assembly to present the manual interface, applying force to the manual interface to rotate the tool and the second anchor about the second axis, and advancing the tool and the second anchor along the second trajectory at the surgical site to a fourth depth greater than the third depth.

Other features and advantages of the embodiments of the present disclosure will be readily appreciated, as the same becomes better understood, after reading the subsequent description taken in conjunction with the accompanying drawings.

BRIEF DESCRIPTION OF THE DRAWINGS

FIG. 5B is another illustrative view of the surgical site of FIG. 5A, shown with the drill bit penetrating the vertebra along the second trajectory to form a pilot hole at a first depth extending through the pedicle and into the vertebral body.

FIG. 11B is another front-side plan view of the end effector of FIG. 11A, shown with the trigger assembly arranged in the second trigger assembly position, with the coupling supporting the drive assembly in the first orientation, and with the handle assembly disposed adjacent to the manual interface.

FIG. 11C is another front-side plan view of the end effector of FIGS. 11A-11B, shown with the trigger assembly arranged in the second trigger assembly position, with the coupling supporting the drive assembly in the first orientation, and with the handle assembly disposed in engagement with the manual interface.

FIG. 11F is another front-side plan view of the end effector of FIGS. 11A-11E, shown with the trigger assembly arranged in a third trigger assembly position, and with the coupling supporting the drive assembly in the third orientation.

FIG. 20A is a perspective view of the retainer of FIG. 17, shown having a plunger disposed in a locked position to restrict movement of the trigger assembly relative to the rotary instrument between the trigger assembly positions.

FIG. 35 is a perspective view of an end effector, according to a fifth embodiment of the present disclosure, which is likewise configured for use with the surgical system of FIG. 1, the end effector shown comprising a mount supporting a rotary instrument to generate torque about a first axis, and a drive assembly with a drive conduit supporting a tool for rotation about a second axis, the tool depicted as a rotary cutting tool with a drill bit.

FIG. 41 is a partial sectional perspective view of the trigger assembly of FIGS. 39A-40, depicted as sectioned generally longitudinally.

FIG. 42A is a side plan view of the end effector of FIGS. 39A-40, shown with a light source operatively attached to a portion of the trigger assembly, with the trigger assembly arranged as depicted in FIG. 39A, and with the light source shown emitting light towards a surgical site along the second axis.

FIG. 49A is a perspective view of an end effector, according to an eighth embodiment of the present disclosure, which is likewise configured for use with the surgical system of FIG. 1, the end effector shown comprising a mount supporting a rotary instrument to generate torque about a first axis, a drive assembly with a drive conduit to support a tool for rotation about a second axis coincident with the first axis, a trigger assembly coupled to the drive assembly, and a retention mechanism having guard cover arranged in a first guard position.

FIG. 58B is another enlarged, partial sectional perspective view of the end effector of FIG. 58A, shown with portions of the rotary driving tool of FIG. 49B supported in the drive conduit of the drive assembly.

FIG. 62A is a partial, sectional perspective view of the rotary driving tool of FIG. 60, depicted as sectioned along a plane (not shown) arranged about the second axis and disposed perpendicular to a longitudinal plane (not shown) likewise arranged about the second axis, shown with the locking subassembly arranged in a driver locked configuration.

FIG. 63F is another partial perspective view of the end effector, the rotary driving tool, and the anchor of FIG. 63E, shown with the rotary driving tool removed from the drive assembly of the end effector and released from the anchor, and shown with the anchor arranged along the trajectory spaced from the end effector and from the rotary driving tool.

It will be appreciated that one or more of the embodiments depicted throughout the drawings may have certain components, structural features, and/or assemblies removed, depicted schematically, and/or shown in phantom for illustrative purposes.

DETAILED DESCRIPTION

Figure 1:
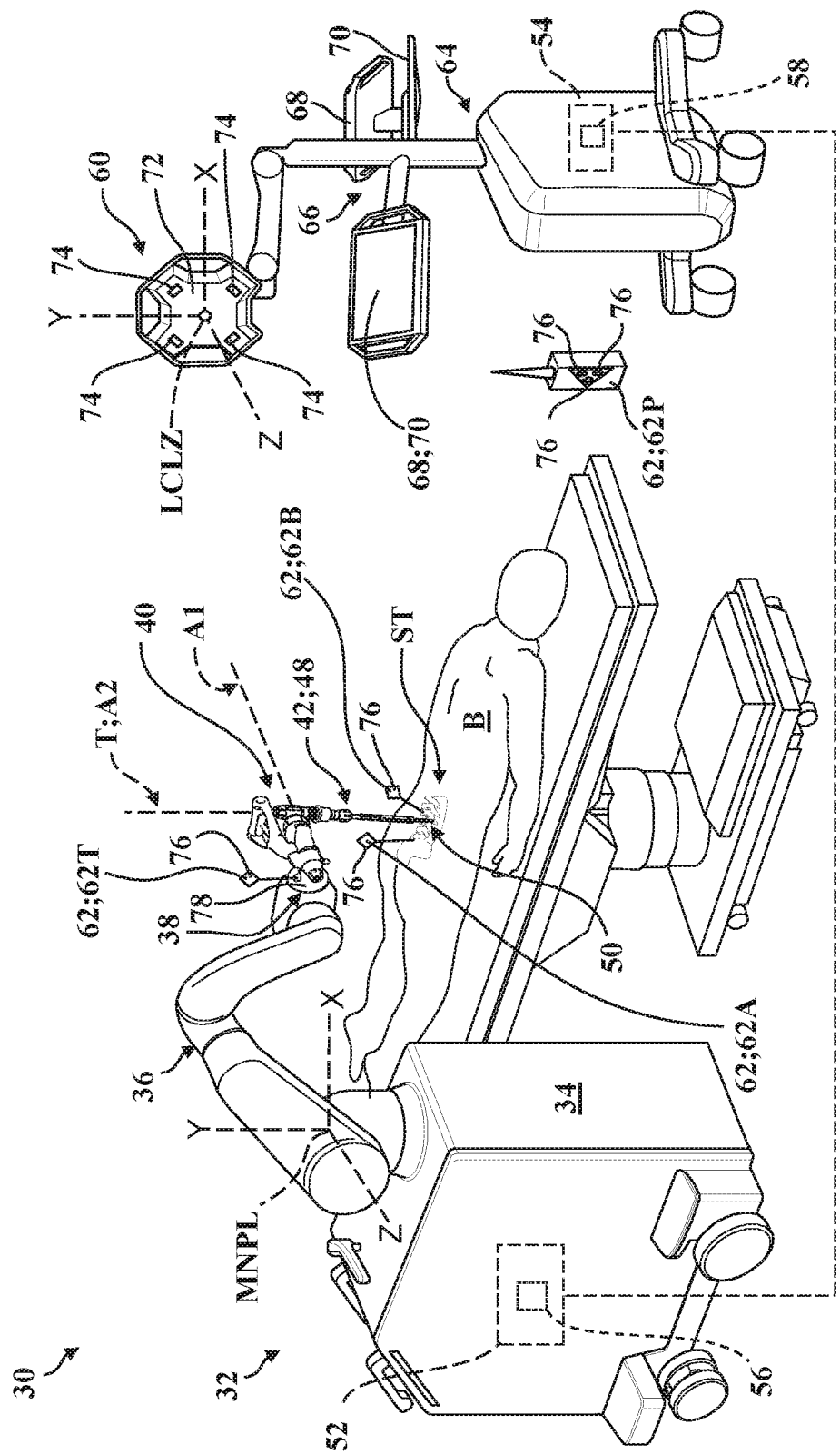
FIG. 1 is a perspective view of a surgical system comprising a surgical robot with a robotic arm supporting an end effector, according to a first embodiment of the present disclosure, to which a tool is secured along a trajectory adjacent to a surgical site on a patient's body.

Referring now to the drawings, wherein like numerals indicate like or corresponding parts throughout the several views, a surgical system 30 comprising a surgical robot 32 is shown in FIG. 1. The surgical robot 32 has a base 34, a robotic arm 36, and a coupler 38. As is described in greater detail below, the robotic arm 36 is supported by the base 34 and is configured to move, guide, drive, maintain, or otherwise control the position and/or orientation of the coupler 38 relative to the base 34 during use. The coupler 38 is adapted to releasably secure an end effector 40 which, in turn, is configured to drive a tool, generally indicated at 42, at a surgical site ST on a patient's body B along one or more trajectories T, as is described in greater detail below. Thus, the surgical robot 32 moves the end effector 40 via the robotic arm 36 to, among other things, assist medical professionals in carrying out various types of surgical procedures with precise control over movement and positioning of the end effector 40 and the tool 42. One exemplary arrangement of the robotic arm 36 is described in U.S. Pat. No. 9,119,655, entitled "Surgical Robotic arm Capable of Controlling a Surgical Instrument in Multiple Modes," the disclosure of which is hereby incorporated by reference in its entirety. It will be appreciated that the robotic arm 36 and other portions of the surgical robot 32 may be arranged in alternative configurations.

The surgical system 30 is configured to help a user (e.g., a surgeon) guide, position, and/or locate one or more types of tools 42, at and/or with respect to the surgical site ST along the trajectory T maintained by the surgical robot 32. As will be appreciated from the subsequent description below of the various embodiments of the present disclosure, tools 42 can be supported by the end effector 40 to, among other things, allow the surgeon to approach and manipulate anatomy of the patient's body B at the surgical site ST with a high level of control relative to the trajectory T maintained by the surgical robot 32. Each of the components of the surgical system 30 introduced above will be described in greater detail below.

Those having ordinary skill in the art will appreciate that conventional surgical procedures routinely involve the use of a number of different types of tools 42. Here, certain types of tools 42 can be characterized as "active," when configured to be driven by the end effector 40 while being supported along the trajectory T (e.g., without limitation, rotary cutting instruments such as drills and burs). On the other hand, certain types of tools 42 can be characterized as "passive," when configured to be guided (but not necessarily driven) by the end effector 40 while being at least partially supported along the trajectory T (e.g., without limitation, dissectors and scalpels). In addition, some types of tools 42 can be characterized as both "active" and "passive" depending on how they are used, as will be appreciated from the subsequent description below.

Figure 4:
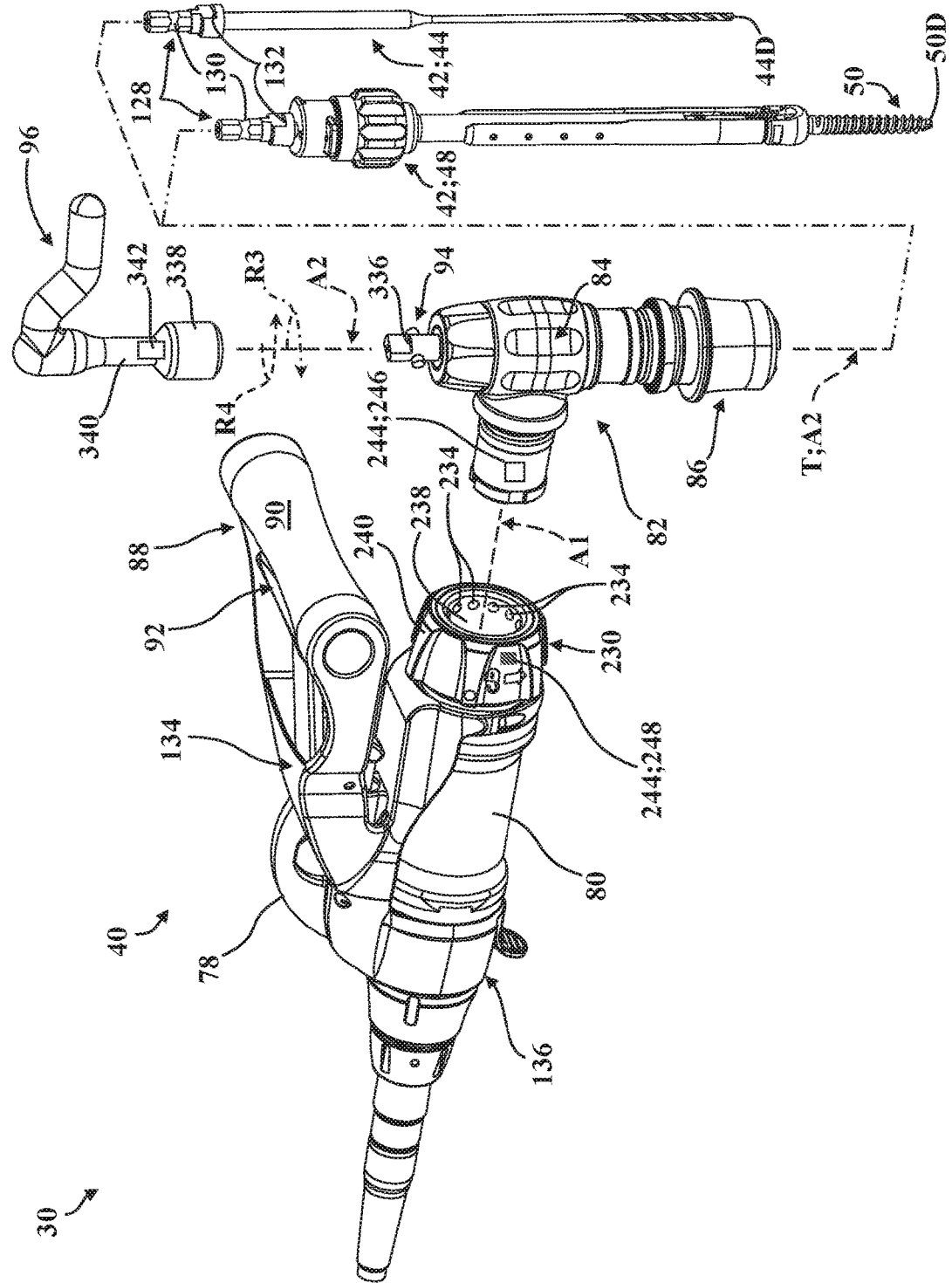
FIG. 4 is a partially-exploded perspective view of the end effector of FIG. 3, shown with the drive assembly spaced from the rotary instrument below the handle assembly and spaced from two tools configured for releasable attachment to the drive assembly, with one of the tools shown as a rotary cutting tool with a drill bit, and with the other of the tools shown as an rotary driving tool supporting an anchor.
Figure 5A:
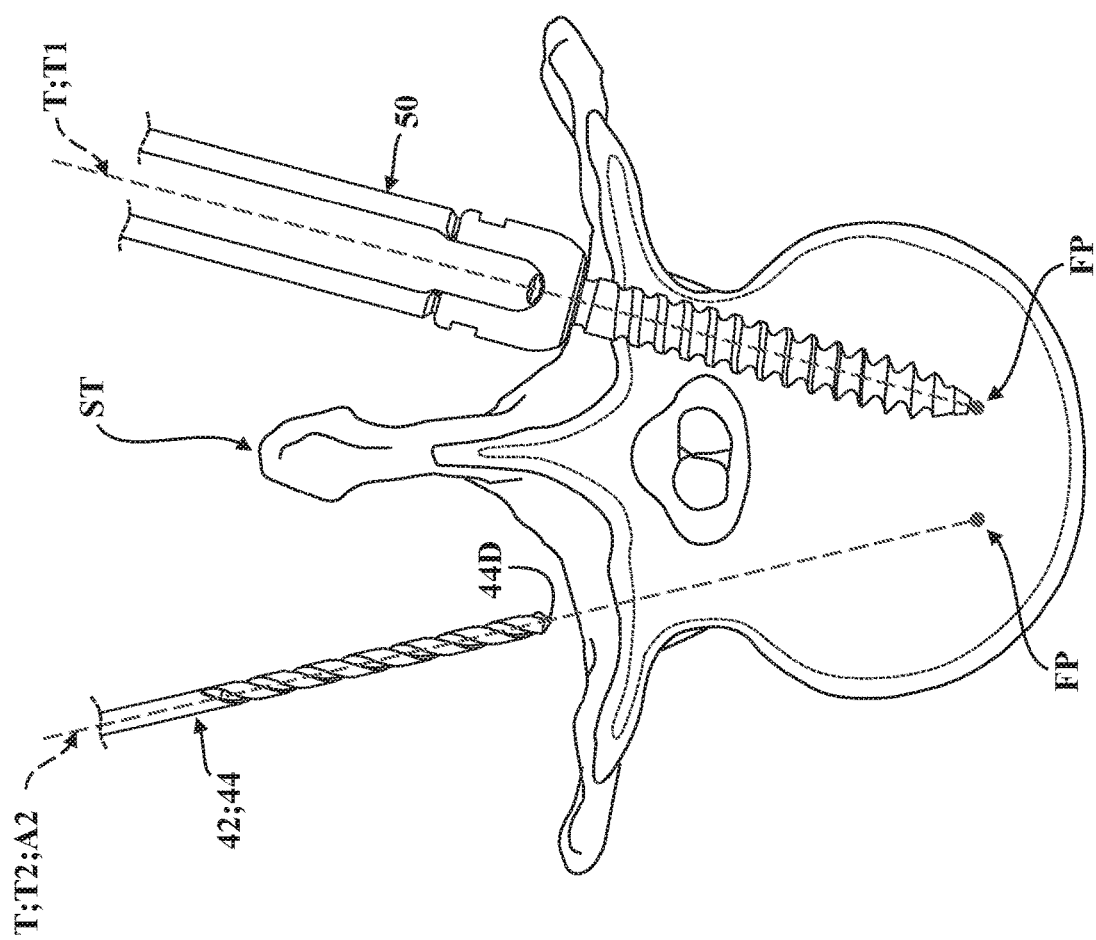
FIG. 5A is an illustrative view of a surgical site taken transversely through a patient's vertebra in connection with a minimally-invasive spinal fusion technique performed with the surgical system of FIGS. 1-4, depicting first and second trajectories arranged bilaterally relative to the spinous process and extending through the respective pedicles into the vertebral body on opposing sides of the foramen and spinal cord, and shown with an anchor installed along the first trajectory and with a drill bit guided along the second trajectory positioned adjacent to the vertebra.
Figure 5C:
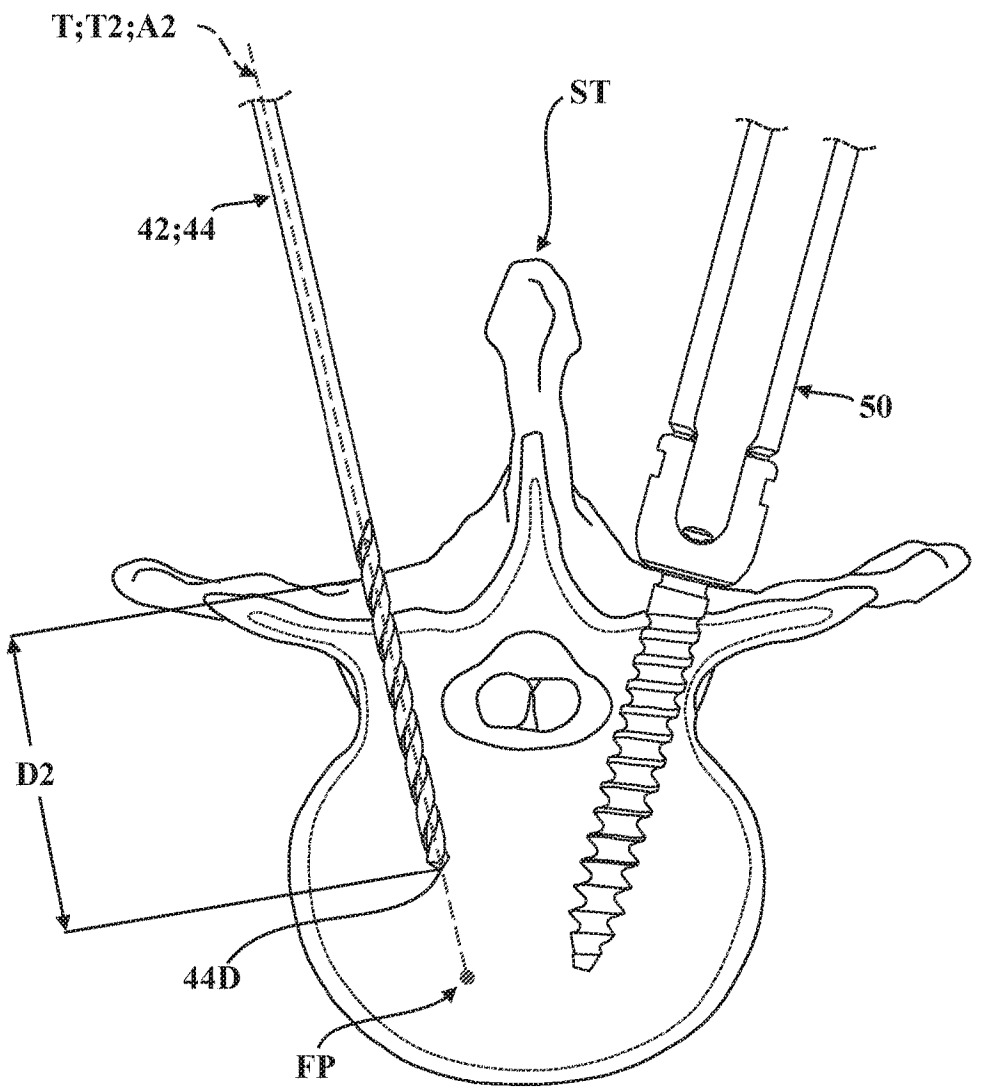
FIG. 5C is another illustrative view of the surgical site of FIGS. 5A-5B, shown with the drill bit advanced further along the trajectory to form the pilot hole at a second depth further into the vertebral body.
Figure 5D:
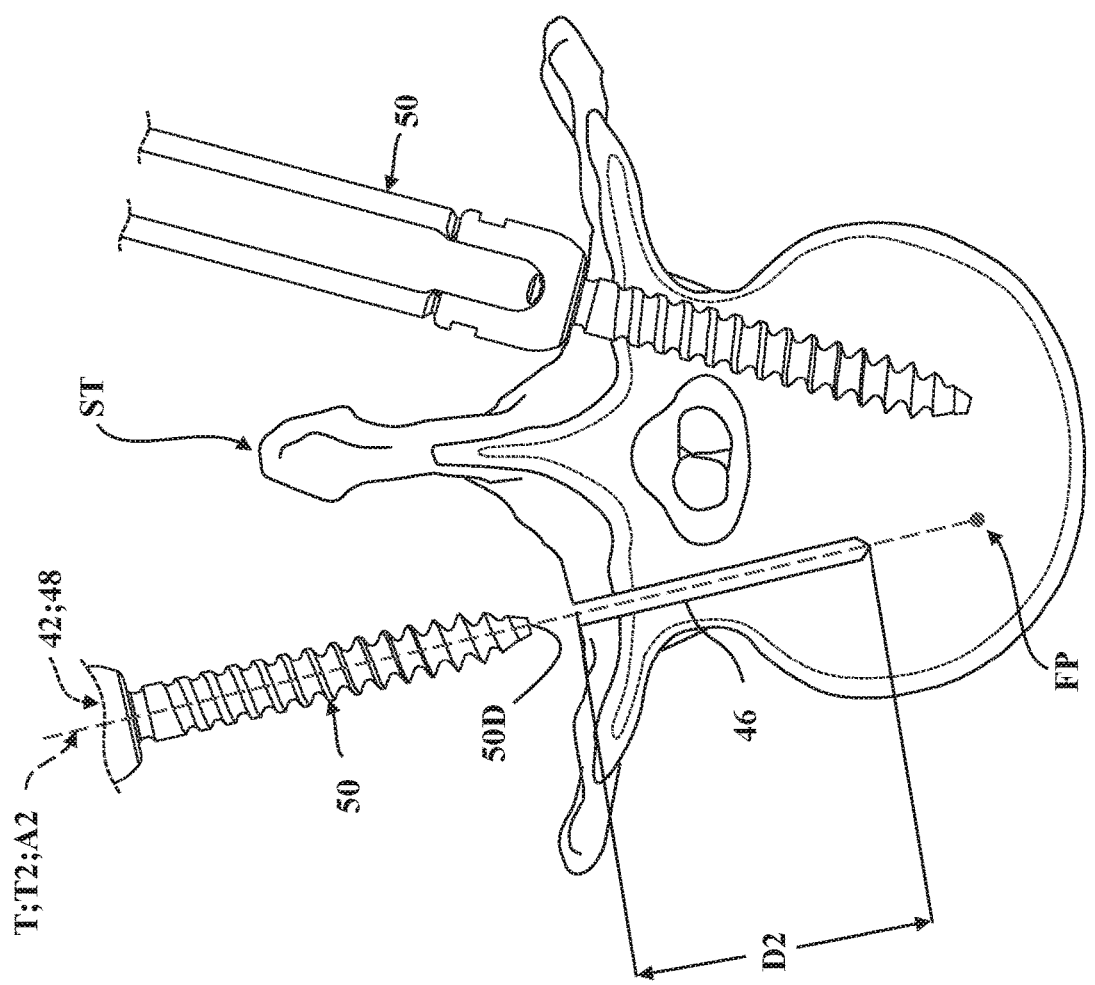
FIG. 5D is another illustrative view of the surgical site of FIGS. 5A-5C, shown with the drill bit removed from the pilot hole and with an anchor supported by an rotary driving tool guided along the second trajectory positioned adjacent to the vertebra.
Figure 5E:
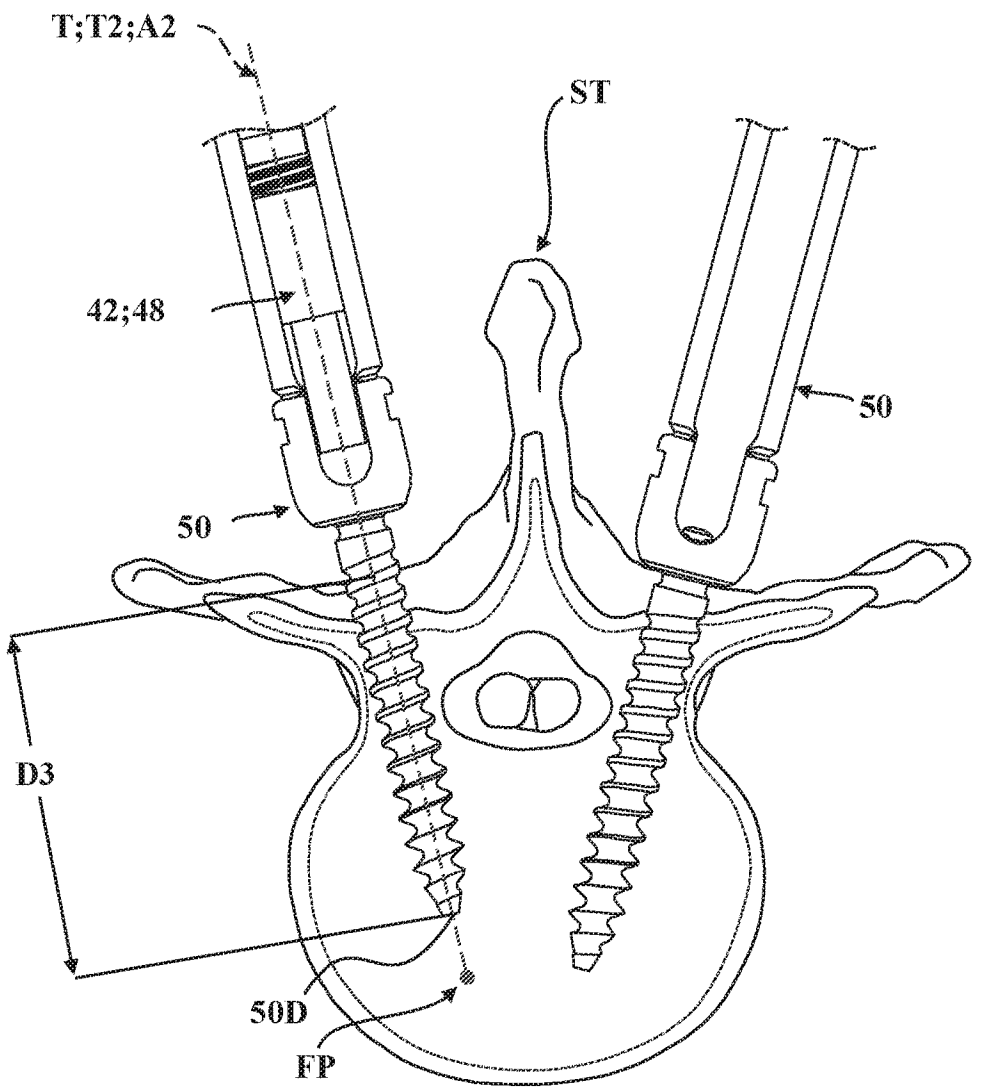
FIG. 5E is another illustrative view of the surgical site of FIGS. 5A-5D, shown with the anchor being installed in the vertebra along the second trajectory to a third depth.
Figure 5F:
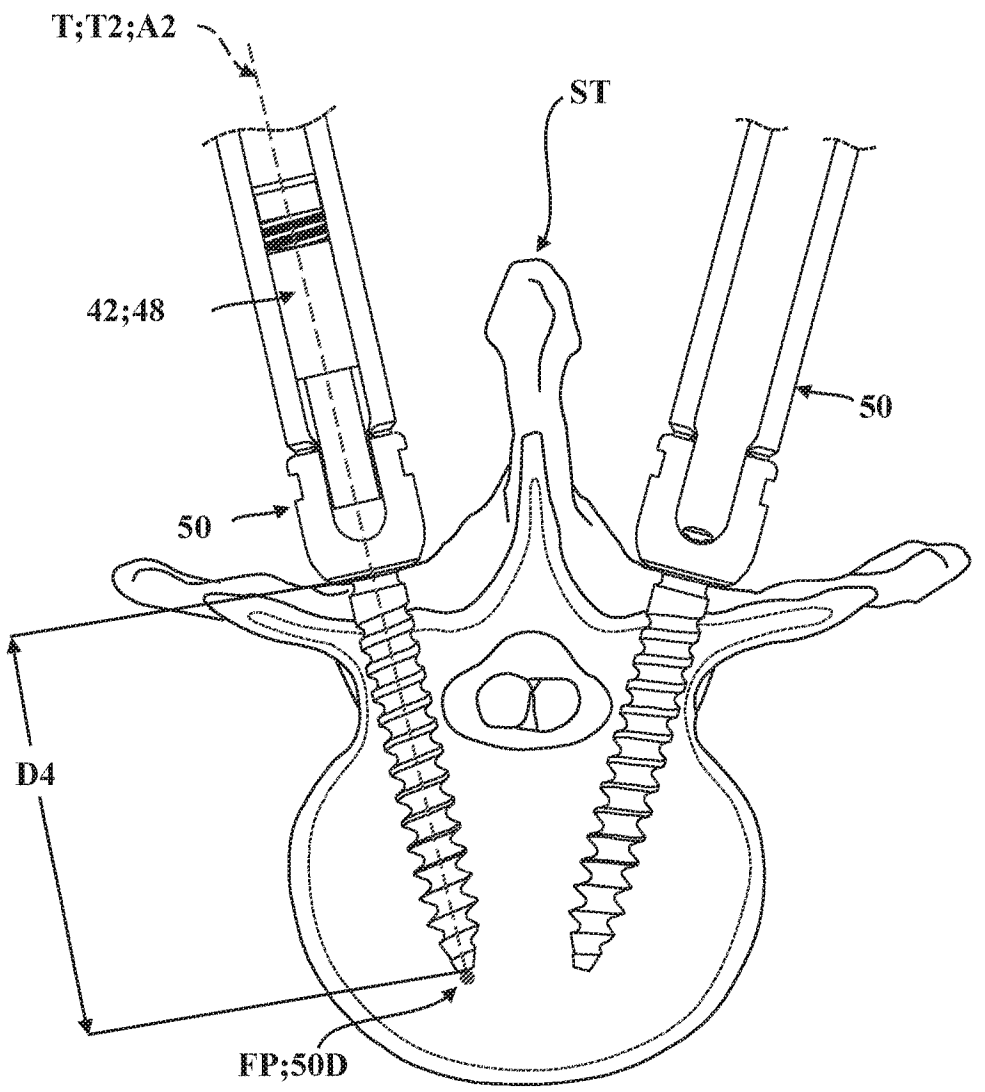
FIG. 5F is another illustrative view of the surgical site of FIGS. 5A-5E, shown with the anchor installed in the vertebra along the second trajectory to a fourth depth.

While a number of different types of "active" tools 42 are contemplated by the present disclosure, two exemplary "active" tools 42 are described herein in connection with FIGS. 4-5F: a rotary cutting tool 44 (e.g., a rotary cutting instrument with a drill bit) to form a pilot hole 46 along the trajectory T at the surgical site ST, and a rotary driving tool 48 (e.g., an anchor driving instrument) configured to releasably secure an anchor 50 (e.g., a polyaxial screw) that is adapted for installation along the trajectory T at the surgical site ST.

The representative embodiments of the end effectors 40 and tools 42 described herein and illustrated in connection with the first embodiment of the end effector 40 are generally configured to assist surgeons in performing various types of minimally-invasive spinal surgical procedures, such as posterior interbody spinal fusions of two or more vertebra in the patient's body B. However, as will be appreciated from the subsequent description below, the surgical system 30 can be used in connection with a number of different types of surgical procedures where it is advantageous to limit movement of tools 42 to rotation about and translation along an axial trajectory T, such as with "active" tools 42 that are driven by the end effector 40 and/or with "passive" tools 42 that are guided by the end effector 40. Here, the term "driven" generally corresponds to rotation of the tool 42 about the trajectory T. However, it will be appreciated that tools 42 supported by end effectors 40 guided by surgical robots 32 can be driven in a number of different ways about and/or relative to the trajectory T and/or the surgical site ST, including without limitation: oscillation, reciprocation, translation, rotation, or combinations thereof.

As noted above, the illustrated surgical system 30 may advantageously be utilized in connection with minimally-invasive spinal surgical procedures such as posterior interbody spinal fusions. In this illustrative example, the rotary cutting tool 44 can be used to form pilot holes 46 in different vertebrae, and the rotary driving tool 48 can be used to install anchors 50 realized as pedicle screws into respective pilot holes 46. Stabilization rods (not shown) may then be mounted between anchors 50 installed in pedicles of two or more vertebrae in the patient's body B to restrict relative movement between those vertebrae and thereby help promote bone growth to fuse the vertebrae together. It will be appreciated that the forgoing example is illustrative, and that other types of surgical procedures are contemplated.

In addition to forming pilot holes 46 for polyaxial pedicle-screw-type anchors 50, the rotary cutting tool 44 may also form holes for other types of fixation hardware (e.g., pins, screws, brackets, plates, rods, and the like), prosthetic components (e.g., artificial joints, bone cages, implants, and the like), and/or medical devices (e.g., guide wires, instrumentation, sensors, trackers, and the like) in some embodiments. Furthermore, the rotary cutting tool 44 may also be configured to help remove portions of vertebra and/or adjacent tissue (e.g., as a bur utilized during a laminectomy or a discectomy) or other bones (e.g., to facilitate grafting bone harvested from the iliac crest) in some embodiments. Thus, the tool 42 may be realized as a number of different types of surgical tools for cutting, removing, manipulating, or treating tissues at surgical sites, and the end effector 40 could be utilized in any suitable type surgical procedure where is advantageous to limit movement of the tool 42 to rotation about and translation along the trajectory T maintained by the surgical robot 32. Other configurations, as noted above, are contemplated.

The surgical system 30 is able to monitor, track, and/or determine changes in the relative position and/or orientation of one or more parts of the surgical robot 32, the robotic arm 36, the end effector 40, and/or the tool 42, as well as various parts of the patient's body B, within a common coordinate system by utilizing various types of trackers (e.g., multiple degree-of-freedom optical, inertial, and/or ultrasonic sensing devices), navigation systems (e.g., machine vision systems, charge coupled device cameras, tracker sensors, surface scanners, and/or range finders), anatomical computer models (e.g., magnetic resonance imaging scans of the lower lumbar region of the spine), data from previous surgical procedures and/or previously-performed surgical techniques (e.g., data recorded by the surgical robot 32 while forming the pilot hole 46 that are subsequently used to facilitate installation of the anchor 50), and the like. To these ends, as is depicted schematically in FIG. 1, the surgical system 30 generally comprises a control system 52 and a navigation system 54 which cooperate to allow the surgical robot 32 maintain alignment of the tool 42 along the trajectory T. The control system 52 comprises an arm controller 56, and the navigation system 54 comprises a navigation controller 58. The controllers 56, 58 may be realized as computers, processors, control units, and the like, and may be discrete components, may be integrated, and/or may otherwise share hardware.

The surgical system 30 employs the control system 52 to, among other things, articulate the robotic arm 36, facilitate driving the tool 42, and the like. Here, the arm controller 56 of the control system 52 is configured to articulate the robotic arm 36 by driving various actuators, motors, and the like disposed at joints of the robotic arm 36 (not shown). The arm controller 56 also gathers sensor data from various sensors such as encoders located along the robotic arm 36 (not shown). Because the specific geometry of each of the components of the surgical robot, end effector 40, and tool 42 are known, these sensor data can be used by the arm controller 56 to reliably adjust the position and/or orientation of the tool 42 within a manipulator coordinate system MNPL (see FIG. 1). The manipulator coordinate system MNPL has an origin, and the origin is located relative to the robotic arm 36. One example of this type of manipulator coordinate system MNPL is described in U.S. Pat. No. 9,119,655, entitled "Surgical Robotic Arm Capable of Controlling a Surgical Instrument in Multiple Modes," previously referenced.

The surgical system 30 employs the navigation system 54 to, among other things, track movement of various objects such as the tool 42 and parts of the patient's body B (e.g., vertebrae located at the surgical site ST). To this end, the navigation system 54 comprises a localizer 60 configured to sense the position and/or orientation of trackers 62 fixed to objects within a localizer coordinate system LCLZ. The navigation controller 58 is disposed in communication with the localizer 60 and gathers position and/or orientation data for each tracker 62 sensed by the localizer 60 in the localizer coordinate system LCLZ.

It will be appreciated that the localizer 60 can sense the position and/or orientation of multiple trackers 62 to track correspondingly multiple objects within the localizer coordinate system LCLZ. By way of example, and as is depicted in FIG. 1, trackers 62 may comprise a pointer tracker 62P, a tool tracker 62T, a first patient tracker 62A, and/or a second patient tracker 62B, as well as additional patient trackers, trackers for additional medical and/or surgical tools, and the like. In FIG. 1, the tool tracker 62T is firmly affixed to the end effector 40, the first patient tracker 62A is firmly affixed to one vertebra at the surgical site ST (e.g., to S1 of the sacrum), and the second patient tracker 62B is firmly affixed to a different vertebra (e.g., to L5 of the lumbar spine). The tool tracker 62T could be fixed to the end effector 40 in different ways, such as by integration into the end effector 40 during manufacture or by releasable attachment to the end effector 40. The patient trackers 62A, 62B are firmly affixed to different bones in the patient's body B, such as by threaded engagement, clamping, or by other techniques. It will be appreciated that various trackers 62 may be firmly affixed to different types of tracked objects (e.g., discrete bones, tools, pointers, and the like) in a number of different ways.

The position of the trackers 62 relative to the anatomy to which they are attached can be determined by known registration techniques, such as point-based registration in which the pointer tracker 62P (e.g., a navigation pointer) is used to touch off on bony landmarks on bone or to touch off on several points across the bone for surface-based registration. Conventional registration techniques can be employed to correlate the pose of the trackers 62 to the patient's anatomy (e.g., each respective vertebra). Other types of registration are also possible, such as by using trackers 62 with mechanical clamps that attach to the spinous process of the vertebra and have tactile sensors (not shown) to determine a shape of the spinous process to which the clamp is attached. The shape of the spinous process can then be matched to a 3D model of the spinous process for registration. A known relationship between the tactile sensors and the three or more markers on the tracker 62 may be entered into or otherwise known by the navigation controller 58. Based on this known relationship, the positions of the markers relative to the patient's anatomy can be determined.

Position and/or orientation data may be gathered, determined, or otherwise handled by the navigation controller 58 using conventional registration/navigation techniques to determine coordinates of each tracker 62 within the localizer coordinate system LCLZ. These coordinates are communicated to the control system 52 to facilitate articulation of the robotic arm 36, as described in greater detail below.

In the representative embodiment illustrated in FIG. 1, the arm controller 56 is operatively attached to the surgical robot 32, and both the navigation controller 58 and the localizer 60 are supported on a mobile cart 64 which is movable relative to the base 34 of the surgical robot 32. The mobile cart 64 also supports a user interface, generally indicated at 66, to facilitate operation of the surgical system 30 by displaying information to, and/or by receiving information from, the surgeon or another user. The user interface 66 is disposed in communication with the navigation system 54 and/or the control system 52, and may comprise one or more output devices 68 (e.g., monitors, indicators, display screens, and the like) to present information to the surgeon (e.g., images, video, data, a graphics, navigable menus, and the like), and one or more input devices 70 (e.g., buttons, touch screens, keyboards, mice, gesture or voice-based input devices, and the like). One type of mobile cart 64 and user interface 66 is described in U.S. Pat. No. 7,725,162, entitled "Surgery System," hereby incorporated by reference in its entirety.

Because the mobile cart 64 and the base 34 of the surgical robot 32 can be positioned relative to each other and also relative to the patient's body B, the surgical system 30 transforms the coordinates of each tracker 62 from the localizer coordinate system LCLZ into the manipulator coordinate system MNPL, or vice versa, so that articulation of the robotic arm 36 can be performed based at least partially on the relative positions and orientations of each tracker 62 within a single, common coordinate system (the manipulator coordinate system MNPL or the localizer coordinate system LCLZ). It will be appreciated that coordinates within the localizer coordinate system LCLZ can be transformed into coordinates within the manipulator coordinate system MNPL, and vice versa, using a number of different conventional coordinate system transformation techniques.

In the illustrated embodiment, the localizer 60 is an optical localizer and includes a camera unit 72 with one or more optical position sensors 74. The navigation system 54 employs the optical position sensors 74 of the camera unit 72 to sense the position and/or orientation of the trackers 62 within the localizer coordinate system LCLZ. In the representative embodiment illustrated herein, the trackers 62 each employ active markers 76 (e.g., light emitting diodes "LEDs"), which emit light that is sensed by the optical position sensors 74 of the camera unit 72. One example of the navigation system 54 of this type is described in U.S. Pat. No. 9,008,757, entitled "Navigation System Including Optical and Non-Optical Sensors," the disclosure of which is hereby incorporated by reference in its entirety. In other embodiments, the trackers 62 may have passive markers, such as reflectors, which reflect light emitted from the camera unit 72. It should be appreciated that other suitable tracking systems and methods not specifically described herein may be utilized (e.g., ultrasonic, electromagnetic, radio frequency, and the like).

In some embodiments, the surgical system 30 is capable of displaying a virtual representation of the relative positions and orientations of tracked objects to the surgeon or other users of the surgical system 30, such as with images and/or graphical representations of the vertebrae and the tool 42 presented on one or more output devices 68 (e.g., a display screen). The arm controller 56 and/or navigation controller 58 may also utilize the user interface 66 to display instructions or request information such that the surgeon or other users may interact with the control system 52 to facilitate articulation of the robotic arm 36. Other configurations are contemplated.

It will be appreciated that the control system 52 and the navigation system 54 can cooperate to facilitate control over the position and/or orientation of the tool 42 in different ways. By way of example, in some embodiments, the arm controller 56 is configured to control the robotic arm 36 (e.g., by driving joint motors) to provide haptic feedback to the surgeon via the robotic arm 36. Here, haptic feedback help constrain or inhibit the surgeon from manually moving the end effector 40 and/or tool 42 beyond predefined virtual boundaries associated with the surgical procedure (e.g., to maintain alignment of the tool 42 along the trajectory T). One type of haptic feedback system and associated haptic objects that define virtual boundaries are described, for example, in U.S. Pat. No. 8,010,180, entitled "Haptic Guidance System and Method," the disclosure of which is hereby incorporated by reference in its entirety. In one embodiment, the surgical system 30 is the RIO™ Robotic Arm Interactive Orthopedic System manufactured by MAKO Surgical Corp. of Fort Lauderdale, Fla., USA.

Referring now to FIGS. 1-11F, as noted above, the surgical system 30 employs the end effector 40 to drive the tool 42 at the surgical site ST along different trajectories T maintained by the surgical robot 32 to assist the surgeon in carrying out various types of surgical procedures with precise control over the relative position and orientation of the tool 42 with respect to the patient's body B.

Figure 3:
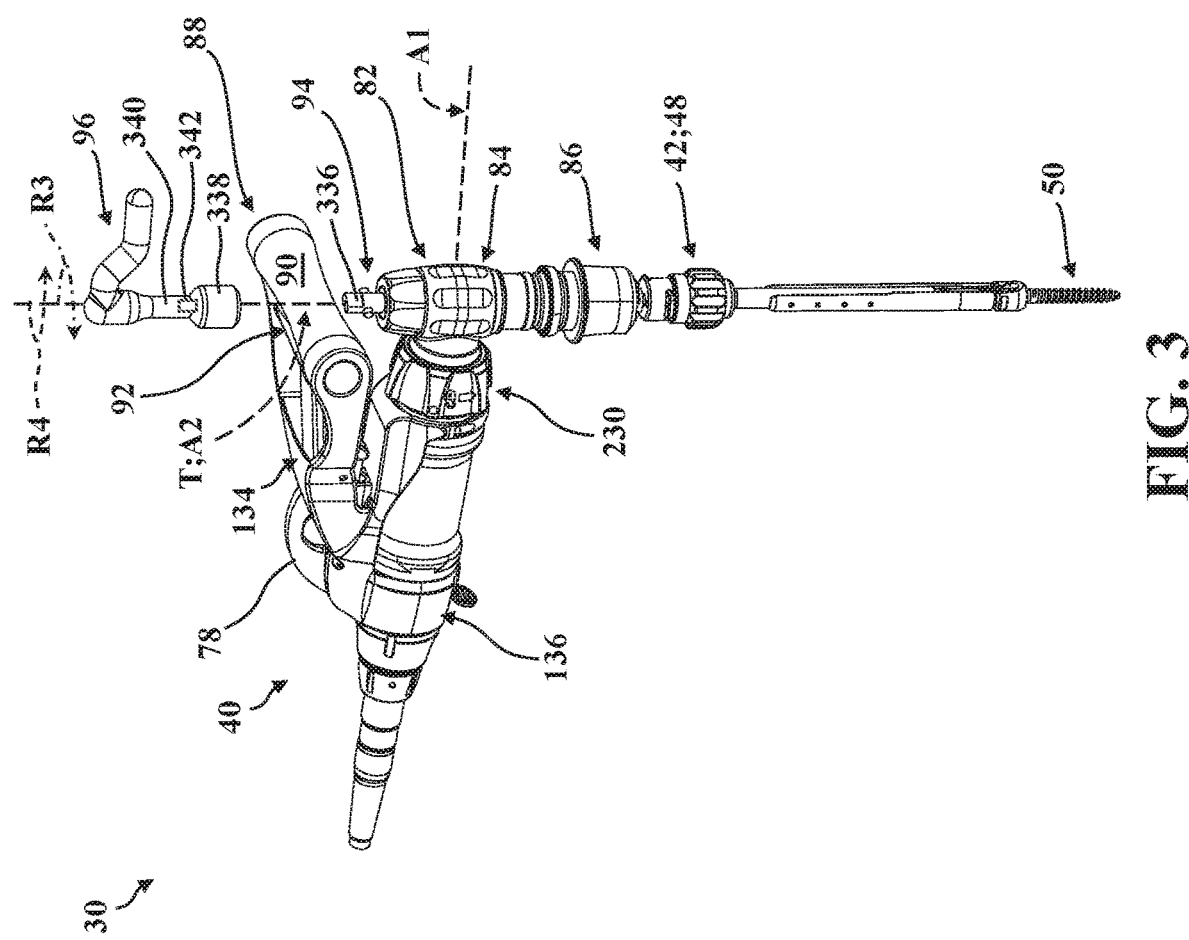
FIG. 3 is a perspective view of the end effector of FIGS. 1-2C, the end effector shown comprising a mount supporting a rotary instrument to generate torque about a first axis and having a coupling, a drive assembly attached to the coupling of the rotary instrument and supporting the tool for rotation about a second axis, a trigger assembly with a grip and an input trigger arranged for engagement by a user to drive the rotary instrument, a manual interface to receive force to rotate the tool about the second axis, and a handle assembly for engagement with the manual interface.

As is best depicted in FIGS. 3-4, the end effector 40 generally comprises a mount 78 which is adapted to attach to the coupler 38 of the robotic arm 36 of the surgical robot 32 for concurrent movement therewith (see FIG. 1). A rotary instrument, generally indicated at 80, is coupled to the mount 78 and is configured to selectively generate rotational torque about a first axis A1 as described in greater detail below. A drive assembly 82 is provided with a geartrain 84 to translate rotation from the rotary instrument 80 about the first axis A1 into rotation about a second axis A2 different from the first axis A1. In the representative embodiment illustrated in connection with the first embodiment of the end effector 40, the second axis A2 intersects and is substantially perpendicular to the first axis A1. However, it will be appreciated that other arrangements of the axes A1, A2 are contemplated. The drive assembly 82 is also provided with a connector, generally indicated at 86, which is configured to releasably secure different types of tools 42 for rotation about the second axis A2. A trigger assembly, generally indicated at 88, is provided with a grip 90 to support a user's hand (e.g., the surgeon's hand), and an input trigger 92 in communication with the rotary instrument 80. The input trigger 92 is arranged for selective engagement by the user to drive the rotary instrument 80 and rotate the tool 42 about the second axis A2 at different rotational speeds. The end effector 40 also comprises a manual interface, generally indicated at 94, to communicate with the drive assembly 82 and to receive and translate applied force from the user into rotational torque to rotate the tool 42 about the second axis A2. To this end, and as is shown in FIGS. 3, 4, 10B, and 11B-11C, a manual handle assembly 96 is provided in the illustrated embodiments for releasable attachment to the manual interface 94. The manual interface 94 and the handle assembly 96 afford the surgeon with the ability to carry out manually-driven operations (e.g., manual drilling, screw driving, and the like) in combination with power-driven operations (e.g., powered drilling, screw driving, and the like) via torque from the rotary instrument 80. Thus, depending on the specific procedure being performed, the types of tools 42 being utilized in the procedure, the preferences of the surgeon, and the like, certain steps of the surgical procedure can be powered via the rotary instrument 80, and other steps can be carried out manually via the handle assembly 96. Each of the components of and for use with the end effector 40 introduced above will be described in greater detail below.

Figure 2A:
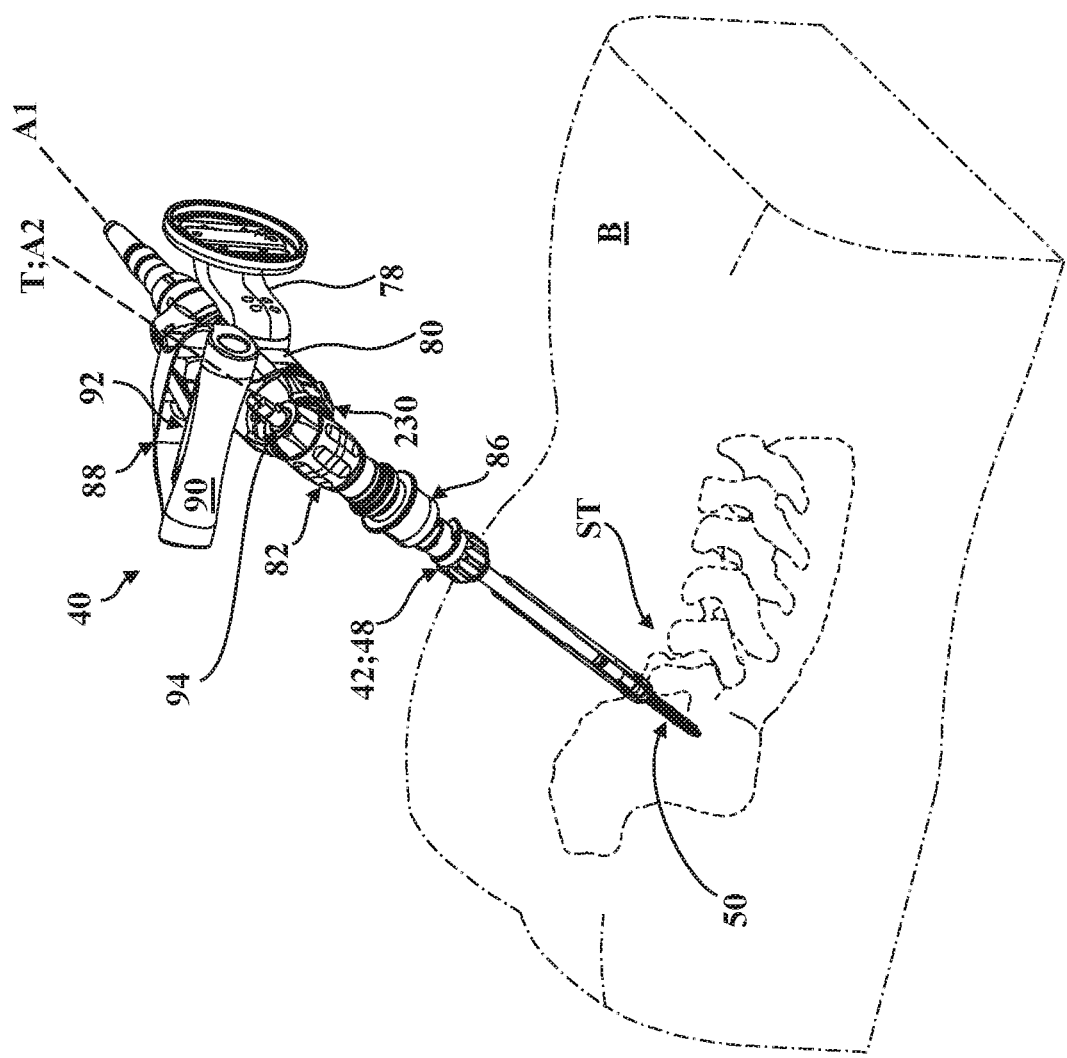
FIG. 2A is a perspective view of the end effector, the tool, and a portion of the patient's body of FIG. 1, with the tool shown supported along a first trajectory.
Figure 2B:
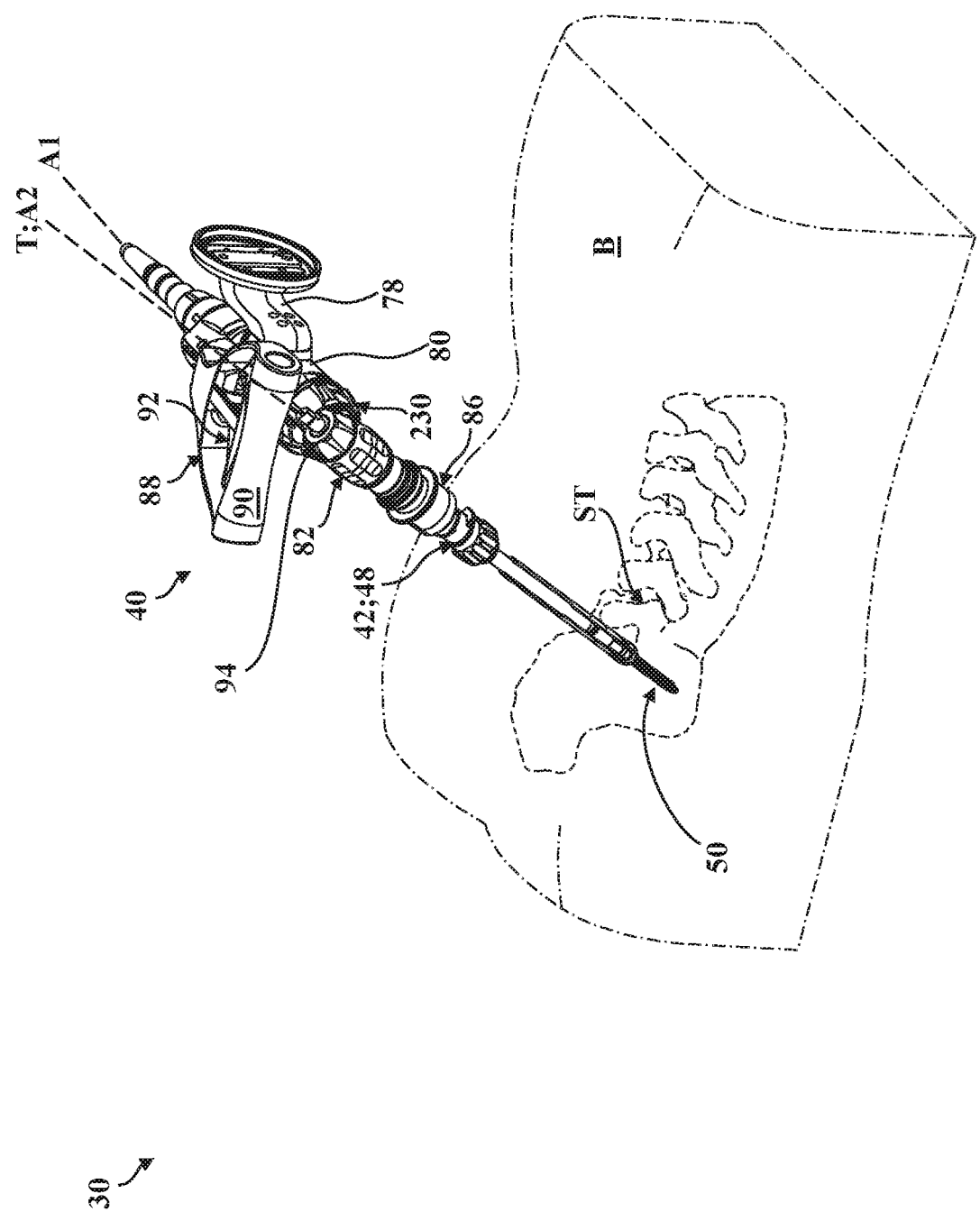
FIG. 2B is another perspective view of the end effector, the tool, and the portion of the patient's body of FIG. 2A, with the tool shown supported along a second trajectory.
Figure 2C:
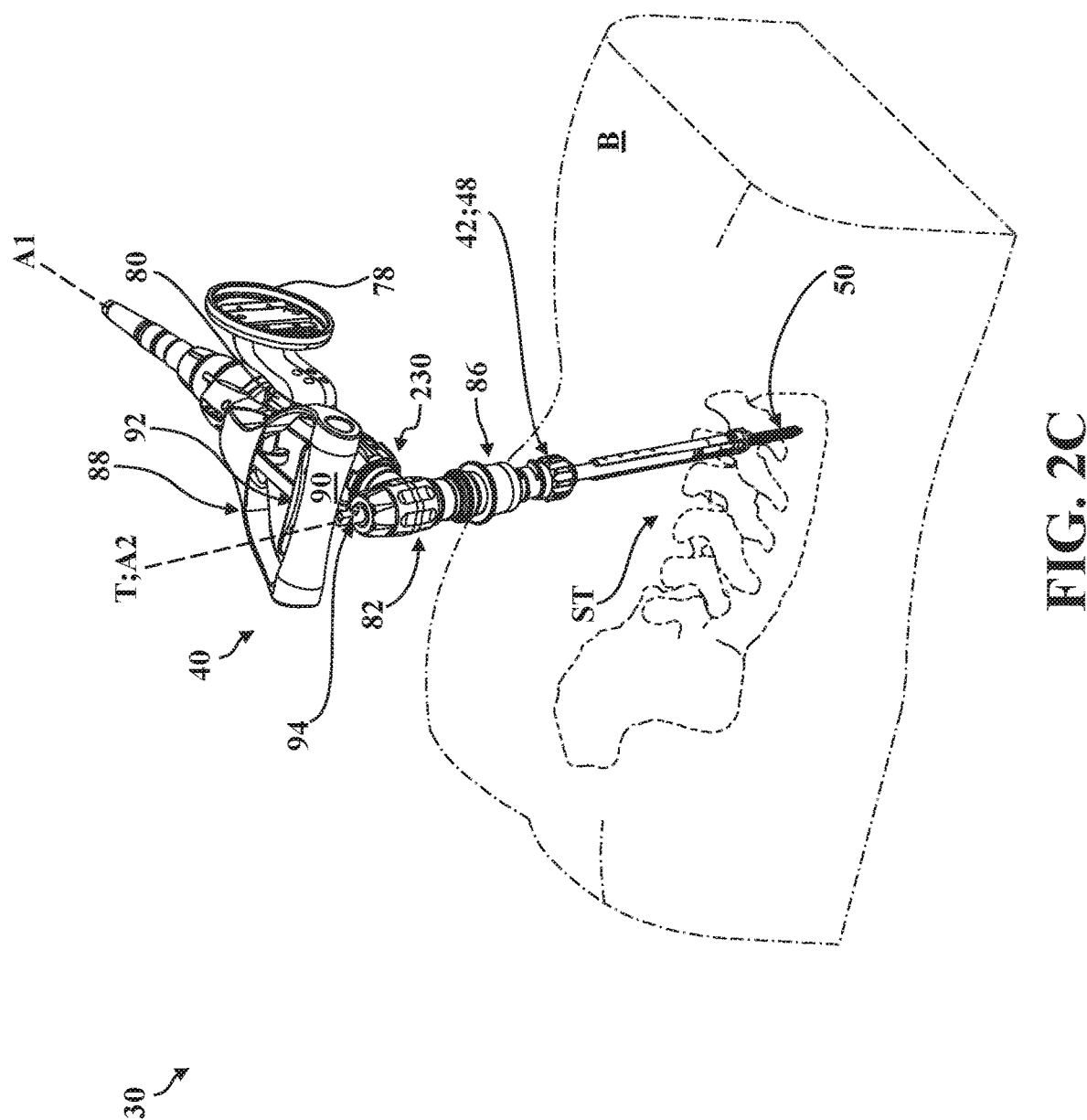
FIG. 2C is another perspective view of the end effector, the tool, and the portion of the patient's body of FIGS. 2A-2B, with the tool shown supported along a third trajectory.

Minimally-invasive spinal fusion techniques (as well as other types of surgical procedures) generally involve installing multiple anchors 50 in two or more vertebra at the surgical site ST. For example, in a posterior lumbar interbody fusion of two adjacent vertebrae (e.g., a fusion of S1 of the sacrum to L5 of the lumbar spine), anchors 50 are typically installed bilaterally into the pedicles on both sides of the spinous process of each vertebra to be fused to support correspondingly bilateral stabilization rods. Thus, fusing two adjacent vertebrae generally involves installing at least four anchors 50, and each additional vertebrae to be fused generally involves installing another two bilateral anchors 50 (e.g., a fusion of S1 of the sacrum to L5 of the lumbar spine combined with a fusion of L5 of the lumbar spine to L4 of the lumbar spine). Moreover, those having ordinary skill in the art will appreciate that anchors 50 must be installed into vertebrae carefully with respect to the spinal cord, nerve roots, and the like, such as to extend entirely through the respective pedicle, from adjacent the lamina into the vertebral body, without passing through the foramen. Thus, as shown in FIGS. 2A-2C, each anchor 50 is installed along a different trajectory T.

FIGS. 5A-5G each transversely depict a vertebra (e.g., L5 of the lumbar spine) and sequentially illustrate how tools 42 supported by the end effector 40 can be utilized to facilitate installation of anchors 50 via the rotary instrument 80 and, in some embodiments, the manual interface 94. In FIG. 5A, first and second trajectories T1, T2 are shown arranged bilaterally relative to the spinous process, each extending through the respective pedicles into the vertebral body on opposing sides of the foramen and spinal cord. One anchor 50 is shown already installed along the first trajectory T1, and a distal cutting end 44D of the rotary cutting tool 44 (e.g., a drill bit tip) is shown adjacent to the surgical site ST. Here, the rotary cutting tool 44 is supported for rotation about the second axis A2, and the surgical robot 32 maintains alignment of the second axis A2 with the second trajectory T2.

FIG. 5B shows the rotary cutting tool 44 advanced along the second trajectory T2 through the pedicle to position the distal cutting end 44D at a first depth D1 into the vertebra at the surgical site ST, and FIG. 5C shows the rotary cutting tool 44 advanced even further along the second trajectory T2 to position the distal cutting end 44D at a second depth D2 greater than the first depth D1.

FIG. 5D shows the pilot hole 46 formed by the rotary cutting tool 44 which extends into the vertebra along the second trajectory T2 to the second depth D2. FIG. 5D also shows a distal tip 50D of another anchor 50 positioned adjacent to the surgical site ST to be installed in the pilot hole 46. Here, the anchor 50 is supported by the rotary driving tool 48 for rotation about the second axis A2 (see FIGS. 3-4), and the surgical robot 32 similarly maintains alignment of the second axis A2 with the second trajectory T2.

FIG. 5E shows the anchor 50 advanced along the second trajectory T2 after having been "threaded" into the pilot hole 46 via rotation of the rotary driving tool 48 about the second axis A2. Here in FIG. 5E, the distal tip 50D of the anchor 50 is positioned at a third depth D3 into the vertebra, which is greater than the second depth D2 in this example but could be the same as or less than the second depth D2.

Figure 5G:
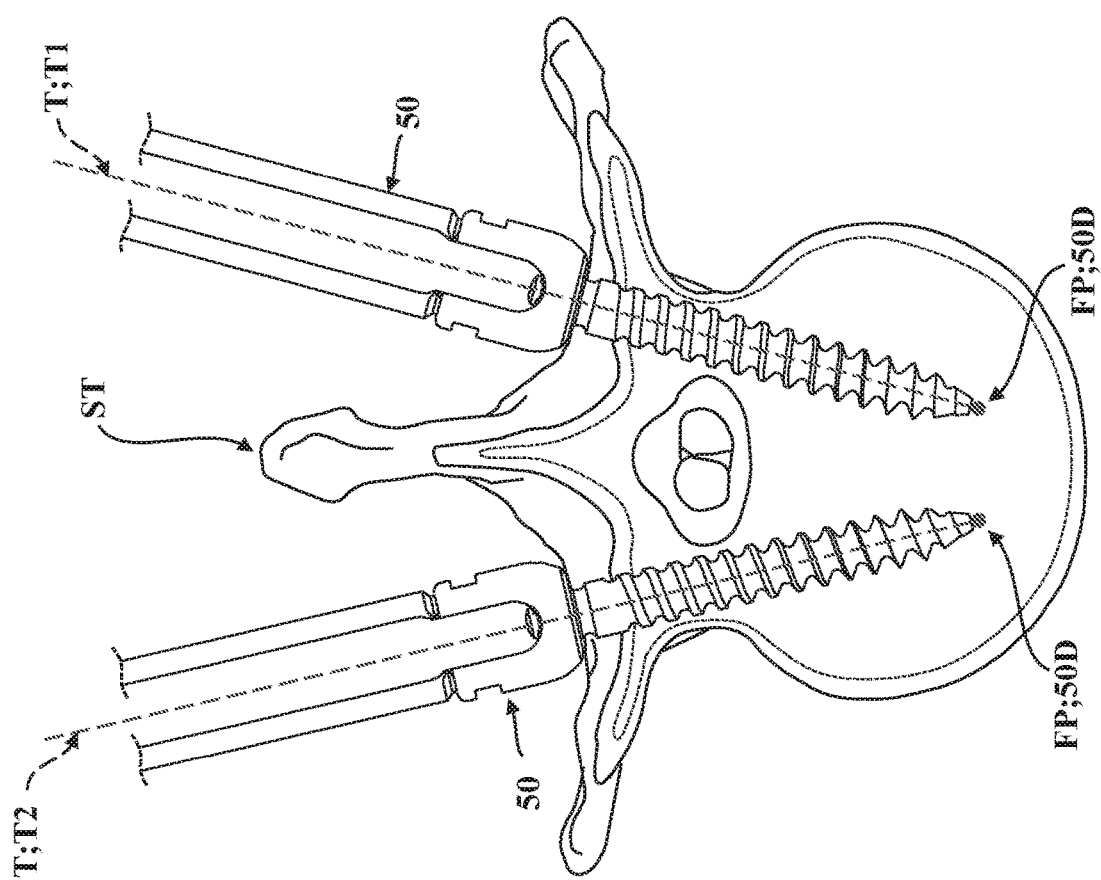
FIG. 5G is another illustrative view of the surgical site of FIGS. 5A-5F, shown with the anchors installed in the vertebra along respective trajectories.
Figure 6:
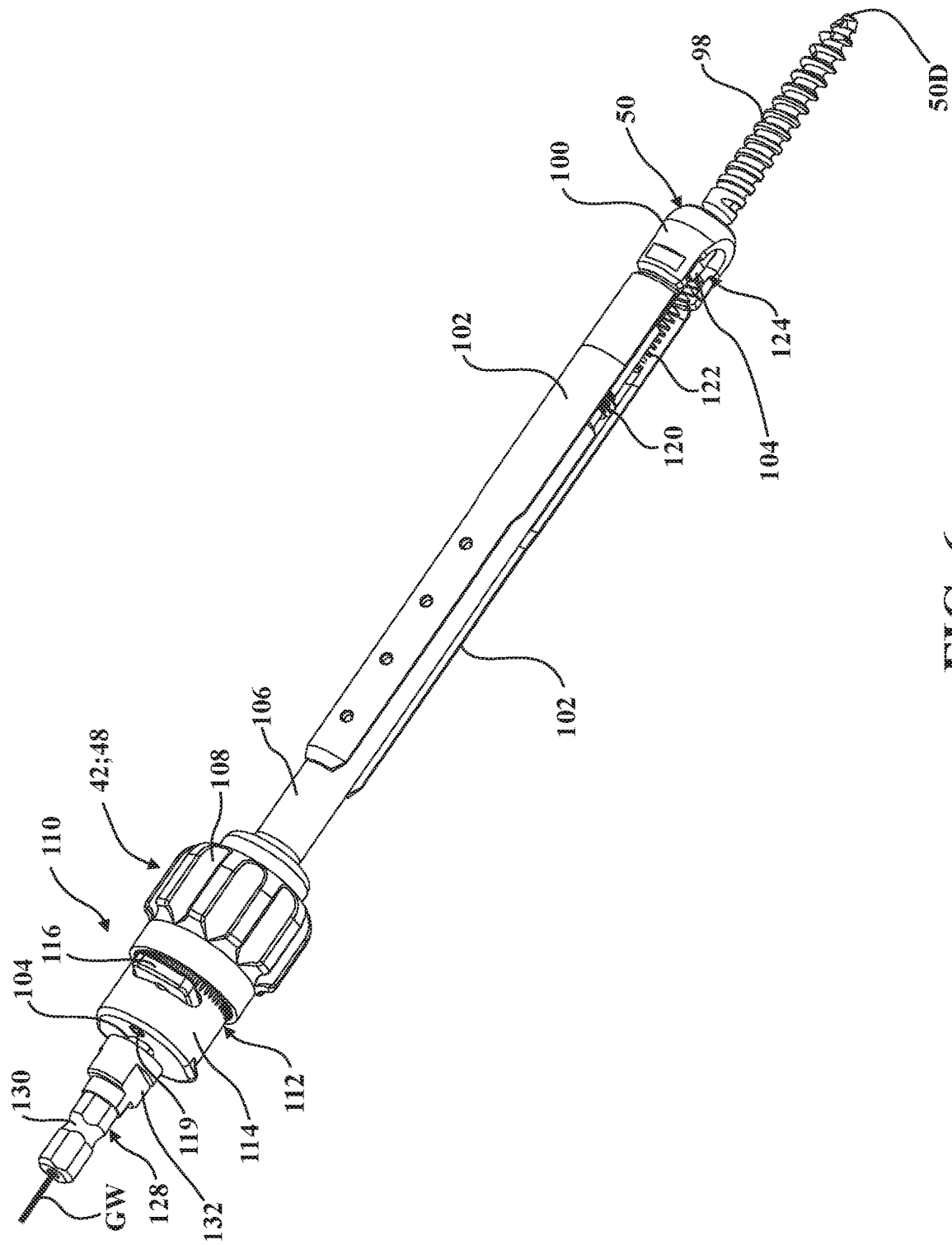
FIG. 6 is a perspective view of the tool supporting the anchor of FIGS. 1-5F.
Figure 7:
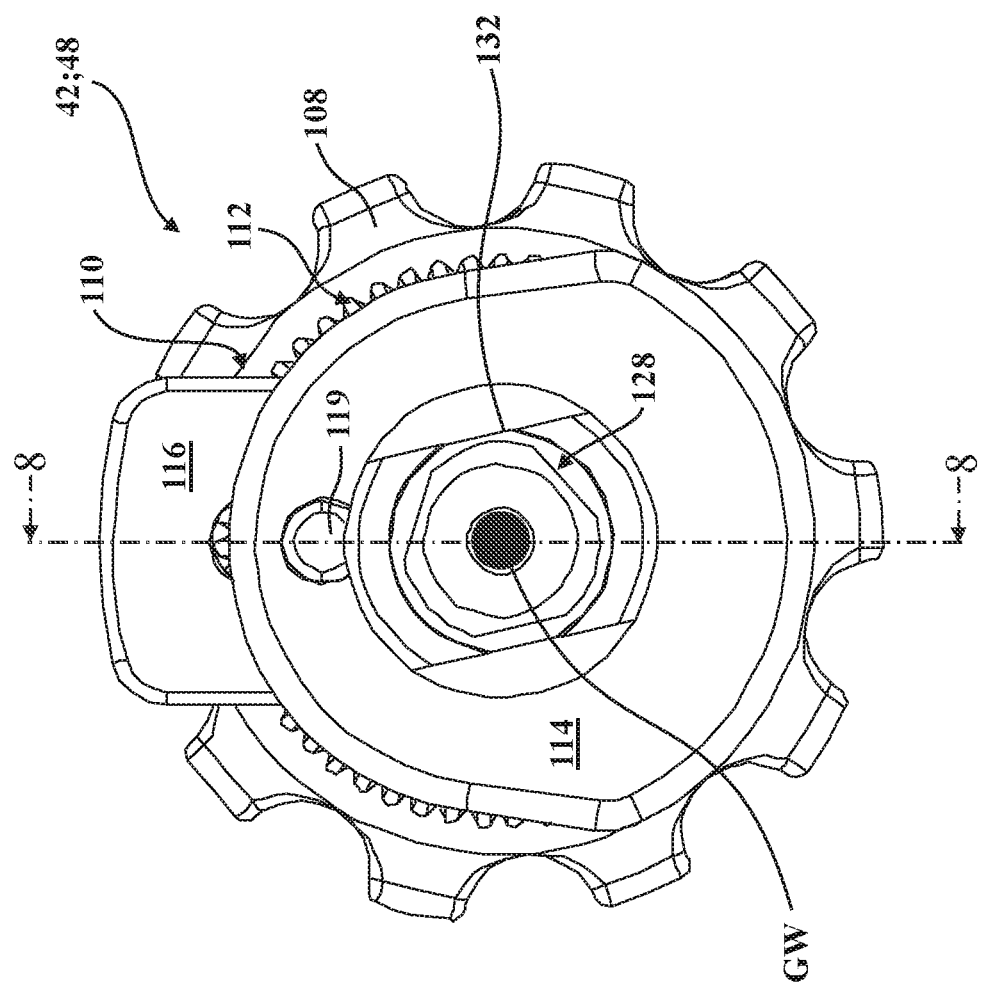
FIG. 7 is a top-side plan view of the tool supporting the anchor of FIGS. 1-6.

In FIG. 5F, the anchor 50 is shown advanced even further along the second trajectory T2 to position the distal tip 50D at a fourth depth D4 greater than the third depth D3. Here, the fourth depth D4 represents the intended final position FP of the installed anchor 50, and the final positions FP of both bilateral anchors are shown in FIG. 5G, with each anchor 50 aligned to its respective trajectory T1, T2.

With continued reference to FIGS. 5A-5G, it will be appreciated that the surgeon can advance the rotary cutting tool 44 or the rotary driving tool 48 along the second trajectory T2 in a number of different ways. Because of the how the illustrated rotary cutting tool 44 and rotary driving tool 48 are configured, rotation of the tools 42 about the second axis A2 tends to advance the distal cutting end 44D and/or the distal tip 50D along the second trajectory T2 in response to engagement with bone. Irrespective of this tendency, the surgeon generally advances the tools 42 along the second trajectory T2 by applying force to the grip 90 of the trigger assembly 88 while operating the surgical robot 32 in a haptic mode to inhibit movement or articulation of the robotic arm 36 which might otherwise bring the second axis A2 out of alignment with the second trajectory T2.

In some embodiments, the surgical system 30 is configured to operate in different ways as one or more of the depths D1, D2, D3, D4 are approached or reached. For example, the surgical system 30 could be configured to allow the surgeon to engage the input trigger 92 to drive the rotary instrument 80 to rotate the rotary cutting tool 44 about the second axis A2 until the first depth D1 is reached (see FIG. 5B). Once the first depth D1 is reached, the surgical system 30 could interrupt rotation to, among other things, allow the surgeon to advance from the first depth D1 to the second depth D2 (see FIG. 5C) manually (e.g., without torque from the rotary instrument 80) via engagement of the handle assembly 96 with the manual interface 94.

The surgical system 30 could similarly interrupt rotation as the anchor 50 is installed, such as when the distal tip 50D reaches the third depth D3 (see FIG. 5E) so that the surgeon can complete installation from the third depth D3 to the fourth depth D4 (see FIG. 5F) manually via engagement of the handle assembly 96 with the manual interface 94. In addition to interrupting rotation at predetermined depths, the surgical system 30 could also slow rotation as certain depths are approached, restrict translation speed along the second trajectory T2, or otherwise afford variable control over rotation and/or translation of the tools 42.

The installation sequence illustrated in FIGS. 5A-5G is intended to be exemplary and non-limiting, and the depths D1, D2, D3, D4 are intended to be arbitrary reference points to help describe how the tools 42 can be utilized, but could also represent actual depths into the vertebra (e.g., determined and set according to a pre-surgical plan). Furthermore, while the forgoing discussion of the depths D1, D2, D3, D4 in connection with FIGS. 5A-5G generally differentiates between rotating the tools 42 with the rotary instrument 80 until one depth is reached (e.g., D1 or D3) before rotating the tools 42 with the manual interface 94 to a final depth (e.g., D2 or D4), it is conceivable that the rotary instrument 80 or the manual interface 94 could be utilized alone to rotate tools 42 to the final depths (e.g., D2 or D4) in some embodiments. By way of illustrative example, the rotary instrument 80 could be used to drive the rotary cutting tool 44 to form the pilot hole all the way to the second depth D2 (and could slow rotation from the first depth D1 to the second depth D2), at which point the surgical system 30 could interrupt rotation of the rotary instrument 80 to prompt the surgeon to switch to the rotary driving tool 48 to install the anchor 50. The rotary driving tool 48 could then be rotated manually via the manual interface 94 all the way to the fourth depth D4 without using torque from the rotary instrument 80. Put differently, it is conceivable that certain tools 42 could be rotated exclusively via torque generated by the rotary instrument 80, exclusively via torque applied manually to the manual interface 94, or sequentially from both the rotary instrument 80 and the manual interface 94. Other configurations are contemplated.

It will be appreciated that the workflow associated with installation of the anchor 50 could vary from the exemplary embodiments described herein based, among other things, on the specific surgical procedure being performed, the configuration of the anchor 50, and the like. By way of non-limiting example, instead of forming the pilot hole 46 to help facilitate installation of the anchor 50 illustrated throughout the drawings, it is contemplated that the anchor 50 could be configured to facilitate a "single-pass" workflow without necessarily requiring formation of the pilot hole 46, such as with anchors 50 that are "self-tapping" or otherwise configured so as to be installed without requiring a preformed pilot hole 46. Other configurations are contemplated.

Referring now to FIGS. 6-9, the rotary driving tool 48 and anchor 50 are shown in greater detail. As noted above, the illustrated anchor 50 is realized as a pedicle screw implant configured for installation into a vertebra in minimally-invasive surgical techniques, and has a threaded body 98 supported by a polyaxial head 100 to which blades 102 are detachably secured.

An exemplary embodiment of the construction of this type of anchor 50 is described in U.S. Pat. No. 9,408,716, entitled "Percutaneous Posterior Spinal Fusion Implant Construction and Method," the disclosure of which is hereby incorporated by reference in its entirety. In some embodiments, the surgical system 30 may facilitate installation of this or other types of anchors 50 as described in U.S. Pat. No. 9,801,686, entitled "Neural Monitor Based Dynamic Haptics," and/or U.S. Patent Application Publication No. US 2018/0042650 A1, entitled "Power Pedicle Screwdriver," the disclosures of which are each hereby incorporated by reference in their entirety. It will be appreciated that other types and configurations of anchors 50, and the associated installation thereof, are contemplated by the present disclosure.

Figure 9:
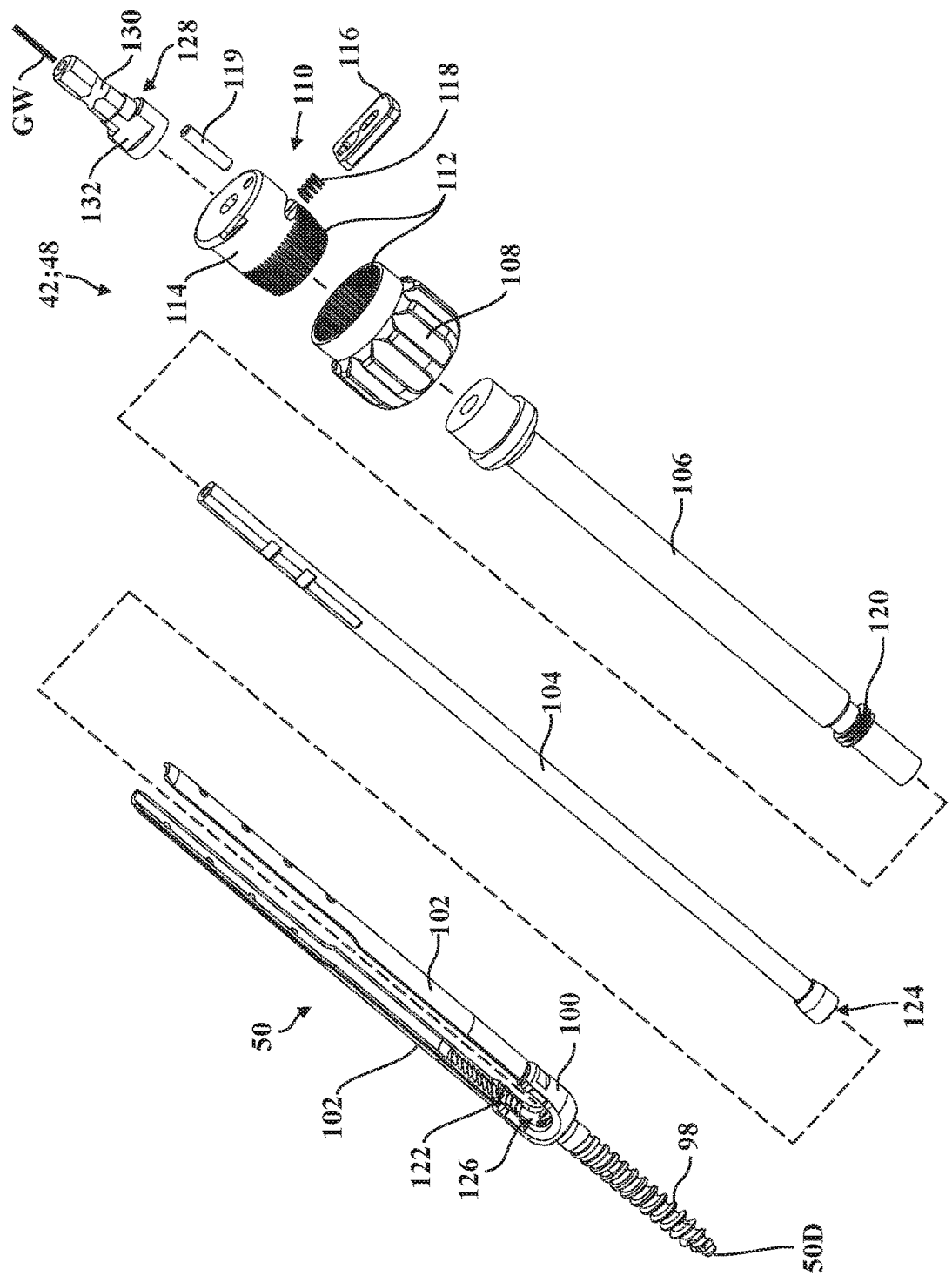
FIG. 9 is an exploded perspective view of the tool shown spaced from the anchor of FIGS. 1-8.
Figure 10A:
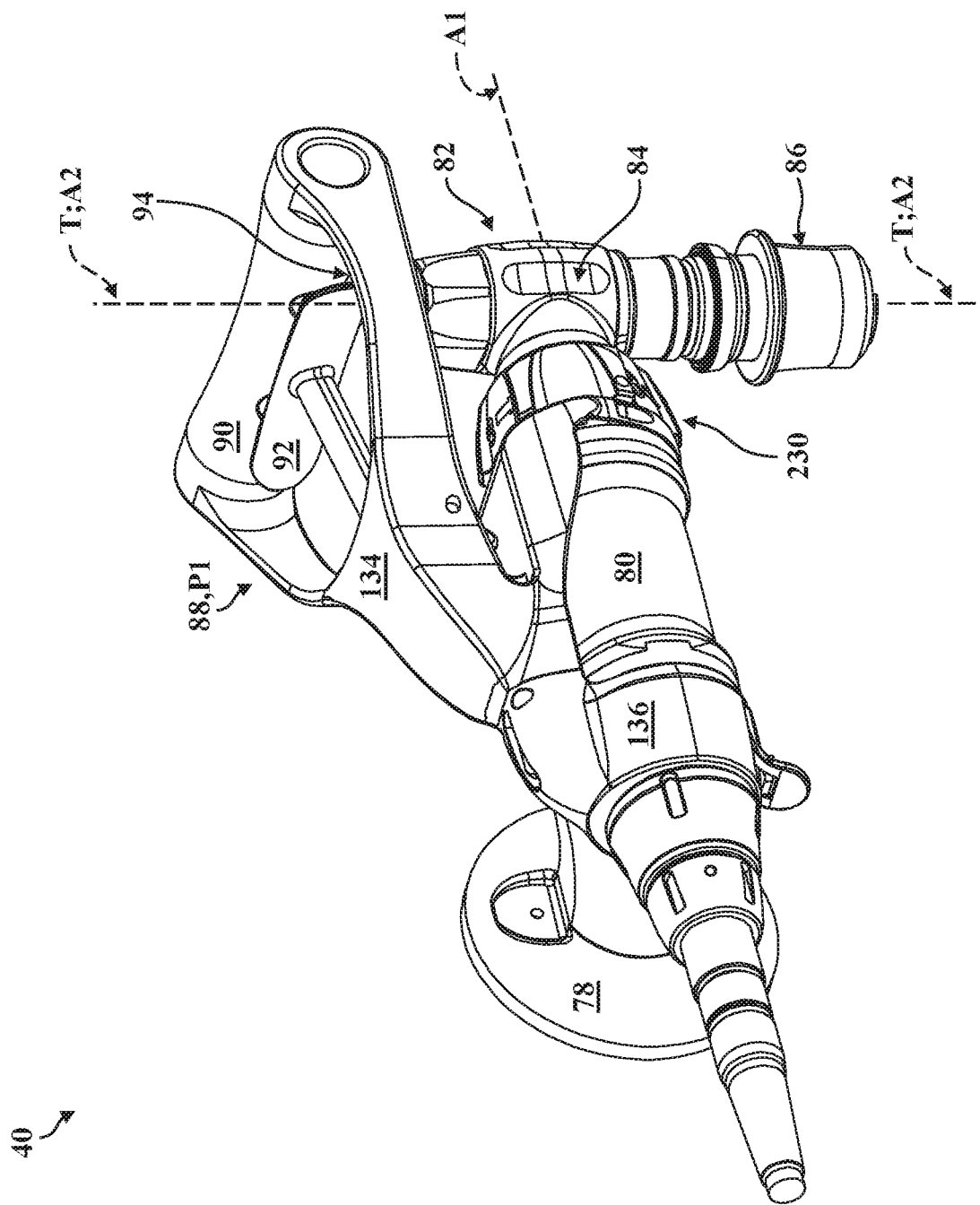
FIG. 10A is a perspective view of the end effector of FIGS. 1-4, shown with the trigger assembly arranged in a first trigger assembly position with the grip and the input trigger disposed above the manual interface adjacent to the drive assembly.
Figure 10B:
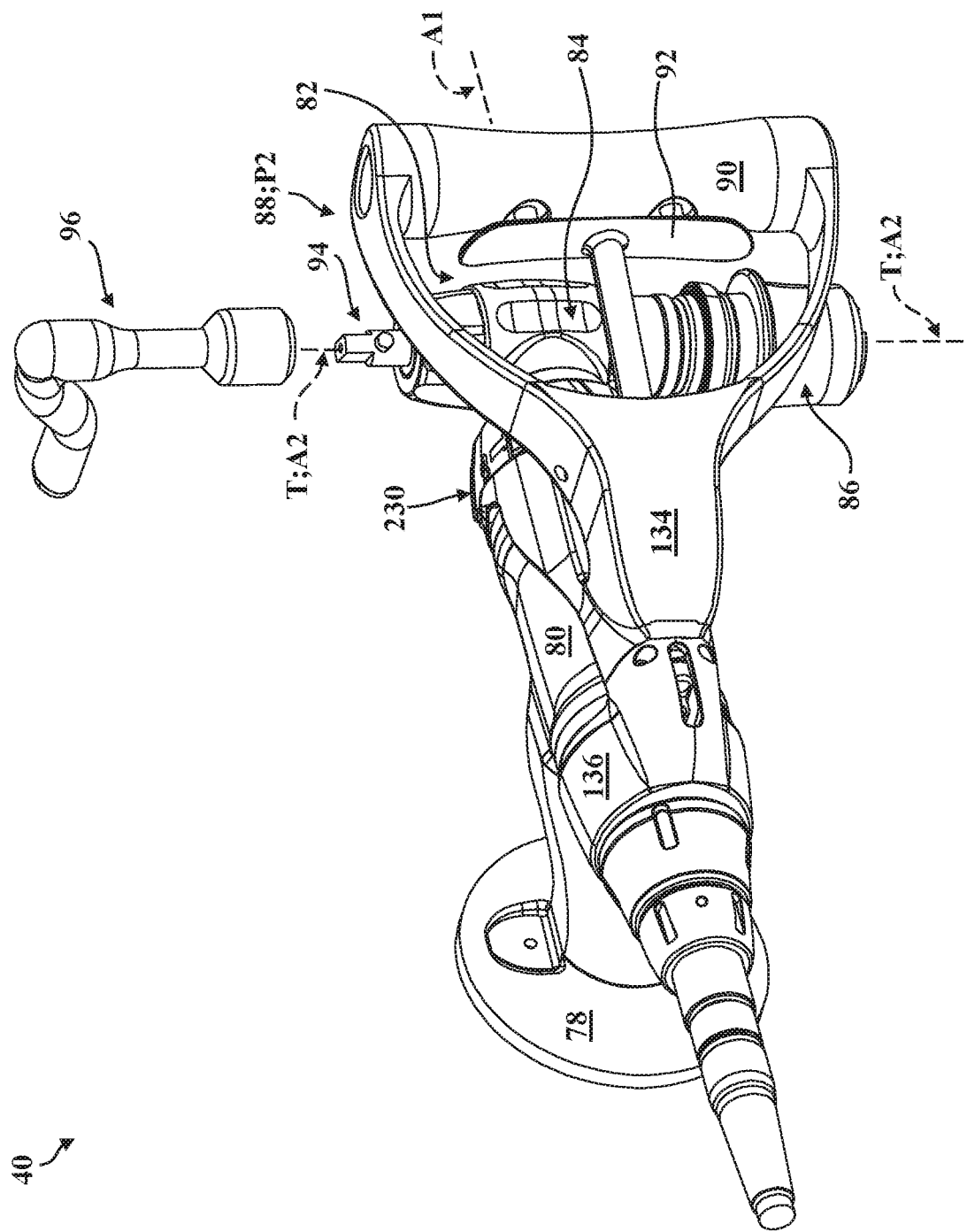
FIG. 10B is another perspective view of the end effector of FIG. 10A, shown with the trigger assembly arranged in a second trigger assembly position with the grip and the input trigger moved to present the manual interface for engagement by the handle assembly.

As is best illustrated in FIG. 9, the rotary driving tool 48 generally comprises a driveshaft 104 which is rotatably supported within a support tube 106. A contoured body 108 is coupled to the support tube 106 for concurrent rotation and is configured for engagement by the surgeon to, among other things, facilitate attaching the rotary driving tool 48 to the anchor 50. The contoured body 108 selectively engages a locking subassembly 110 for concurrent rotation via splined engagement, generally indicated at 112.

The locking subassembly 110 is configured to selectively restrict axial movement of the driveshaft 104 relative to the support tube 106. To this end, the locking subassembly 110 comprises a locking body 114 that supports a slider 116 for movement transverse to the driveshaft 104. The slider 116 is biased by a spring 118 and is retained relative to the locking body 114 via a pin 119 in the illustrated embodiment. The support tube 106 comprises external threads 120 which engage corresponding internal threads 122 formed in the blades 102 of the anchor 50, and a distal end of the driveshaft 104 comprises a driver key 124 which engages a correspondingly-shaped driven key 126 formed in the proximal end of the threaded body 98 of the anchor 50 adjacent to the polyaxial head 100. The rotary driving tool 48 is thus releasably attachable to the anchor 50 via engagement between the driver key 124 and the driven key 126 and via engagement between the external threads 120 and the internal threads 122. One exemplary embodiment of this type of rotary driving tool 48 and anchor 50 are described in U.S. Pat. No. 8,002,798, entitled "System and Method for Spinal Implant Placement," the disclosure of which is hereby incorporated by reference in its entirety.

Figure 8:
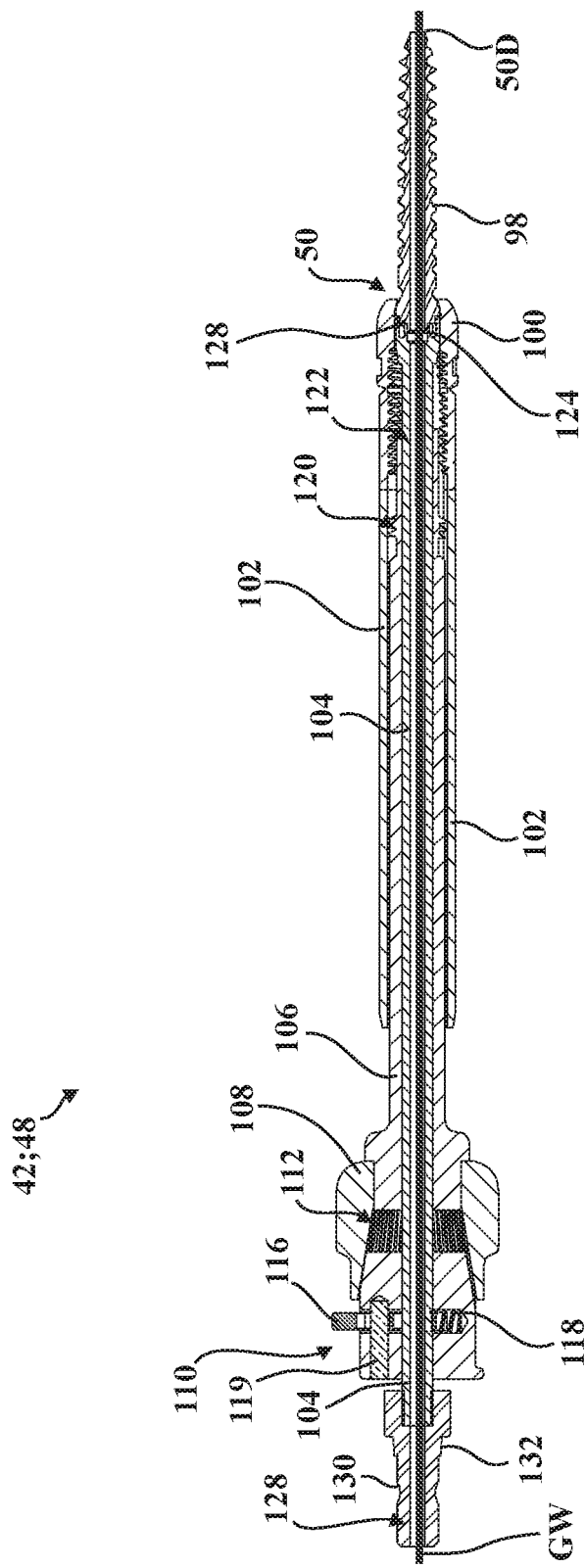
FIG. 8 is a section view taken along line 8-8 of FIG. 7.

A bit interface, generally indicated at 128, is coupled to the proximal end of the driveshaft 104 adjacent to the locking subassembly 110. The bit interface 128 is configured to be releasably attached to the connector 86 of the drive assembly 82 of the end effector 40 and comprises an axial retainer 130 and a rotational retainer 132 which engage to connector 86 to restrict translation and rotation, respectively, of the rotary driving tool 48 relative to the connector 86, as described in greater detail below. As is best depicted in FIG. 8, the threaded body 98 of the anchor 50, as well as the driveshaft 104 and bit interface 128 of the rotary driving tool 48, are cannulated to, among other things, allow a guidewire GW (e.g., a "K-Wire") to extend therethrough (not shown in detail).

Referring now to FIGS. 1-24, as noted above, the end effector 40 is configured to facilitate rotation of the tool 42 about the second axis A2 via torque from either the rotary instrument 80 or the manual interface 94 as the surgical robot 32 maintains alignment of the second axis A2 with the trajectory T and allows the end effector 40 and the tool 42 to concurrently translate along the second axis A2, such as in response to force applied by the surgeon to the grip 90 of the trigger assembly 88. As is best depicted in FIGS. 10A-12, the mount 78 is configured to support the various other components of the end effector 40 to advantageously position the second axis A2 relative to the coupler 38 of the robotic arm 36 (see FIG. 1) to, among other things, promote rigidity and stiffness of the end effector 40 while, at the same time, affording advantages relating to the usability, stability, and accuracy of the surgical system 30.

In the representative embodiment of the trigger assembly 88 illustrated in connection with the first embodiment of the end effector 40, the grip 90 has a generally cylindrical profile and is configured for generally pronate or supernate hand engagement. Thus, when the surgeon is actuating the trigger assembly 88 to generate torque with the rotary instrument 80, the surgeon's hand is positioned above the drive assembly 82 such that the second axis A2 generally extends through the grip 90 (see FIGS. 10A and 11A). This advantageously allows the surgeon's hand to be positioned along the trajectory T while the trigger assembly 88 is being engaged, which can help the surgeon to apply force to the end effector 40 in a direction substantially aligned with the trajectory T to advance the tool 42. Furthermore, this configuration allows the surgeon to engage the grip 90 without substantially obstructing the surgeon's view of the drive assembly 82, the tool 42, or the surgical site ST. However, it will be appreciated that the trigger assembly 88 and/or grip 90 could be configured in other ways, such as where the grip 90 is shaped and arranged for generally neutral (as opposed to pronate or supernate) hand engagement, and could be arranged either in-line with or offset from the trajectory T when engaged to drive the rotary instrument 80. Other configurations are contemplated.

While the illustrated embodiment of the trigger assembly 88 depicted throughout the drawings advantageously positions the surgeon's hand along the trajectory T when the grip 90 is engaged to drive the rotary instrument 80 as noted above (see FIGS. 10A and 11A), it will be appreciated that this configuration necessarily positions the grip 90 in a way that at least partially inhibits access to the manual interface 94. In order to promote access to the manual interface 94, the trigger assembly 88 comprises a frame, generally indicated at 134, which supports the grip 90 and the input trigger 92 for movement relative to the rotary instrument 80 between a plurality of trigger assembly positions including a first trigger assembly position P1 where the grip 90 and the input trigger 92 are arranged for engagement by the surgeon to drive the rotary instrument 80 to rotate the tool 42 about the second axis A2 (see FIGS. 10A, 11D, 11E, and 19A-19B), and a second trigger assembly position P2 where the grip 90 and the input trigger 92 are positioned so as to promote access to the manual interface 94 which is thereby arranged to receive applied force from the user to rotate the tool 42 about the second axis A2 (see FIGS. 10B and 11B-11C). As is described in greater detail below, other trigger assembly positions are contemplated.

As is best depicted in FIGS. 15, 17, and 19A-19C, the trigger assembly 88 comprises a retainer, generally indicated at 136, which is operatively coupled to the frame 134 for concurrent movement. In the illustrated embodiment, the retainer 136 is formed as a separate component from the frame 134 to facilitate assembly of the end effector 40, but could be formed integrally with the frame 134 in other embodiments.

Figure 19A:
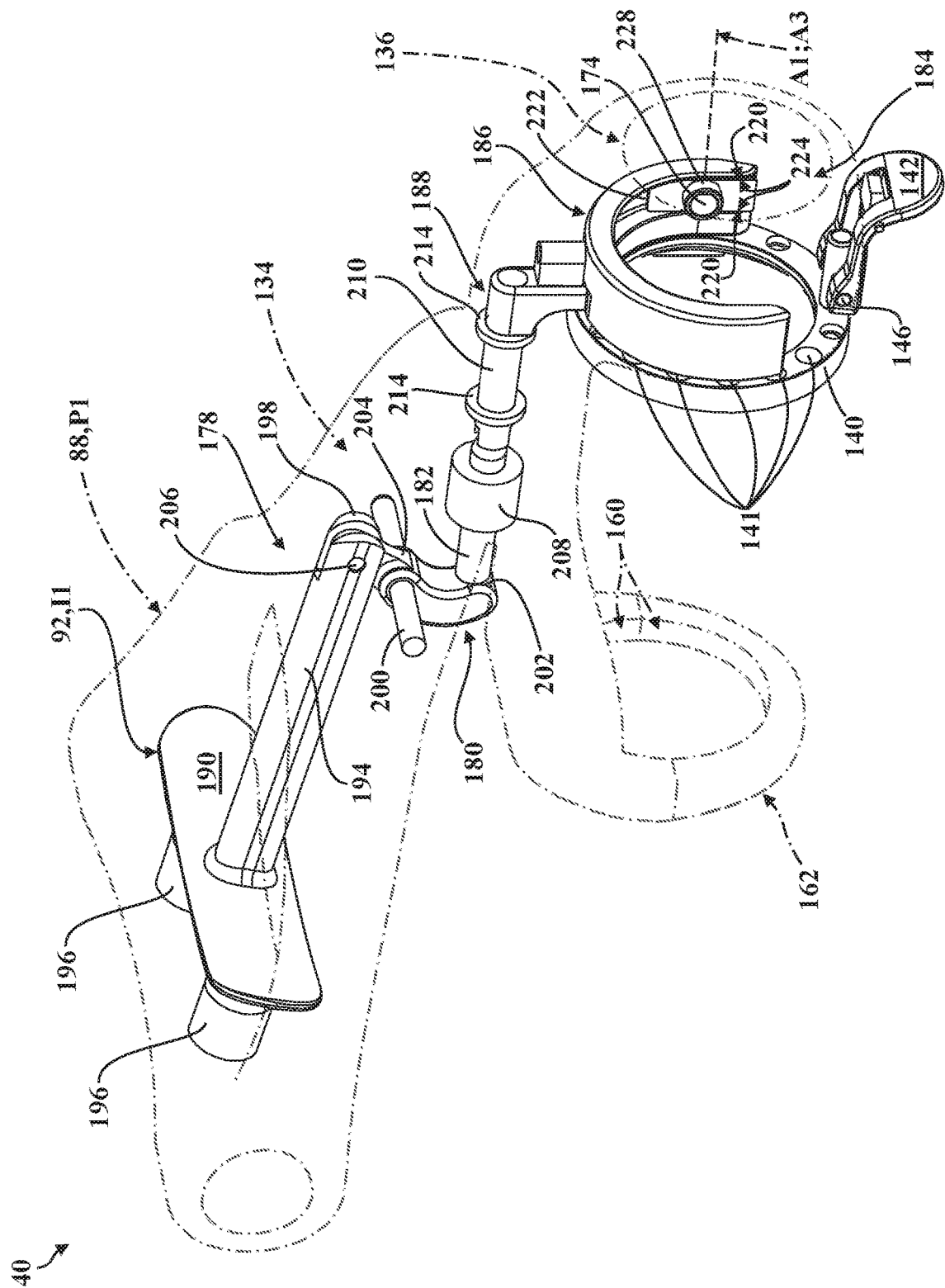
FIG. 19A is a perspective view of portions of the retainer and the trigger assembly of the end effector of FIGS. 11A-18, shown with the trigger assembly arranged in the first trigger assembly position, with the input trigger arranged in a first input position, and shown with portions of the trigger assembly depicted in phantom.
Figure 19B:
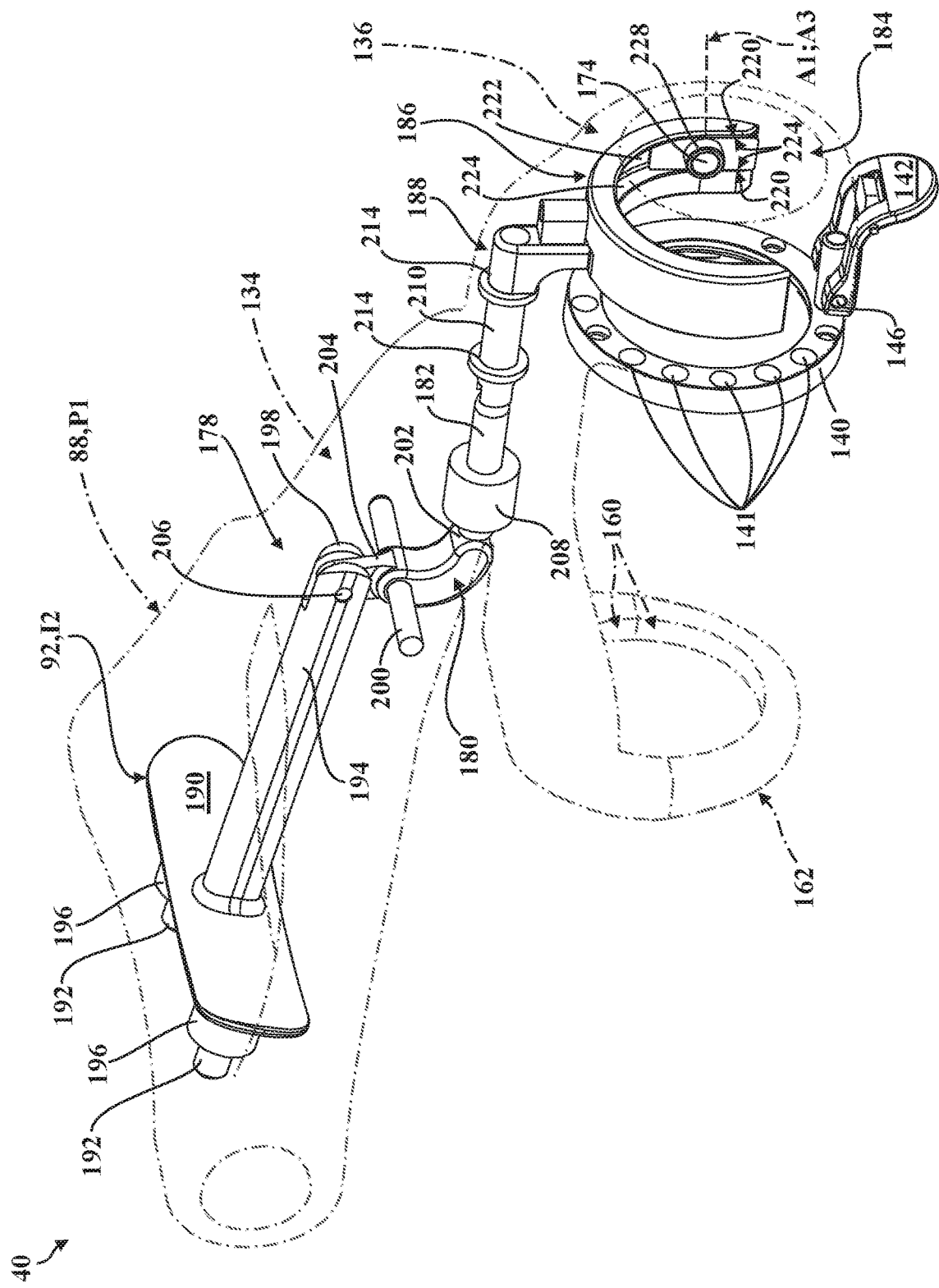
FIG. 19B is another perspective view of the portions of the retainer and the trigger assembly of the end effector of FIG. 19A, shown with the trigger assembly arranged in the first trigger assembly position, with the trigger arranged in a second input position, and shown with portions of the trigger assembly depicted in phantom.
Figure 19C:
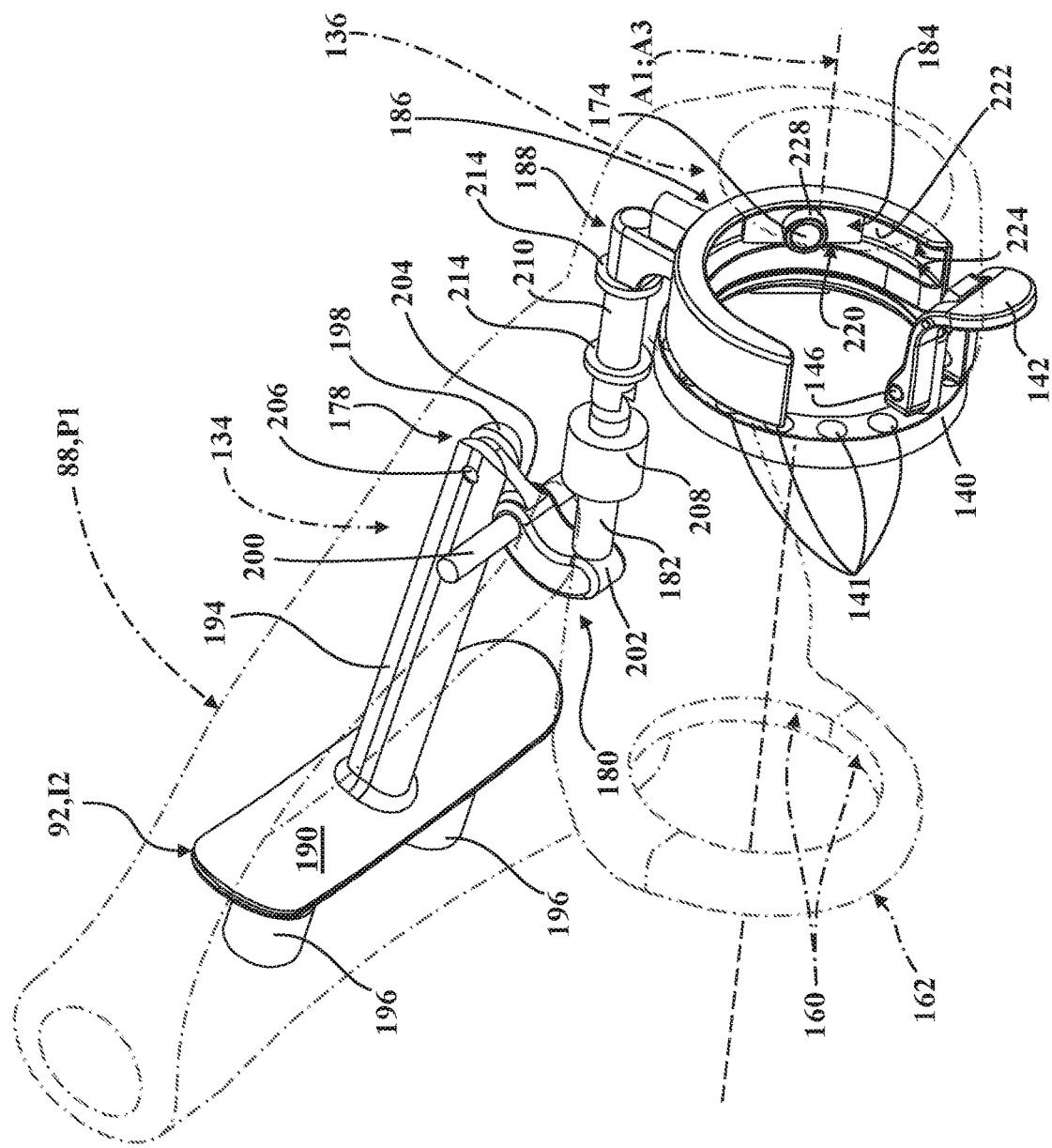
FIG. 19C is another perspective view of the portions of the retainer and the trigger assembly of the end effector of FIGS. 19A-19B, shown with the trigger assembly arranged in the third trigger assembly position, with the trigger arranged in the first input position, and shown with portions of the trigger assembly depicted in phantom.

The retainer 136 is configured to prevent the grip 90 of the trigger assembly 88 from inadvertently moving relative to the rotary instrument 80. To this end, the retainer 136 comprises a plunger 138 which is selectively movable between a locked position 138L (see FIG. 20A; see also FIG. 15) and an unlocked position 138U (see FIG. 20B). A catch, generally indicated at 140, is operatively attached to the rotary instrument 80 (e.g., via fasteners) and has a plurality of receptacles 141 each shaped to receive the plunger 138 of the retainer 136 in the locked position 138L to define one of the trigger assembly positions P1, P2. As is best depicted in FIGS. 19A-19C, the catch 140 has a generally annular profile, and the receptacles 141 each have a generally cylindrical profile and are radially spaced from each other about the catch 140. It will be appreciated that the arrangement of the retainer 136 and the catch 140 could be interchanged such that the plunger could remain stationary relative to the rotary instrument 80 instead of moving concurrently with the trigger assembly 88.

Figure 15:
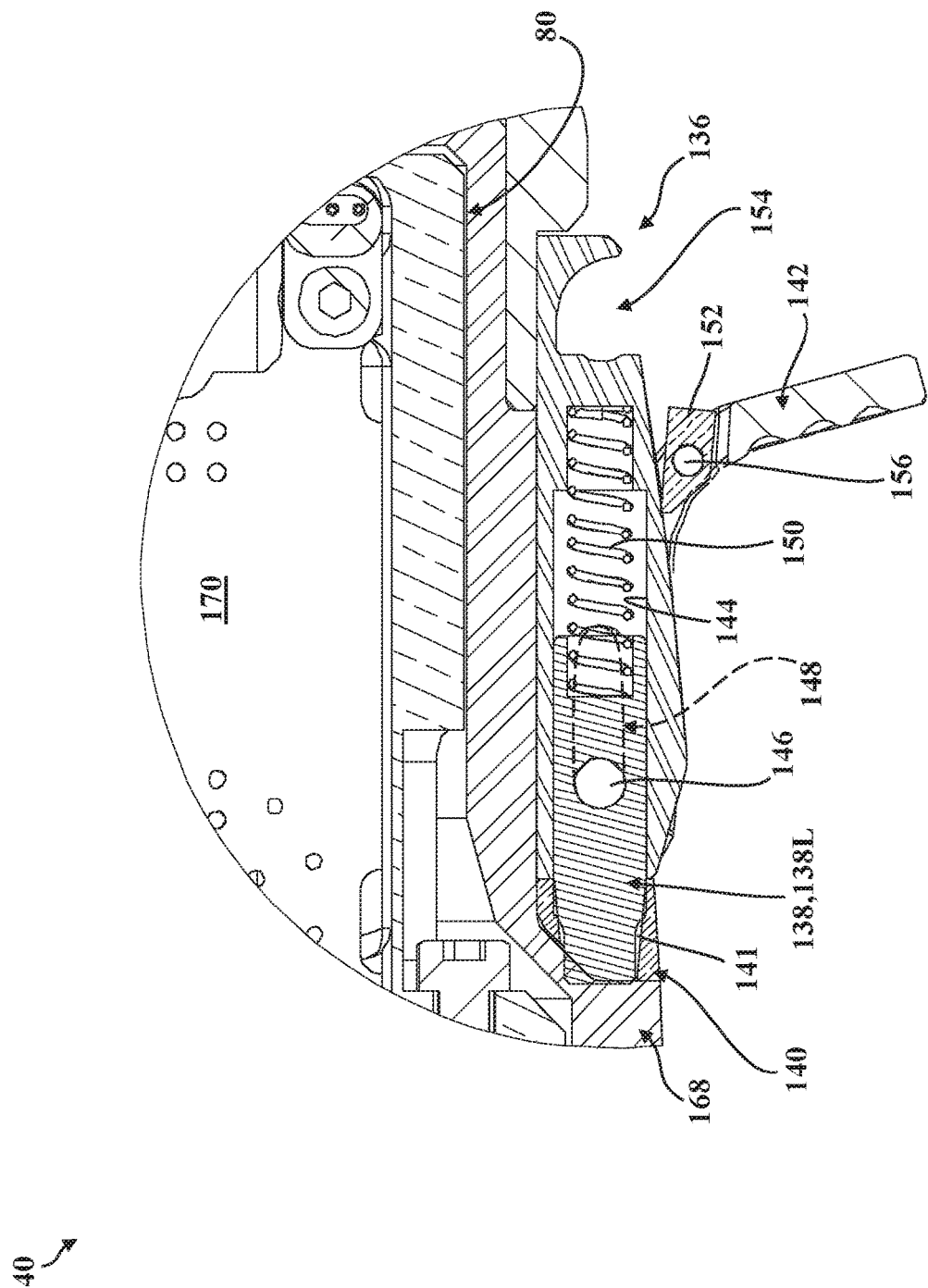
FIG. 15 is an enlarged section view taken along indicia 15 of FIG. 13.
Figure 20B:
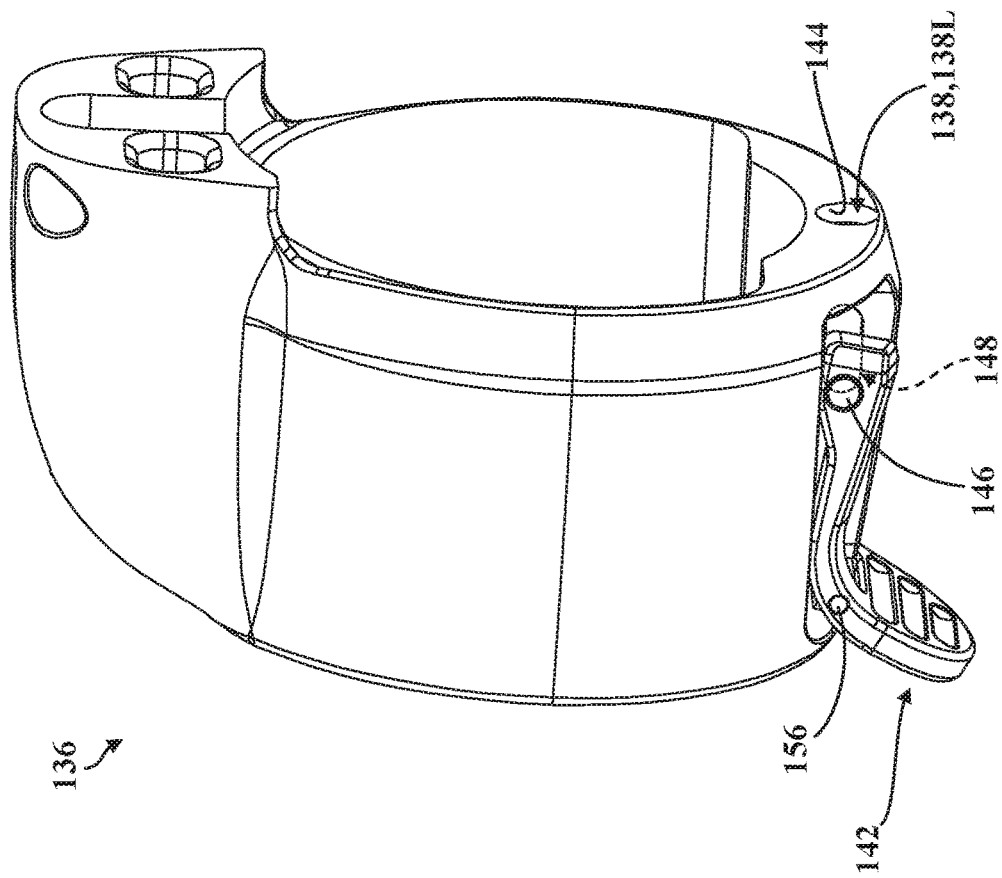
FIG. 20B is another perspective view of the retainer of FIG. 20A, shown with the plunger disposed in an unlocked position to permit movement of the trigger assembly relative to the rotary instrument between the trigger assembly positions.
Figure 21:
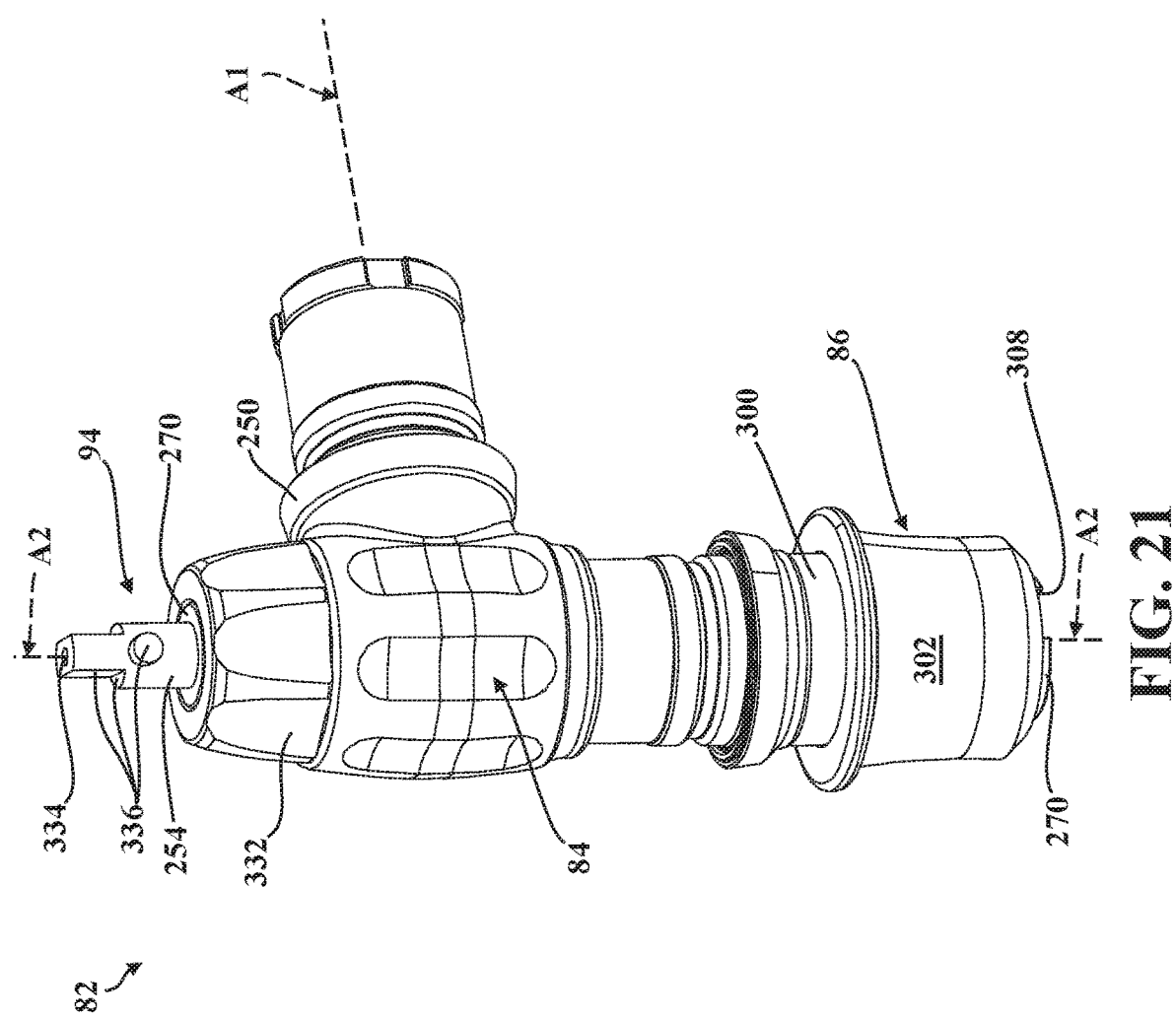
FIG. 21 is a perspective view of the drive assembly of FIGS. 1-4, shown with the manual interface and the connector arranged along the second axis.
Figure 22:
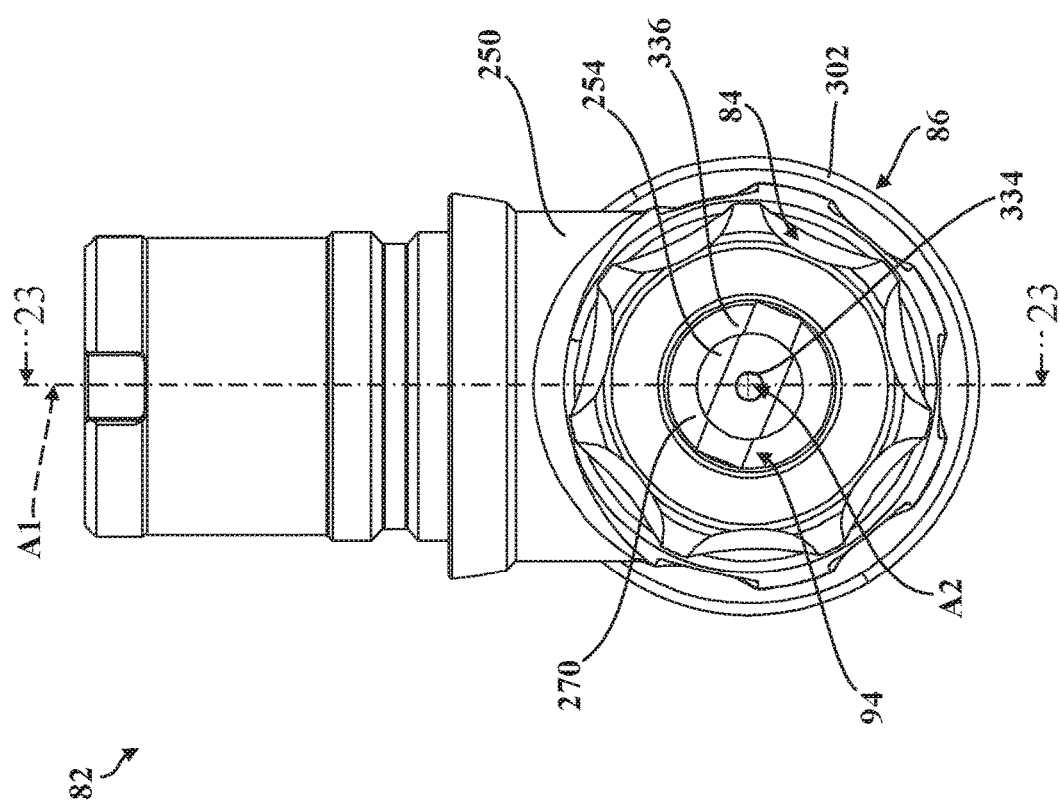
FIG. 22 is a top-side plan view of the drive assembly of FIG. 21.

Referring now to FIGS. 15 and 20A-20B, the retainer 136 comprises a release lever 142 in communication with the plunger 138. The release lever 142 is arranged for engagement by the surgeon or another user to facilitate movement of the plunger 138 between the locked position 138L (see FIG. 20A) and the unlocked position (see FIG. 20B). The plunger 138 is supported for movement along a plunger bore 144 formed in the retainer 136, and is coupled to the release lever 142 via a lever guide pin 146 which, in turn, is supported for translation along a retainer slot 148 (depicted in phantom in FIGS. 20A-20B) formed in the retainer 136. A plunger biasing element 150 (see FIG. 15), such as a compression spring, is interposed between the plunger 138 and the retainer 136 to urge the plunger 138 into the locked position 138L. In order to move the plunger 138 to the unlocked position 138U, the release lever 142 supports a clasp element 152 which can be selectively positioned into a correspondingly-shaped clasp pocket 154 formed in the retainer 136. The clasp element 152 is attached to the release lever 142 via a clasp pin 156.

In order to move to the plunger 138 to the unlocked position 138U, the surgeon or another user can apply force to the release lever 142 in a direction generally away from the catch 140 to compress the plunger biasing element 150 as the lever guide pin 146 translates along the retainer slot 148 until the clasp element 152 is placed into the clasp pocket 154. The corresponding shapes of the clasp element 152 and the clasp pocket 154 keep the plunger 138 in the unlocked position 138U until the surgeon or another user subsequently applies force to the release lever 142 in a direction generally toward the catch 140 to remove the clasp element 152 from the clasp pocket 154, whereby energy stored in the plunger biasing element 150 then returns the plunger 138 to the locked position 138L. It will be appreciated that other configurations of the retainer 136, the plunger 138, and the catch 140 are contemplated.

Figure 17:
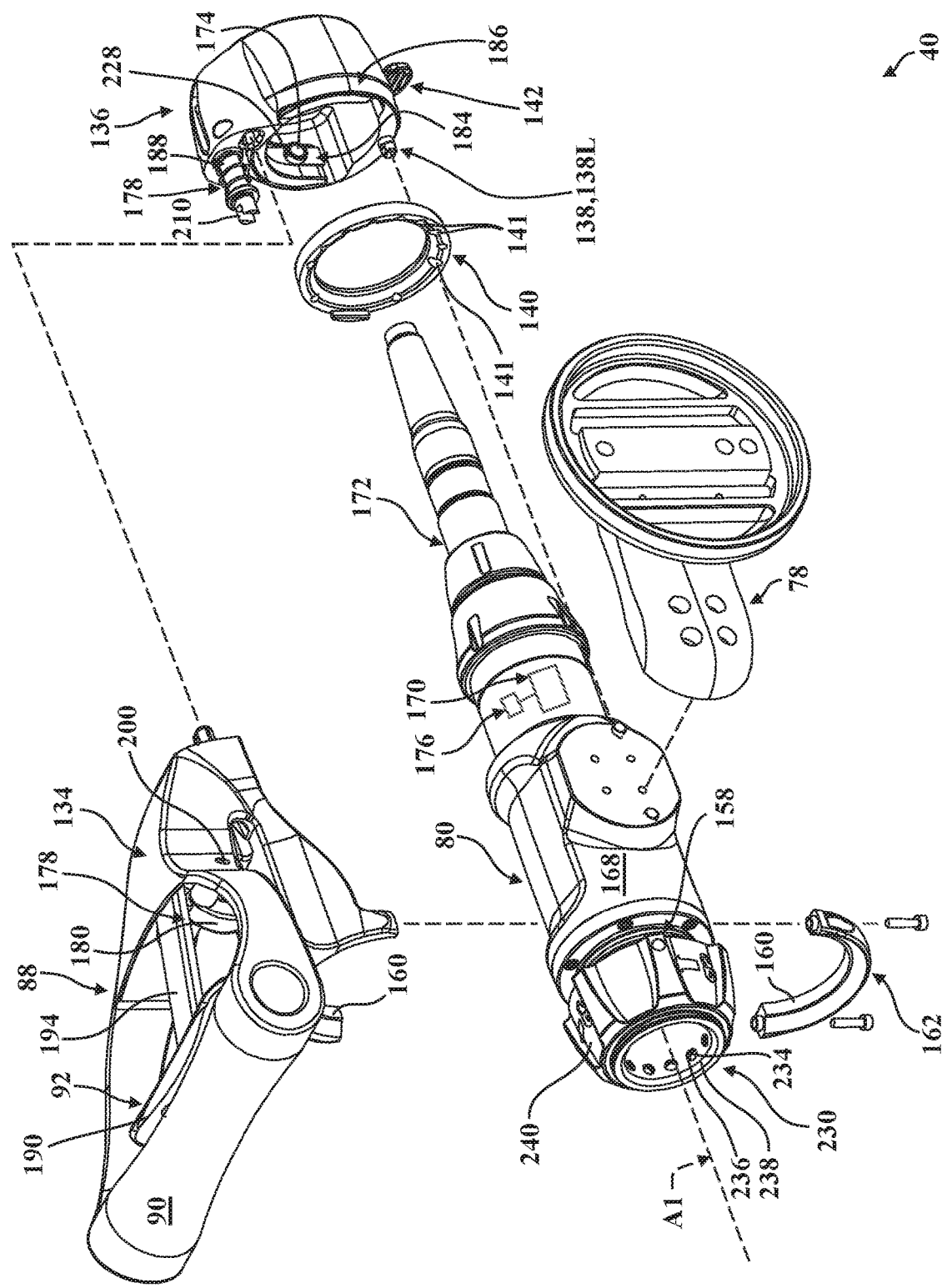
FIG. 17 is a partially-exploded perspective view of the end effector of FIG. 16, shown with the trigger assembly, the mount, and a retainer each spaced from the rotary instrument.

As shown in FIG. 17, the rotary instrument 80 comprises a journal, generally indicated at 158, and the trigger assembly 88 comprises a bearing surface 160 operatively attached to the frame 134 which is disposed in engagement with the journal 158 such that the trigger assembly 88 is selectively movable relative to the rotary instrument 80 between the trigger assembly positions P1 (see FIGS. 10A, 11A, and 19A-19B), P2 (see FIGS. 10B and 11B-11C), P3 (see FIGS. 11F and 19C) about a trigger axis A3 (see FIGS. 19A-19C). Put differently, in the illustrated embodiment, the frame 134 supports the trigger assembly 88 for rotational movement relative to the rotary instrument 80 between the trigger assembly positions P1, P2, P3. As shown in FIG. 17, the bearing surface 160 is defined by a cap element 162 that attaches to the frame 134 via fasteners, as well as by a portion of the frame 134 adjacent to the cap element 162. Other journals and bearing surfaces may be provided at other locations along the rotary instrument 80 and trigger assembly 88, respectively, to promote smooth rotational movement therebetween (e.g., adjacent to the retainer 136). While the illustrated embodiment is directed toward rotational movement of the trigger assembly 88 between the first and second trigger assembly positions P1, P2, it will be appreciated that other types of movement are contemplated. By way of illustrative example, pivoting movement, sliding movement, translation, and/or combinations thereof could be utilized in some embodiments.

Figure 11A:
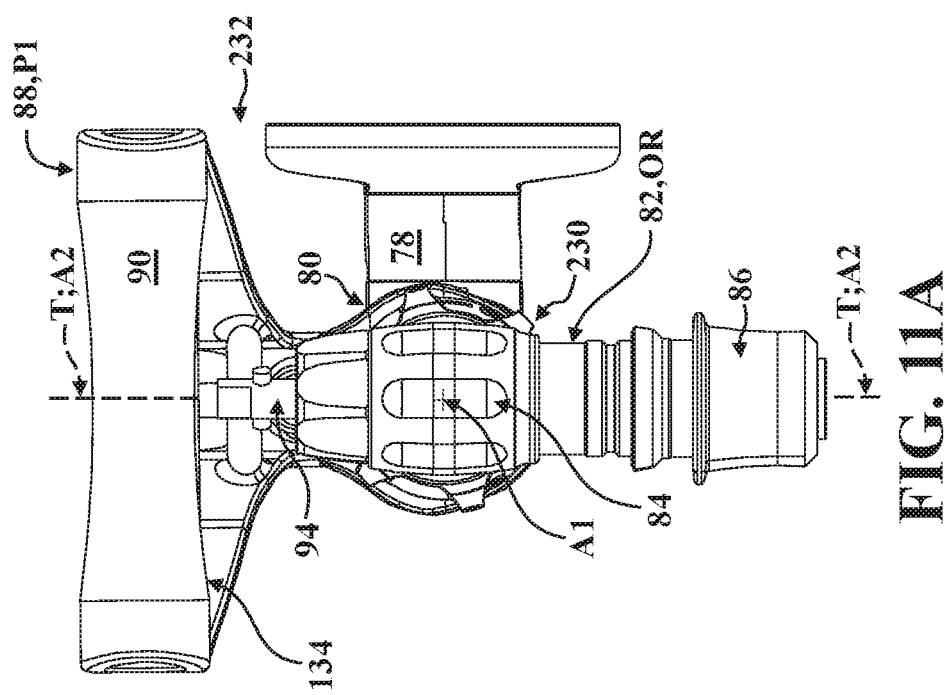
FIG. 11A is a front-side plan view of the end effector of FIGS. 10A-10B, shown with the trigger assembly arranged in the first trigger assembly position, and with the coupling supporting the drive assembly in a first orientation.

As noted above, the grip 90 of the trigger assembly 88 is arranged in the illustrated embodiment to support the surgeon's hand along the trajectory T as the surgeon engages the input trigger 92 to drive the rotary instrument 80. In one embodiment, the second axis A2 intersects at least a portion of the trigger assembly 88 in the first trigger assembly position P1 (see FIG. 10A). Furthermore, as shown in FIG. 11A, when the trigger assembly 88 is in the first trigger assembly position P1, the grip 90 is substantially perpendicular to the second axis A2. Conversely, and as shown in FIG. 11B, when the trigger assembly 88 is in the second trigger assembly position P2, the grip 90 is substantially parallel to (and offset from) the second axis A2. Thus, movement from the first trigger assembly position P1 to the second trigger assembly position P2 comprises rotating the trigger assembly 88 approximately 90-degrees relative to the rotary instrument 80 in the illustrated embodiment. Thus, as shown in FIGS. 19A-19C, the receptacles 141 of the catch 140 which define the first and second trigger assembly positions P1, P2 are arranged 90-degrees apart from each other relative to the trigger axis A3. Furthermore, additional receptacles 141 are provided to define other trigger assembly positions, such as a third trigger assembly position P3 (see FIGS. 11F and 19C) between the first and second trigger assembly positions P1, P2. It will be appreciated that any suitable number of receptacles 141 could be provided to define a corresponding number of discrete trigger assembly positions spaced from each other in a number of different ways.

Figure 16:
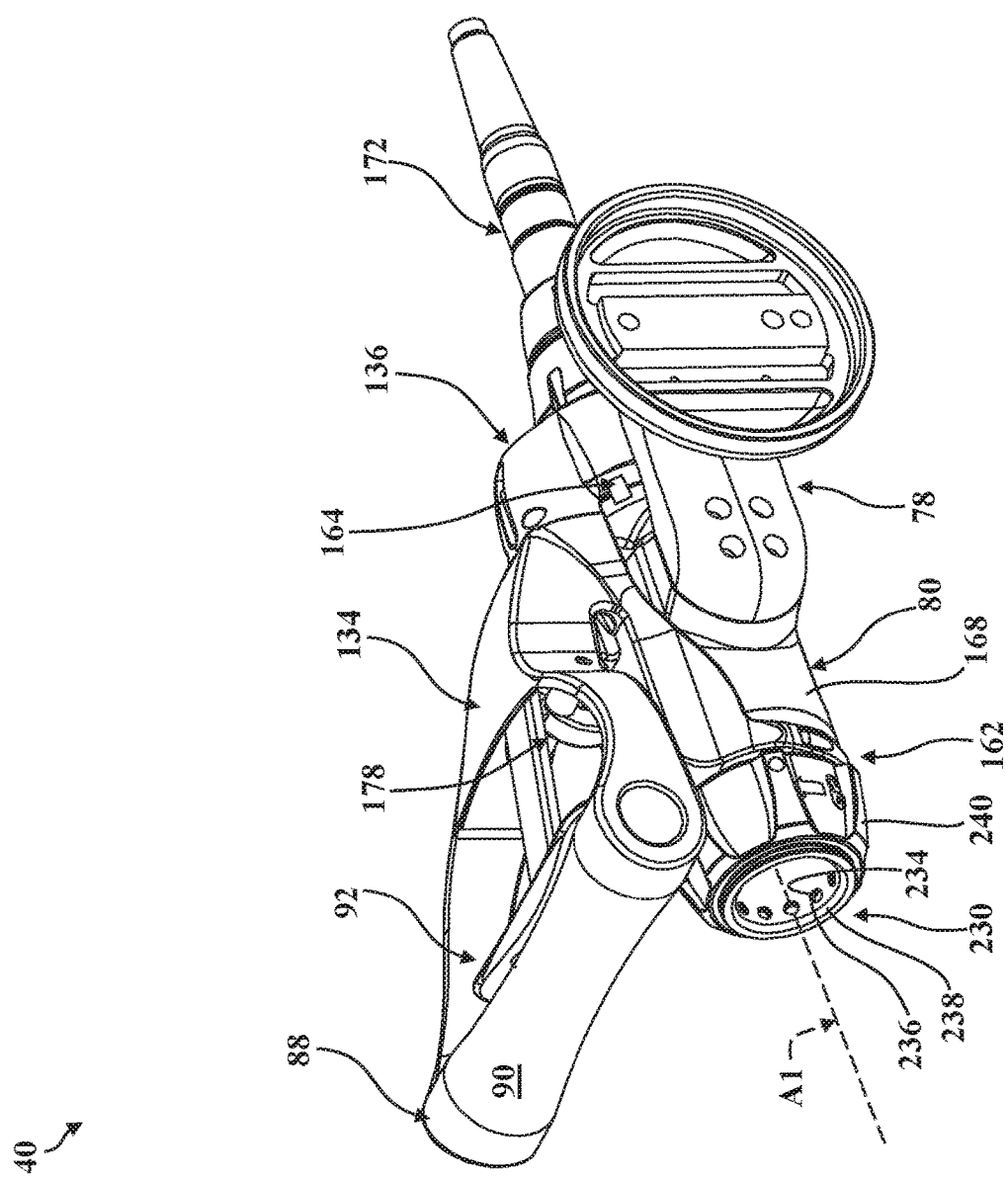
FIG. 16 is a perspective view of the mount, the rotary instrument, the trigger assembly, and the coupling of the end effector of FIG. 12.

As is depicted schematically in FIG. 16, in one embodiment the end effector 40 is provided with an assembly sensor arrangement, generally indicated at 164, interposed between the rotary instrument 80 and the trigger assembly 88 to determine a position of the trigger assembly 88 relative to the rotary instrument 80 between the trigger assembly positions P1, P2, P3 (see FIGS. 11A, 11B, and 11F). The assembly sensor arrangement 164 may be of any suitable configuration sufficient to differentiate between positions (e.g., an encoder, a sensor/emitter arrangement, and the like), and may communicate with the control system 52 to, among other things, allow the rotary instrument 80 to be controlled in different ways depending on how the trigger assembly 88 is positioned relative to the rotary instrument 80. Other configurations and arrangements are contemplated.

As noted above, the input trigger 92 of the trigger assembly 88 is arranged for engagement by the surgeon to facilitate driving the rotary instrument 80. As is depicted generically in FIG. 13, the rotary instrument 80 comprises an actuator 166 (e.g., an electric motor) which is supported within an instrument housing 168 which, in turn, defines the journal 158 and rigidly attaches to the mount 78. The actuator 166 is disposed in communication with an actuator driver, generally indicated at 170 (e.g., a motor controller supported on a printed circuit board) which, in turn, is disposed in communication with the control system 52 via an actuator interface, generally indicated at 172 (e.g., a wiring harness connected to the arm controller 56). Those having ordinary skill in the art will appreciate that the actuator 166, the actuator driver 170, and/or the actuator interface 172 could be arranged or configured in a number of different ways sufficient to power, control, or otherwise enable the rotary instrument 80 to selectively generate rotational torque about the first axis A1 in response to engagement of the input trigger 92. Furthermore, and as will be appreciated from the subsequent description below, certain embodiments of the end effector 40 illustrated in connection with the first embodiment of the end effector 40 and described herein are configured such that rotary instrument 80 has a generally modular configuration (e.g., removable from one or more portions of the drive assembly 82), while other embodiments of the end effector 40 are less modular (e.g., integrated with one or more portions of the drive assembly 82). Thus, unless otherwise indicated, the terms "actuator 166" and "rotary instrument 80" may be used interchangeably.

Referring now to FIGS. 13-19C, the input trigger 92 of the trigger assembly 88 is disposed in communication with the actuator driver 170 to facilitate how rotational torque is generated by the actuator 166. To this end, the input trigger 92 is arranged for movement relative to the grip 90 between a first input position I1 (see FIG. 19A) and a second input position I2 (see FIG. 19B) to control rotational torque generated by the rotary instrument 80. In the illustrated embodiment, the first input position I1 corresponds to an absence of engagement with the input trigger 92, and the second input position I2 corresponds to full engagement of the input trigger 92. It will be appreciated that the input trigger 92 is also movable to other input positions between the first and second input positions I1, I2, such as to facilitate variable speed control of the actuator 166.

In order to communicate the physical position of the input trigger 92 between the first and second input positions I1, I2 to the actuator driver 170, the trigger assembly 88 comprises a trigger emitter 174 (see FIGS. 17-19C) disposed in communication with the input trigger 92, and the rotary instrument 80 comprises a trigger detector 176 (see FIGS. 17-18; depicted schematically) disposed in communication with the actuator driver 170 to determine a position of the trigger emitter 174 corresponding to movement of the input trigger 92 between the first and second input positions I1, I2. In one embodiment, the trigger emitter 174 is further defined as a magnet, and the trigger detector 176 is responsive to predetermined changes in magnetic fields generated by the magnet to determine the relative position of the trigger emitter 174. In this illustrative example, the trigger detector 176 may be of any suitable type sufficient to sense and respond to changes in magnetic fields. Moreover, it is conceivable that the trigger emitter 174 could be manufactured from an iron-based material and the trigger detector 176 could be a hall-effect sensor that responds to changes in magnetic fields due to interaction of the iron-based material of the trigger emitter 174. Thus, it is conceivable that the trigger emitter 174 may also be realized as a ferrous enamel, coating, paint, or the like. Other configurations are contemplated.

Referring now to FIGS. 17-19C, a linkage 178 is interposed between the input trigger 92 and the trigger emitter 174 to translate movement of the input trigger 92 between the first and second input positions I1, I2 into corresponding movement of the trigger emitter 174 which can be sensed by the trigger detector 176. The linkage 178 generally comprises a cam member 180, a piston 182, a carrier 184, a fork 186, and a fork guide 188. The input trigger 92, in turn, comprises a trigger handle 190, a pair of guide shafts 192, and an extension member 194. The guide shafts 192 extend from the trigger handle 190 and are supported for sliding movement within respective bushings 196 disposed in the grip 90. The extension member 194 similarly extends from the trigger handle 190, away from the guide shafts 192, to a notched end 198. The cam member 180 is interposed between the piston 182 and the notched end 198 of the input trigger 92, and pivots about a support shaft 200 which is coupled to the frame 134. On opposing sides of the support shaft 200, the cam member 180 has an engagement face 202 which abuts the piston 182, and a slotted projection 204 in which an extension pin 206 travels. The extension pin 206 is attached to the notched end 198 of the extension member 194 to pivot the cam member 180 about the support shaft 200 as the input trigger 92 moves.

The piston 182 is slidably supported in a piston bushing 208 attached to the frame 134. In addition to contacting the engagement face 202 of the cam member 180, the piston 182 also contacts a fork guide shaft 210 of the fork guide 188 which, in turn, supports a trigger biasing element 212 between a pair of washers 214 and a keeper 216 (see FIG. 18). The keeper 216 attaches to the fork guide shaft 210 and engages one of the washers 214 to retain the trigger biasing element 212 between the washers 214. The washers 214 help facilitate translation of the fork guide shaft 210 in response to movement of the piston 182. Here, the trigger biasing element 212 is arranged to compress between one of the washers 214 and the frame 134 as the input trigger moves from the first input position I1 to the second input position I2, and energy stored in the trigger biasing element 212 urges the input trigger toward the first input position I1.

The fork guide 188 moves concurrently with the fork 186 which, in the illustrated embodiment, is disposed within the retainer 136 for translation along the first axis A1 as the input trigger 92 moves between the first and second input positions I1, I2 (compare FIG. 19A with FIG. 19B). As shown in FIG. 17, the retainer 136 is shaped to rotate concurrently with the fork 186 about the first axis A1 as the trigger assembly 88 moves between the first and second trigger assembly positions P1, P2.

Figure 18:
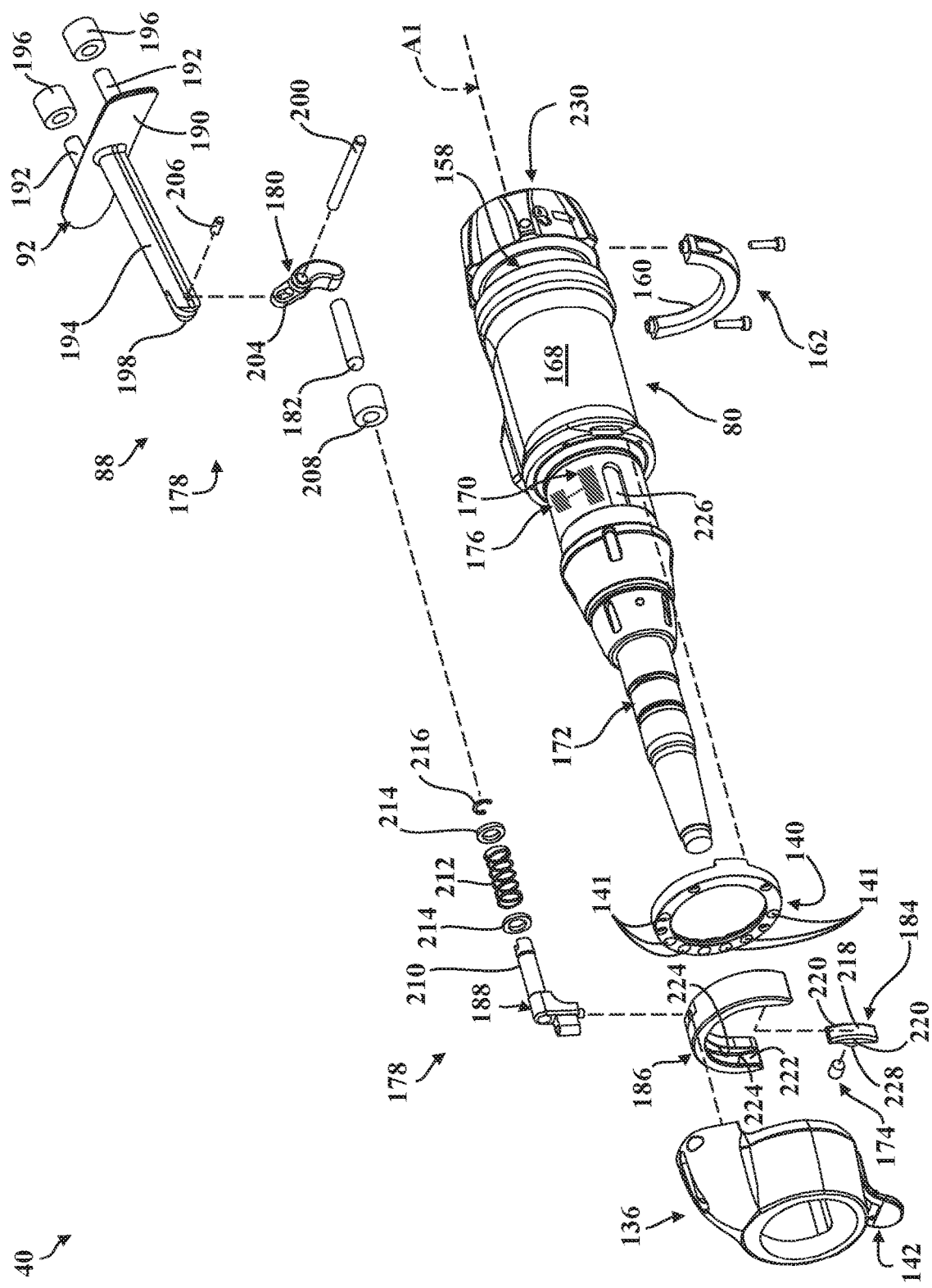
FIG. 18 is another partially-exploded perspective view of the end effector of FIG. 16, shown with portions of the retainer and the trigger assembly each spaced from the rotary instrument.

The carrier 184 is operatively attached to or otherwise supports the trigger emitter 174 for concurrent movement, and defines an outer sliding contact surface 218 (see FIG. 18) and a pair of outer blocking surfaces 220. The fork 186, in turn, defines an inner sliding contact surface 222 and a pair of inner blocking surfaces 224. The outer sliding contact surface 218 of the carrier 184 engages the inner sliding contact surface 222 of the fork 186 to permit rotational movement of the fork 186 about the first axis A1 without moving the carrier 184, and the outer blocking surfaces 220 of the carrier 184 engage the inner blocking surfaces 224 of the fork 186 to facilitate concurrent translation of the fork 186 and the carrier 184 along the first axis A1 (compare FIGS. 19A-19C). As shown in FIG. 18, the instrument housing 168 of the rotary instrument 80 defines a slot 226 which is arranged adjacent to the trigger detector 176 (depicted schematically in FIG. 18). The carrier 184 comprises a boss 228 which is supported along the slot 226 for translation in response to corresponding translation of the fork 186 along the first axis A1 effected by movement of the input trigger 92 between the first and second input positions I1, I2. It will be appreciated that other configurations beyond those illustrated in the drawings are contemplated for the various components of the linkage 178 and/or the trigger assembly 88.

Referring again to FIGS. 1-24, the end effector 40 employs a coupling 230 operatively attached to the rotary instrument 80. The coupling 230 is configured to releasably secure the drive assembly 82 to the rotary instrument 80 in a plurality of orientations to selectively position the second axis A2 relative to the rotary instrument 80 along different trajectories maintained by the surgical robot 32. This functionality affords the surgeon with a more consistent approach along each discrete trajectory T in that the grip 90 can generally be positioned similarly irrespective of how the second axis A2 is orientated relative to the rotary instrument 80 and, thus, relative to the mount 78 of the end effector 40 (compare FIGS. 2A-2C).

The functionality described above is further illustrated throughout FIGS. 11A-11F by comparing the orientation of the second axis A2 with the orientation of the mount 78. Here, the mount 78 has a reference portion, generally indicated at 232, which in this illustrative example is realized as a vertical line defined by a generally planar face of the mount 78 which abuts the coupler 38 of the robotic arm 36. However, it will be appreciated that the reference portion 232 could be defined by other components of the end effector 40 which remain fixed relative to the mount 78, or could be defined in other ways (e.g., vertically with respect to the environment, such as by gravity).

Figure 11D:
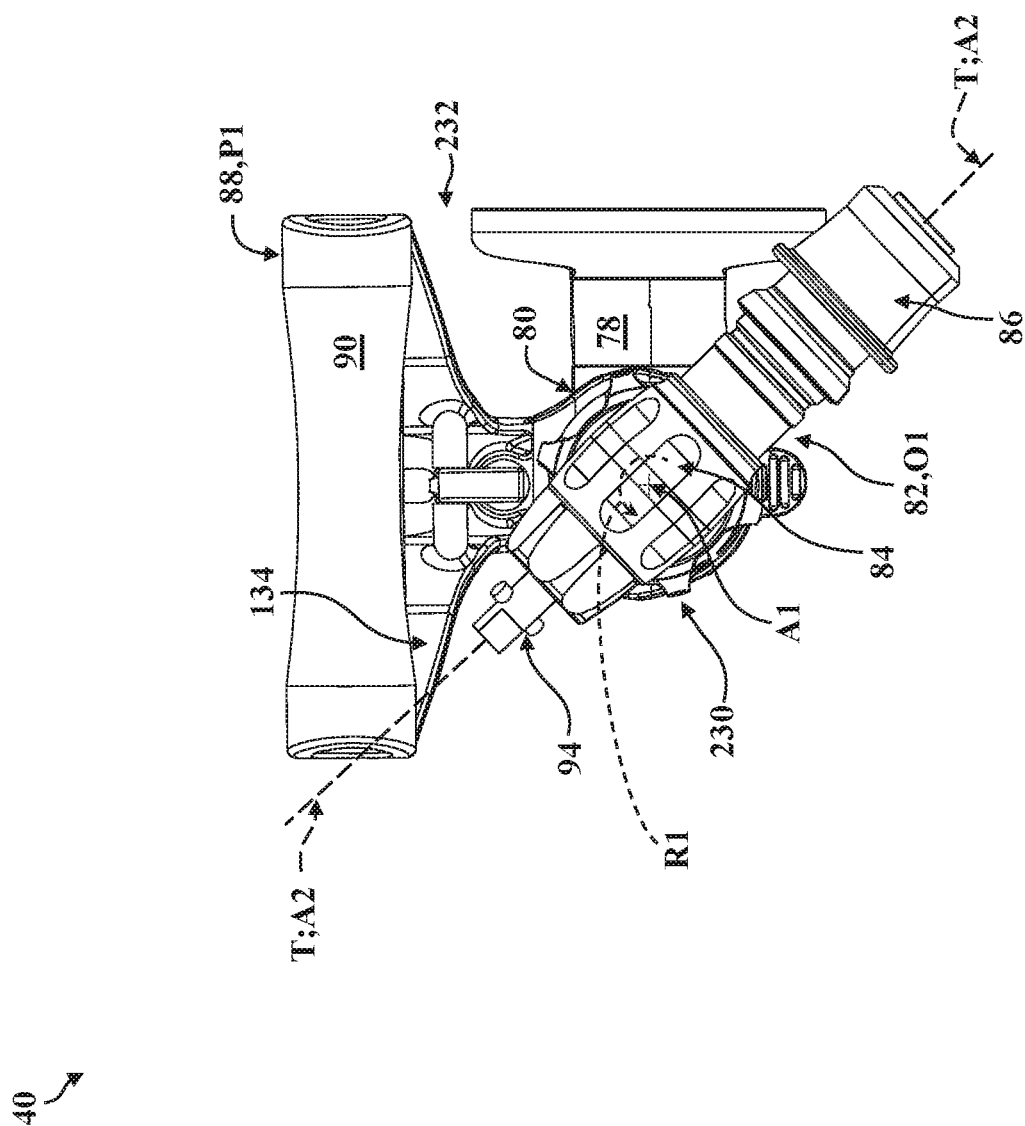
FIG. 11D is another front-side plan view of the end effector of FIGS. 11A-11C, shown with the trigger assembly arranged in the first trigger assembly position, and with the coupling supporting the drive assembly in a second orientation.
Figure 11E:
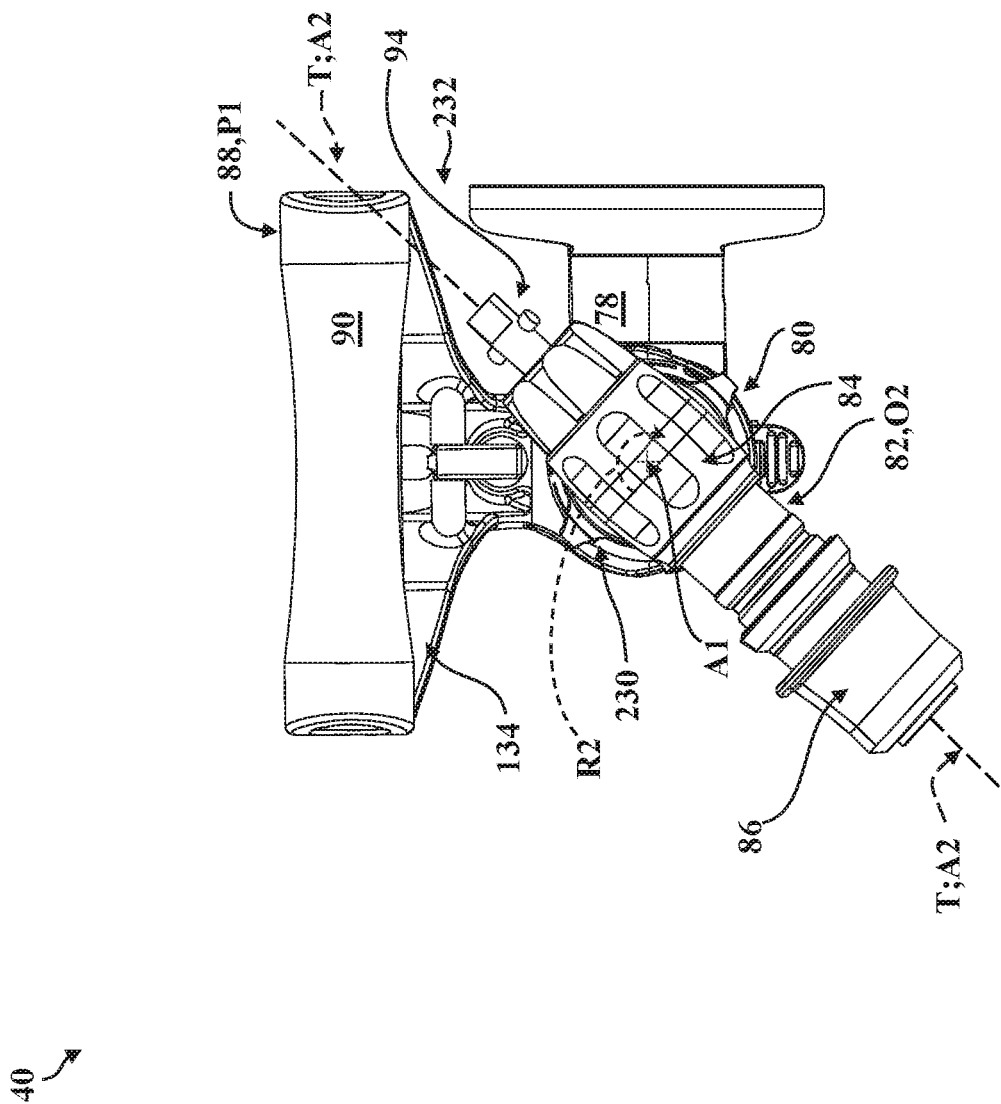
FIG. 11E is another front-side plan view of the end effector of FIGS. 11A-11D, shown with the trigger assembly arranged in the first trigger assembly position, and with the coupling supporting the drive assembly in a third orientation.
Figure 12:
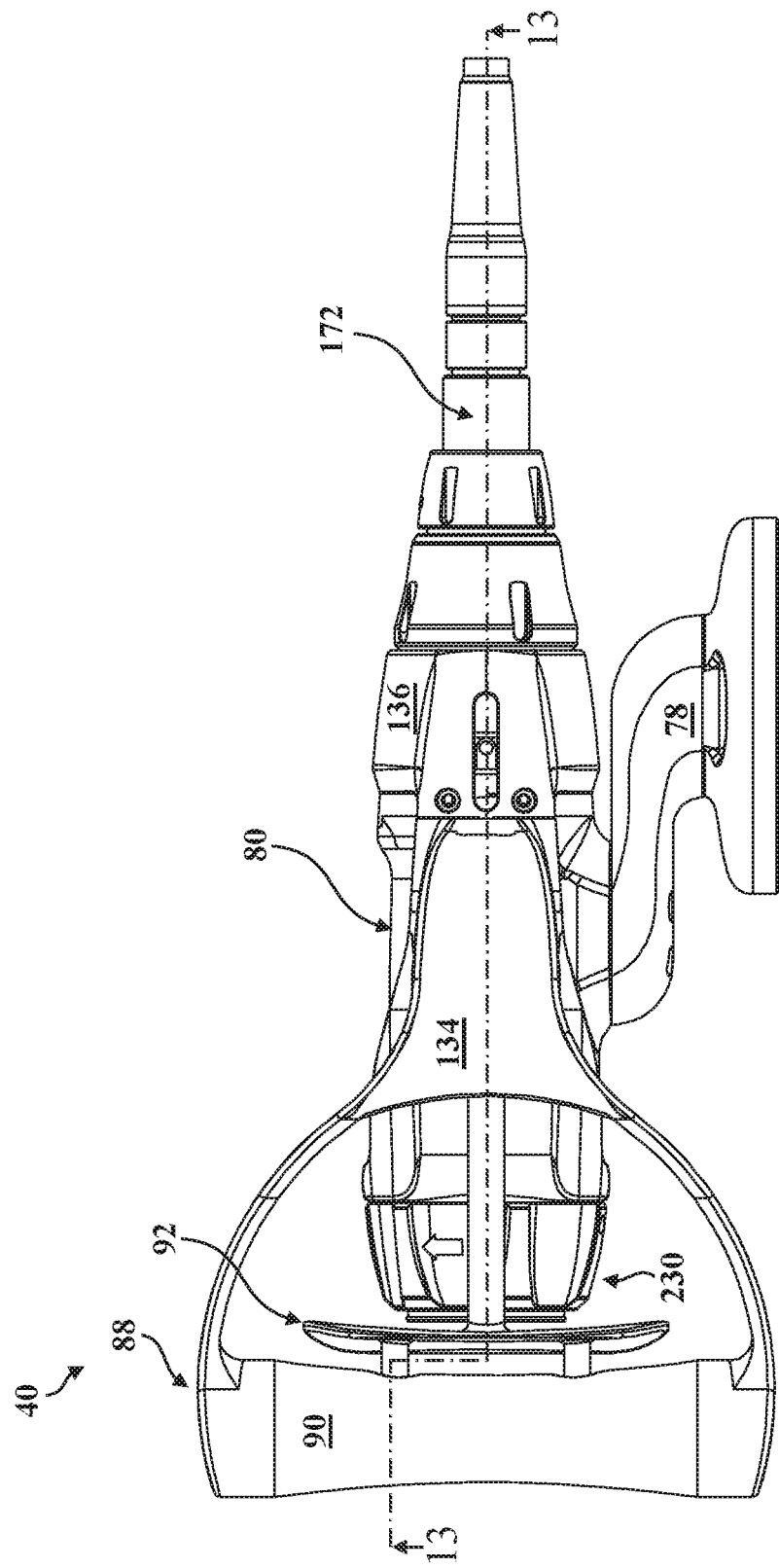
FIG. 12 is a top-side plan view of the mount, the rotary instrument, the trigger assembly, and the coupling of the end effector of FIGS. 1-4.

In FIGS. 11A-11C, the drive assembly 82 is arranged in a reference orientation OR defined between the second axis A2 and the reference portion 232 of the mount 78. Thus, the second axis A2 is parallel with the reference portion 232 when in the reference orientation OR. In FIG. 11D, however, the drive assembly 82 is arranged in a different, first orientation O1 defined by rotation of the drive assembly 82 relative to the rotary instrument 80 about the first axis A1 in a first rotational direction R1. Moreover, in FIGS. 11E and 11F, the drive assembly 82 is arranged in a second orientation O2 defined by rotation of the drive assembly 82 relative to the rotary instrument 80 about the first axis A1 in an opposite, second rotational direction R2.

From the perspective depicted in FIGS. 11A-11F, the first rotational direction R1 is counter-clockwise and the second rotational direction R2 is clockwise. Thus, when in the first orientation O1 depicted in FIG. 11D, the drive assembly 82 has been rotated counter-clockwise about the first axis A1 +45-degrees relative to the reference portion 232. When in the second orientation O2 depicted in FIGS. 11E-11F, the drive assembly 82 has been rotated clockwise about the first axis A1 −45-degrees relative to the reference portion 232. As such, there is a 90-degree difference between the first orientation O1 and the second orientation O2. However, it will be appreciated that the first and second orientations O1, O2 could be defined in a number of different ways to facilitate consistent positioning of the grip 90. Moreover, it will be appreciated that the coupling 230 could support the drive assembly 82 in other orientations.

Figure 13:
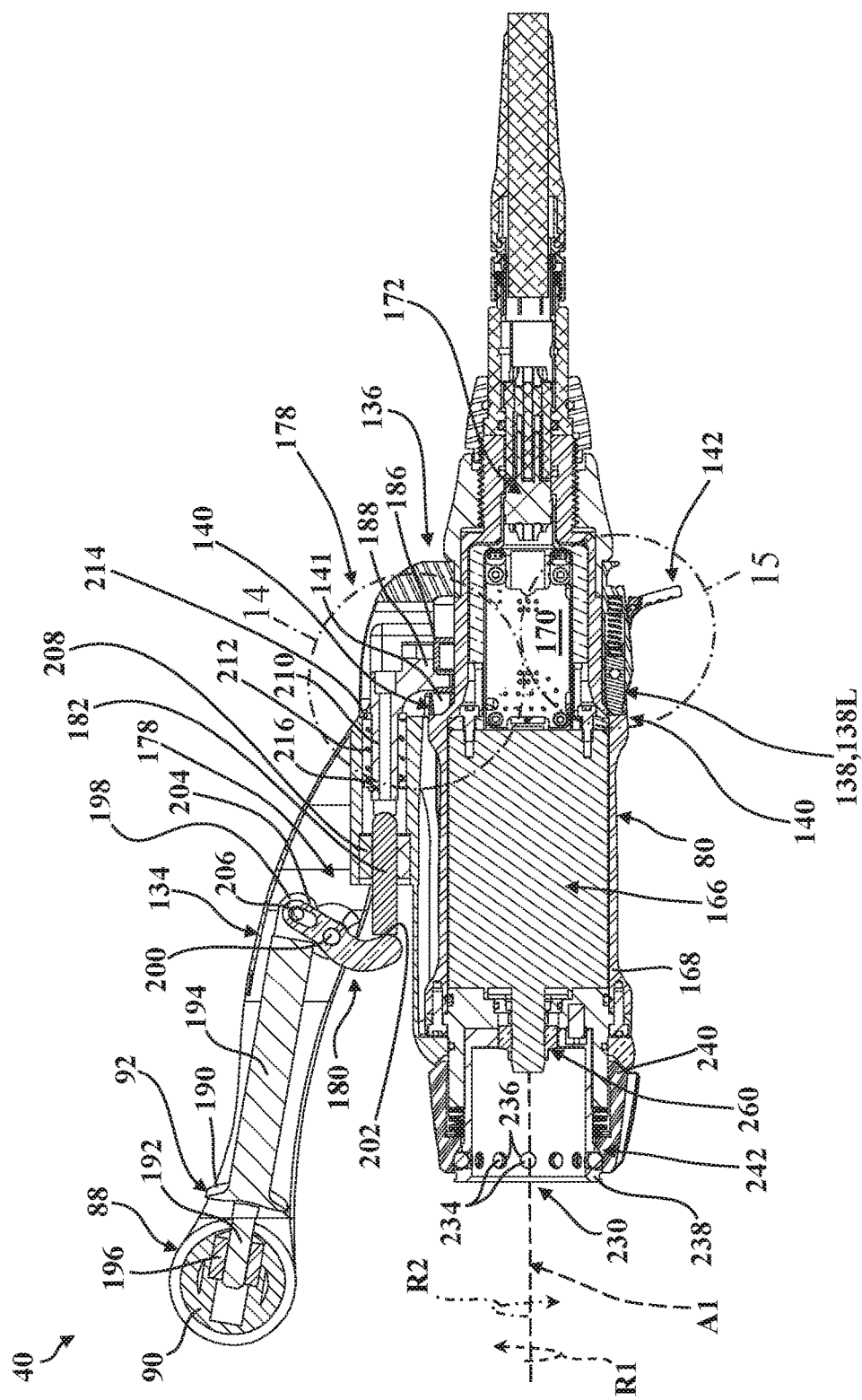
FIG. 13 is an offset section view taken along line 13-13 of FIG. 12.
Figure 14:
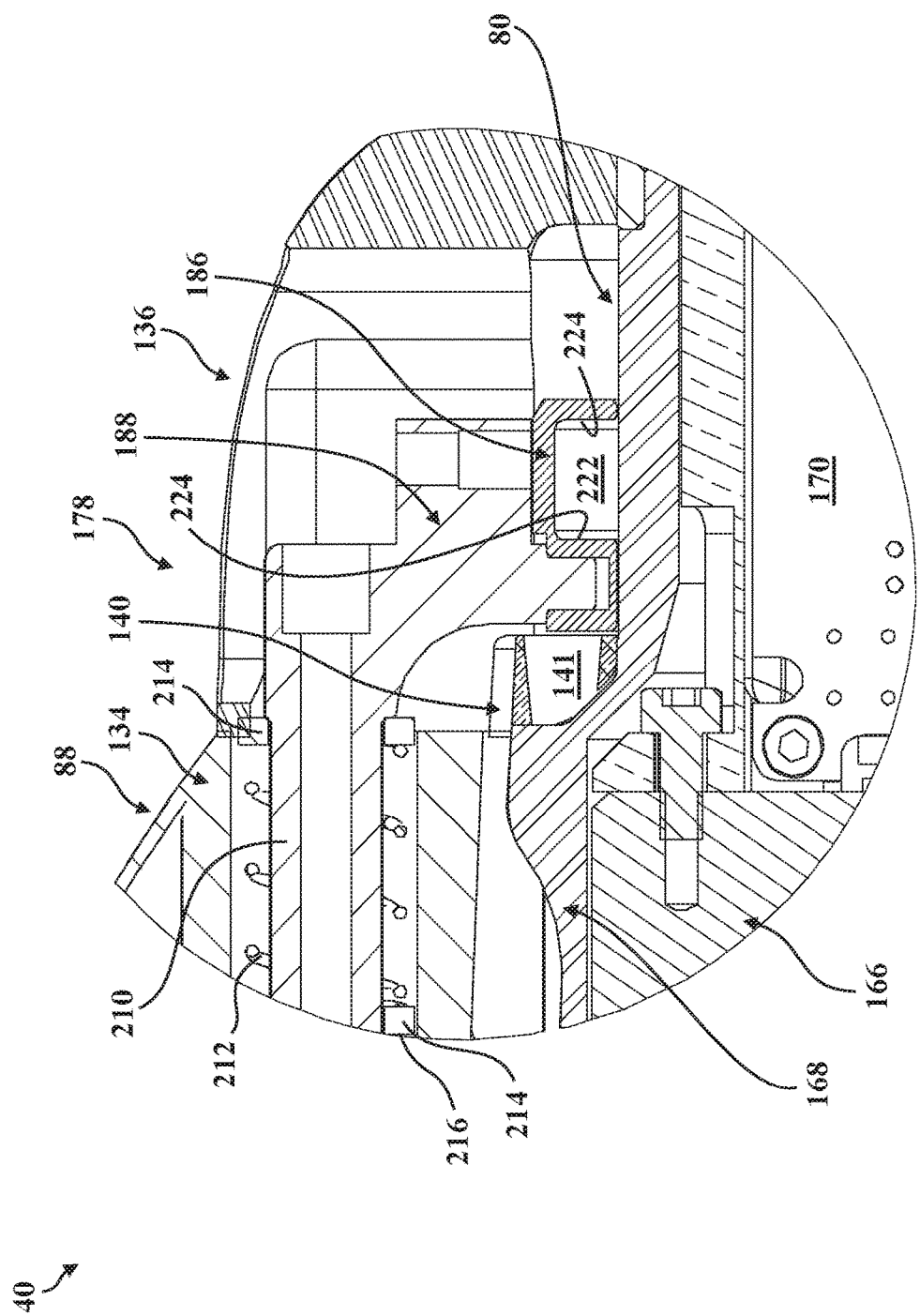
FIG. 14 is an enlarged section view taken along indicia 14 of FIG. 13.

Referring now to FIG. 13, in the representative embodiment illustrated herein, the coupling 230 comprises a plurality of coupling elements 234 (e.g., ball bearings) which are supported for radial movement relative to the first axis A1 along respective coupling pockets 236 formed in a carrier ring 238. The coupling 230 also comprises a lock collar 240 with an inner ramp surface 242 that contacts the coupling elements 234. The lock collar 240 is arranged for selective rotation about the first axis A1 via force applied thereto from the surgeon. The carrier ring 238 is configured to translate axially relative to the rotary instrument 80 in response to rotation of the lock collar 240 relative to the instrument housing 168, such as via threaded engagement between the lock collar 240 and the carrier ring 238 (threaded engagement not shown in detail).

When the lock collar 240 is rotated about the first axis A1 in the second rotational direction R2, the carrier ring 238 translates along the first axis A1 toward the actuator 166 concurrently with the coupling elements 234. Because of the shape of the inner ramp surface 242 contacting the coupling elements 234, translation toward the actuator 166 urges the coupling elements 234 radially inwardly toward the first axis A1 to press against the drive assembly 82 and thereby maintain the orientation of the drive assembly 82 relative to the mount 78. Conversely, when the lock collar 240 is rotated about the first axis A1 in the first rotational direction R1, the carrier ring 238 translates along the first axis A1 away from the actuator 166 concurrently with the coupling elements 234, and the coupling elements 234 are then able to move radially away from the first axis A1 along their respective coupling pockets 236. It will be appreciated that other configurations of the coupling 230 are contemplated. Moreover, the coupling 230 could be configured to secure the drive assembly 82 to the rotary instrument 80 in any number of different orientations, or in only predefined orientations (e.g., via a lock or detent mechanism).

It will be appreciated that the coupling 230 effectively creates an additional joint between the base 34 of the surgical robot 32 and the tool 42. In order to communicate the orientation of the drive assembly 82 relative to the mount 78, an orientation sensor arrangement, depicted schematically at 244 in FIG. 4, is interposed between the rotary instrument 80 and the drive assembly 82 to determine the orientation of the drive assembly 82 relative to the rotary instrument 80. To this end, the orientation sensor arrangement 244 comprises an orientation emitter 246 operatively attached to the drive assembly 82, and an orientation detector 248 operatively attached to the rotary instrument 80 to determine a position of the orientation emitter 246 relative to the rotary instrument 80. Here too, the orientation sensor arrangement 244 could be of a number of different types, configurations, and/or arrangements. Alternatively, a selected orientation could be inputted into the surgical system 30 manually, such as via the input device 70 of the user interface 66 (see FIG. 1).

Referring now to FIGS. 21-24, as noted above, the drive assembly 82 is employed to translate rotation to the tool 42 attached to the connector 86, through the geartrain 84, from either the rotary instrument 80 or the manual interface 94. To this end, the drive assembly 82 comprises a generally L-shaped drive body 250 which, as described in greater detail below, supports a driver input shaft 252 along the first axis A1 (see FIG. 23A), and also supports a manual input shaft 254, a retention shaft 255, and an intermediate shaft 256 along the second axis A2. The driver input shaft 252 comprises a driver coupling 258 which is shaped to engage a corresponding actuator coupling 260 (see FIG. 13) coupled to the actuator 166 for concurrent rotation (e.g., as an interference-type "dog clutch"). The driver input shaft 252, the manual input shaft 254, the retention shaft 255, and the intermediate shaft 256 are each generally supported for rotation relative to the drive body 250 via one or more bearings 262 (e.g., sealed ball bearings), washers 264, keepers 266, and/or spring shims 268 (arrangements generally illustrated in FIGS. 23A-23B and 24, but not described in detail). The drive assembly 82 further comprises seals 270 disposed adjacent to the exposed ends of each of the driver input shaft 252, the manual input shaft 254, and the retention shaft 255.

In order to translate rotation about the first axis A1 into rotation about the second axis A2, the geartrain 84 comprises at least one bevel gearset, generally indicated at 272, interposed in rotational communication between the rotary instrument 80 and the connector 86. The bevel gearset 272 comprises an input gear 274 and an output gear 276. The input gear 274 rotates concurrently with the driver input shaft 252 via a key and keyway arrangement, generally indicated at 278. The input gear 274 is arranged to mesh with the output gear 276 (see FIG. 23A) as described in greater detail below. The output gear 276 rotates concurrently with the intermediate shaft 256 via a splined arrangement, generally indicated at 280. Here, the intermediate shaft 256 comprises outer splines 282 which engage corresponding inner splines 284 of the output gear 276 as described in greater detail below.

In the illustrated embodiment, the geartrain 84 of the drive assembly 82 comprises at least one reduction gearset, generally indicated at 286, interposed in rotational communication between the rotary instrument 80 and the connector 86 such that rotation of the actuator 166 of the rotary instrument 80 occurs at a different (e.g., higher or lower) speed than rotation of the tool 42 attached to the connector 86. More specifically, the reduction gearset 286 is interposed in rotational communication between the bevel gearset 272 and the connector 86, and is arranged such that the intermediate shaft 256 (which can be rotated via the rotary instrument 80 or the manual interface 94) rotates at a higher speed than the retention shaft 255 (which rotates concurrently with the tool 42 about the second axis A2). While rotation of the actuator 166 about the first axis A1 occurs at a higher speed than rotation of the tool 42 about the second axis A2 in the first embodiment of the end effector 40, other configurations are contemplated and the term "reduction gearset" as used herein may refer to either a reduction in rotational speed (with an increase in torque) or a reduction in torque (with an increase in rotational speed) unless specifically noted otherwise.

Figure 23A:
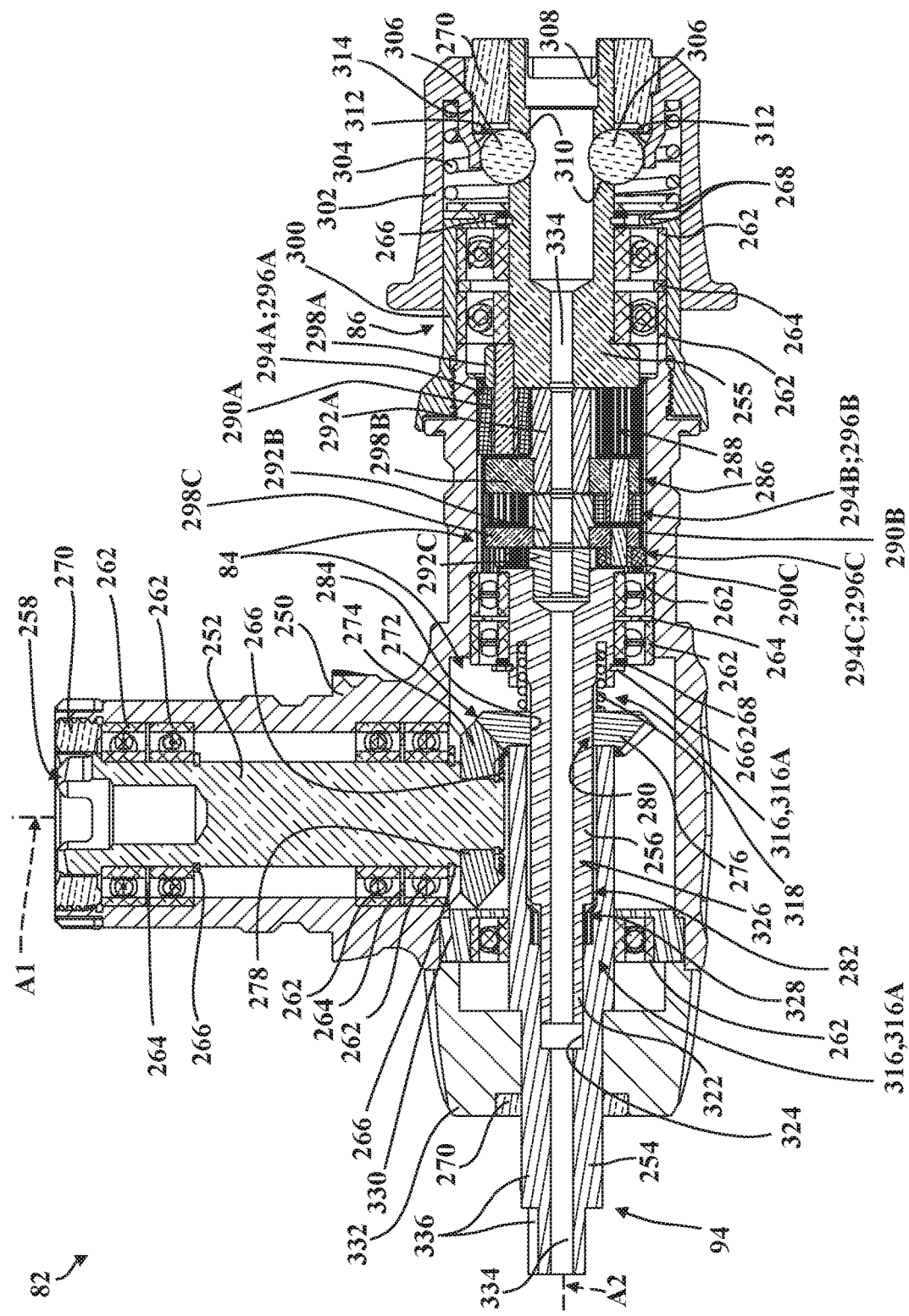
FIG. 23A is a section view taken along line 23-23 of FIG. 22, shown with the drive assembly comprising a geartrain to translate torque from the rotary instrument toward the connector to rotate the tool, and a clutch mechanism interposed between the manual interface and the geartrain, shown with the clutch mechanism operating in a first mode to effect rotation of the connector via torque from the rotary instrument without rotating the manual interface.
Figure 23B:
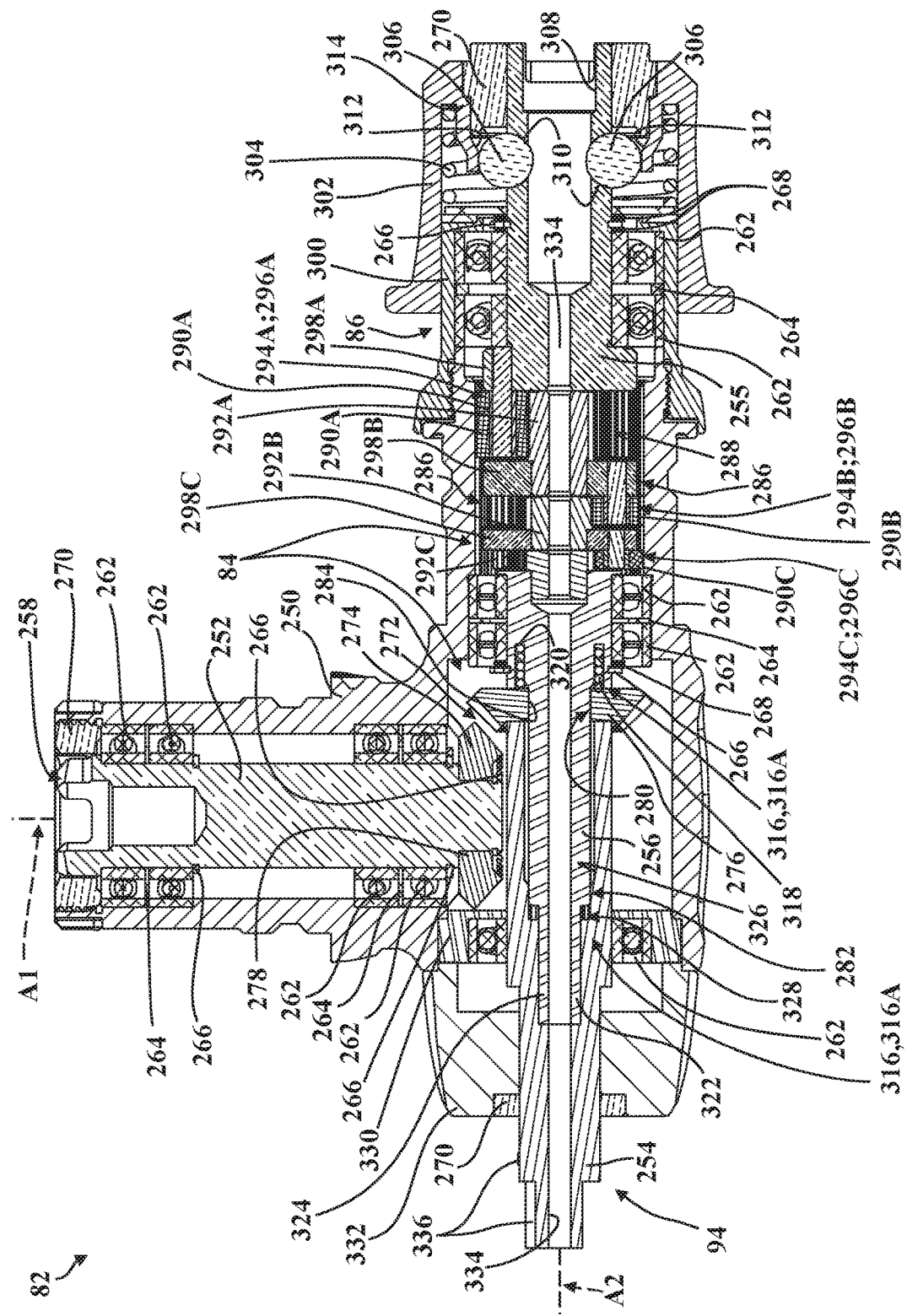
FIG. 23B is another section view depicting the of the geartrain, the clutch mechanism, and the connector of the drive assembly of FIG. 23A, shown with the clutch mechanism operating in a second mode to effect rotation of the connector from force applied to the manual interface.
Figure 24:
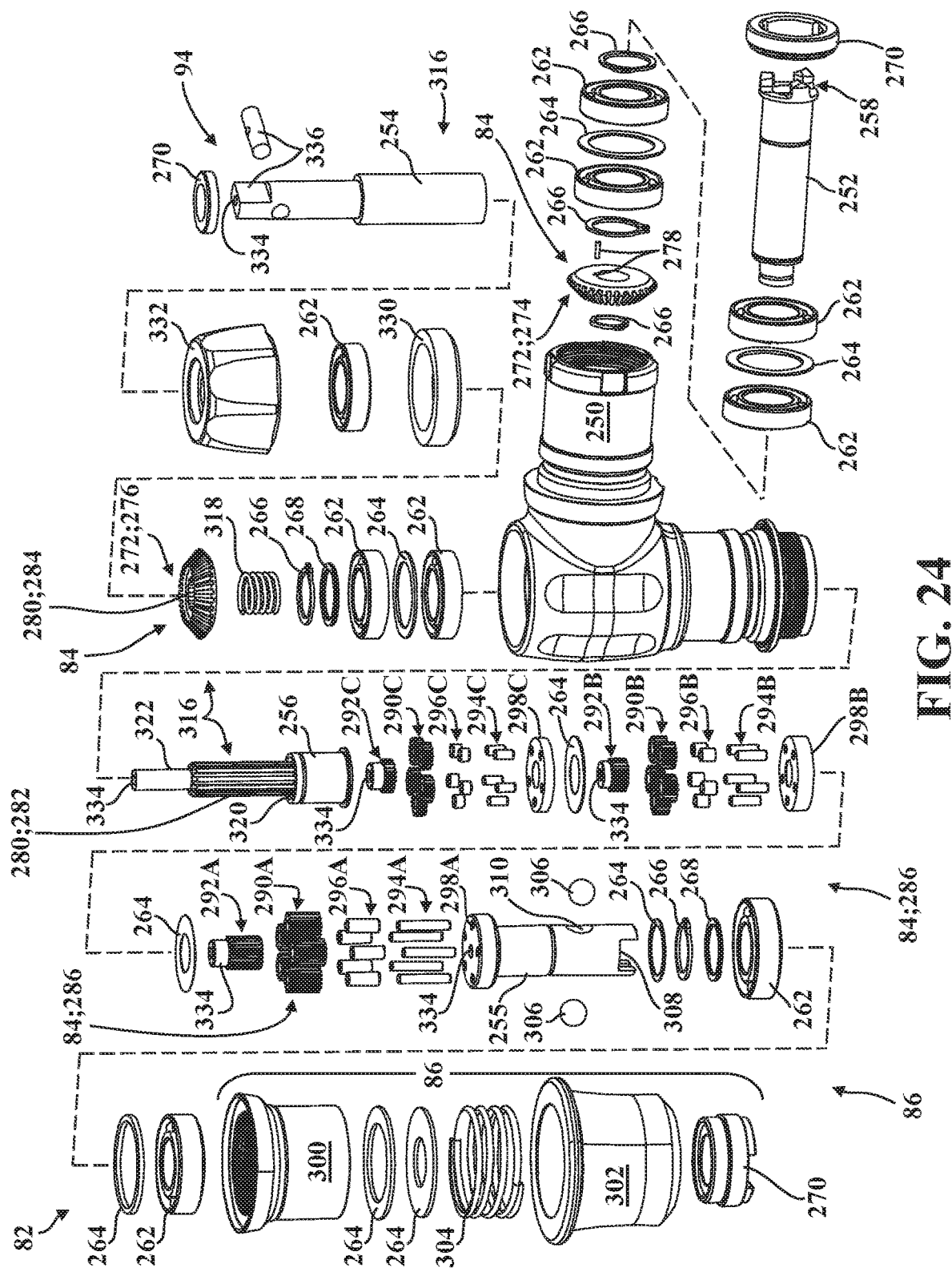
FIG. 24 is an exploded perspective view of the drive assembly of FIGS. 21-23B.

Referring now to FIGS. 23A-24, in the illustrated embodiment, the reduction gearset 286 comprises a compound planetary reduction gearset with a fixed ring gear 288 formed in the drive body 250 (see FIGS. 23A-23B) disposed in meshed engagement with first, second, and third sets of planet gears 290A, 290B, 290C each respectively disposed in meshed engagement with first, second, and third sun gears 292A, 292B, 292C. First, second, and third sets of pins 294A, 294B, 294C cooperate with first, second, and third sets of bushings 296A, 296B, 296C to rotatably support the planet gears of the respective sets of planet gears 290A, 290B, 290C for rotation. The sets of pins 294A, 294B, 294C are each fixed to respective first, second, and third carriers 298A, 298B, 298C. The first carrier 298A is defined by or otherwise operatively attached to the retention shaft 255 and carries the first set of planet gears 290A, which are also disposed in meshed engagement with the first sun gear 292A. The first sun gear 292A is coupled to the second carrier 298B for concurrent rotation, and the second carrier 298B carries the second set of planet gears 290B, which are also disposed in meshed engagement with the second sun gear 292B. The second sun gear 292B is coupled to the third carrier 298C for concurrent rotation, and the third carrier 298C carries the third set of planet gears 290C, which are also disposed in meshed engagement with the third sun gear 292C. The third sun gear 292C is coupled to the intermediate shaft 256 for concurrent rotation. Washers 264 may be provided adjacent to one or more of the carriers 298A, 298B, 298C to help reduce friction with adjacent sets of planet gears 290A, 290B, 290C. Those having ordinary skill in the art will appreciate that the reduction gearset 286 could be arranged or configured in a number of different ways, such as with fewer or more than three planetary reductions, or without any planetary reductions. Other configurations are contemplated.

With continued reference to FIGS. 23A-24, in order to facilitate releasable attachment to the bit interface 128 of the tool 42, the connector 86 of the drive assembly 82 generally comprises a connector body 300, a flange member 302, a connector biasing element 304, a pair of axial connector elements 306, and a rotational connector element 308. The connector body 300 is operatively attached to the drive body 250 (e.g., via threaded engagement) and accommodates bearings 262 which rotatably support the retention shaft 255 about the second axis A2. The retention shaft 255 comprises connector element pockets 310 which each accommodate one of the axial connector elements 306 to engage against the axial retainer 130 of the bit interface 128 of the tool 42 to inhibit relative axial movement between the tool 42 and the retention shaft 255.

In order to release the tool 42, the flange member 302 is arranged for translation along the second axis A2 and can slide along the connector body 300 in response to force applied by the surgeon. The flange member 302 comprises an axial ramp surface 312 which contacts the axial connector elements 306. The connector biasing element 304 is interposed between the connector body 300 and the flange member 302 so as to urge the flange member 302 axially away from the connector body 300. The flange member 302 is prevented from disengaging from the connector body via a stepped surface 314 of the seal 270 coupled to the retention shaft 255. Because of the engagement between the axial connector elements 306 and the axial ramp surface 312 of the flange member 302, the biasing afforded by the connector biasing element 304 urges the axial connector elements 306 radially inwardly toward the second axis A2 and into engagement with the axial retainer 130 of the bit interface 128 of the tool 42, which effects axial retention of the tool 42 relative to the drive assembly 82. In the illustrated embodiment, the rotational connector element 308 of the connector 86 is formed at the distal end of the retention shaft 255 and is shaped to abut the rotational retainer 132 of the bit interface 128 of the tool 42, which effects concurrent rotation of the tool 42 and the retention shaft 255. Other configurations of the connector 86 are contemplated.

With continued reference to FIGS. 23A-24, the drive assembly 82 comprises a clutch mechanism, generally indicated at 316, interposed between the manual interface 94 and the geartrain 84. The clutch mechanism 316 is operable between a first mode 316A (see FIG. 23A) and a second mode 316B (see FIG. 23B). In the first mode 316A, rotational torque generated by the actuator 166 of the rotary instrument 80 translates through the geartrain 84 to rotate the tool 42 about the second axis A2 without rotating the manual interface 94. In the second mode 316B, force applied to the manual interface 94 is translated as torque through the geartrain 84 to rotate the tool 42 about the second axis S2. As is described in greater detail below, the clutch mechanism 316 moves from the first mode 316A to the second mode 316B in response to force applied to the manual interface 94, and comprises a clutch biasing element 318 arranged to urge the clutch mechanism from the second mode 316B toward the first mode 316A.

As is best depicted in FIGS. 23A-23B, the clutch biasing element 318 is supported in a clutch pocket 320 formed in the intermediate shaft 256 adjacent to the outer splines 282. The clutch biasing element 318 is also disposed in engagement with the output gear 276 of the bevel gearset 272 of the geartrain 84. Because the output gear 276 employs the inner splines 284 to engage the outer splines 282 of the intermediate shaft 256 and is not axially fixed to the intermediate shaft 256, the clutch biasing element 318 urges the output gear 276 along the second axis A2 into meshed engagement with the input gear 274 to facilitate operating the clutch mechanism 316 in the first mode 316A (see FIG. 23A).

In order to facilitate alignment with the second axis A2, the proximal end of the intermediate shaft 256 comprises a pilot shaft region 322 adjacent to the outer splines 282 which is slidably received within a correspondingly-shaped pilot bore 324 formed in the manual input shaft 254 of the manual interface 94 (see FIGS. 23A-23B). The manual input shaft 254 also comprises an idle bore 326 at its distal end, and a linking spline arrangement 328 is arranged axially between the idle bore 326 and the pilot bore 324. The outer surface of the manual input shaft 254 is rotatably supported by a bearing 262 which, in turn, is accommodated in a seat 330 attached to the drive body 250. The manual input shaft 254 extends through an upper cover 332 also attached to the drive body 250 such that the proximal end of the manual input shaft 254 can be engaged by the handle assembly 96, as described in greater detail below.

When the clutch mechanism 316 is in the first mode 316A (see FIG. 23A), the idle bore 326 of the manual input shaft 254 contacts but does not rotate with the outer splines 282 of the intermediate shaft 256. Moreover, because of how the idle bore 326 and the linking spline arrangement 328 are positioned, rotation of the intermediate shaft 256 is not translated to the manual input shaft 254 when the clutch mechanism 316 is in the first mode 316A, and the gears 274, 276 of the bevel gearset 272 remain meshed so that rotation of the driver input shaft 252 translates to the intermediate shaft 256. However, when force is applied axially to the manual interface 94, the manual input shaft 254 translates concurrently with the output gear 276 along the second axis A2 toward the connector 86. As shown in FIG. 23B, this causes the output gear 276 to come out of meshed engagement with the input gear 274, thereby interrupting rotation between the axes A1, A2, and also brings the linking spline arrangement 328 of the manual input shaft 254 into engagement with the outer splines 282 of the intermediate shaft 256, thereby facilitating concurrent rotation of the manual input shaft 254 and the intermediate shaft 256.

Thus, axial force applied to the manual interface 94 moves the clutch mechanism 316 from the first mode 316A (see FIG. 23A) to the second mode 316B (see FIG. 23B). This configuration effectively prevents the translation of rotational torque between the rotary instrument 80 and the manual interface 94. Put differently, driving the rotary instrument 80 will not rotate the manual interface 94 when the clutch mechanism 316 is in the first mode 316A, and applying force to rotate the manual interface 94 will not back-drive the rotary instrument 80. Other configurations of the clutch mechanism 316 are contemplated beyond those illustrated in connection with the first embodiment of the end effector 40 and described herein.

As is depicted in FIGS. 23A-23B, the illustrated embodiment of the drive assembly 82 and manual interface 94 cooperate to define a guide bore, generally indicated at 334, extending along the second axis A2 from the manual interface 94 and through the various components of the drive assembly 82 to the connector 86. Here, like the cannulated anchor 50 and rotary driving tool 48, the guide wire GW (e.g., a "K-Wire") can extend through the guide bore 334 (not shown in detail, but generally known in the related art).

Referring now to FIGS. 11B-11C, as noted above, the handle assembly 96 is employed to attach to the manual interface 94 to, among other things, manually rotate the tool 42 about the second axis A2 and translate the manual input shaft 254 along the second axis A2 in response to force applied by the surgeon to the handle assembly 96. To this end, the manual interface 94 comprises a head 336 arranged for rotation about the second axis A2, and the handle assembly 96 generally comprises a driver 338 and a handle body 340. The head 336 is arranged at the proximal end of the manual input shaft 254, and the driver 338 is shaped to receive the head 336 for concurrent rotation about the second axis A2 in response to force applied to the handle body 340 by the surgeon. As is depicted schematically in FIGS. 11B-11C, the handle assembly 96 may comprise a ratcheting mechanism 342 interposed between the handle body 340 and the driver 338 to permit concurrent rotation of the handle body 340 and the driver 338 about the second axis A2 in a third rotational direction R3, and to interrupt rotation of the driver 338 relative to the handle body 340 about the second axis A2 in a fourth rotational direction R4 opposite to the third rotational direction R3. It will be appreciated that the ratcheting mechanism 342 may be of a number of different types and configurations (e.g., with a ratchet and pawl arrangement, with one or more resiliently flexible members, and the like). Furthermore, while the handle assembly 96 is releasably attachable to the manual interface 94 in the illustrated embodiments, it is conceivable that the handle assembly 96 could be permanently affixed to the manual interface 94 (e.g., with a foldable or otherwise articulable handle body 340).

The present disclosure is also directed toward a method of forming the pilot hole 46 at the surgical site ST along the trajectory T maintained by the surgical robot 32. The method comprises different steps, including attaching the end effector 40 to the surgical robot 32, with the end effector 40 supporting the rotary instrument 80, the drive assembly 82, the manual interface 94, and the trigger assembly 88. The method also comprises attaching the rotary cutting tool 44 to the drive assembly 82 along the second axis A2, aligning the second axis A2 with the trajectory T to position the rotary cutting tool 44 at the surgical site, and engaging the trigger assembly 88 to generate rotational torque with the rotary instrument 80 about the first axis A1 and to translate torque from the rotary instrument 80 about the first axis A1 through the drive assembly 82 to rotate the rotary cutting tool 44 about the second axis A2. The method further comprises advancing the rotary cutting tool 44 along the trajectory T at the surgical site ST to the first depth D1, and interrupting rotation about the first axis A1. The method also comprises positioning the trigger assembly 88 to present or otherwise promote access to the manual interface 94, applying force to the manual interface 94 to rotate the rotary cutting tool 44 about the second axis A2, and advancing the rotary cutting tool 44 along the trajectory T at the surgical site ST to a second depth D2 greater than the first depth D1.

The present disclosure is also directed toward a method of installing the anchor 50 at the surgical site ST along the trajectory T maintained by the surgical robot 32. The method comprises different steps, including attaching the end effector 40 to the surgical robot 32, with the end effector 40 supporting the rotary instrument 80, the drive assembly 82, the manual interface 94, and the trigger assembly 88. The method also comprises attaching the tool 42 to the drive assembly 82 along the second axis A2, attaching the anchor 50 to the tool 42, and aligning the second axis A2 with the trajectory to position the anchor 50 adjacent to the surgical site ST. The method further includes engaging the trigger assembly 88 to generate rotational torque with the rotary instrument 80 about the first axis A1 and to translate torque from the rotary instrument 80 about the first axis A1 through the drive assembly 82 to rotate the tool 42 and the anchor 50 about the second axis A2. The method also includes advancing the tool 42 and the anchor 50 along the trajectory at the surgical site ST to the first depth D1, interrupting rotation about the first axis A1, and positioning the trigger assembly 88 to present or otherwise promote access to the manual interface 94. The method further comprises applying force to the manual interface 94 to rotate the tool 42 and the anchor 50 about the second axis A2, and advancing the anchor 50 along the trajectory at the surgical site ST to the second depth D2 greater than the first depth D1.

The present disclosure is also directed toward a method of installing first and second anchors 50 at the surgical site ST along respective first and second trajectories T1, T2 maintained by the surgical robot 32. The method comprises different steps, including attaching the end effector 40 to the surgical robot 32, with the end effector 40 supporting the rotary instrument 80, the drive assembly 82, the manual interface 94, and the trigger assembly 88. The method also comprises attaching the tool 42 to the drive assembly 82 along the second axis A2, attaching the first anchor 50 to the tool 42, aligning the second axis A2 with the first trajectory to position the first anchor 50 adjacent to the surgical site ST, and engaging the trigger assembly 88 to generate rotational torque with the rotary instrument 80 about the first axis A1 and to translate torque from the rotary instrument 80 about the first axis A1 through the drive assembly 82 to rotate the tool 42 and the first anchor 50 about the second axis A2. The method further comprises advancing the tool 42 and the first anchor 50 along the first trajectory at the surgical site ST to the first depth D1, interrupting rotation about the first axis A1, and positioning the trigger assembly 88 to present or otherwise promote access to the manual interface 94. The method also comprises applying force to the manual interface 94 to rotate the tool 42 and the first anchor 50 about the second axis A2, advancing the tool 42 and the first anchor 50 along the first trajectory at the surgical site ST to the second depth D2 greater than the first depth D1, and releasing the first anchor 50 from the tool 42. The method further comprises attaching the second anchor 50 to the tool 42, aligning the second axis A2 with the second trajectory to position the second anchor 50 adjacent to the surgical site ST, and engaging the trigger assembly 88 to generate rotational torque with the rotary instrument 80 about the first axis A1. The method also comprises translating torque from the rotary instrument 80 about the first axis A1 through the drive assembly 82 to rotate the tool 42 and the second anchor 50 about the second axis A2, advancing the tool 42 and the second anchor 50 along the second trajectory at the surgical site ST to the third depth D3, interrupting rotation about the first axis A1, and positioning the trigger assembly 88 to present or otherwise promote access to the manual interface 94. The method further comprises applying force to the manual interface 94 to rotate the tool 42 and the second anchor 50 about the second axis A2, and advancing the tool 42 and the second anchor 50 along the second trajectory at the surgical site ST to the fourth depth D4 greater than the third depth D3.

As noted above, a second embodiment of the end effector of the surgical system 30 is shown in FIGS. 25A-28. In the description that follows, the structure and components of the second embodiment that are the same as or that otherwise correspond to the structure and components of the first embodiment of the end effector 40 are provided with the same reference numerals increased by 2000. Because many of the components and features of the second embodiment of the end effector 2040 are substantially similar to those of the first embodiment of the end effector 40 described above, for the purposes of clarity, consistency, and brevity, only certain specific differences between the second embodiment of the end effector 2040 and the first embodiment of the end effector 40 will be described below, and only some of the components and features common between the embodiments will be discussed herein and depicted in the drawings. Thus, unless otherwise indicated below, the description of the first embodiment of the end effector 40 may be incorporated by reference with respect to the second embodiment of the end effector 2040 without limitation.

Referring now to FIGS. 25A-28, the second embodiment of the end effector 2040 is generally shown comprising the mount 2078, the rotary instrument 2080 and its actuator 2166 (depicted schematically), and the drive assembly 2082. When compared with the first embodiment described above, the second embodiment of the end effector 2040 generally employs a differently-configured rotary instrument 2080, drive assembly 2082, and trigger assembly 2088, each of which will be described in greater detail below.

Figure 25A:
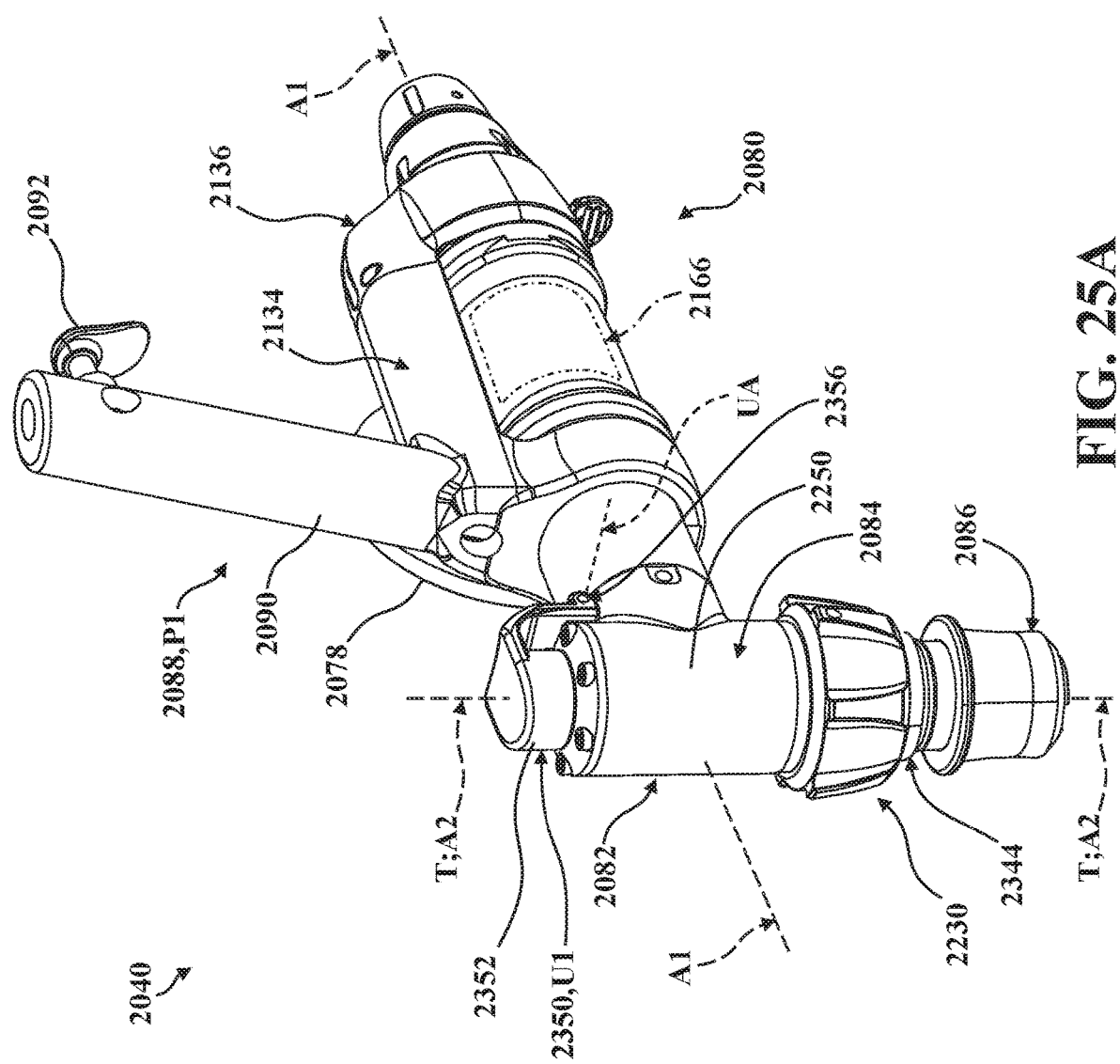
FIG. 25A is a perspective view of an end effector, according to a second embodiment of the present disclosure, which is likewise configured for use with the surgical system of FIG. 1, the end effector shown comprising a mount supporting a rotary instrument to generate torque about a first axis, a trigger assembly arranged in a first trigger assembly position, a drive assembly with a connector to support a tool for rotation about a second axis, and a guard cover arranged in a first guard position.
Figure 25B:
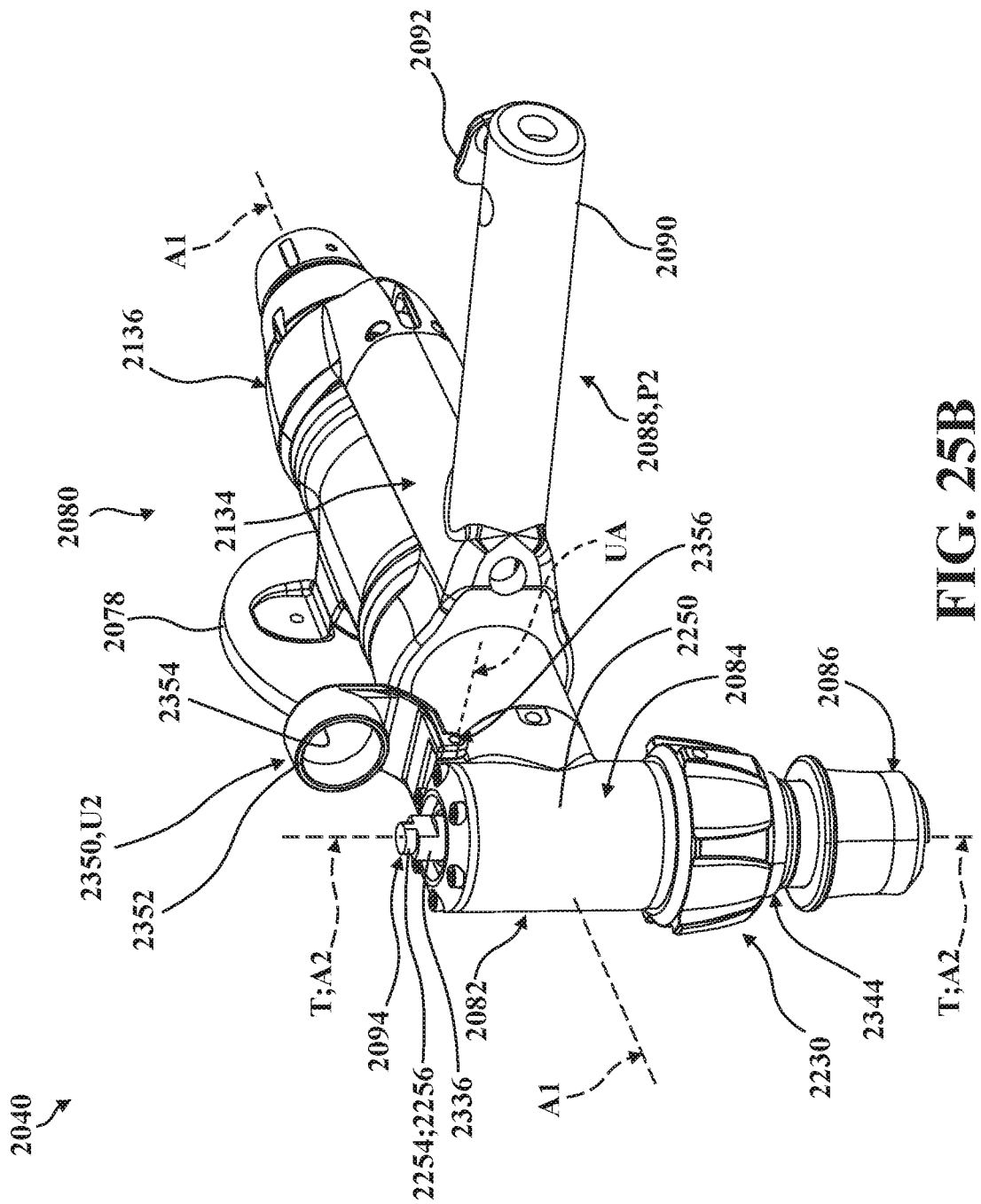
FIG. 25B is another perspective view of the end effector of FIG. 25A, shown with the trigger assembly arranged in a second trigger assembly position, and with the guard cover arranged in a second guard position to promote access to a manual interface.
Figure 26:
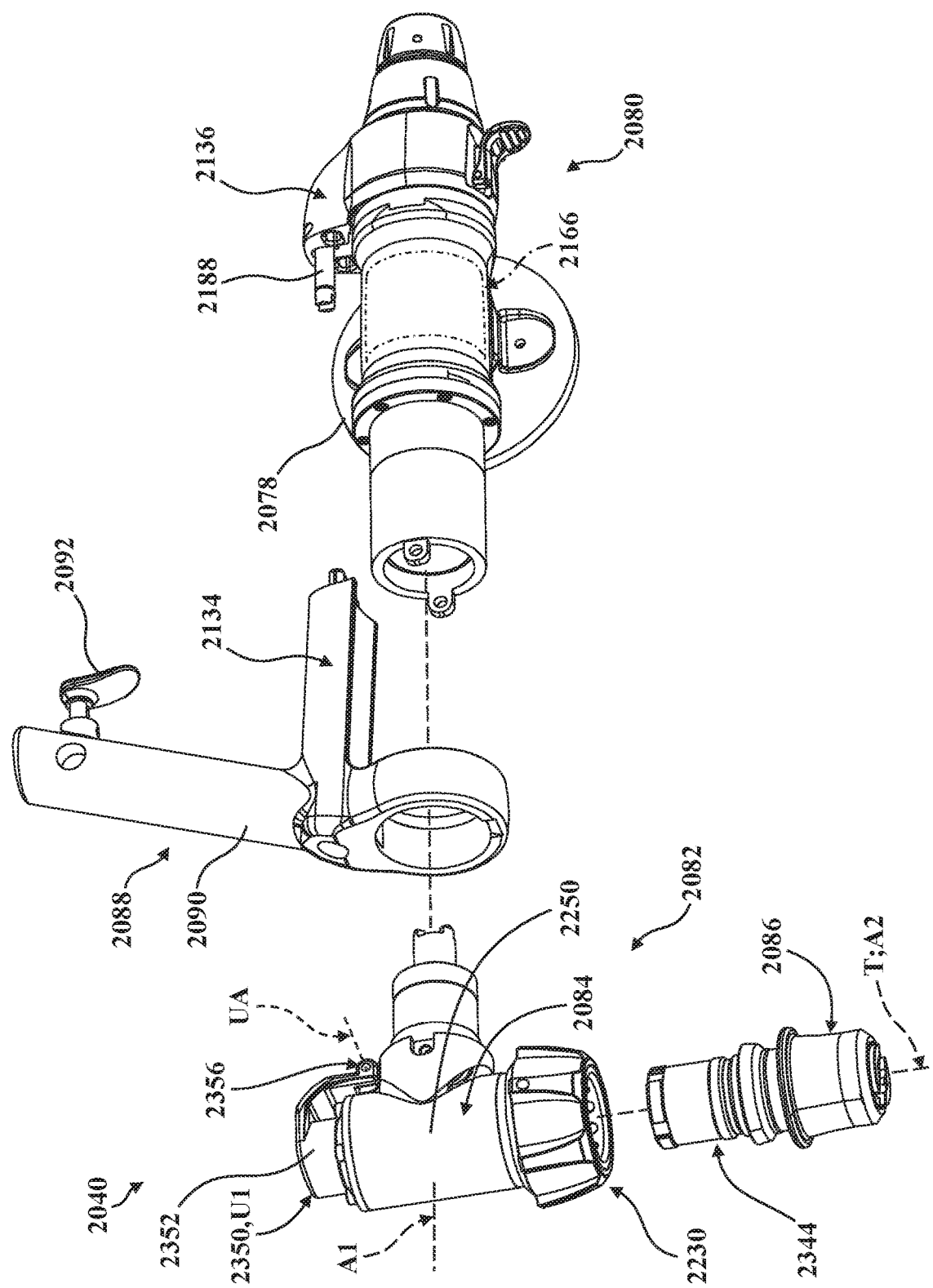
FIG. 26 is an exploded perspective view of the end effector of FIGS. 25A-25B, shown with trigger assembly spaced between the drive assembly and the rotary instrument.
Figure 28:
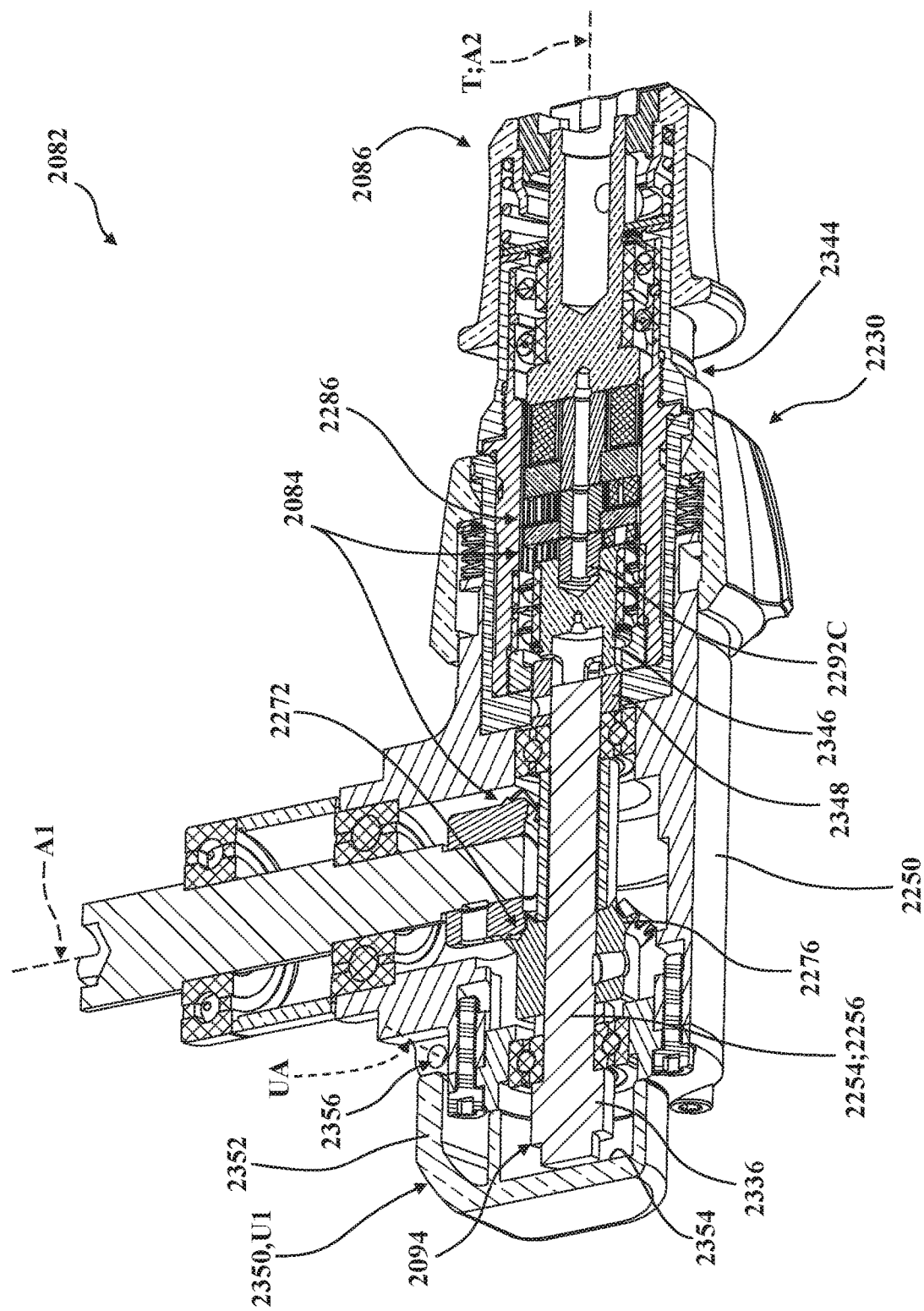
FIG. 28 is a sectional perspective view of the drive assembly of FIGS. 25A-26, depicted as sectioned generally longitudinally.

As is best shown in FIGS. 25A-26, in the second embodiment, the rotary instrument 2080 and the drive assembly 2082 are configured such that the second axis A2 is fixed relative to the first axis A1. Put differently, in this embodiment, the drive body 2250 of the drive assembly 2082 is not arranged for movement relative to the rotary instrument 2080. Here, the coupling 2230 is operatively attached to the drive assembly 2082 to releasably secure a drive subassembly, generally indicated at 2344, along the second axis A2. As is best shown in FIG. 28, the drive subassembly 2344 comprises the reduction gearset 2286, which similarly has a planetary configuration and is interposed between the connector 2086 and a drive subassembly coupler 2346 that is coupled to the third sun gear 2292C. When the drive subassembly 2344 is operatively attached to the coupling 2230, the drive subassembly coupler 2346 engages an intermediate output coupler 2348 coupled to the intermediate shaft 2256 of the drive assembly 2082 which, in this embodiment, also serves as the manual input shaft 2254. While not shown in the drawings of the second embodiment of the end effector 2040, it will be appreciated that the connector 2086 of the drive subassembly 2344 can releasably secure different types of tools in the same way as the connector 86 described above in connection with the first embodiment of the end effector 40.

Here in the second embodiment, the intermediate shaft 2256 of the drive assembly 2082 defines the head 2336 of the manual interface 2094 and is coupled to the output gear 2276 of the bevel gearset 2272 of the geartrain 2084. The head 2336 of the manual interface 2094 is likewise arranged to receive and translate applied force from the user into rotational torque used to rotate tools (not shown in FIGS. 25A-28) about the second axis A2. As is described in greater detail below, the trigger assembly 2088 of the second embodiment of the end effector 2040 is not configured so as to limit access to the manual interface 2094 in any of the trigger assembly positions P1, P2. Rather, in this embodiment, the end effector 2040 further comprises a guard cover, generally indicated at 2350, which is operatively attached to the drive assembly 2082 and is arranged for movement relative to the second axis A2 between a first guard position U1 (see FIG. 25A) and a second guard position U2 (see FIG. 25B).

In the first guard position U1, the second axis A2 intersects at least a portion of the guard cover 2350 to limit access to the manual interface 2094 (see FIG. 25A). In the second guard position U2, the guard cover 2350 is spaced from the second axis A2 to promote access to the manual interface 2094 (see FIG. 25B). To this end, and as is best shown in FIGS. 25A-25B and 28, the guard cover 2350 comprises a guard body 2352 that defines a guard pocket 2354 shaped to accommodate or otherwise inhibit access to at least a portion of the manual interface 2094 in the first guard position U1. The guard body 2352 is provided with a guard hinge 2356 that is operatively attached to the drive assembly 2082 for pivoting movement about a guard axis UA between the first guard position U1 (see FIG. 25A) and the second guard position U2 (see FIG. 25B). In the illustrated embodiment, the guard axis UA is arranged substantially perpendicular to both the first axis A1 and the second axis A2.

It will be appreciated that utilization of the guard cover 2350 allows the end effector 2040 to limit or otherwise inhibit access to the manual interface 2094 without necessarily relying on movement of the trigger assembly 2088. Thus, in the second embodiment, while the trigger assembly 2088 is nevertheless arranged for movement with the retainer 2136 between the first trigger assembly position P1 (see FIG. 25A) and the second trigger assembly position P2 (see FIG. 25B), no portion of the trigger assembly 2088 limits or otherwise inhibits access to the manual interface 2094 in either of the trigger assembly positions P1, P2.

The grip 2090 of the trigger assembly 2088 has a generally cylindrical profile and is configured for generally neutral hand engagement when in the first trigger assembly position P1 (see FIG. 25A), and for generally pronate or supernate hand engagement when in the second trigger assembly position P2 (see FIG. 25B). Here too in this embodiment, the trigger assembly 2088 is arranged for concurrent movement with the retainer 2136 such that the input trigger 2092 can be moved between the first input position I1 (see FIG. 27A) and the second input position I2 (see FIG. 27B) irrespective of whether the trigger assembly 2088 is arranged in the first trigger assembly position P1 (see FIG. 25A) or the second trigger assembly position P2 (see FIG. 25B).

Figure 27A:
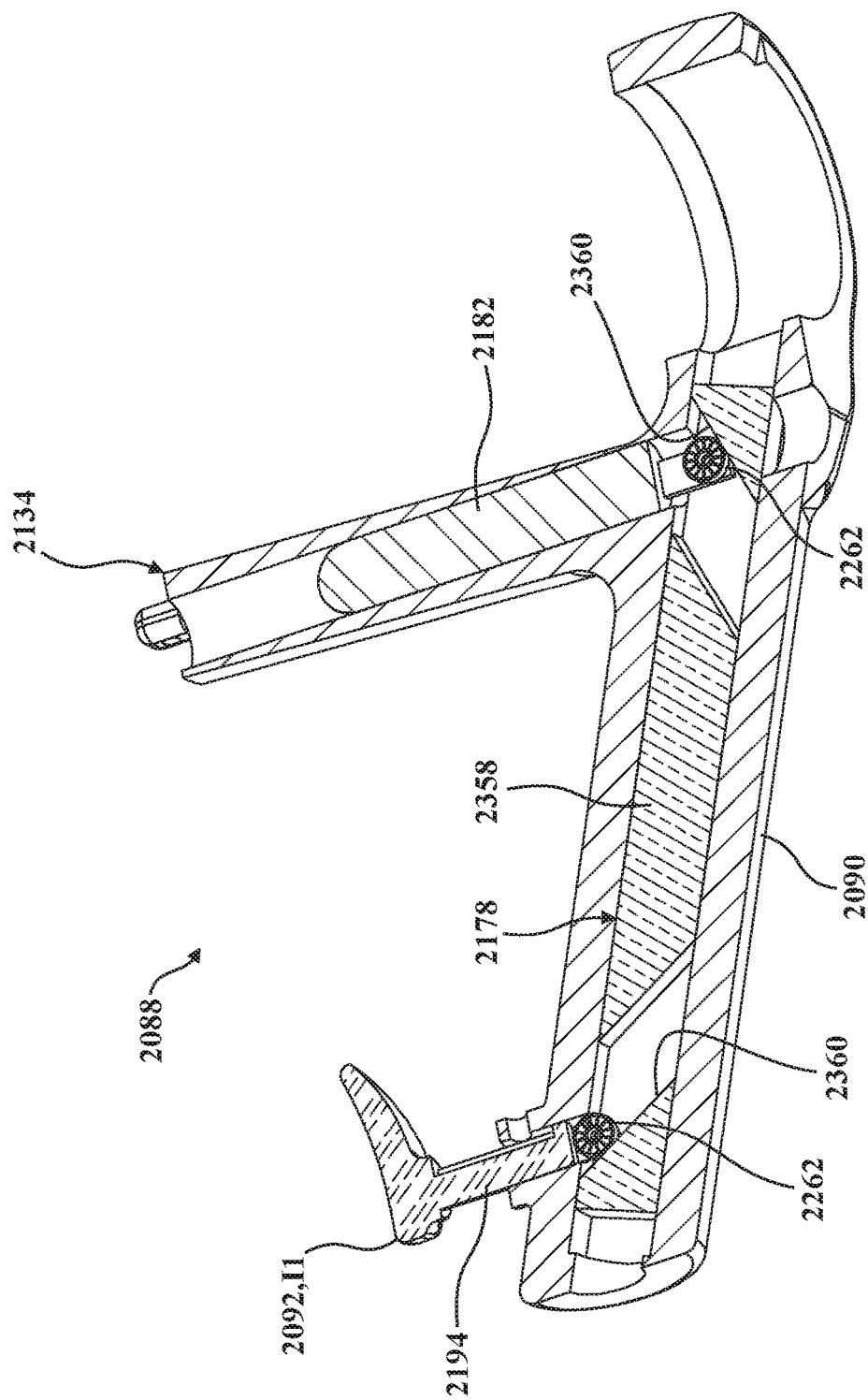
FIG. 27A is a sectional perspective view of the trigger assembly of FIGS. 25A-26, depicted as sectioned generally longitudinally, and shown having an input trigger arranged in a first input position.
Figure 27B:
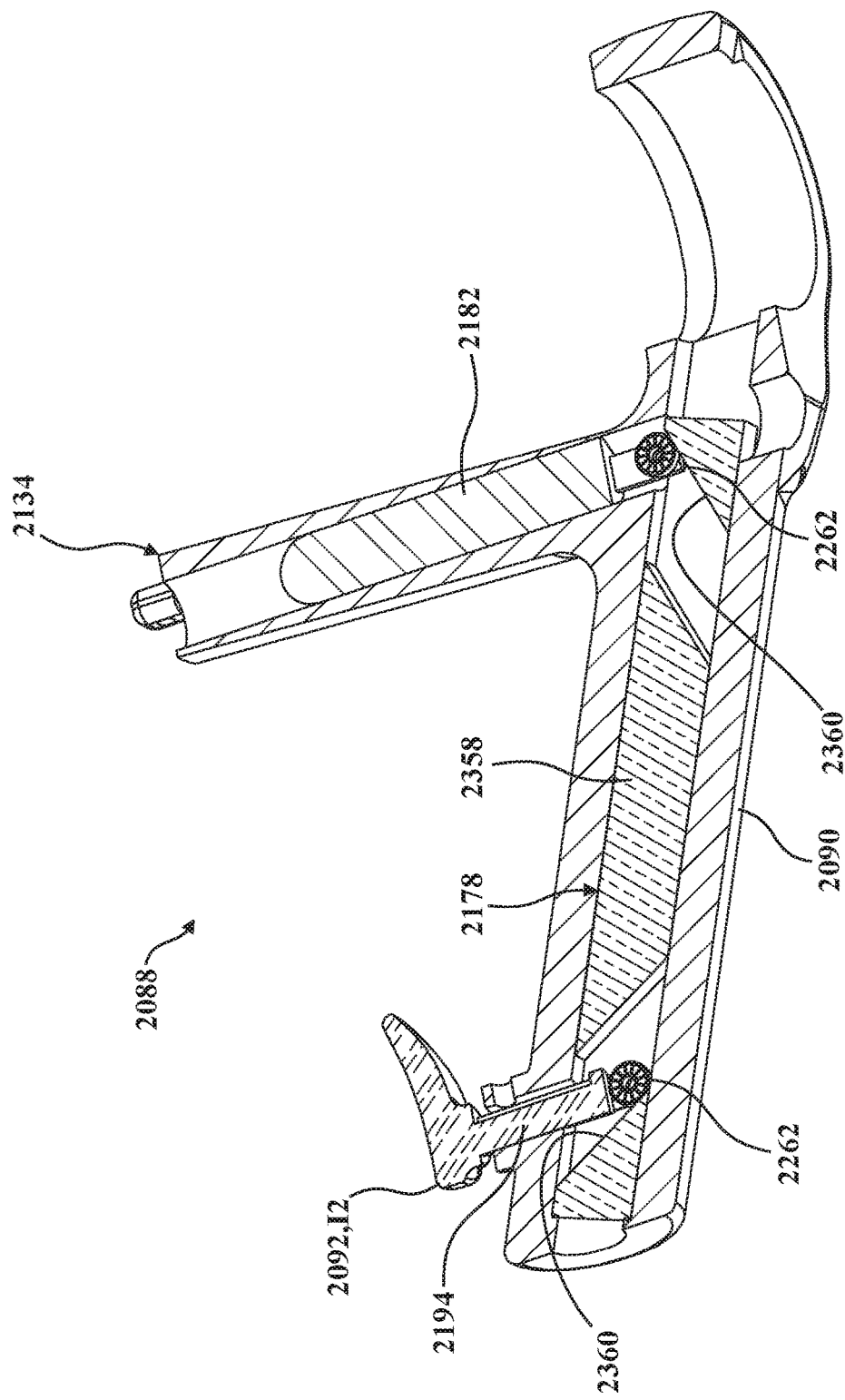
FIG. 27B is another sectional perspective view of the trigger assembly of FIG. 27A, shown with the input trigger arranged in a second input position.

Referring now to FIGS. 26-27B, the trigger assembly 2088 in this embodiment is similarly configured such that movement of the input trigger 2092 effects corresponding movement of the piston 2182 (see FIGS. 27A-28B) which, in turn, engages and moves the fork guide 2188 of the retainer 2136 (see FIG. 26). As shown in FIGS. 27A-27B, the linkage 2178 in this embodiment comprises a slide member 2358 supported within the grip 2090 for concurrent movement with the input trigger 2092 between the first and second input positions I1, I2. Here, the slide member 2358 defines two slide ramps 2360 which engage against respective bearings 2262 supported on the piston 2182 and on the extension member 2194 of the input trigger 2092 to effect translation of motion from the input trigger 2092 to the piston 2182 (compare FIGS. 27A-27B). While not shown, it will be appreciated that the linkage 2178 may comprise additional components (e.g., biasing elements, bushings, fasteners, seals, and the like). Other configurations are contemplated.

As noted above, a third embodiment of the end effector of the surgical system 30 is shown in FIGS. 29A-31B. In the description that follows, the structure and components of the third embodiment that are the same as or that otherwise correspond to the structure and components of the first embodiment of the end effector 40 are provided with the same reference numerals increased by 3000. Because many of the components and features of the third embodiment of the end effector 3040 are substantially similar to those of the first embodiment of the end effector 40 described above, for the purposes of clarity, consistency, and brevity, only certain specific differences between the third embodiment of the end effector 3040 and the first embodiment of the end effector 40 will be described below, and only some of the components and features common between the embodiments will be discussed herein and depicted in the drawings. Thus, unless otherwise indicated below, the description of the first embodiment of the end effector 40 may be incorporated by reference with respect to the third embodiment of the end effector 3040 without limitation.

Referring now to FIGS. 29A-31B, the third embodiment of the end effector 3040 is generally shown comprising the mount 3078, the rotary instrument 3080 and its actuator 3166 (depicted schematically), and the drive assembly 3082. When compared with the first embodiment described above, the third embodiment of the end effector 3040 generally employs a differently-configured trigger assembly 3088 and drive assembly 3082, and is configured to secure tools 3042 with different types of bit interfaces 3128, each of which will be described in greater detail below.

Figure 29A:
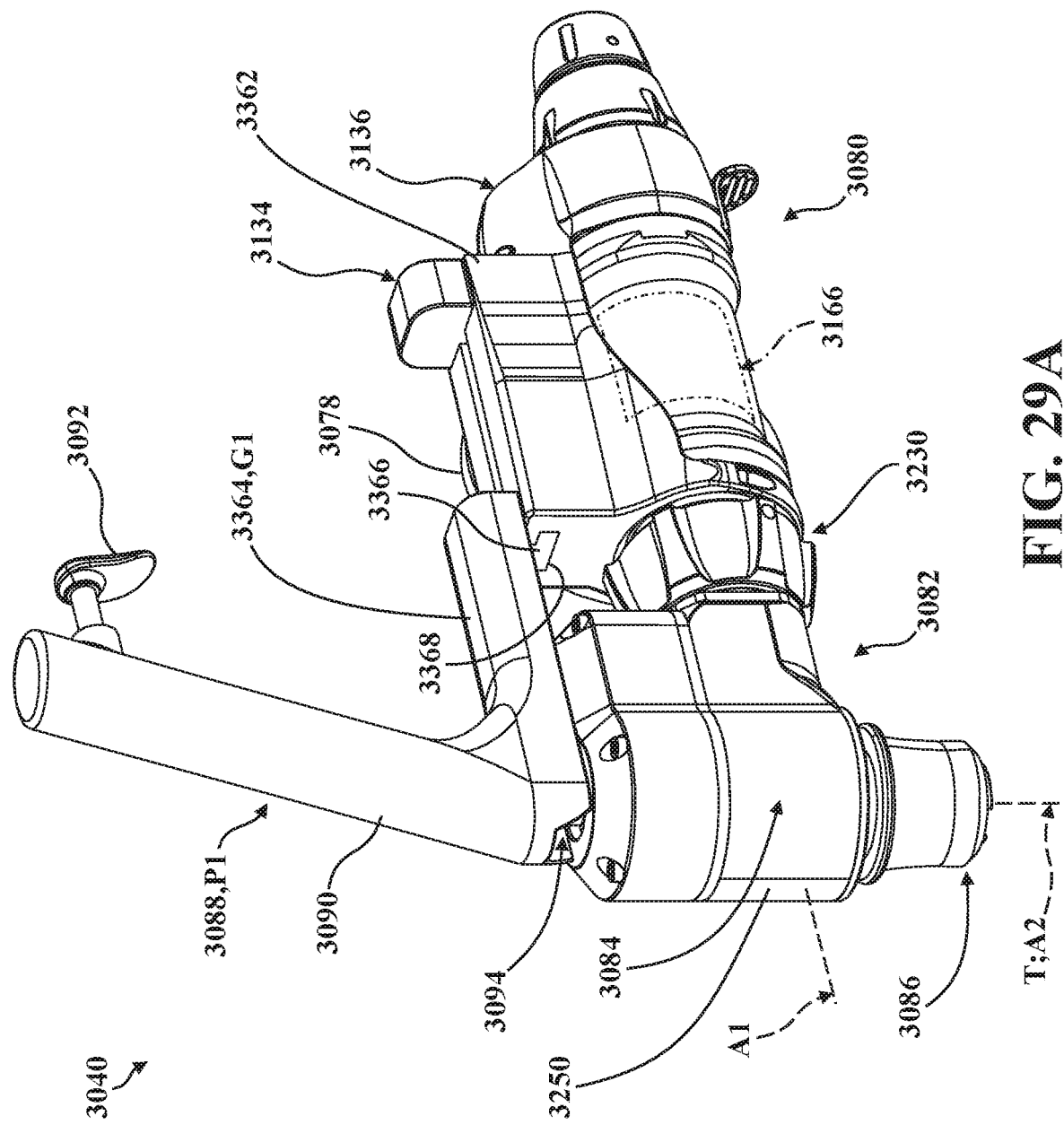
FIG. 29A is a perspective view of an end effector, according to a third embodiment of the present disclosure, which is likewise configured for use with the surgical system of FIG. 1, the end effector shown comprising a mount supporting a rotary instrument to generate torque about a first axis, a drive assembly with a connector to support a tool for rotation about a second axis, and a trigger assembly arranged in a first trigger assembly position and shown having a first and second frame bodies, with the second frame body disposed in a first grip position to limit access to a manual interface.
Figure 29B:
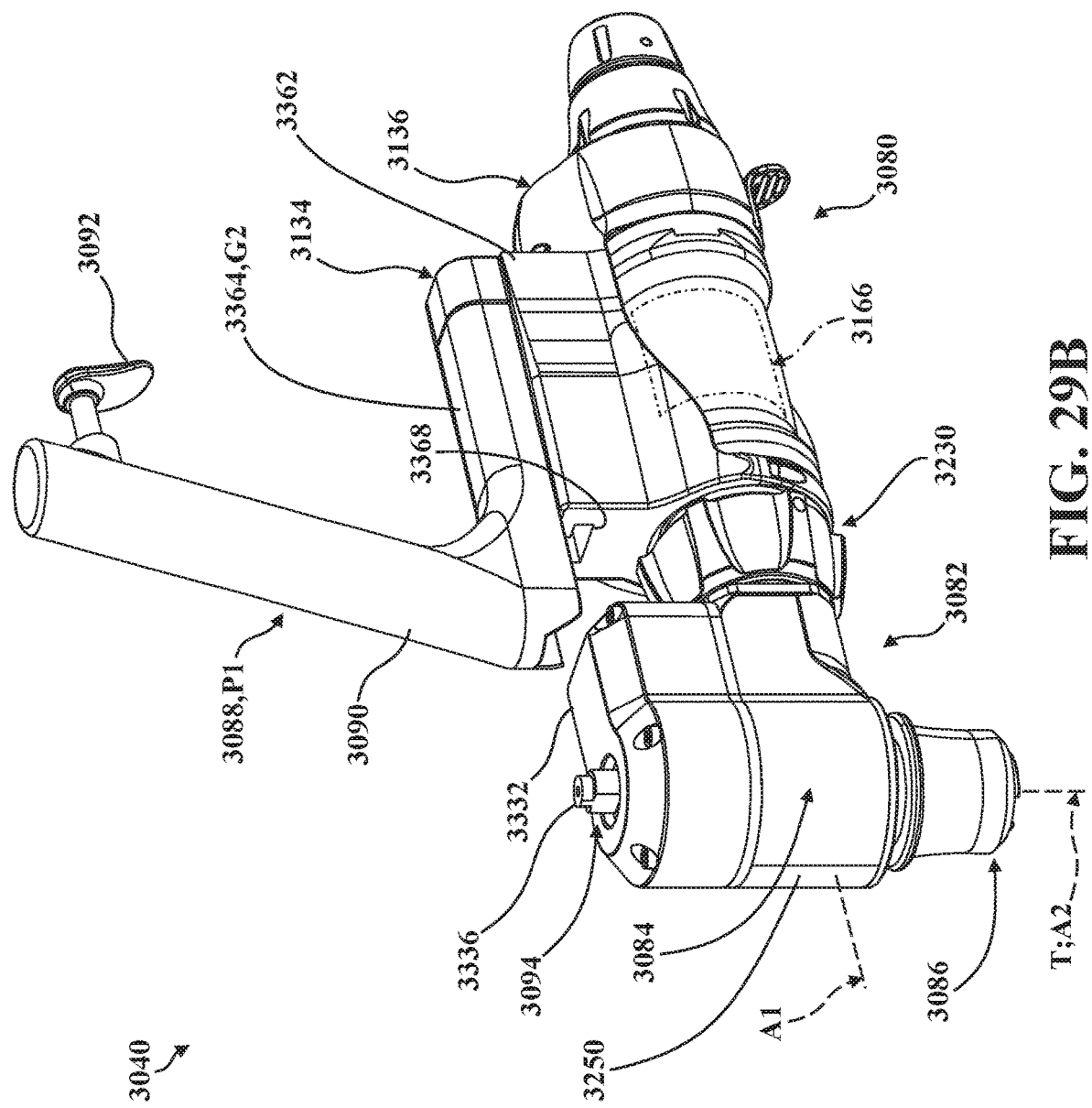
FIG. 29B is another perspective view of the end effector of FIG. 29A, shown with the second frame body disposed in a second grip position to promote access to the manual interface.
Figure 30:
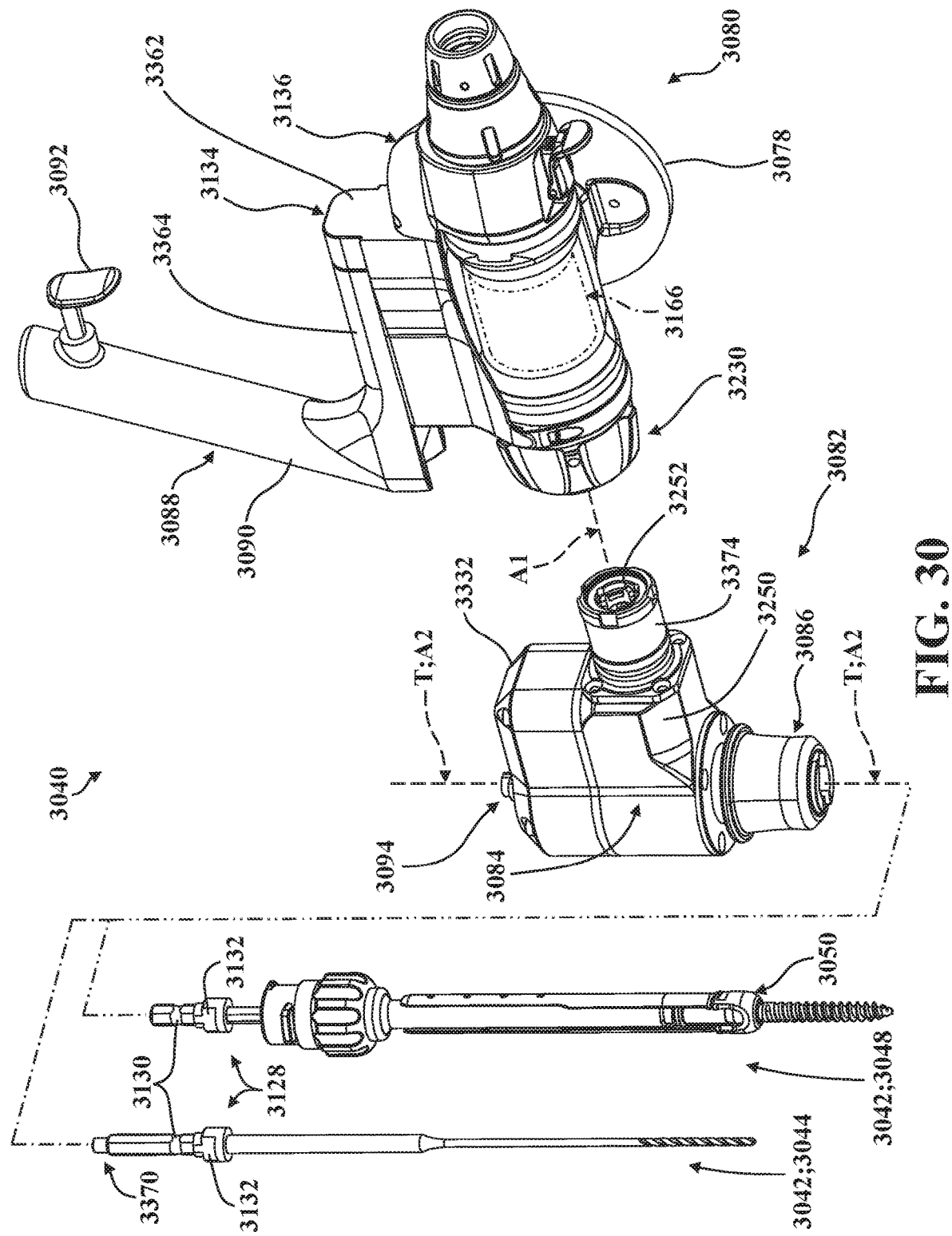
FIG. 30 is an exploded perspective view of the end effector of FIGS. 29A-29B, shown with the drive assembly spaced from the rotary instrument and the trigger assembly, and shown with two tools configured for releasable attachment to the drive assembly, with one of the tools shown as a rotary cutting tool with a drill bit, and with the other of the tools shown as an rotary driving tool supporting an anchor.

As is best shown in FIGS. 29A-30, in the third embodiment, the drive assembly 3082 is similarly configured for releasable attachment to the rotary instrument 3080 via the coupling 3230 such that the second axis A2 can be moved relative to the first axis A1 by positioning the drive assembly 3082 in different ways about the first axis A1. The trigger assembly 3088 in the third embodiment employs a grip 3090 and an input trigger 3092 which are similar in construction to the second embodiment of the trigger assembly 2088 described above. However, in the third embodiment, the frame 3134 of the trigger assembly 3088 generally comprises a first frame body 3362 coupled to the retainer 3136 for concurrent movement between the plurality of trigger assembly positions (first trigger assembly position P1 shown in FIGS. 29A-29B), and a second frame body 3364 supporting the grip 3090 and the input trigger 3092 for movement relative to the first frame body 3362 between a plurality of grip positions, including a first grip position G1 (see FIG. 29A) and a second grip position G2 (see FIG. 29B).

When in the first grip position G1 as shown in FIG. 29A, at least a portion of the second frame body 3364 limits access to the manual interface 3094, and the input trigger 3092 is arranged for engagement by the user to drive the rotary instrument 3080 to rotate whichever tool 3042 is secured to the connector 3086 about the second axis A2, as described in greater detail below. However, when in the second grip position G2 as shown in FIG. 29B, the second frame body 3364 is disposed in spaced relation to the manual interface 3094 to facilitate receiving applied force from the user to rotate the tool 3042 about the second axis A2. While not illustrated in connection with the third embodiment, the second frame body 3364 is also arranged for concurrent movement with the first frame body 3362 between the plurality of trigger assembly positions (first trigger assembly position P1 shown in FIGS. 29A-29B) independent of movement between the plurality of grip positions (e.g., the first and second grip positions G1, G2).

In the third embodiment of the end effector 3040, the second frame body 3364 is arranged for translational movement between the first and second grip positions G1, G2, the movement being substantially parallel to the first axis A1. To this end, the second frame body 3364 comprises a rider 3366 which is supported for sliding movement along a track 3368 defined in the first frame body 3362. It will be appreciated that this configuration is exemplary, and that the first and second frame bodies 3362, 3364 could be configured in a number of different ways sufficient to permit the second frame body 3364 to move relative to the first frame body 3362 to selectively inhibit access to and/or promote access to the manual interface 3094. By way of illustrative example, movement between the first and second grip positions G1, G2 could be defined by other types of translational movement (e.g., sliding along a curved path or in a direction that is non-parallel to the first axis A1), rotational movement, or other types of movement. Other configurations are contemplated.

Figure 31A:
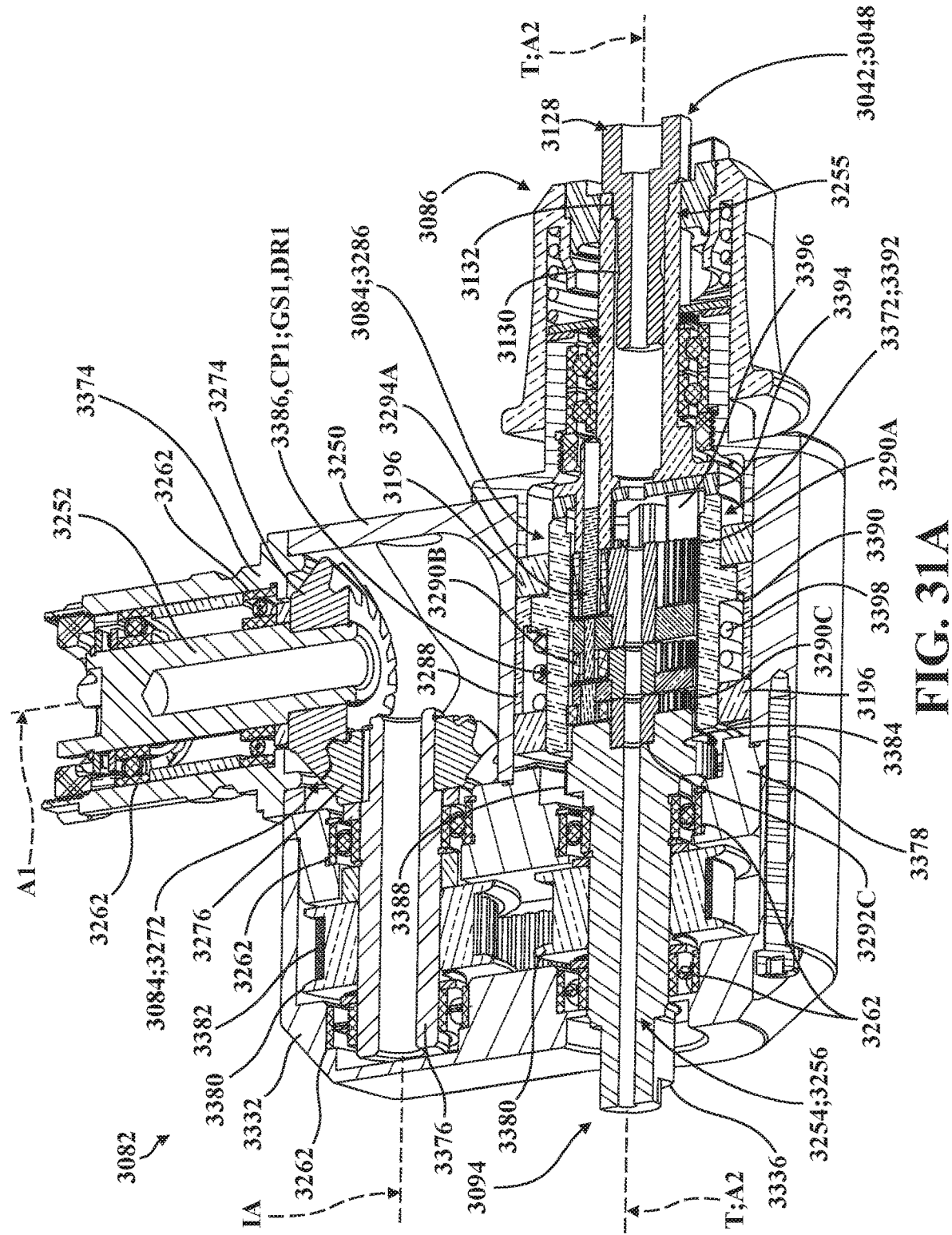
FIG. 31A is a sectional perspective view of the drive assembly and a portion of the rotary driving tool of FIG. 30, depicted as sectioned generally longitudinally, shown with a transmission having a shift collar arranged in a first collar position to engage a first gearset of the transmission.
Figure 31B:
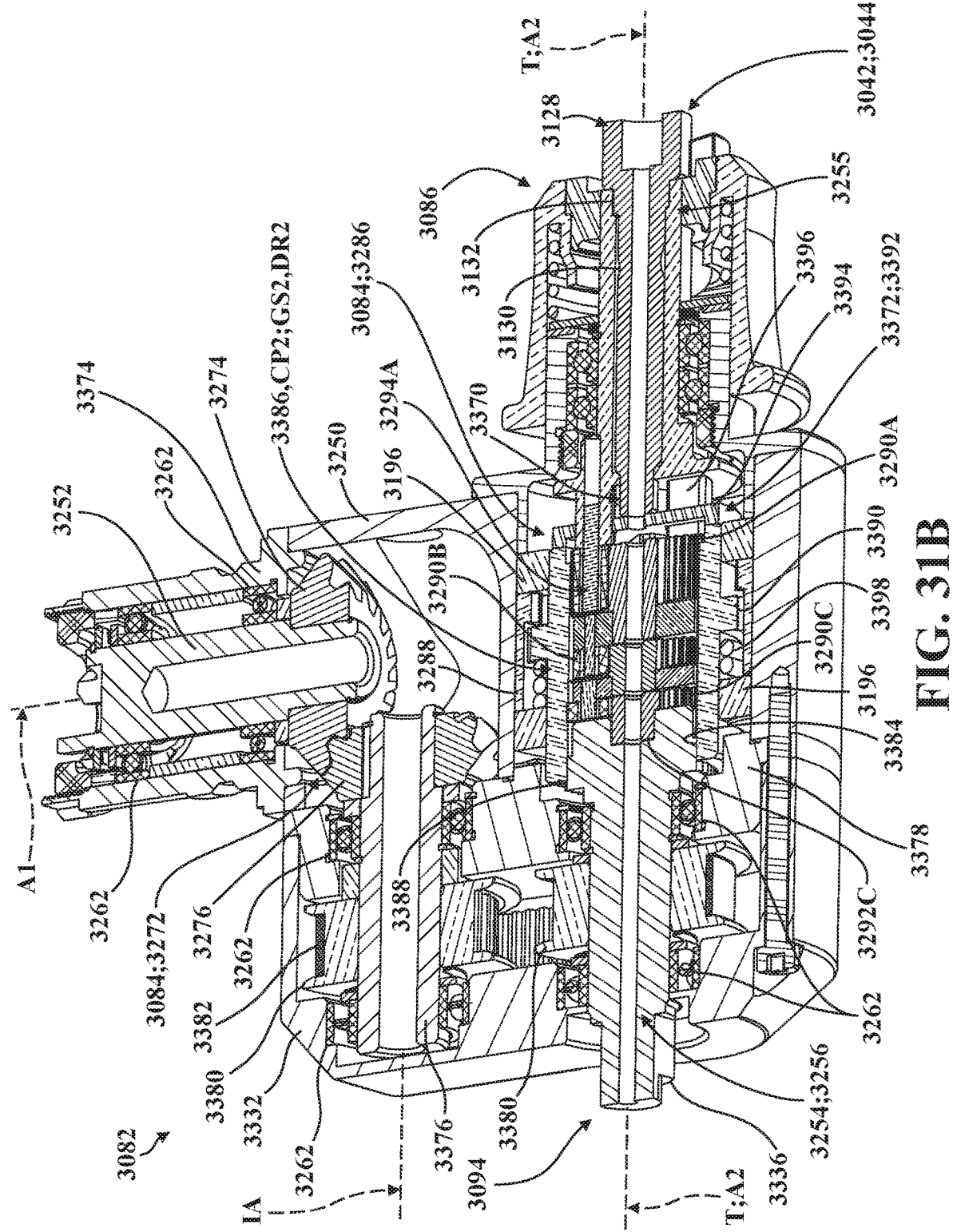
FIG. 31B is a sectional perspective view of the drive assembly and a portion of the rotary cutting tool of FIG. 30, depicted as sectioned generally longitudinally, shown with a transmission having a shift collar arranged in a second collar position to engage a second gearset of the transmission, with a portion of the rotary cutting tool disposed in engagement with a selector operatively attached to the shift collar.

Referring now to FIGS. 30-31B, as noted above, the third embodiment of the end effector 3040 is configured to secure tools 3042 with different types of bit interfaces 3128 via the connector 3086. FIG. 30 depicts two representative tools 3042 realized as the rotary cutting tool 3044 (e.g., a drill bit), and the rotary driving tool 3048 (e.g., a polyaxial screwdriver) supporting an anchor 3050 (e.g., a polyaxial screw). While the bit interface 3128 of the rotary driving tool 3048 is configured in the same way as the bit interface 128 used with the first embodiment of the end effector 40, the bit interface 3128 of the illustrated rotary cutting tool 3044 includes an extension portion 3370 extending away from the axial retainer 3130 and the rotational retainer 3132. As is described in greater detail below, the extension portion 3370 of the bit interface 3128 of the rotary cutting tool 3044 in the third embodiment cooperates with a transmission, generally indicated at 3372, of the drive assembly 3082 to facilitate operating the geartrain 3084 of the drive assembly 3082 at different drive ratios.

As is best shown in FIGS. 31A-31B, for the drive assembly 3082 of the third embodiment of the end effector 3040, the driver input shaft 3252 is supported by bearings 3262 seated in an input body 3374 that is operatively attached to the drive body 3250 (e.g., via fasteners). Here too, the input gear 3274 of the bevel gearset 3272 is coupled to the driver input shaft 3252 and is arranged for rotation about the first axis A1. However, the output gear 3276 of the bevel gearset 3272 is coupled to an idler shaft 3376 in this embodiment. Here, the idler shaft 3376 is supported by bearings 3262 seated in the upper cover 3332 and in an intermediate body 3378 arranged between the upper cover 3332 and the drive body 3250. The idler shaft 3376 rotates about an idler axis IA that is arranged substantially parallel to and spaced from the second axis A2. The intermediate shaft 3256 of the drive assembly 3082 which, in this embodiment, also serves as the manual input shaft 3254, is similarly supported by bearings 3262 seated in the upper cover 3332 and the intermediate body 3378, rotates about the second axis A2, and is coupled to the third sun gear 3292C of the reduction gearset 3286. Pulleys, generally indicated at 3380, are respectively supported on the intermediate shaft 2256 and the idler shaft 3376 and are interconnected via an endless belt 3382 such that the intermediate shaft 3256 and the idler shaft 3376 rotate concurrently. While the pulleys 3380 have the same configuration as each other in the illustrated embodiment, it will be appreciated that differently-sized pulleys could be utilized in some embodiments, such as to provide an increase in rotational speed or torque between the intermediate shaft 3256 and the idler shaft 3376. Furthermore, while not depicted herein, it will be appreciated that the drive assembly 3082 could employ a tensioner to remove slack in the endless belt 3382 in some embodiments. Moreover, in other embodiments, it is contemplated that a chain and sprocket arrangement could be used in place of the illustrated endless belt 3382 and pulley 3380 arrangement. Other configurations are contemplated.

While the drive assembly 3082 of the third embodiment of the end effector 3040 similarly employs a planetary configuration for the reduction gearset 3286, various components are arranged differently so as to effect operation of the transmission 3372. To this end, rather than being disposed in meshed engagement with the ring gear 3288, the first, second, and third sets of planet gears 3290A, 3290B, 3290C are each respectively disposed in meshed engagement with inner teeth 3384 of a shift collar 3386 of the transmission 3372. As is described in greater detail below, the inner teeth 3384 of the shift collar 3386 are also arranged to selectively engage shaft teeth 3388 of the intermediate shaft 3256 in splined engagement, and the shift collar 3386 further comprises outer teeth 3390 which are arranged selectively engage the ring gear 3288 in splined engagement. Moreover, in this embodiment, the ring gear 3288 is formed as a discrete component that is supported within the drive body 3250 between a pair of bushings 3196.

With continued reference to FIGS. 31A-31B, the transmission 3372 of the drive assembly 3082 is generally configured so as to be interposed in rotational communication between the rotary instrument 3080 (see FIGS. 29A-30) and the connector 3086, and comprises a first gearset GS1, a second gearset GS2, and the shift collar 3386. Here, the shift collar 3386 is arranged for movement, along the second axis A2, between a first collar position CP1 (see FIG. 31A) and a second collar position CP2 (see FIG. 31B).

In the first collar position CP1, the shift collar 3386 engages the first gearset GS1 to translate rotation between the rotary instrument 3080 and the connector 3086 at a first drive ratio DR1. In this embodiment, the first gearset GS1 is defined by splined engagement between the ring gear 3288 and the outer teeth 3390 of the shift collar 3386 such that the shift collar 3386 is effectively "fixed" to the drive body 3250 (see FIG. 31A). Thus, in the first collar position CP1, rotation of the intermediate shaft 3256, caused either from torque generated via the rotary instrument 3080 or force applied to the head 3336 of the manual interface 3094, is translated through the planetary reduction gearset 3286 to the retention shaft 3255 of the connector 3086.

In the second collar position CP2, the shift collar 3386 engages the second gearset GS2 to translate rotation between the rotary instrument 3080 and the connector 3086 at a second drive ratio DR2 that is different from the first drive ratio DR1. In this embodiment, the second gearset GS2 is defined by splined engagement between the inner teeth 3384 of the shift collar 3386 and the shaft teeth 3388 of the intermediate shaft 3256 such that the shift collar 3386 rotates concurrently with the intermediate shaft 3256 about the second axis A2 within the drive body 3250 (see FIG. 31B). Thus, in the second collar position CP2, rotation of the intermediate shaft 3256, caused either from torque generated via the rotary instrument 3080 or force applied to the head 3336 of the manual interface 3094, effectively bypasses the planetary reduction gearset 3286 and is translated directly through the shift collar 3386 to the retention shaft 3255 of the connector 3086. Put differently, in the second collar position CP2, the intermediate shaft 3256 rotates at the same speed as the connector 3086 (and, thus, the secured tool 3042).

In the illustrated embodiment, the transmission 3372 comprises a transmission linkage, generally indicated at 3392, that is operatively attached to the shift collar 3386 for concurrent movement between the first and second collar positions CP1, CP2. Here in this embodiment, the transmission linkage 3392 comprises a selector 3394 that is supported for movement by braces 3396 operatively attached to the retention shaft 3255 of the connector 3086. The selector 3394 is shaped and arranged for sliding movement along the braces 3396 which, in turn, respectively support the pins of the first set of pins 3294A of the reduction gearset 3286 in this embodiment.

As is best shown in FIG. 31B, the selector 3394 is also arranged to engage the extension portion 3370 of the bit interface 3128 of the rotary cutting tool 3044 to move the shift collar 3386 to the second collar position CP2 when the rotary cutting tool 3044 is secured to the connector 3086 of the drive assembly 3082. Conversely, and as is shown in FIG. 31A, the selector 3394 is arranged to move the shift collar 3386 to the first collar position CP1 when the rotary driving tool 3048 is secured to the connector 3086 of the drive assembly 3082 because no portion of the bit interface 3128 of the rotary driving tool 3048 engages the selector 3394, unlike the extension portion 3370 of the bit interface 3128 of the rotary cutting tool 3044 depicted in FIG. 31B. In the illustrated embodiment, the transmission 3372 also comprises a linkage biasing element 3398 (e.g., a compression spring, one or more spring washers, and the like) that is arranged to urge the shift collar 3386 toward the first collar position CP1 (see FIG. 31A).

It will be appreciated that the functionality afforded by the transmission 3372 allows the drive assembly 3082 to drive tools 3042 at either the first drive ratio DR1 or the second drive ratio DR2 depending on the presence or absence of the extension portion 3370. As such, tools 3042 can be designed with or without the extension portion 3370 based, among other things, on their intended rotational speed range during use. Moreover, this configuration advantageously allows the transmission 3372 to "shift" between the gearsets GS1, GS2 "automatically" based on the configuration of the secured tool 3042, without requiring additional user interaction beyond securing the tool 3042 to the connector 3086 (e.g., to shift "manually" or otherwise select a gearset).

While the transmission 3372 affords "automatic" shifting between the gearsets GS1, GS2 to facilitate driving different tools 3042 at different drive ratios DR1, DR2, it will be appreciated that the drive assembly 3082 can be configured to facilitate driving at different drive ratios DR1, DR2 without necessarily utilizing the transmission 3372, as is described in greater detail below in connection with other embodiments. Furthermore, while the transmission 3372 described above is configured to facilitate movement of the shift collar 3386 via engagement between the selector 3394 and the extension portion 3370 of the tool 3042, it will be appreciated that the selector 3394 could be configured to engage different portions of tools 3042 besides the extension portion 3370 illustrated in FIGS. 30 and 31B. Other configurations are contemplated.

As noted above, a fourth embodiment of the end effector of the surgical system 30 is shown in FIGS. 32-34C. In the description that follows, the structure and components of the fourth embodiment that are the same as or that otherwise correspond to the structure and components of the first embodiment of the end effector 40 are provided with the same reference numerals increased by 4000. Because many of the components and features of the fourth embodiment of the end effector 4040 are substantially similar to those of the first embodiment of the end effector 40 described above, for the purposes of clarity, consistency, and brevity, only certain specific differences between the fourth embodiment of the end effector 4040 and the first embodiment of the end effector 40 will be described below, and only some of the components and features common between the embodiments will be discussed herein and depicted in the drawings.

Thus, unless otherwise indicated below, the description of the first embodiment of the end effector 40 may be incorporated by reference with respect to the fourth embodiment of the end effector 4040 without limitation. Likewise, certain components and features of the fourth embodiment of the end effector 4040 that are similar to corresponding components and features of previously-described embodiments may be referred to or otherwise depicted in the drawings as provided with the same reference numerals increased by 1000 plus another 1000 for every intervening embodiment (e.g., for the fourth embodiment, components described in connection with the third embodiment would be increased by 1000, and components described in connection with the second embodiment would be increased by 2000).

Referring now to FIGS. 32-34C, the fourth embodiment of the end effector 4040 is generally shown comprising the mount 4078, the rotary instrument 4080 and its actuator 4166 (depicted schematically), and the drive assembly 4082. When compared with the first embodiment described above, the fourth embodiment of the end effector 4040 generally employs a differently-configured trigger assembly 4088 and drive assembly 4082, interacts with a differently-configured handle assembly 4096, and is configured to secure tools 4042 with different types of bit interfaces 4128, each of which will be described in greater detail below.

Figure 32:
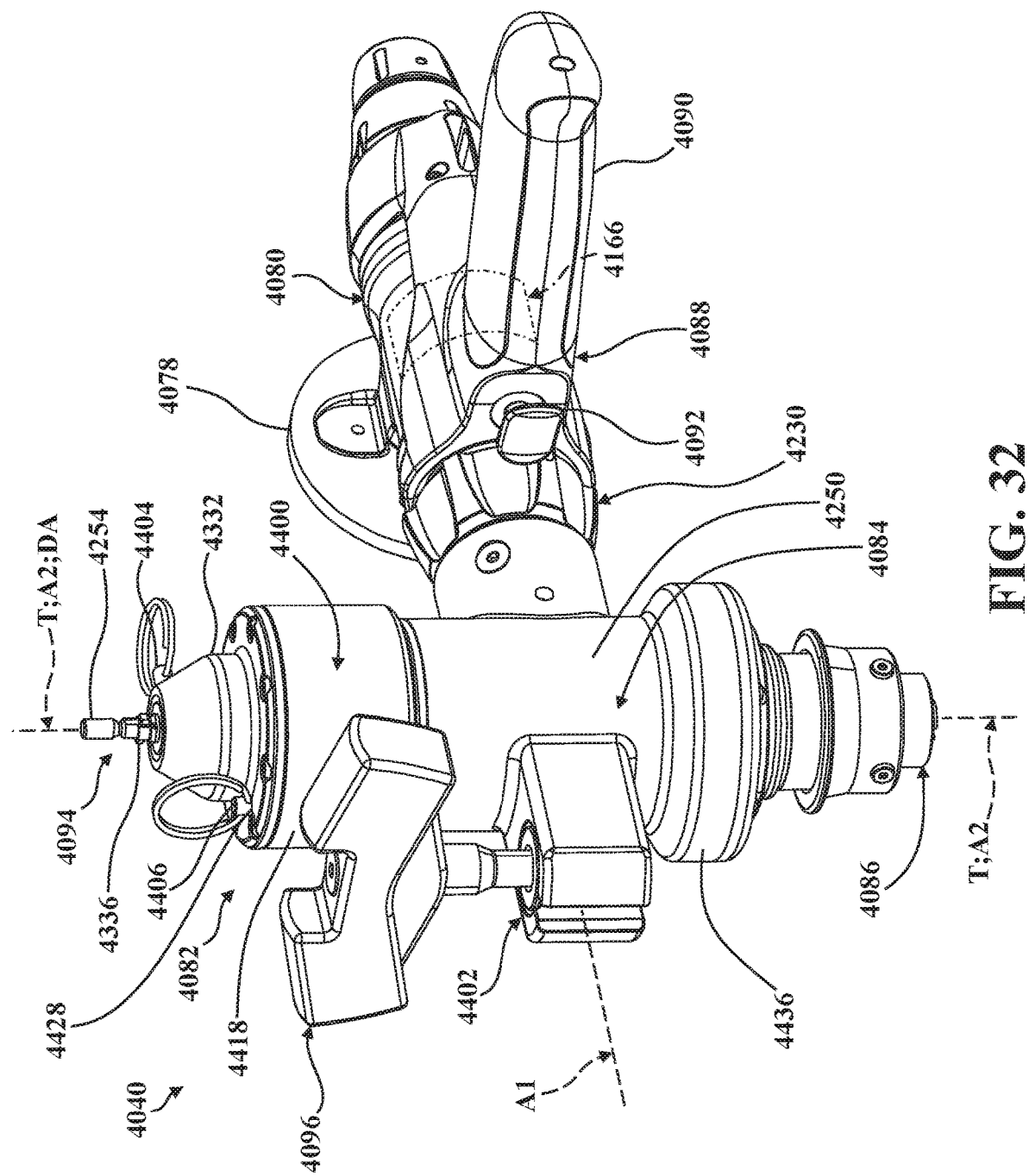
FIG. 32 is a perspective view of an end effector, according to a fourth embodiment of the present disclosure, which is likewise configured for use with the surgical system of FIG. 1, the end effector shown comprising a mount supporting a rotary instrument to generate torque about a first axis, a drive assembly with a connector to support a tool for rotation about a second axis, a differential assembly, a pair of pins, and a handle assembly supported in a dock.
Figure 33:
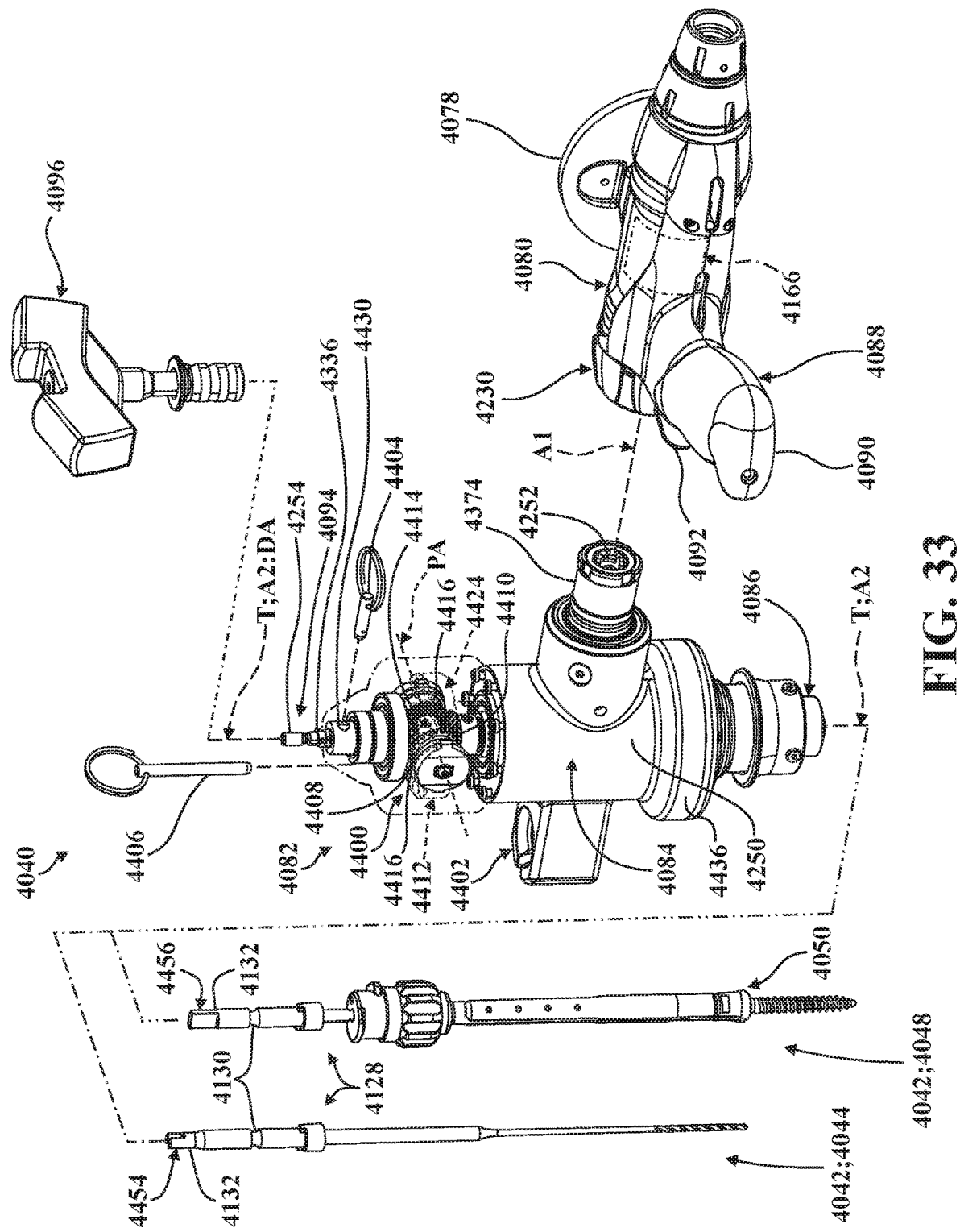
FIG. 33 is an exploded perspective view of the end effector of FIG. 32, shown with the drive assembly spaced from the rotary instrument, the pins, and the handle assembly, and shown with two tools configured for releasable attachment to the drive assembly, with one of the tools shown as a rotary cutting tool with a drill bit, and with the other of the tools shown as an rotary driving tool supporting an anchor.

As is best shown in FIGS. 32-33, in the fourth embodiment, the drive assembly 4082 is similarly configured for releasable attachment to the rotary instrument 4080 via the coupling 4230 such that the second axis A2 can be moved relative to the first axis A1 by positioning the drive assembly 4082 in different ways about the first axis A1. The trigger assembly 4088 in the third embodiment employs a grip 4090 with a contoured profile, and an input trigger 4092 which is similar in construction to the second embodiment of the trigger assembly 2088 described above. As will be appreciated from the subsequent description below, the trigger assembly 4088 depicted in FIGS. 32-33 is exemplary in the fourth embodiment, and the drive assembly 4082 can be utilized with a number of different types of trigger assemblies 4088 which may be configured so as to be movable to limit and/or promote access to the manual interface 4094 (movement not shown in the fourth embodiment).

With continued reference to FIGS. 32-33, the handle assembly 4096 in the fourth embodiment has a different configuration than the handle assembly 96 described in connection with the first embodiment. Specifically, the handle assembly 4096 has a more symmetric profile and is generally configured to selectively lock, both rotatably and axially, to the head 4336 of the manual interface 4094 (locking not shown). In this embodiment, the drive assembly 4082 further comprises a differential assembly 4400 interposed between the rotary instrument 4080, the connector 4086, and the manual interface 4094. As is described in greater detail below, the differential assembly 4400 is operable in a haptic torque mode 4400H (see FIG. 34A; not shown in detail) where the handle assembly 4096 can be engaged by the user while driving the tool 4042 via the rotary instrument 4080 as a way to provide the user with tactile torque feedback. When not being utilized (e.g., as the end effector 4040 is being repositioned), the handle assembly 4096 can be stowed in a dock 4402 formed on the drive body 4250 of the drive assembly 4082 (see FIG. 32).

In addition to allowing the user to sense tactile torque feedback through the handle assembly 4096 at the manual interface 4094 in the haptic torque mode 4400H, the differential assembly 4400 also affords functionality that is similar to the clutch mechanism 316 described above in connection with the first embodiment of the end effector 40. Specifically, the differential assembly 4400 is also operable between a first interrupt mode 4400A (see FIG. 34B; not shown in detail) and a second interrupt mode 4400B (see FIG. 34C; not shown in detail). In the first interrupt mode 4400A, rotational torque generated by the rotary instrument 4080 translates through the differential assembly 4400 to the connector 4086 to rotate the tool 4042 about the second axis A2 without translating rotational torque to the head 4336 of the manual interface 4094. In the second interrupt mode 4400B, rotational torque generated as force is applied to the head 4336 of the manual interface 4094 translates through the differential assembly 4400 to the connector 4086 to rotate the tool 4042 without translating rotational torque to the rotary instrument 4080.

Figure 34A:
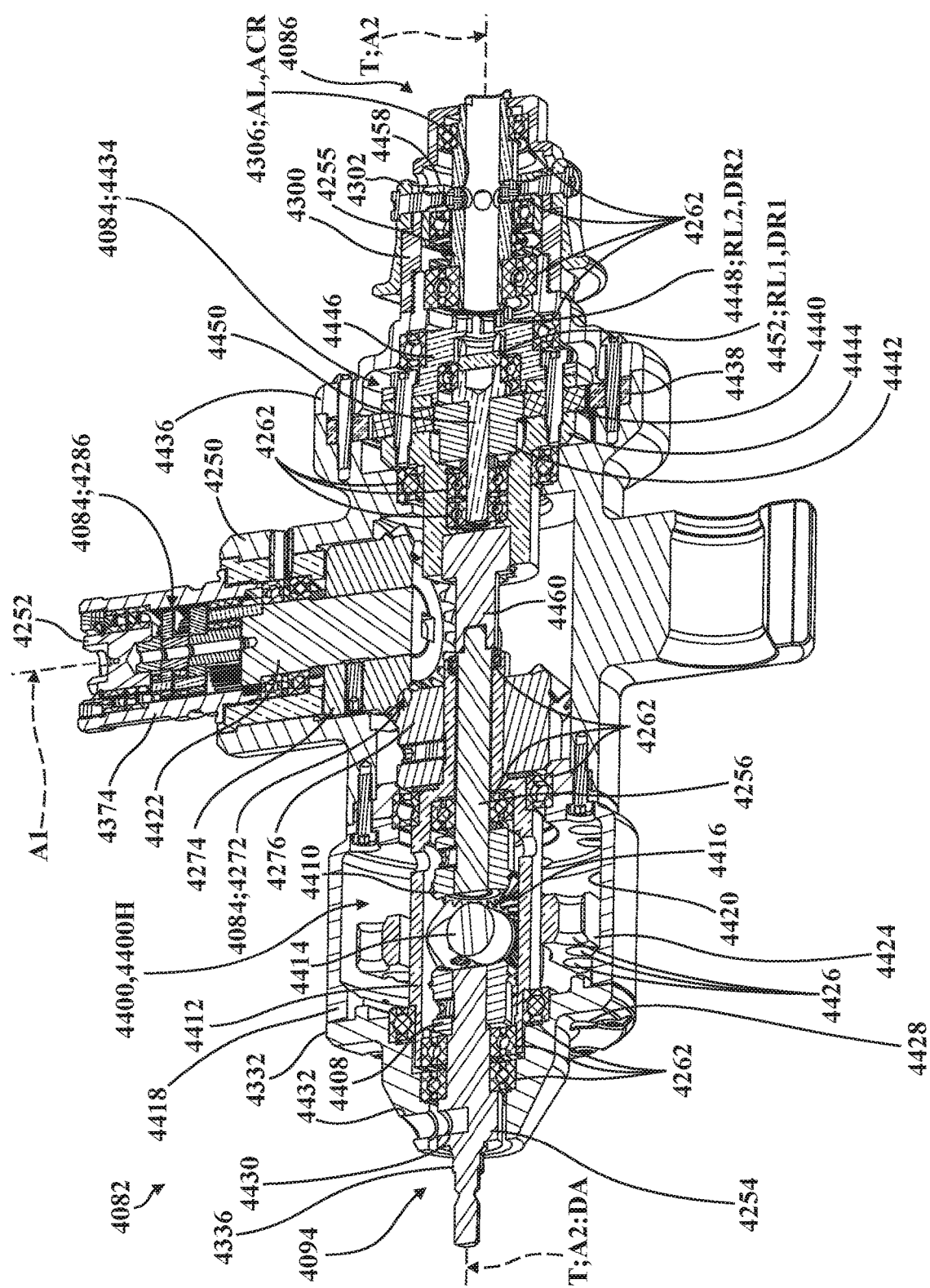
FIG. 34A is a sectional perspective view of the drive assembly of FIG. 33, depicted as sectioned generally longitudinally, shown with the differential assembly in communication with first and second rotational locks of the drive assembly.
Figure 34B:
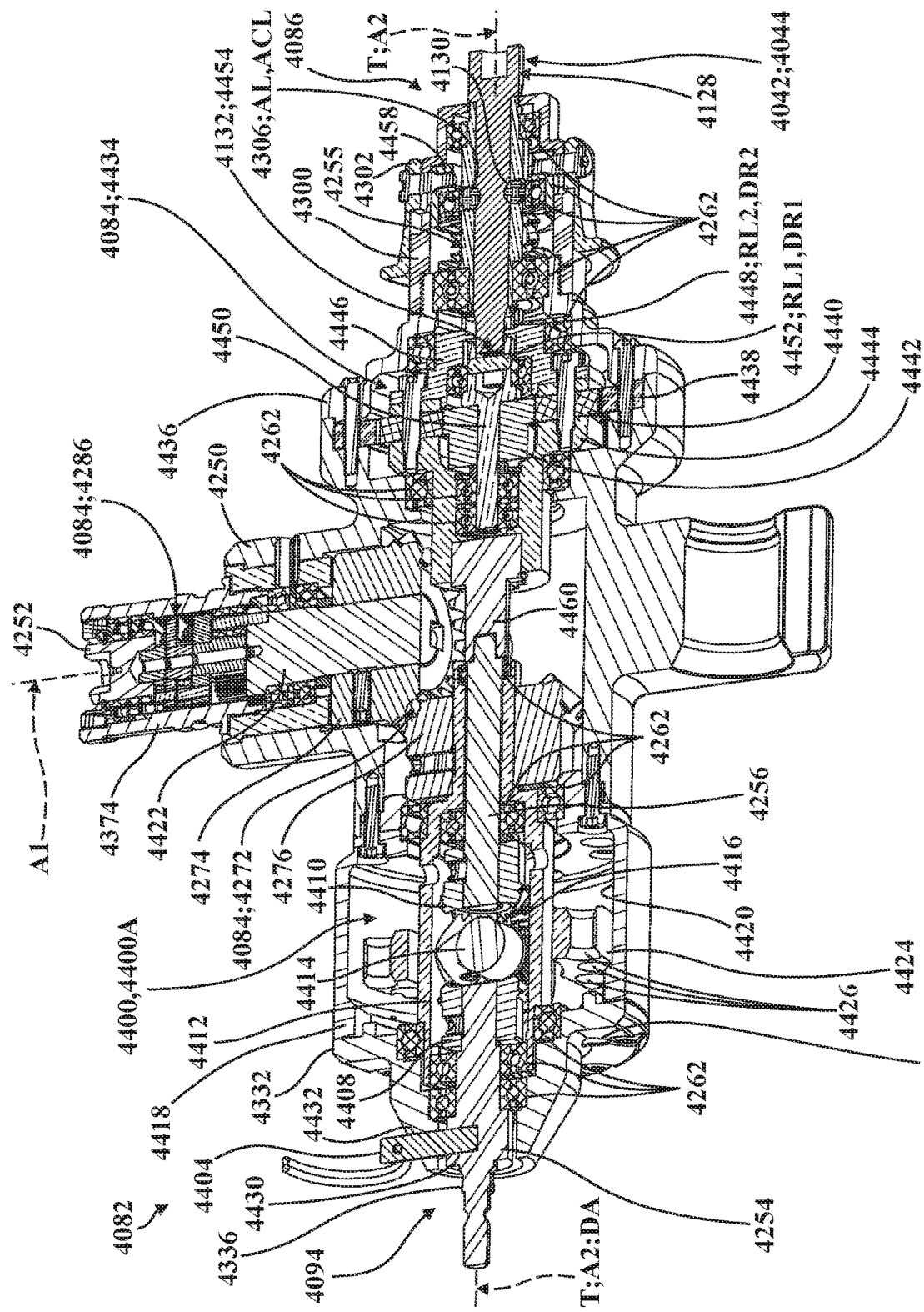
FIG. 34B is another sectional perspective view of the drive assembly of FIG. 34A, shown with a portion of the rotary cutting tool depicted in FIG. 33 disposed in engagement with the first rotational lock of the drive assembly for rotation about the second axis, and shown with one of the pins engaging a portion of the differential assembly.

Operation of the differential assembly 4400 in the first interrupt mode 4400A is achieved by selectively locking the manual input shaft 4254 to the upper cover 4332 of the drive assembly 4082 via a first pin 4404 (see FIG. 34B; not shown in detail). Similarly, operation of the differential assembly 4400 in the second interrupt mode 4400B is achieved by selectively locking the differential assembly 4400 to the upper cover 4332 of the drive assembly 4082 via a second pin 4406 (see FIG. 34C; not shown in detail). Furthermore, operation of the differential assembly 4400 in the haptic torque mode 4400H is achieved by selectively removing the first and second pins 4404, 4406 from the upper cover 4332 of the drive assembly 4082 (see FIG. 34A; not shown in detail) and connecting the handle assembly 4096 to the head 4336 of the manual interface 4094 to prevent rotation of the head 4336 about the second axis A2 as the rotary instrument 4080 is driven to rotate the tool 4042 about the second axis A2.

Figure 34C:
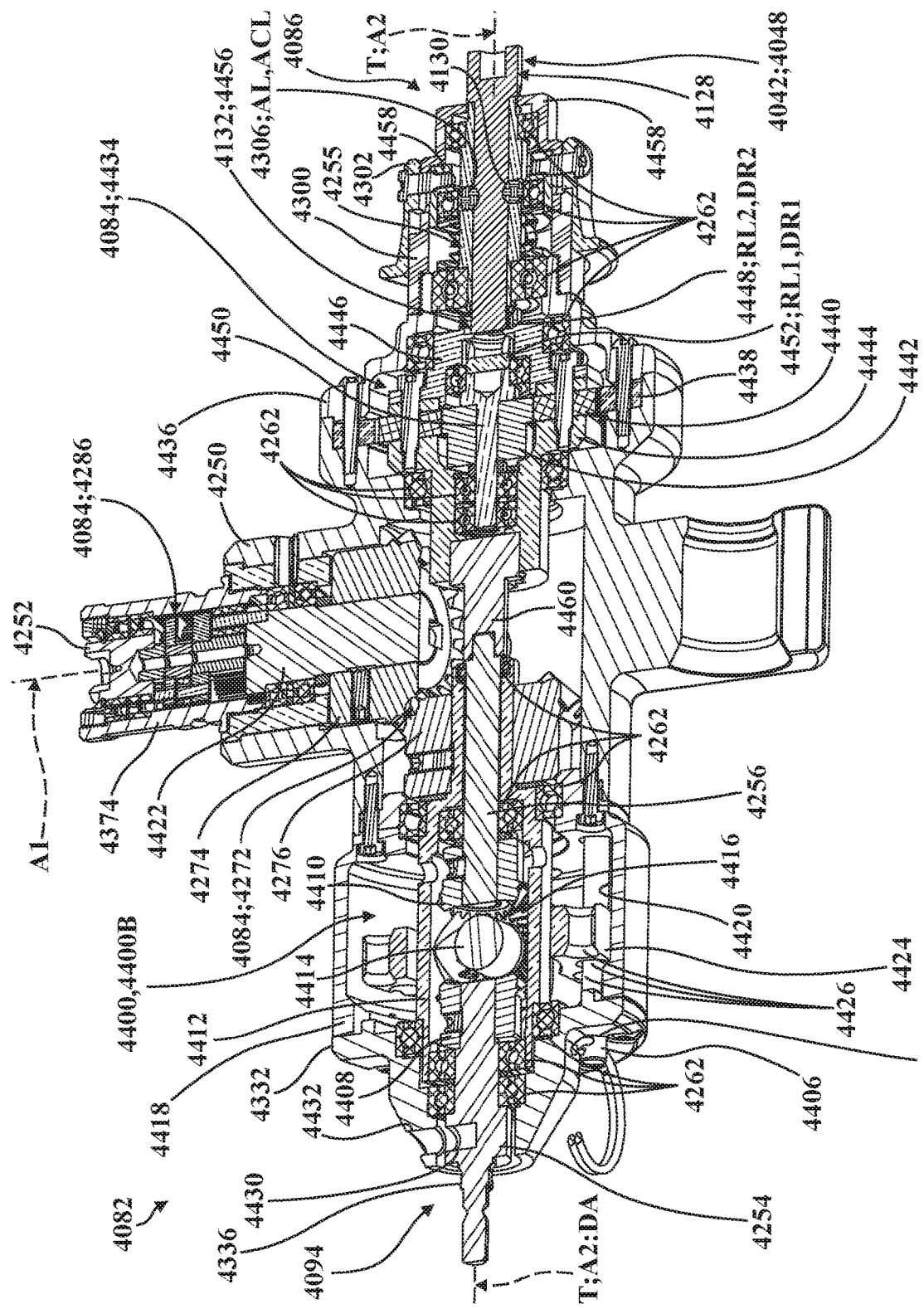
FIG. 34C is another sectional perspective view of the drive assembly of FIGS. 34A-34B, shown with a portion of the rotary driving tool depicted in FIG. 33 disposed in engagement with the second rotational lock of the drive assembly for rotation about the second axis, and shown with the other of the pins engaging another portion of the differential assembly.

Referring now to FIGS. 34A-34C, the differential assembly 4400 of the drive assembly 4082 generally comprises an interface-side gear 4408 disposed in rotational communication with the manual interface 4094, a connector-side gear 4410 disposed in rotational communication with the connector 4086, a differential case 4412 disposed in rotational communication with the rotary instrument 4080, a pinion shaft 4414 operatively attached to the differential case 4412 for concurrent movement, and a pair of pinion gears 4416 each supported by the pinion shaft 4414 and disposed in meshed engagement with the interface-side gear 4408 and the connector-side gear 4410. A differential housing 4418 operatively attached to the drive assembly 4082 defines a differential chamber 4420 shaped to accommodate at least a portion of the differential case 4412 of the differential assembly 4400 therein. Each of the components of the differential assembly 4400 introduced above will be described in greater detail below.

Here too in the fourth embodiment of the end effector 4040, the geartrain 4084 of the drive assembly 4082 similarly employs a planetary reduction gearset 4286 and the bevel gearset 4272. However, in this embodiment, the reduction gearset 4286 is interposed in rotational communication between the rotary instrument 4080 (see FIGS. 32-33) and the bevel gearset 4272. More specifically, the components of the planetary reduction gearset 4286 are supported in the input body 4374 and are generally arranged about the first axis A1 between the driver input shaft 4252 and a carrier shaft 4422. Here, the input gear 4274 of the bevel gearset 4272 is coupled to the carrier shaft 4422 for concurrent rotation about the first axis A1, and the output gear 4276 of the bevel gearset 4272 is coupled to the differential case 4412 for concurrent rotation about the second axis A2.

The differential case 4412 is rotatably supported by bearings 4262 disposed in the drive body 4250, the differential housing 4418, and the upper cover 4332, and has an annular hub 4424 supported by ribs (not shown in detail) that is provided with a plurality of hub apertures 4426 shaped to receive the second pin 4406 when aligned with a radial cover aperture 4428 formed in the upper cover 4332 so as to facilitate operation in the second interrupt mode 4400B. The manual input shaft 4254 is similarly supported by bearings 4262 disposed in the upper cover 4332 and the differential case 4412, is coupled to the interface-side gear 4408, and is provided with an interface aperture 4430 shaped to receive the first pin 4404 when aligned with a transverse cover aperture 4432 formed in the upper cover 4332 so as to facilitate operation in the first interrupt mode 4400A. The pinion shaft 4414 is carried by the differential case 4412 and rotatably supports the pinion gears 4416, which are disposed in meshed engagement with the interface-side gear 4408 and the connector-side gear 4410, as noted above. Here, the connector-side gear 4410 is coupled to the intermediate shaft 4256 which, in this embodiment, is rotatably supported by bearings 4262 disposed in the differential case 4412.

The differential housing 4418 of the differential assembly 4400 defines a differential axis DA which, in the illustrated embodiment, is coincident with the second axis A2. Here, rotation of the differential case 4412 is permitted relative to the differential housing 4418 when in the first interrupt mode 4400A. Conversely, rotation of the differential case 4412 is inhibited relative to the differential housing 4418 when in the second interrupt mode 4400B. Furthermore, rotation of both the interface-side gear 4408 and the connector-side gear 4410 is permitted about the differential axis DA when in the second interrupt mode 4400B. However, when in the first interrupt mode 4400A, rotation of the connector-side gear 4410 about the differential axis DA is permitted, but rotation of the interface-side gear 4408 about the differential axis DA is inhibited. Moreover, the pinion shaft 4414 defines a pinion axis PA about which the pinion gears 4416 are permitted to rotate in the first interrupt mode 4400A, the second interrupt mode 4400B, and the haptic torque mode 4400H. In the illustrated embodiment, the pinion axis PA is substantially perpendicular to the differential axis DA.

As noted above, when operating in the haptic torque mode 4400H with the handle assembly 4096 connected to the head 4336 of the manual interface 4094, the user can grasp the handle assembly 4096 to prevent rotation of the head 4336 about the second axis A2 as the rotary instrument 4080 is driven to rotate the tool 4042 about the second axis A2. When driven by the actuator 4166, the manual input shaft 4254 and the intermediate shaft 4256 each experience the same amount of torque but can rotate at different speeds.

Thus, because the differential assembly 4400 is interposed between the rotary instrument 4080 and the tool 4042 as a part of the geartrain 4084, if the user prevents the manual input shaft 4254 from rotating about the second axis A2 by grasping the handle assembly 4096, haptic (or "tactile") torque feedback is translated to the user's hand. Even though the handle assembly 4096 does not rotate when grasped, the user will nevertheless experience torque feedback that is substantially equivalent to the amount of torque being applied to the tool 4042. Thus, if the driven tool 4042 comprises the rotary driving tool 4048 with the anchor 4050, the user would "feel" torque in the handle assembly 4096 that is equivalent to torque in the anchor 4050. This torque feedback advantageously provides the user with a relative sense of the resistance to rotation being experienced by the anchor 4050 while using the rotary instrument 4080 to drive the anchor 4050.

With continued reference to FIGS. 34A-34C, in the fourth embodiment of the end effector 4040, the geartrain 4084 further comprises an auxiliary gearset, generally indicated at 4434, which is interposed between the intermediate shaft 4256 and the connector 4086. The auxiliary gearset 4434 is disposed within an auxiliary housing 4436 secured to the drive body 4250 with fasteners, with an auxiliary ring gear 4438 arranged therebetween. A total of four auxiliary planet gears 4440 are disposed in meshed engagement with the auxiliary ring gear 4438 and also with an auxiliary sun gear 4442. The auxiliary planet gears 4440 are secured via fasteners to an auxiliary carrier 4444 and to a first interface body 4446 which, in turn, are supported by bearings 4262 respectively disposed in the drive body 4250 and the auxiliary housing 4436.

The first interface body 4446 comprises a cross recess 4448 which defines a rotational lock that is shaped to engage the bit interface 4128 of the rotary driving tool 4048 illustrated in FIG. 33, as described in greater detail below. A second interface body 4450 is coupled to the auxiliary sun gear 4442 and is supported by bearings 4262 disposed in the auxiliary carrier 4444 and the first interface body 4446. A peg 4452 is operatively attached to the second interface body 4450 and defines another rotational lock that is shaped to engage the bit interface 4128 of the rotary cutting tool 4044 illustrated in FIG. 33, as described in greater detail below.

In the representative embodiment illustrated herein, the peg 4452 defines a first rotational lock RL1 (see FIG. 34B), and the cross recess 4448 defines a second rotational lock RL2. Here, the peg 4452 of the first rotational lock RL1 is arranged closer to the manual interface 4094 than the cross recess 4448 of the second rotational lock RL2. This arrangement corresponds to the configurations of the bit interfaces 4128 of the rotary driving tool 4048 and the rotary cutting tool 4044 illustrated in FIG. 33. The bit interfaces 4128 shown in FIG. 33 each employ axial retainers 4130 that are similar to those previously described in connection with the bit interface 128 utilized with the first embodiment of the end effector 40. However, in the fourth embodiment, the rotational retainers 4132 are different, both from each other and from the first embodiment. More specifically, in the fourth embodiment, the bit interface 4128 of the rotary cutting tool 4044 comprises a notch element 4454 that is shaped to engage the first rotational lock RL1 (see FIG. 34B), and the bit interface 4128 of the rotary driving tool 4048 comprises a key element 4456 that is configured to engage the second rotational lock RL2 (see FIG. 34C). The key element 4456 has a rounded, generally rectangular profile that is shaped to engage in the cross recess 4448 such that the rotary driving tool 4048 rotates concurrently about the second axis A2 with the first interface body 4446 of the auxiliary gearset 4434 when secured to the connector 4086 (see FIG. 34C). The notch element 4454 is provided with a profile that is configured so as to pass through the cross recess 4448 before engaging on opposing sides of the peg 4452 such that the rotary cutting tool 4044 rotates concurrently about the second axis A2 with the second interface body 4450 when secured to the connector 4086 (see FIG. 34B).

While the drive assembly 4082 comprises the first rotational lock RL1 and the second rotational lock RL2 in the fourth embodiment, it will be appreciated that other embodiments described herein may employ only the first rotational lock RL1. Furthermore, rotational locks could be of a number of different configurations including, for example, similar to the rotational connector element 308 formed in the retention shaft 255 of the connector 86 of the drive assembly 82 described above in connection with the first embodiment of the end effector 40. Other configurations are contemplated Here in the fourth embodiment, axial retention of tools 4042 secured to the connector 4086 is achieved with an axial lock AL configured to releasably secure one of the rotary cutting tool 4044, the rotary driving tool 4048, or another tool 4042 for concurrent translation with the drive assembly 4082 along the trajectory T maintained by the surgical robot 32 (see FIG. 1). To this end, the axial lock AL is operable between a release configuration ACR (see FIG. 34A) and a lock configuration ACL (see FIGS. 34B-34C). When the axial lock AL operates in the release configuration ACR shown in FIG. 34A, relative movement between the drive assembly 4082 and the tool 4042 secured to either of the first and second rotational locks RL1, RL2 (tools 4042 not shown in FIG. 34A) is permitted along the second axis A2. When the axial lock AL operates in the lock configuration ACL as shown in FIGS. 34B-34C, relative movement between the drive assembly 4082 and the tool 4042 secured to either the first rotational lock RL1 (see FIG. 34B) or the second rotational lock RL2 (see FIG. 34C) is restricted along the second axis A2.

The axial lock AL is realized in the fourth embodiment by generally spherical axial connector elements 4306 which form part of the connector 4086 and operate in substantially the same way as the first embodiment of the end effector 40. Here, however, the retention shaft 4255 of the connector 4086 is supported by bearings 4262 disposed in the connector body 4300 and also disposed in a rider body 4458 that moves concurrently with the flange member 4302. When in the lock configuration ACL, the axial connector elements 4306 are supported by the bearing 4262 and also engage the axial retainer 4130 of the bit interfaces 4128 of the rotary cutting tool 4044 and the rotary driving tool 4048 to restrict relative movement therebetween along the second axis A2. When the flange member 4302 of the connector 4086 is engaged by the user to move to the release configuration ACR, movement of the flange member 4302 along the second axis A2 brings the axial connector elements 4306 out of engagement with the axial retainer 4130 and out of support with the bearing 4262. This arrangement permits concurrent rotation of the retention shaft 4255 and the bit interface 4128 of the tool 4042 when secured to the axial lock AL in the lock configuration ACL, and allows the retention shaft 4255 to rotate independent of the first and second rotational locks RL1, RL2 when tools 4042 are removed from the connector 4086.

Here too, it will be appreciated that axial locks could be of a number of different configurations including, for example, similar to the axial connector elements 306 disposed in the connector element pockets 310 formed in the retention shaft 255 of the connector 86 of the drive assembly 82 described above in connection with the first embodiment of the end effector 40. Other configurations are contemplated.

In the fourth embodiment of the end effector 4040, the auxiliary gearset 4434 effectively acts as a speed increaser between the intermediate shaft 4256 and the second interface body 4450 such that the peg 4452 of the first rotational lock RL1 is driven at the first drive ratio DR1, while the cross recess 4448 of the second rotational lock RL2 is driven at the second drive ratio DR2 and rotates concurrently with the intermediate shaft 4256. Here, rotation of the intermediate shaft 4256 is translated through an intermediate coupler 4460 to the auxiliary carrier 4444. Rotation of the auxiliary carrier 4444 causes the auxiliary planet gears 4440 to orbit the second axis A2 and rotate about their own axes while remaining in meshed engagement with the auxiliary ring gear 4438 and the auxiliary sun gear 4442 such that the auxiliary sun gear 4442 rotates about the second axis A2 faster than the auxiliary carrier 4444. Thus, as noted above, different tools 4042 can be driven by the drive assembly 4082 at different, predetermined drive ratios without necessarily requiring a transmission to "shift" between different gearsets.

As noted above, a fifth embodiment of the end effector of the surgical system 30 is shown in FIGS. 35-38B. In the description that follows, the structure and components of the fifth embodiment that are the same as or that otherwise correspond to the structure and components of the first embodiment of the end effector 40 are provided with the same reference numerals increased by 5000. Because many of the components and features of the fifth embodiment of the end effector 5040 are substantially similar to those of the first embodiment of the end effector 40 described above, for the purposes of clarity, consistency, and brevity, only certain specific differences between the fifth embodiment of the end effector 5040 and the first embodiment of the end effector 40 will be described below, and only some of the components and features common between the embodiments will be discussed herein and depicted in the drawings.

Thus, unless otherwise indicated below, the description of the first embodiment of the end effector 40 may be incorporated by reference with respect to the fifth embodiment of the end effector 5040 without limitation. Likewise, certain components and features of the fifth embodiment of the end effector 5040 that are similar to corresponding components and features of previously-described embodiments may be referred to or otherwise depicted in the drawings as provided with the same reference numerals increased by 1000 plus another 1000 for every intervening embodiment (e.g., for the fifth embodiment, components described in connection with the fourth embodiment would be increased by 1000, components described in connection with the third embodiment would be increased by 2000, and components described in connection with the second embodiment would be increased by 3000).

Referring now to FIGS. 35-38B, the fifth embodiment of the end effector 5040 is generally shown comprising the mount 5078, the rotary instrument 5080 and its actuator 5166 (depicted schematically), and the drive assembly 5082. When compared with the first embodiment described above, the fifth embodiment of the end effector 5040 generally employs a differently-configured trigger assembly 5088 and drive assembly 5082, and is configured to secure tools 5042 in a "top loading" manner through a drive conduit 5462 which forms part of the geartrain 5084. Each of these components will be described in greater detail below.

Figure 36:
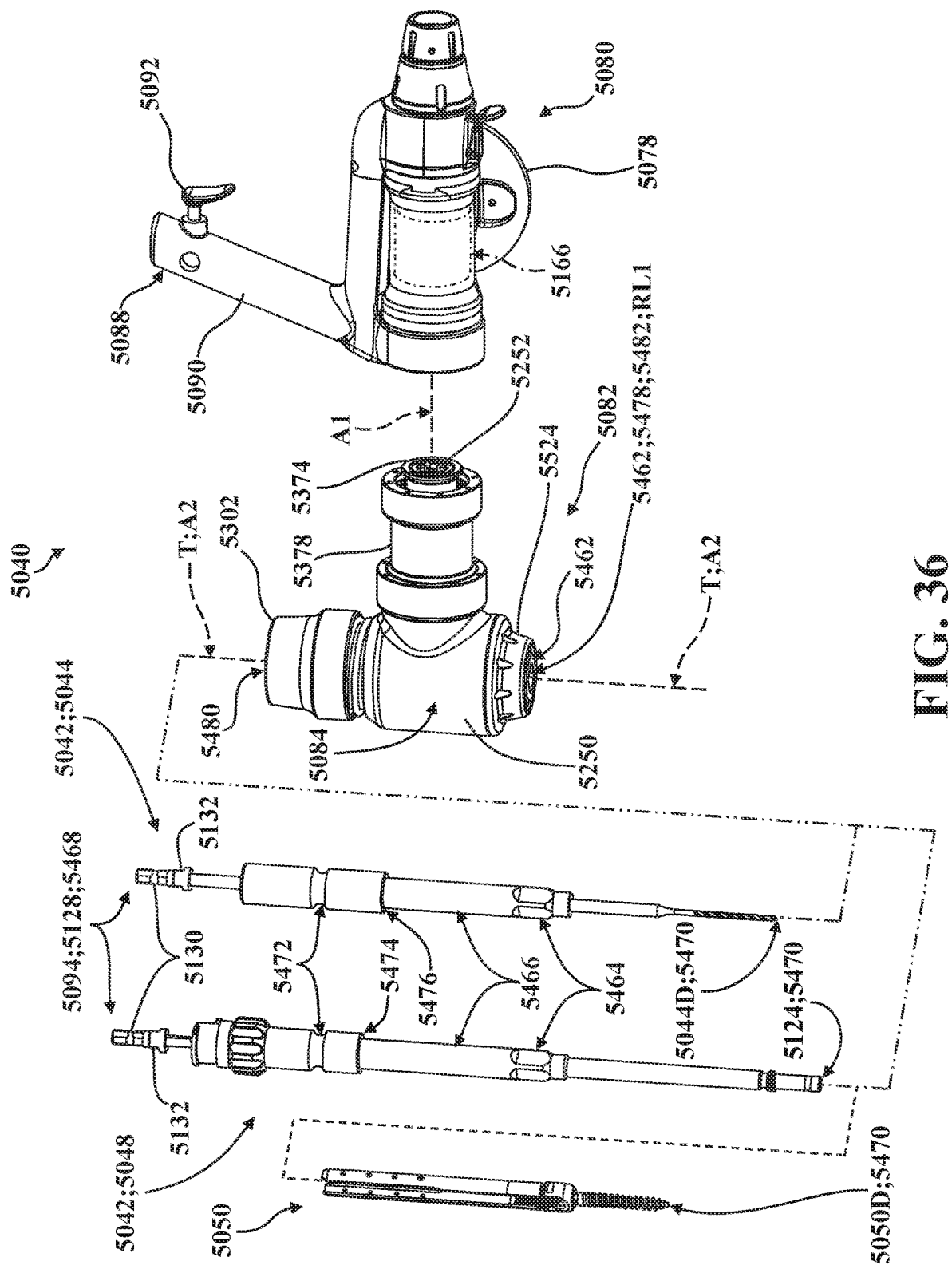
FIG. 36 is an exploded perspective view of the end effector of FIG. 35, shown with the drive assembly spaced from the rotary instrument and the rotary cutting tool, and shown spaced from another tool depicted as an rotary driving tool for driving an anchor.

As is best shown in FIGS. 35-36, the fifth embodiment of the end effector 5040 is provided with the same trigger assembly 5088, grip 5090, and input trigger 5092 as described above in connection with the second embodiment of the end effector 2040. Also like the second embodiment described above, in the fifth embodiment of the end effector 5040, the rotary instrument 5080, and the drive assembly 5082 are configured such that the second axis A2 is fixed relative to the first axis A1. Put differently, here too in this embodiment, the drive body 5250 of the drive assembly 5082 is not arranged for movement relative to the rotary instrument 5080. However, as will be appreciated from the subsequent description below, the drive assembly 5082 and/or the rotary instrument 5080 could be configured differently, such as to permit relative positioning about the first axis A1 in ways similar to the first embodiment of the end effector 40. Other configurations are contemplated.

Because the drive assembly 5082 of the fifth embodiment of the end effector 5040 is provided with the drive conduit 5462 to facilitate "top loading" of different types of tools 5042, as noted above and as is described in greater detail below, the manual interface 5094 of the fifth embodiment is realized by the bit interface 5128 of whichever tool 5042 is secured to the drive assembly 5082 rather than as a portion of the drive assembly 5082 itself. However, this configuration is exemplary, and as will be appreciated from the subsequent description below, the end effector 5040 could be provided with a separate manual interface 5094 which forms part of the drive assembly 5082 while still utilizing the drive conduit 5462 to permit "top loading" of tools 5042. Other configurations are contemplated.

Referring now to FIGS. 36-38B, in the fifth embodiment of the end effector 5040, the drive conduit 5462 of the drive assembly 5082 is supported for rotation about the second axis A2 and is operatively attached to the output gear 5276 of the bevel gearset 5272. Thus, here too in this embodiment, the first axis A1 is different from the second axis A2 (see also FIG. 35). More specifically, the first axis A1 is substantially perpendicular to the second axis A2 in this embodiment. However, and as will be appreciated from the eighth embodiment described below, it is contemplated that the first axis A1 could be arranged differently, such as parallel to or even coincident with the second axis A2. Other configurations are contemplated. In the fifth embodiment, the bevel gearset 5272 also provides a reduction in that the output gear 5276 is different in configuration than the input gear 5274. Thus, in addition to translating rotation about the first axis A1 into rotation about the second axis A2, the bevel gearset 5272 also adjusts rotational torque between the first and second axes A1, A2 in this embodiment.

Similar to the fourth embodiment of the end effector 4040 described above, the geartrain 5084 in the fifth embodiment also employs a planetary reduction gearset 5286 arranged along the first axis A1. Here, the reduction gearset 5286 is interposed in rotational communication between the actuator of the rotary instrument 5080 (see FIG. 35; actuator not shown in detail) and the drive conduit 5462 of the drive assembly 5082 such that rotation about the first axis A1 occurs at a different (e.g., higher) speed than rotation of the first rotational lock RL1 about the second axis A2. Furthermore, and similar to the third embodiment of the end effector 3040 described above, a transmission 5372 is provided to facilitate "shifting" between first and second gearsets GS1, GS2 in order to drive different types of tools 5042 at correspondingly different drive ratios DR1, DR2. The specific arrangement of each of these components will be described in greater detail below.

The drive assembly 5082 of the fifth embodiment of the end effector 5040 employs the first rotational lock RL1 and the axial lock AL to facilitate securing tools 5042 about the second axis A2. The first rotational lock RL1 is operatively attached to the drive conduit 5462 for concurrent rotation about the second axis A2. The axial lock AL is provided to releasably secure the tool 5042 for concurrent translation with the drive conduit 5462 along the trajectory T maintained by the surgical robot 32 (see FIG. 1), and is operable between the release configuration ACR where relative movement between the drive assembly 5082 and the tool 5042 is permitted along the second axis A2 (see FIG. 37A; tool 5042 not shown), and the lock configuration ACL where relative movement between the drive assembly 5082 and the tool 5042 is restricted along the second axis A2 (see FIGS. 37B-37C). The configuration of the axial lock AL in the fifth embodiment will be described in greater detail below The first rotational lock RL1 comprises a keyed bore in the fifth embodiment, with a generally "square" profile that is shaped to engage correspondingly-shaped conduit rotational retainer 5464 formed in a tool body 5466 arranged between an interface end 5468 and a working end 5470 of each of the tools 5042 (see FIG. 36). As will be appreciated from the subsequent description below, the tool body 5466 could be defined by any suitable number of components between the interface end 5468 and the working end 5470. Similarly, it will be appreciated that the interface end 5468 and/or the working end 5470 could be defined as a part of the tool body 5466 itself, a separate component that is operatively attached to the tool body 5466, and/or a component that is releasably attached to the tool 5042 (e.g., an anchor, a handle assembly, and the like). Other configurations are contemplated. Also formed in the tool body 5466 of each of the tools 5042 is a conduit axial retainer 5472 arranged between the interface end 5468 and the working end 5470 that is engaged by the axial lock AL in the lock configuration ACL (see FIGS. 37B-37C). In this embodiment, the working end 5470 of the rotary cutting tool 5044 corresponds, generally, to the distal cutting end 5044D, and the working end 5470 of the rotary driving tool 5048 corresponds, generally, to the distal tip 5050D of the anchor 5050 secured thereto (see FIG. 36; not shown secured). Further, in this embodiment, the interface end 5468 corresponds, generally, to the bit interface 5128 of either the rotary cutting tool 5044, the rotary driving tool 5048, or another type of tool 5042 secured to the drive assembly 5082 for rotation about the second axis A2.

While similar in configuration, it will be appreciated that the conduit rotational retainer 5464 and the conduit axial retainer 5472 of the tool body 5466 are different from the rotational retainer 5132 and the axial retainer 5130 of the bit interface 5128. Specifically, in the fifth embodiment, rotational retainer 5132 and the axial retainer 5130 of the bit interface 5128 form part of the manual interface 5094 to releasably secure to the handle assembly (not shown in this embodiment), whereas the conduit rotational retainer 5464 and the conduit axial retainer 5472 of the tool body 5466 facilitate releasable attachment of the tool 5042 to the drive assembly 5082 via engagement with the first rotational lock RL1 and the axial lock AL, which effectively serve as the connector in this embodiment. Furthermore, in the fifth embodiment, each of the tools 5042 are configured to engage the same first rotational lock RL1 and the same axial lock AL.

In order to facilitate cooperation with the transmission 5372 to "shift" between the first and second gearsets GS1, GS2, as noted above and described in greater detail below, the tool body 5466 of the rotary driving tool 5048 comprises a first shaft portion 5474, and the tool body 5466 of the rotary cutting tool 5044 comprises a second shaft portion 5476. Both the first shaft portion 5474 and the second shaft portion 5476 are arranged between the interface end 5468 and the working end 5470 of the tool body 5466 (more specifically, between the conduit axial retainer 5472 and the conduit rotational retainer 5464 in this embodiment). Both the first and second shaft portions 5474, 5476 are shaped and arranged to abut, engage, or otherwise contact at least a portion of the selector 5394 of the transmission linkage 5392 of the transmission 5372. As is described in greater detail below, the selector 5394 has a generally tubular profile with a stepped outer profile and a cylindrical inner profile arranged along the second axis A2. Because the second shaft portion 5476 depends further toward the working end 5470 than the first shaft portion 5474 (compare FIGS. 37B-37C), abutment between the selector 5394 of the transmission 5372 and the first shaft portion 5474 facilitates engagement of the first gear set GS1 (see FIG. 37B), whereas abutment between the selector 5394 and the second shaft portion 5476 facilitate engagement of the second gear set GS2 (see FIG. 37C), as described in greater detail below.

Referring now to FIGS. 35-37C, the drive conduit 5462 of the drive assembly 5082 defines a drive bore, generally indicated at 5478, that is shaped for receiving the working end 5470 of the tool 5042 therethrough and along the second axis A2. Put differently, the drive bore 5478 is larger in size than the driver key 5124 of the rotary driving tool 5048 or the distal cutting end 5044D of the rotary cutting tool 5044. Here, the drive assembly 5082 generally defines a proximal inlet 5480 and an opposing distal outlet 5482 with the drive conduit 5462 interposed in communication between the proximal inlet 5480 and the distal outlet 5482 for permitting the working end 5470 of the tool 5042 to be inserted along the second axis A2 into the proximal inlet 5480 and advanced through the drive bore 5478 and out of the distal outlet 5482 toward the surgical site ST (see FIG. 1) when the axial lock AL is in the release configuration ACR. As is best depicted in FIG. 37A, the drive conduit 5462 in this embodiment defines the distal outlet 5482 of the drive bore 5478, but the proximal inlet 5480 is defined by another portion of the drive assembly 5082 as described in greater detail below. However, other configurations are contemplated, and it will be appreciated that the drive conduit 5462 could alternatively define the proximal inlet 5480 or even the entire drive bore 4478 in some embodiments.

In the fifth embodiment, at least a portion of the drive bore 5478 arranged adjacent to the distal outlet 5482 defines the first rotational lock RL1, which is shaped to engage at least a portion of the tool 5042 (here, the conduit rotational retainer 5464) between the interface end 5468 and the working end 5470 when the axial lock AL is in the lock configuration ACL such that the working end 5470 of the tool 5042 is arranged distal to the distal outlet 5482 of the drive bore 5478. Here too, the interface end 5468 of the tool 5042 is arranged proximal to the proximal inlet 5480 of the drive bore 5478 when the axial lock AL is in the lock configuration ACL.

As noted above, the geartrain 5084 of the drive assembly 5082 in the fifth embodiment of the end effector 5040 is provided with the transmission 5372 interposed in rotational communication between the actuator of the rotary instrument 5080 (see FIG. 35; actuator not shown in detail) and the drive conduit 5462. Here too, the transmission 5372 comprises the first gearset GS1, the second gearset GS2, and the shift collar 5386, which is similarly arranged for movement between the first collar position CP1 (see FIG. 37B) and the second collar position CP2 (see FIG. 37C). In the first collar position CP1 shown in FIG. 37B, the shift collar 5386 engages the first gearset GS1 to translate rotation between the actuator of the rotary instrument 5080 (see FIG. 35; actuator not shown in detail) and the drive conduit 5462 at the first drive ratio DR1. In the second collar position CP2 shown in FIG. 37C, the shift collar 5386 engages the second gearset GS2 to translate rotation between the actuator of the rotary instrument 5080 (see FIG. 35; actuator not shown in detail) and the drive conduit 5462 at the second drive ratio DR2.

Figure 37A:
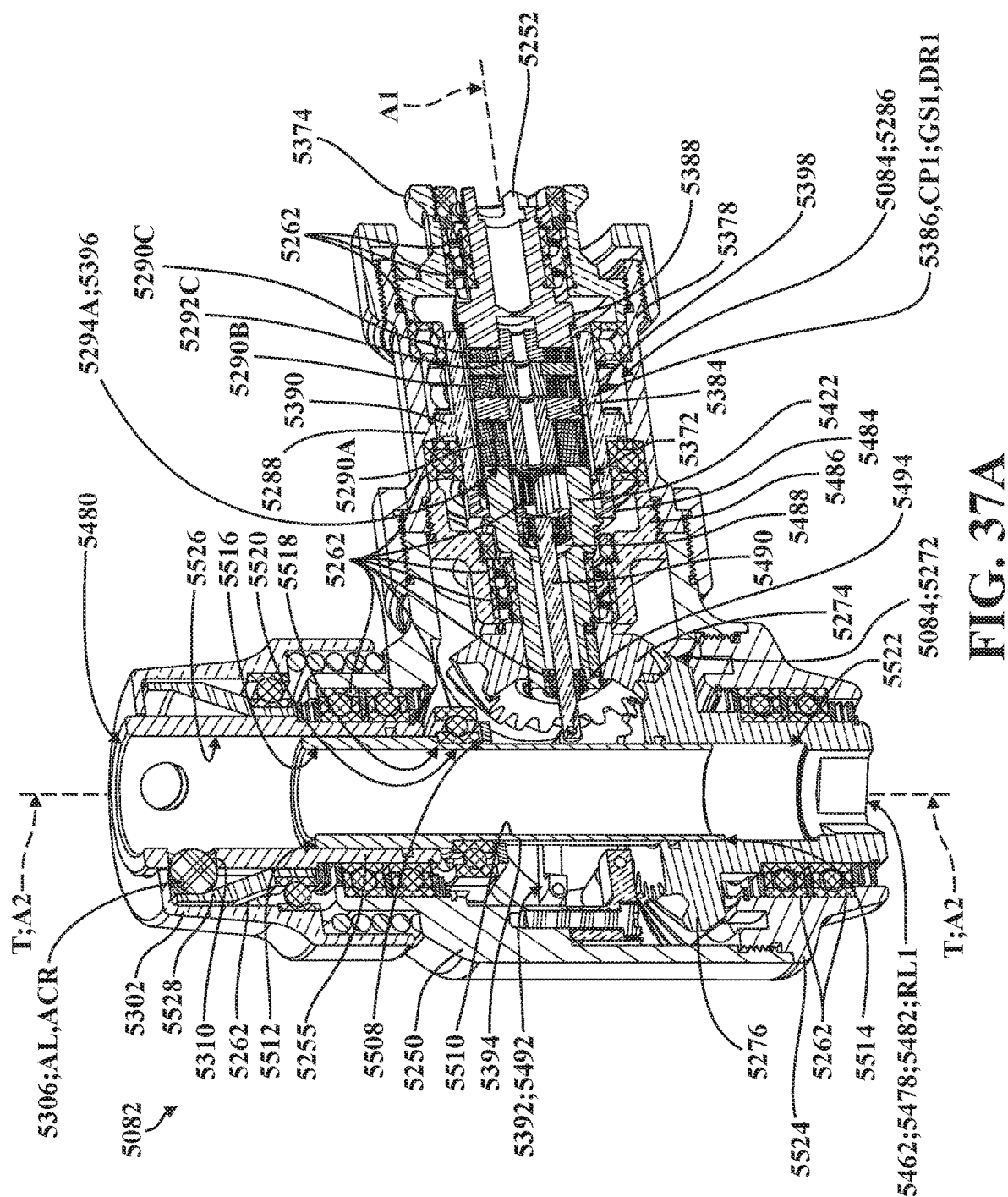
FIG. 37A is a sectional perspective view of the drive assembly of FIG. 36, depicted as sectioned generally longitudinally, shown having a transmission with first and second gearset disposed in rotational communication with the drive conduit.
Figure 37B:
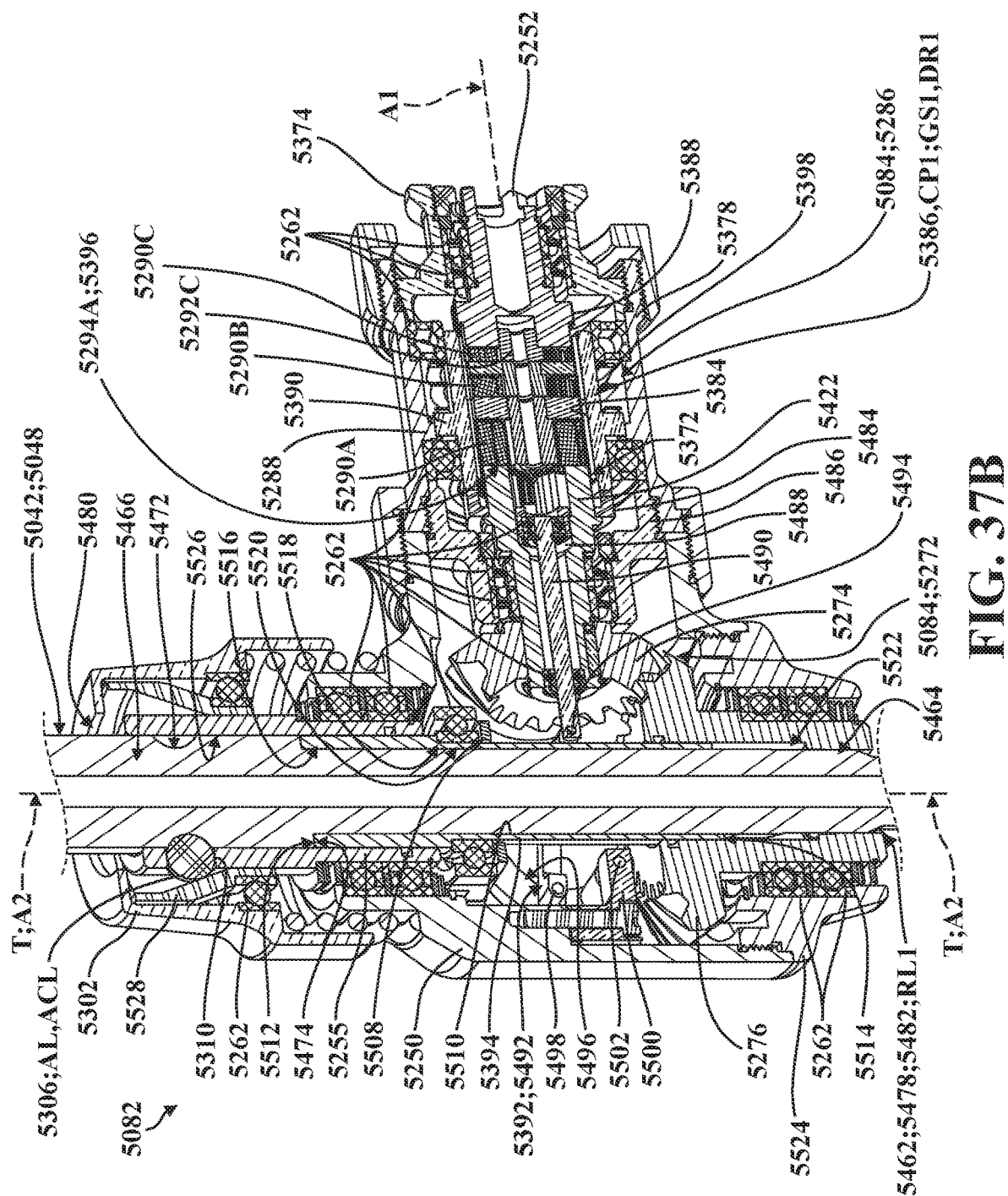
FIG. 37B is another sectional perspective view of the drive assembly of FIG. 37A, partially depicting portions of the rotary driving tool of FIG. 36 secured in the drive conduit and engaging a selector operatively attached to a shift collar of the transmission, and shown with the shift collar disposed in a first collar position to engage the first gearset.
Figure 37C:
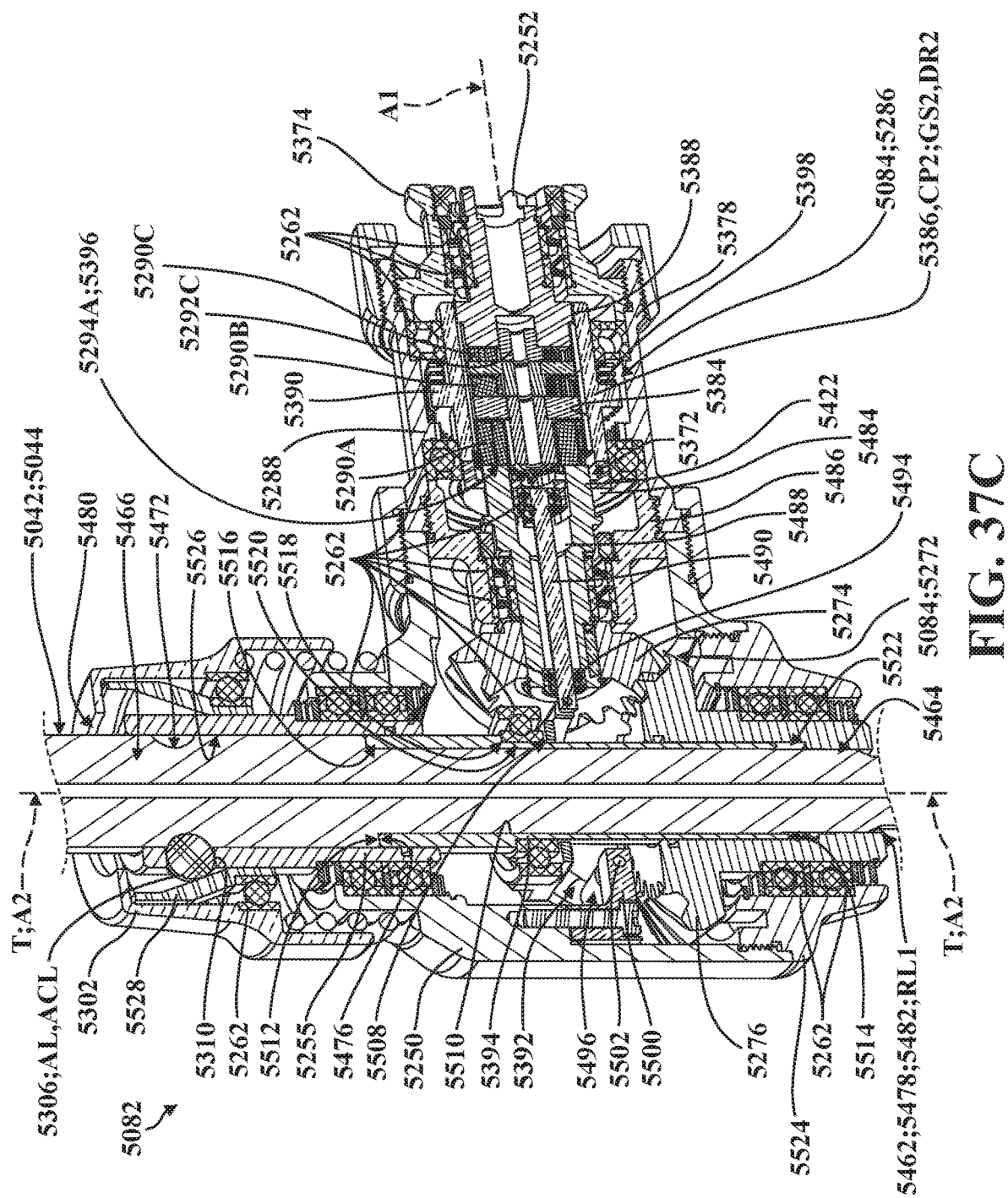
FIG. 37C is another sectional perspective view of the drive assembly of FIG. 37A, partially depicting portions of the rotary cutting tool of FIGS. 35-36 secured in the drive conduit and engaging a selector operatively attached to a shift collar of the transmission, and shown with the shift collar disposed in a second collar position to engage the second gearset.
Figure 38A:
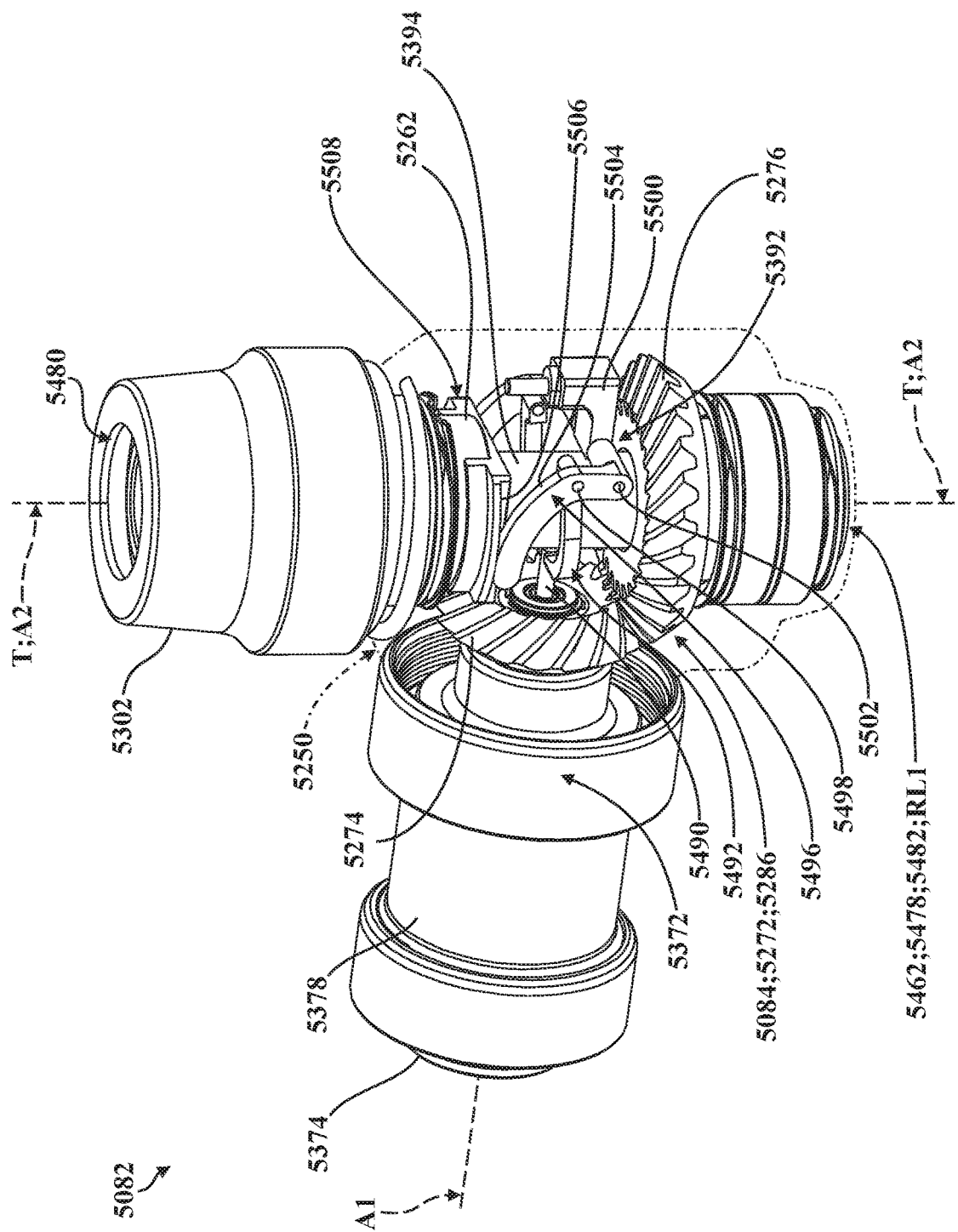
FIG. 38A is a perspective view of the drive assembly of FIGS. 35-37C, shown with the selector of the transmission arranged as depicted in FIG. 37B.
Figure 38B:
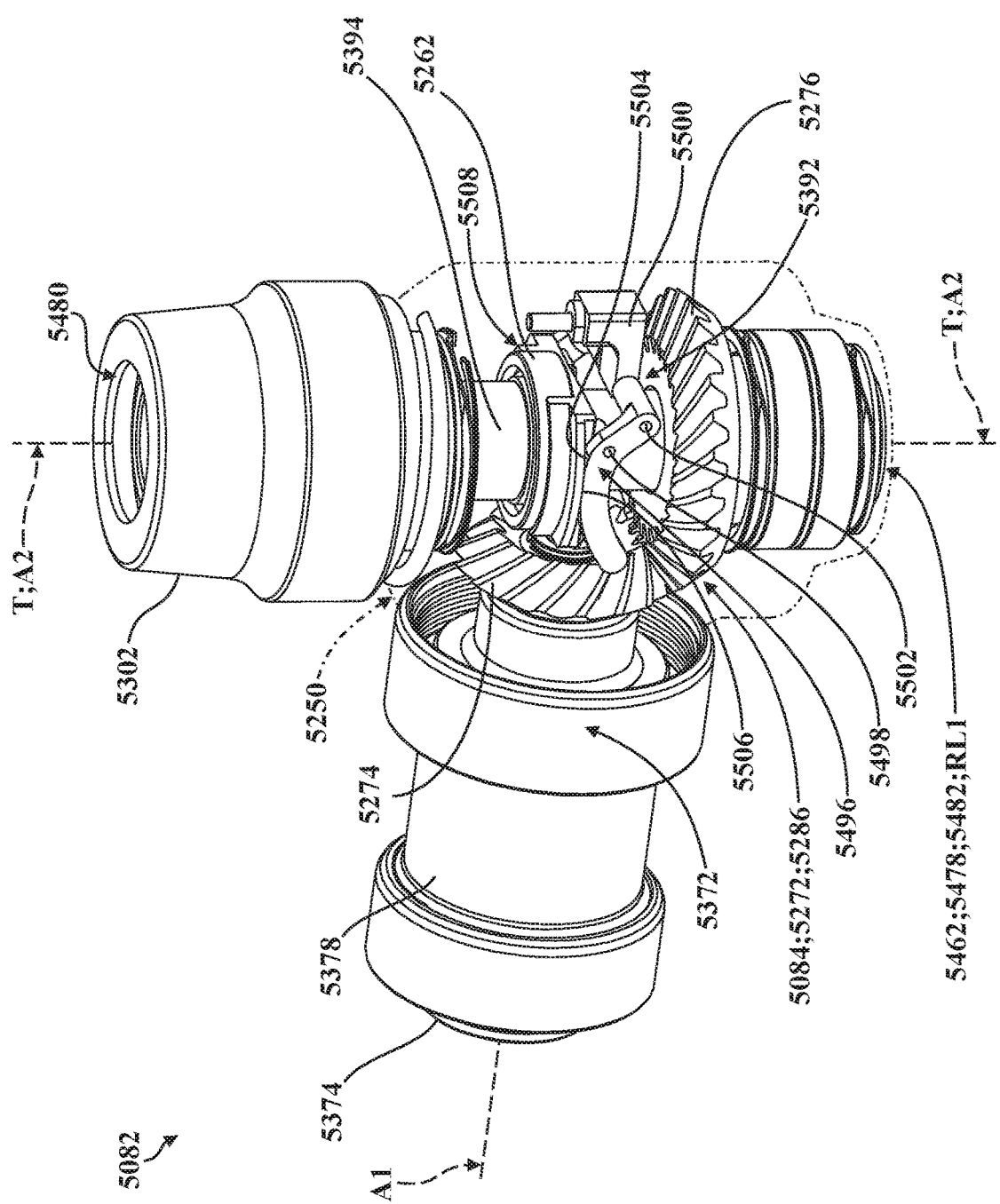
FIG. 38B is a perspective view of the drive assembly of FIGS. 35-37C, shown with the selector of the transmission arranged as depicted in FIG. 37C.

As is best shown in FIGS. 37A-37C, like the third embodiment described above, here too in the fifth embodiment of the end effector 5040, rather than being disposed in meshed engagement with the ring gear 5288, the first, second, and third sets of planet gears 5290A, 5290B, 5290C are each respectively disposed in meshed engagement with the inner teeth 5384 of the shift collar 5386 of the transmission 5372. In this embodiment, however, the inner teeth 5384 of the shift collar 5386 are also arranged to selectively engage the shaft teeth 5388 of the driver input shaft 5252 in splined engagement when the shift collar 5386 is in the second collar position CP2 (see FIG. 37C), whereas in the third embodiment the shaft teeth 3388 are formed on the intermediate shaft 3256. Rotation of the driver input shaft 5252, which is facilitated by bearings 5262 disposed in the input body 5374, occurs concurrently with the third sun gear 5292C. Here too in this embodiment, the outer teeth 5390 of the shift collar 5386 are similarly arranged to selectively engage the ring gear 5288 in splined engagement when the shift collar 5386 is in the first collar position CP1 (see FIGS. 37A-37B).

The ring gear 5288 is formed on the intermediate body 5378 in this embodiment, and movement of the shift collar 5386 occurs substantially within the intermediate body 5378 along the first axis A1 (compare FIGS. 37B-37C). To this end, a selector guide 5484 abuts and moves concurrently with the shift collar 5386 and is similarly shaped so as to permit the braces 5396 to pass therethrough and provide support to the first set of pins 5294A. In this embodiment, the braces 5396 that support the first set of pins 5294A are formed on the carrier shaft 5422, rather than on the retention shaft 3255 as described in connection with the third embodiment of the end effector 3040. The linkage biasing element 5398 is disposed within the intermediate body 5378 in this embodiment, and abuts the shift collar 5386 so as to urge the shift collar 5386 along the first axis A1 toward the first collar position CP1 when the axial lock AL is in the release configuration ACL (see FIG. 37A) or when tools 5042 are not otherwise disposed within the drive conduit 5462.

The input gear 5274 of the bevel gearset 5272 is coupled to the carrier shaft 5422 which, in turn, is supported for rotation by bearings 5262 disposed in a carrier support body 5486 operatively attached to the drive body 5250 and to the intermediate body 5378. The carrier shaft 5422 defines a carrier bore 5488 into which a portion of the selector guide 5484 is disposed and through which a piston element 5490 extends along the first axis A1. The piston element 5490, like the selector guide 5484, forms part of the transmission linkage 5392 in this embodiment. The piston element 5490 is supported by bearings 5262 disposed in the carrier bore 5488 and in the selector guide 5484, and moves concurrently with the selector guide 5484 and the shift collar 5386 between the first and second collar positions CP1, CP2.

Referring now to FIGS. 37A-38B, in order to facilitate concurrent movement of the piston element 5490 and the selector guide 5484 along the first axis A1 in response to corresponding movement of the selector 5394 along the second axis A2, the transmission linkage 5392 also comprises piston link members 5492 pivotally coupled to the piston element 5490 by piston pins 5494. The piston link members 5492 are generally disposed within the drive body 5250 and extend around the selector 5394 in a "wishbone" arrangement. The piston link members 5492 are pivotally connected to respective cam link members 5496 by link pins 5498, and the cam link members 5496 are pivotally coupled to a pivot mount 5500 by cam pins 5502. The pivot mount 5500 is coupled to the drive body 5250 by a fastener and is shaped such that the cam pins 5502 are generally arranged closer to the output gear 5276 than the link pins 5498. The cam link members 5496 each define a respective cam link surface 5504 (see FIGS. 38A-38B) that is disposed in engagement with and slides along a corresponding bearing seat surface 5506 defined by a bearing seat 5508. Here, the bearing seat 5508 supports a bearing 5262 about the second axis A2 which, in turn, supports the selector 5394.

As noted above, the selector 5394 has a stepped outer profile and a generally cylindrical inner profile in the fifth embodiment. More specifically, the selector 5394 comprises a selector bore 5510 that extends between a proximal selector end 5512 and a distal selector end 5514, with a first outer portion 5516 that extends from the proximal selector end 5512 to a selector step 5518, and with a second outer portion 5520 that extends from the selector step 5518 to the distal selector end 5514. Here, the second outer portion 5520 extends through the bearing 5262 disposed on the bearing seat 5508 with the selector step 5518 disposed in abutment with the bearing 5262.

The second outer portion 5520 of the selector 5394 has a generally cylindrical profile and is shaped so as to be received within a second cylindrical region 5522 of the drive bore 5478 arranged above the first rotational lock RL1. As noted above, both the drive bore 5478 and the first rotational lock RL1 are defined by the output gear 5276 in this embodiment. The output gear 5276 is rotatably supported by bearings 5262 disposed in a lower cover 5524 that is operatively attached to the drive body 5250. At least a portion of the second outer portion 5520 of the selector 5394 remains disposed within the cylindrical region 5522 defined by the output gear 5276 when the shift collar 5386 is in either of the collar positions CP1, CP2 (see FIGS. 38A-38C). While the selector 5394 is not specifically arranged for concurrent rotation with the output gear 5276 in the illustrated embodiment, it will be appreciated that the selector bore 5510 can be considered to effectively be an extension of the drive bore 5478 in that it is similarly shaped to receive a portion of the tool 5042 along the second axis A2 in a "top loading" manner. Here too, it will be appreciated that the selector 5394 can be considered to effectively be an extension of the drive conduit 5462 in the fifth embodiment of the end effector 5040.

The first outer portion 5516 of the selector 5394 also has a generally cylindrical profile and is shaped so as to be received within a first cylindrical region 5526 of the retention shaft 5255 which, in this embodiment, is rotatably supported by bearings 5262 disposed in the drive body 5250 and serves as a part of the axial lock AL to engage the conduit axial retainer 5472 formed in the tool body 5466 of the tool 5042. Here in this embodiment, the first cylindrical region 5526 of the retention shaft 5255 defines the proximal inlet 5480 of the drive assembly 5082 and, like the selector bore 5510, can be considered to effectively be an extension of the drive bore 5478 in that it is similarly shaped to receive a portion of the tool 5042 along the second axis A2 in a "top loading" manner. Here too, it will be appreciated that the retention shaft 5255 can be considered to effectively be an extension of the drive conduit 5462 in the fifth embodiment of the end effector 5040.

As shown in FIGS. 37A-37C, in this embodiment the connector element pockets 5310 are formed in the retention shaft 5255 adjacent to the proximal inlet 5480, and are shaped so as to accommodate the axial connector elements 5306 therein. The axial connector elements 5306 are provided with a substantially spherical configuration and move radially with respect to the second axis A2 in response to movement of the flange member 5302 along the second axis A2 (compare FIGS. 37A-37C). Here in this embodiment, the axial ramp surface 5312 is defined by a ramp member 5528 formed as a separate component from the flange member 5302 and supported for rotation relative thereto by a bearing 5262. The ramp member 5528 moves concurrently with the flange member 5302 such that movement of the axial ramp surface 5312 relative to the retention shaft 5255 causes the axial connector elements 5306 to move radially with respect to the second axis A2. The flange member 5302, the ramp member 5528, the retention shaft 5255, and the axial connector elements 5306 cooperate to define the axial lock AL in the fifth embodiment of the end effector 5040, whereby the axial connector elements 5306 move into engagement with the conduit axial retainer 5472 of the tool 5042 when in the lock configuration ACL (see FIGS. 37B-37C), and move away from the second axis A2 so as to come out of engagement with the conduit axial retainer 5472 when in the release configuration ACR (see FIG. 37A; tool 5042 not shown).

Referring now to FIGS. 36-38B, as noted above, the conduit rotational retainer 5464 and the conduit axial retainer 5472 are spaced relative to each other along the tool body 5466 in the same way for both of tools 5042 (here, the rotary cutting tool 5044 and the rotary driving tool 5048) and in a way that corresponds to the relative spacing between the axial lock AL and the first rotational lock RL1 of the drive assembly 5082. However, because the first shaft portion 5474 of the rotary driving tool 5048 and the second shaft portion 5476 of the rotary cutting tool 5044 extend in different ways along the tool bodies 5466 of the respective tools 5042 between the conduit rotational retainer 5464 and the conduit axial retainer 5472, engagement with the proximal selector end 5512 causes the selector 5394 to move to different positions along the second axis A2 depending on which tool 5042 is secured to the axial lock AL (compare FIGS. 37A-37C). In the illustrated embodiment, because the second shaft portion 5476 is arranged closer to the conduit rotational retainer 5464 than the first shaft portion 5474 (see FIG. 36), the selector 5394 moves closer to the first rotational lock RL1 when the rotary cutting tool 5044 is secured to the axial lock AL than when the rotary driving tool 5048 is secured to the axial lock AL (compare FIG. 37C with FIG. 37B).

Because movement of the selector 5394 along the second axis A2 results in corresponding movement of the shift collar 5386 along the first axis A1 via the transmission linkage 5392, it will be appreciated that the transmission 5372 in the fifth embodiment similarly "automatically shifts" between the gearsets GS1, GS2 based on the configuration of the tool 5042 and without requiring the user to "manually shift" the transmission 5372. Rather, movement of the selector 5394 along the second axis A2 also moves the bearing seat 5508, which causes the cam link members 5496 to pivot about the cam pins 5502 secured to the pivot mount 5500 as the cam link surfaces 5504 slide against the bearing seat surfaces 5506 (compare FIGS. 38A-38B). This movement of the cam link members 5496 causes the piston link members 5492 to pivot about the link pins 5498 coupled to the cam link members 5496 which, in turn, causes the piston element 5490 to move within the carrier bore 5488 of the carrier shaft 5422 via the connection afforded by the piston pins 5494. As a result, the piston element 5490 moves concurrently with the selector guide 5484 and the shift collar 5386 between the first and second collar positions CP1, CP2 (compare FIGS. 38B-38C).

As noted above, the drive conduit 5462 of the drive assembly 5082 is configured to releasably secure different types of tools 5042 in a "top loading" manner. This configuration affords significant advantages for certain types of surgical procedures and/or with certain types of tools 5042 based, among other things, on the amount of articulation available via the robotic arm 36 relative to the base 34 and/or relative to the surgical site ST (see FIG. 1). More specifically, "top loading" may advantageously be utilized in scenarios where it is undesirable or impractical to substantially move or otherwise reposition the end effector to provide sufficient clearance relative to the surgical site ST in order to remove one tool and/or subsequently attach another tool, or where the approach utilized by the surgeon results in the robotic arm 36 having been articulated relative to the base 34 in a way that is sufficient for one type of tool but may not be desirable or viable for a different type of tool. Put differently, it is contemplated that certain types of tools may require less overall movement of the robotic arm 36 to facilitate attachment in a "top loading" manner than in a "bottom loading" manner, and it is contemplated that the "top loading" manner can provide improved opportunities for utilizing the articulation range of the robotic arm 36 relative to the base 34 and the surgical site ST than could otherwise be utilized in a "bottom loading" manner.

It will be appreciated that the forgoing examples are illustrative and non-limiting, and that the "bottom loading" manner described in connection with the first, second, third, and fourth embodiments can also be utilized with different tools that are sequentially utilized during a surgical procedure, and may even be preferable to the "top loading" manner in certain situations. Similarly, it will be appreciated that movement of the end effector along the trajectory T in order to facilitate changing between tools may occur or may even be desirable in certain scenarios, both for end effectors that are configured to secure tools in the "bottom loading" manner and also for end effectors that are configured to secure tools in the "top loading" manner. Nevertheless, the "top loading" manner afforded by the fifth embodiment of the end effector 5040 may be particularly advantageous where different, sequentially-utilized tools 5042 differ in length enough that an undesirable amount of movement along the trajectory T would otherwise be needed to completely remove one tool 5042 and provide sufficient clearance to attach another tool 5042 in a "bottom loading" manner.

As noted above, a sixth embodiment of the end effector of the surgical system 30 is shown in FIGS. 39A-44B. In the description that follows, the structure and components of the sixth embodiment that are the same as or that otherwise correspond to the structure and components of the first embodiment of the end effector 40 are provided with the same reference numerals increased by 6000. Because many of the components and features of the sixth embodiment of the end effector 6040 are substantially similar to those of the first embodiment of the end effector 40 described above, for the purposes of clarity, consistency, and brevity, only certain specific differences between the sixth embodiment of the end effector 6040 and the first embodiment of the end effector 40 will be described below, and only some of the components and features common between the embodiments will be discussed herein and depicted in the drawings.

Thus, unless otherwise indicated below, the description of the first embodiment of the end effector 40 may be incorporated by reference with respect to the sixth embodiment of the end effector 6040 without limitation. Likewise, certain components and features of the sixth embodiment of the end effector 6040 that are similar to corresponding components and features of previously-described embodiments may be referred to or otherwise depicted in the drawings as provided with the same reference numerals increased by 1000 plus another 1000 for every intervening embodiment (e.g., for the sixth embodiment, components described in connection with the fifth embodiment would be increased by 1000, components described in connection with the fourth embodiment would be increased by 2000, components described in connection with the third embodiment would be increased by 3000, and components described in connection with the second embodiment would be increased by 4000).

Referring now to FIGS. 39A-44B, the sixth embodiment of the end effector 6040 is generally shown comprising the mount 6078, the rotary instrument 6080 and its actuator 6166 (depicted schematically), and the drive assembly 6082. When compared with the first embodiment described above, the sixth embodiment of the end effector 6040 generally employs a differently-configured trigger assembly 6088 and drive assembly 6082, and is configured to secure tools 6042 in a "top loading" manner through the drive conduit 6462 in a way that is similar to the fifth embodiment. Each of these components will be described in greater detail below.

Figure 39A:
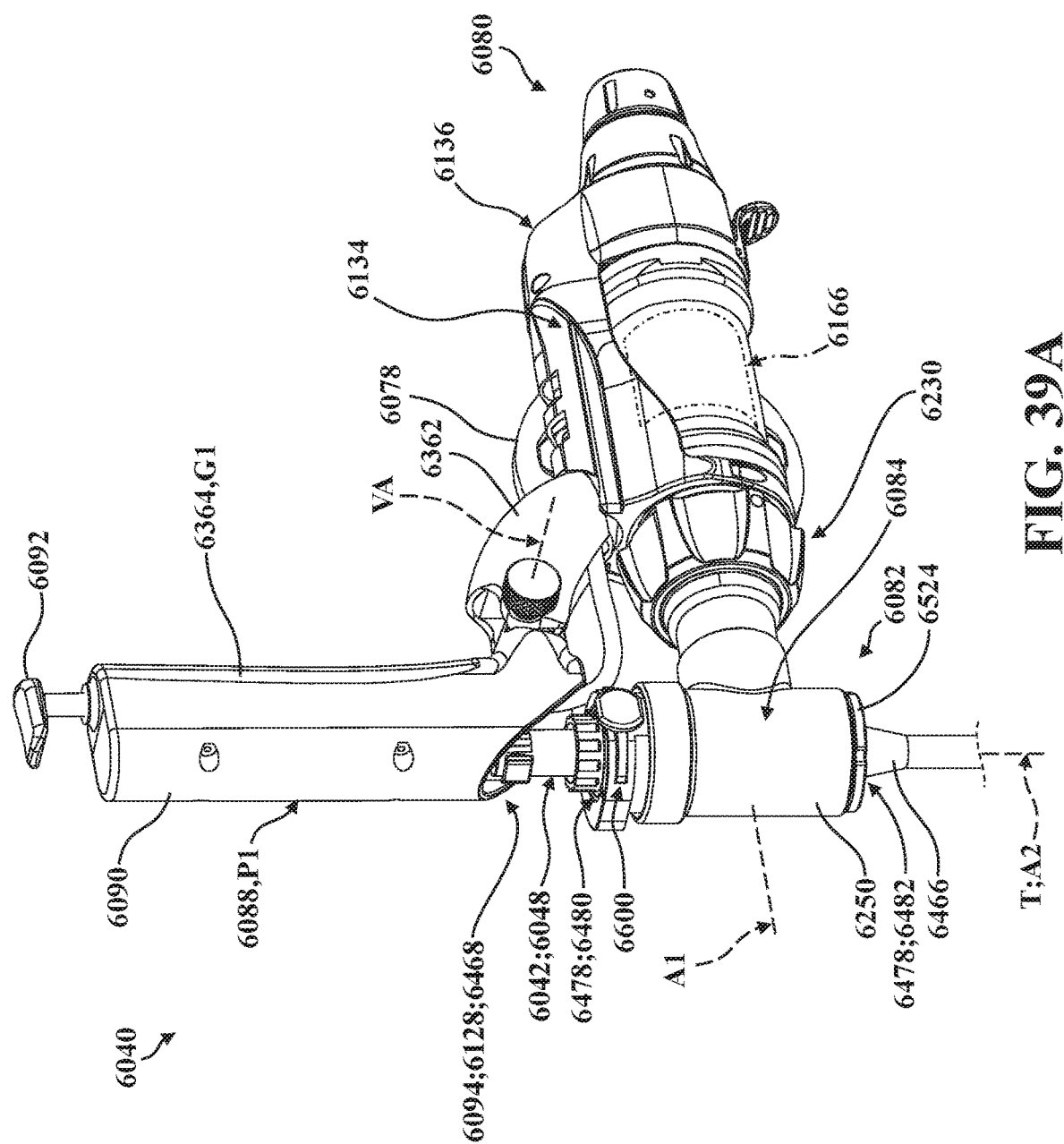
FIG. 39A is a perspective view of an end effector, according to a sixth embodiment of the present disclosure, which is likewise configured for use with the surgical system of FIG. 1, the end effector shown comprising a mount supporting a rotary instrument to generate torque about a first axis, a drive assembly with a drive conduit supporting a tool for rotation about a second axis, and a trigger assembly arranged in a first trigger assembly position and shown having a first and second frame bodies, with the second frame body disposed in a first grip position to limit access to a manual interface defined by the tool.
Figure 39B:
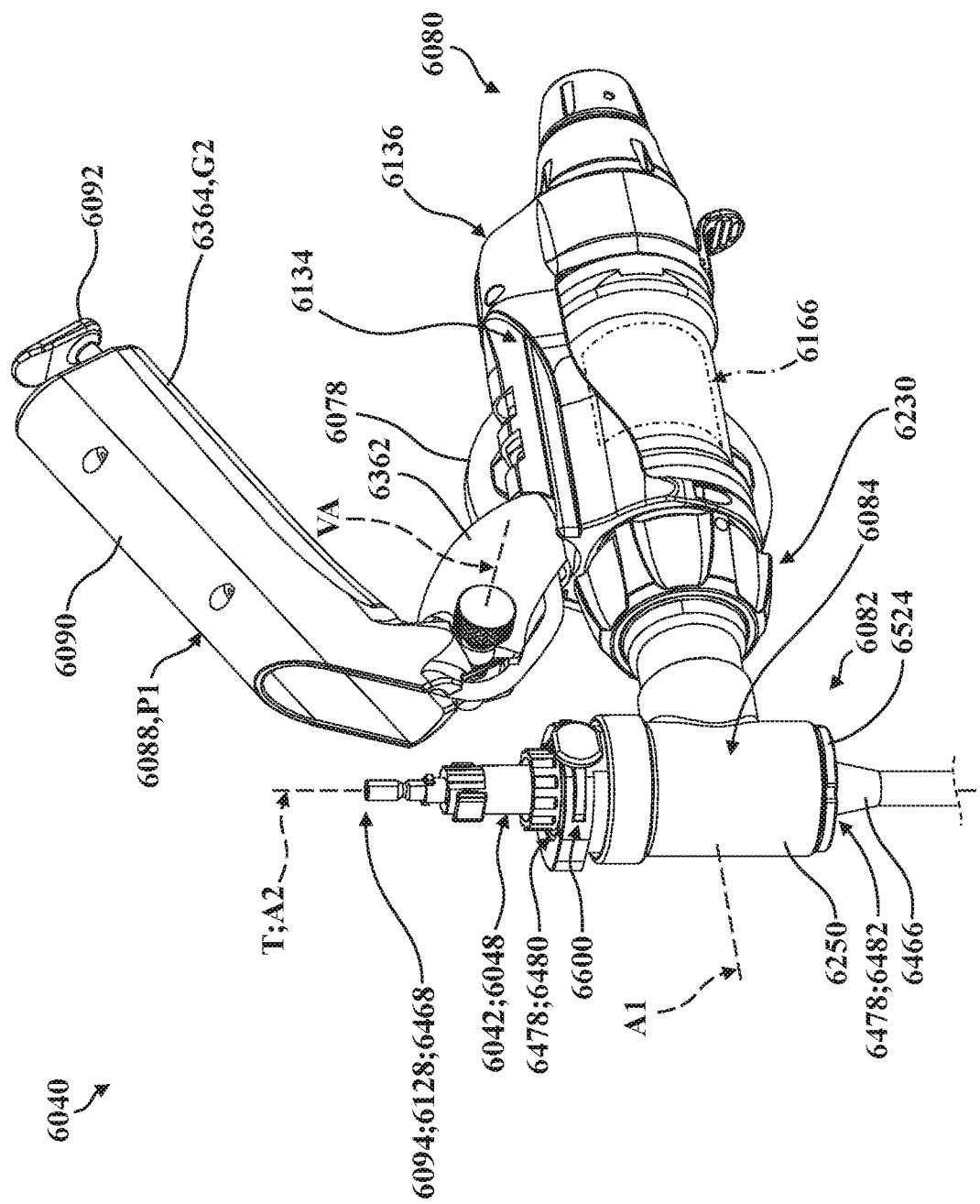
FIG. 39B is another perspective view of the end effector of FIG. 39A, shown with second frame body disposed in a second grip position to promote access to the manual interface defined by the tool.
Figure 39C:
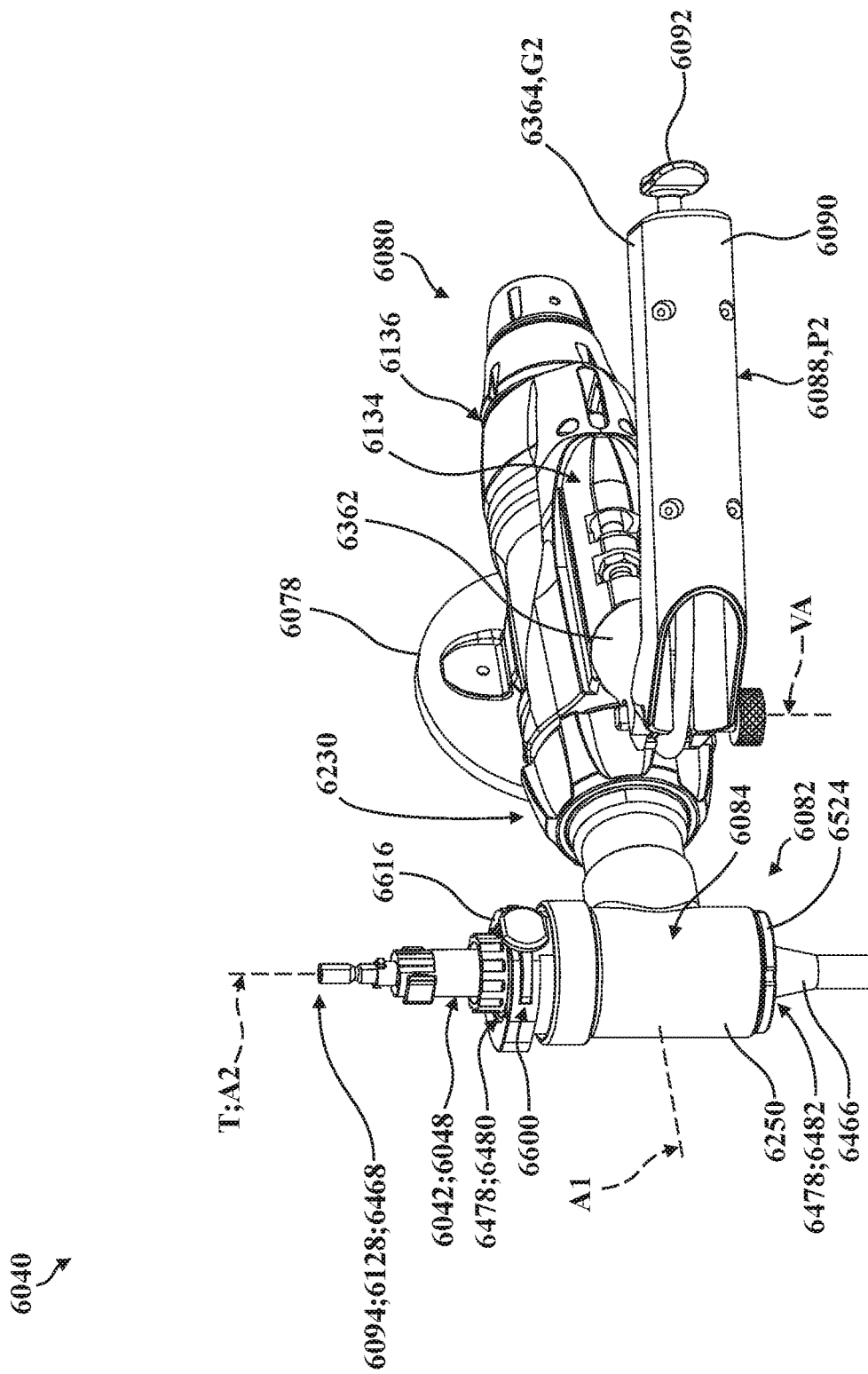
FIG. 39C is another perspective view of the end effector of FIGS. 39A-39B, shown with the trigger assembly arranged in a second trigger assembly position, and shown with the second frame body disposed in the second grip position.
Figure 40:
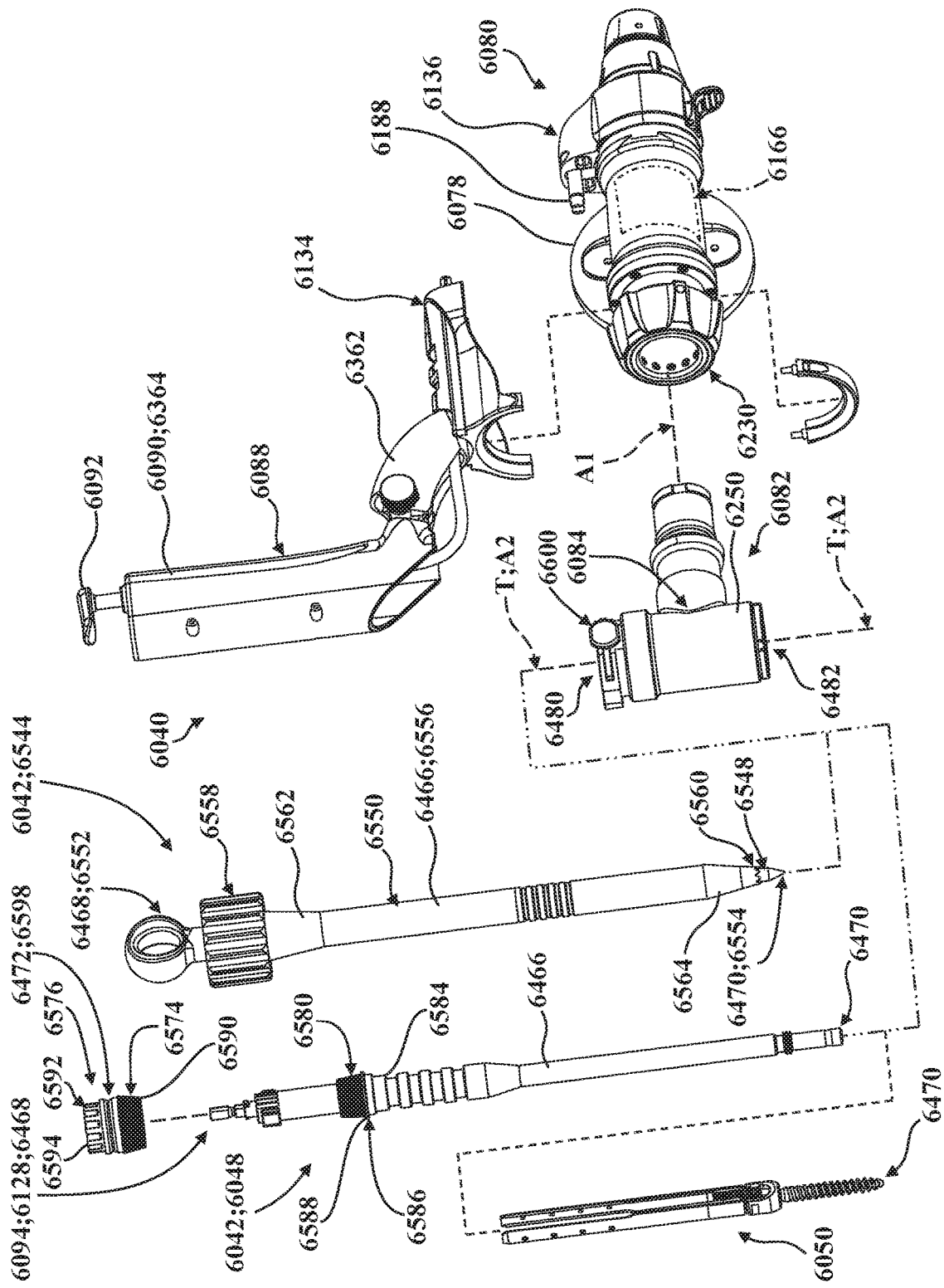
FIG. 40 is an exploded perspective view of the end effector of FIGS. 39A-39C, shown with the trigger assembly and the drive assembly spaced from the rotary instrument, and shown with two tools configured for releasable attachment to the drive conduit of the drive assembly, with one of the tools shown as an rotary driving tool for supporting an anchor to be driven by the rotary instrument along the trajectory maintained by the surgical robot, and with the other of the tools shown as a dissector tool to be guided along the trajectory maintained by the surgical robot.

As is best shown in FIGS. 39A-40, in the sixth embodiment, the drive assembly 6082 is similarly configured for releasable attachment to the rotary instrument 6080 via the coupling 6230 such that the second axis A2 can be moved relative to the first axis A1 by positioning the drive assembly 6082 in different ways about the first axis A1. The trigger assembly 6088 in the sixth embodiment employs a grip 6090 and an input trigger 6092 which are similar in construction to the third embodiment of the trigger assembly 3088 described above. Here too, the frame 6134 of the trigger assembly 6088 is provided with the first frame body 6362 and the second frame body 6364. The first frame body 6362 is similarly coupled to the retainer 6136 for concurrent movement between the plurality of trigger assembly positions, including the first trigger assembly position P1 (see FIGS. 39A-39B) and the second trigger assembly position P2 (see FIG. 39C). Moreover, the second frame body 6364 likewise supports the grip 6090 and the input trigger 6092 for movement relative to the first frame body 6362 between the plurality of grip positions, including the first grip position G1 (see FIG. 39A) and the second grip position G2 (see FIGS. 39B-39C). However, in this embodiment, the second frame body 6364 is arranged for pivoting movement relative to the first frame body 6362 between the first and second grip positions G1, G2 as opposed to the translational movement described and illustrated in connection with the third embodiment.

When in the first grip position G1 as shown in FIG. 39A, at least a portion of the second frame body 6364 limits access to the manual interface 6094 which, like the fifth embodiment described above, is realized by the bit interface 6128 of the tool 6042 that is secured to the drive conduit 6462 in the "top loading" manner in this embodiment. Furthermore, when in the first grip position G1, the input trigger 6092 is similarly arranged for engagement by the user to drive the rotary instrument 6080 to rotate whichever tool 6042 is secured to the drive conduit 6462 about the second axis A2, as described in greater detail below. However, when in the second grip position G2 as shown in FIG. 39B, the second frame body 6364 is disposed in spaced relation to the manual interface 6094 to facilitate receiving applied force from the user to rotate the tool 6042 about the second axis A2. The second frame body 6364 is also arranged for concurrent movement with the first frame body 6362 between the plurality of trigger assembly positions P1, P2 independent of movement between the plurality of grip positions G1, G2 (compare FIGS. 39A-39C).

In the sixth embodiment of the end effector 6040, the second frame body 6364 is arranged for pivoting movement between the first grip position G1 (see FIG. 39A) and the second grip position G2 (see FIG. 39B), the pivoting movement occurring along pivot axis VA arranged substantially perpendicular to both the first axis A1 and the second axis A2. To this end, and as is best shown in FIG. 41, a pivot pin 6530 pivotally couples the first frame body 6362 and the second frame body 6364 together, and a tensioner 6532 operatively attached to the first frame body 6362 extends into a tensioner slot 6534 formed in the second fame body 6364 to limit movement of the second frame body 6364 relative to the first frame body 6362. Here, the tensioner slot 6534 has an arc-shaped profile that effectively defines the first and second grip positions G1, G2, and can also be utilized to provide an adjustable amount of resistance to rotation about the pivot axis VA, or to otherwise "lock" the second frame body 6364 relative to the first frame body 6362 at or between the first and second grip positions G1, G2.

As shown in FIG. 41, in the sixth embodiment, the linkage 6178 of the trigger assembly 6088 employs a cable arrangement, generally indicated at 6536, to facilitate movement of the piston 6182 in response to corresponding movement of the input trigger 6092 between the first and second input positions I1, I2 (first input position I1 shown in FIG. 41). To this end, the cable arrangement 6536 comprises a flexible conduit 6538 that extends between a pair of tensioner assemblies 6540 respectively coupled to the first and second frame bodies 6362, 6364. A wire 6542 (depicted schematically in FIG. 41) is coupled to the input trigger 6092 and the piston 6182, and extends through the tensioner assemblies 6540 and the flexible conduit 6538 such that movement of the input trigger 6092 results in corresponding movement of the piston 6182 which, in turn, engages against and moves the fork guide 6188 of the rotary instrument 6080 (see FIG. 40). This configuration facilitates the pivoting movement of the second frame body 6364 relative to the first frame body 6362 while ensuring that the input trigger 6092 can be moved between the first and second input positions I1, I2 in either the first grip position G1 (see FIG. 39A), the second grip position G2 (see FIG. 39B), or any other grip position therebetween.

Figure 42B:
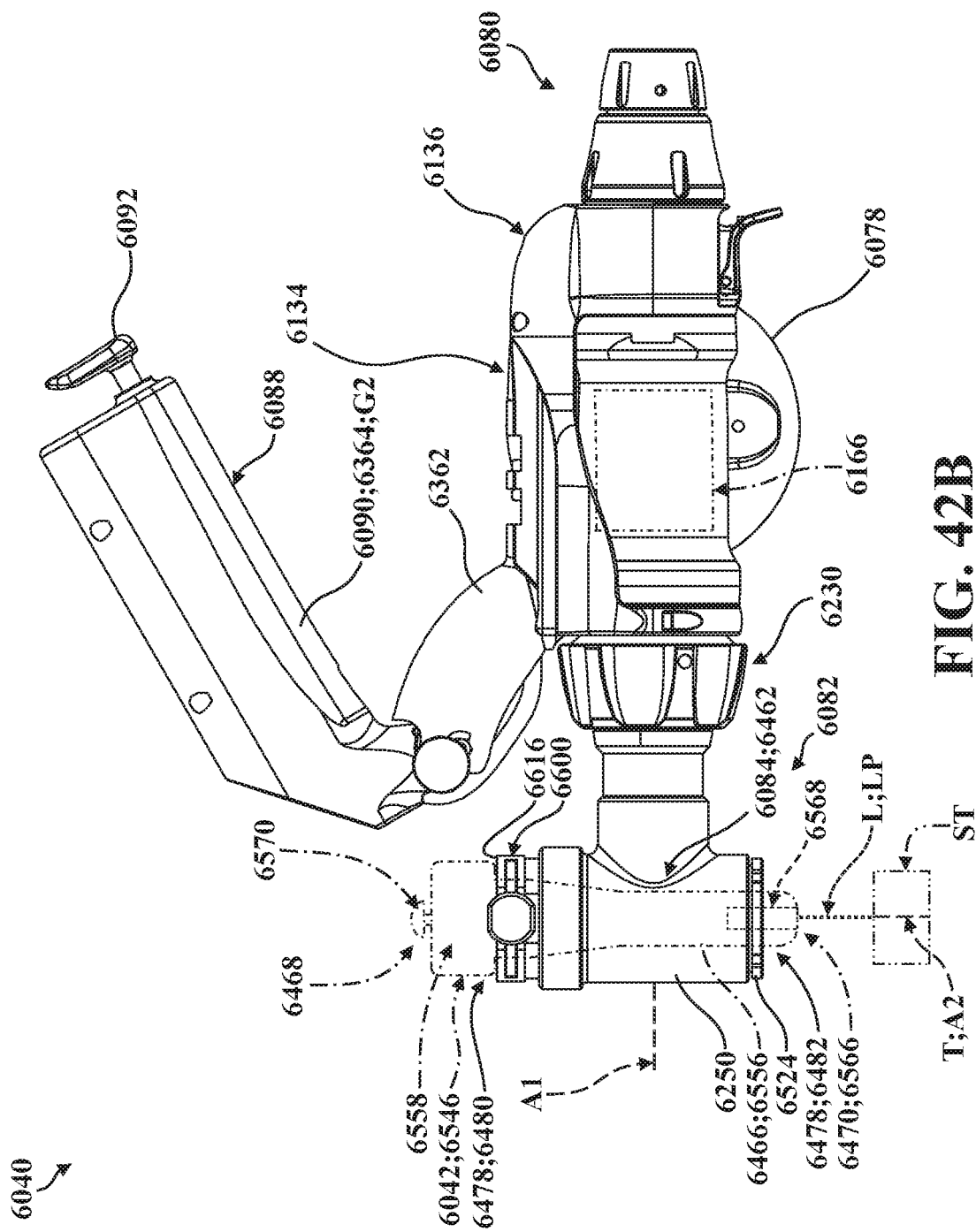
FIG. 42B is a side plan view of the end effector of FIGS. 39A-40, shown with a tool comprising a light source supported in the drive conduit of the drive assembly, with the trigger assembly arranged as depicted in FIG. 39B, and with the light source shown emitting light towards a surgical site along the second axis.

Referring now to FIGS. 40 and 42B, a total of three different exemplary types of tools 6042 are depicted in connection with the sixth embodiment of the end effector 6040, each of which are configured for "top loading" into the drive conduit 6462 of the drive assembly 6082 along the second axis A2 like the fifth embodiment of the end effector 5040 described above. More specifically FIG. 40 shows a dissector tool 6544 and a version of the rotary driving tool 6048 for use in driving the anchor 6050, and FIG. 42B schematically depicts an alignment tool 6546. As is described in greater detail below, the rotary driving tool 6048 has structural differences compared to previously-described embodiments, but is nevertheless configured for releasable attachment to the first rotational lock RL1 and the axial lock AL of the drive assembly 6082 in a "top loading" manner so as to extend through the drive conduit 6462 and be driven about the second axis A2 via the rotary instrument 6080. The dissector tool 6544 and the alignment tool 6546, while still configured to be received within the drive conduit 6462 along the second axis A2, are not configured to attach to the first rotational lock RL1 or the axial lock AL in the illustrated embodiment. Here, the dissector tool 6544 and the alignment tool 6546 are realized as "passive" tools 6042 in that they can be inserted into the drive conduit 6462 along the second axis A2 and positioned relative to the surgical site ST by the surgical robot 32 (see FIG. 1), but are not driven by the rotary instrument 6080 as "active" tools 6042 like the rotary driving tool 6048. Other types of "active" and/or "passive" tools 6042, besides those introduced above, are contemplated by the present disclosure.

In the representative examples illustrated in connection with the sixth embodiment, "passive" tools 6042 such as the dissector tool 6544 and the alignment tool 6546 are permitted to freely rotate about the second axis A2 independent of the drive conduit 6462, and can translate away from the drive conduit 6462 along the second axis A2. Put differently, the "passive" tools 6042 do not engage either the first rotational lock RL1 or the axial lock AL in this embodiment, but can nevertheless be inserted into the drive conduit 6462 along the second axis A2 and can be removed from the drive conduit 6462 without requiring the user to interact with the axial lock AL. In contrast to "passive" tools 6042, "active" tools 6042 do engage both the first rotational lock RL1 and the axial lock AL, rotate concurrently with the drive conduit 6462 about the second axis A2, and require the user to interact with the axial lock AL to facilitate removal from the drive conduit 6462.

While the "passive" tools 6042 illustrated in connection with the sixth embodiment are configured so as to be received within the drive conduit 6462 along the second axis A2 without engaging the first rotational lock RL1 or the axial lock AL, it is contemplated that certain types of "passive" tools 6042 could be configured to engage the axial lock AL but not the first rotational lock RL1 such that free rotation would be permitted about the second axis A2, but translation along the second axis A2 would be inhibited.

Figure 43A:
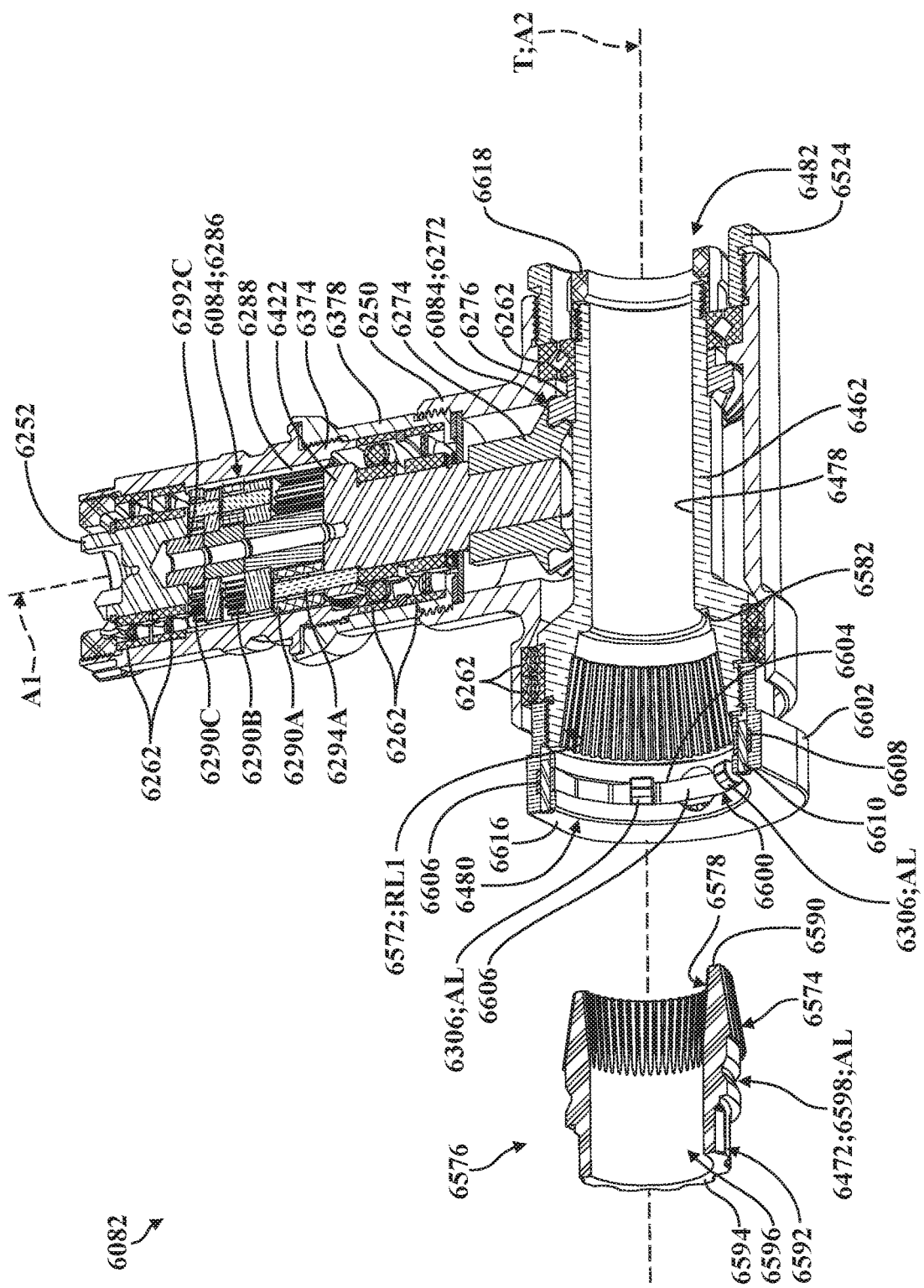
FIG. 43A is a partially-exploded, sectional perspective view of the drive assembly of FIGS. 39A-40, depicted as sectioned generally longitudinally, and shown with an axial lock to releasably secure the rotary driving tool of FIG. 40.
Figure 43B:
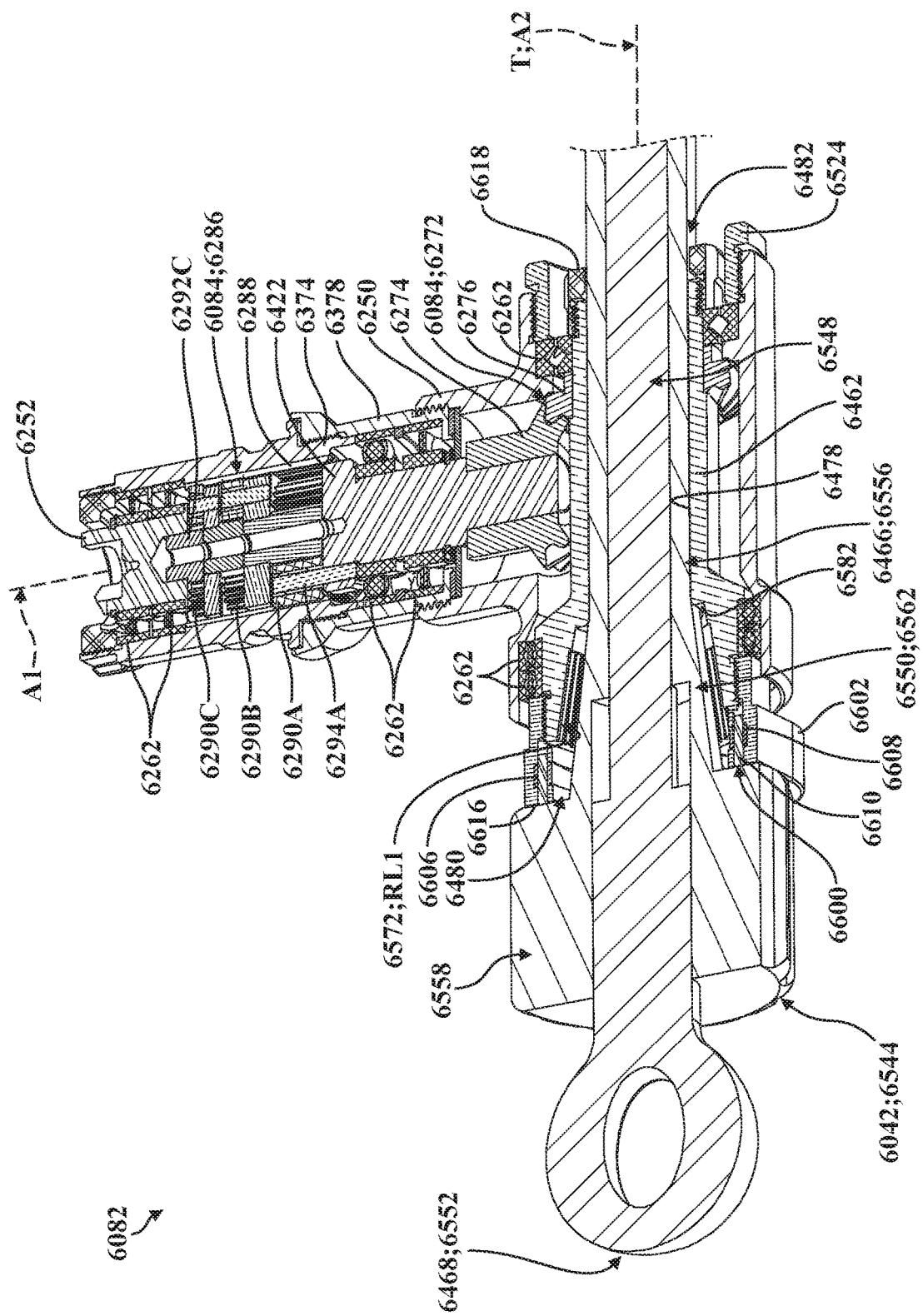
FIG. 43B is a sectional perspective view of the drive assembly of FIG. 43A, shown with the dissector tool of FIG. 40 disposed in the drive conduit.

As is best depicted in FIGS. 40 and 43B, the dissector tool 6544 generally comprises a dissection shaft 6548 and a dissection cannula 6550. The dissection shaft 6548 is shaped to extend through the dissection cannula 6550 between a knob 6552 arranged at the interface end 6468 and a pointed tip 6554 arranged at the working end 6470. The dissection cannula 6550, in turn, comprises a guide body 6556 which extends from a stop element 6558 to a toothed end 6560, with a generally cylindrical profile delineated by a first tapered step 6562 adjacent to the stop element 6558 and a second tapered step 6564 adjacent to the toothed end 6560. Here, the guide body 6556 of the dissection cannula 6550 serves as the tool body 6466 and can be inserted into the drive conduit 6462 along the second axis A2 until abutment between the stop element 6558 and the drive assembly 6082 limits further translational movement along the second axis A2. The dissection cannula 6550 can rotate freely within the drive conduit 6462. The dissection shaft 6548 can be inserted into the dissection cannula 6550 along the second axis A2 until the pointed tip 6554 of the dissection shaft 6548 extends beyond the toothed end 6560 of the guide body 6556. Here too, the dissection shaft 6548 can be rotated freely about the second axis A2 within the dissection cannula 6550. The knob 6552 of the dissection shaft 6548 is shaped and arranged so as to be grasped by the user, such as to facilitate advancing or retracting the dissection shaft 6548 through the dissection cannula 6550. It is also contemplated that the knob 6552 could be employed to facilitate moving or otherwise positioning the end effector 6040 relative to the base 34 of the surgical robot 32 (see FIG. 1) such as in various types of "haptic" or "free" modes that allow articulation of the robotic arm 36 in response to applied force acting on the end effector 6040, which may be utilized during certain steps of surgical procedures to permit movement relative to the surgical site ST (e.g., along the trajectory T or based on various types of virtual boundaries). Thus, the user can grasp the knob 6552 and apply force in certain directions to move the end effector 6040 when the surgical robot 32 (see FIG. 1) operates in one or more "haptic" or "free" modes.

Referring now to FIG. 42B, the alignment tool 6546 is schematically depicted as being disposed within the drive conduit 6462 of the drive assembly 6082. In this illustrative embodiment, the guide body 6556 of the alignment tool 6546 is analogous to the tool body 6466 and extends from the stop element 6558 to a module end 6566 arranged distal to the drive conduit 6462 along the second axis A2 when the stop element 6558 abuts the drive assembly 6082. However, as will be appreciated from the subsequent description below, the module end 6566 could be arranged differently, such as to be disposed within the drive bore 6478, without departing from the scope of the present disclosure.

A light source, generally indicated at 6568, is coupled to the guide body 6556 adjacent to the module end 6566 of the alignment tool 6546 in the illustrated embodiment. The light source 6568 is configured to emit light L toward the surgical site ST along a light path LP that is substantially aligned with the second axis A2 (and, thus, the trajectory T) when the alignment tool 6546 is inserted along the second axis A2 into the drive conduit 6462 of the drive assembly 6082. Here, an activation button 6570 is coupled to the stop element 6558 may be disposed in electrical communication with the light source 6568 to facilitate selectively emitting light L when actuated by the user. A battery or another type of power source (not shown) may be disposed within the guide body 6556 to power the light source 6568. The light source 6568 may be configured as a laser diode in some embodiments. Depending on the specific configuration of the light source 6568, emitted light L may visualized as a "dot" aligned along the trajectory T that is projected onto the surgical site ST, and may also be visualized as a "beam" aligned along the light path LP (and, thus, along the trajectory T) in some embodiments. It will be appreciated that the light source 6568 can be configured to emit light L at any suitable wavelength sufficient to be visualized in any suitable way. By way of non-limiting example, light L can be visualized directly (e.g., within the visible spectrum) and/or visualized indirectly (e.g., with a camera feed presented on a display screen).

Furthermore, it will be appreciated that a variety of different types of light sources 6568 may be utilized, in addition to or in the place of the light sources 6568 illustrated throughout the drawings and described herein. By way of non-limiting example, light sources may be provide to direct or otherwise emit light L generally toward the surgical site ST, such as for general illumination purposes. In some embodiments, light sources 6568 may be configured similar to as is described in U.S. Patent Application Publication No. US 2013/0053648 A1, entitled "Surgical Tool for Selectively Illuminating a Surgical Volume," the disclosure of which is hereby incorporated by reference in its entirety. It will be appreciated that other types and configurations of anchors 50, and the associated installation thereof, are contemplated by the present disclosure. Furthermore, it will be appreciated that other types of optical devices (e.g., cameras) could be employed in some embodiments. Other configurations are contemplated.

Because the alignment tool 6546 is configured for removable attachment to the drive conduit 6462 of the drive assembly 6082, the light source 6568 and/or the entire alignment tool 6546 may be configured as a "single use" component that is discarded for recycling or reprocessing after the surgical procedure. Alternatively, the light source 6568 and/or the alignment tool 6546 may be configured as a "multiple use" component that is sterilized after the surgical procedure. Other configurations are contemplated.

In the representative embodiment illustrated in FIG. 42A, the light source 6568 is not configured for removable attachment to the drive conduit 6462 of the drive assembly 6082. Rather, in this embodiment, light source 6568 and the activation button 6570 are coupled to the second frame body 6364 of the trigger assembly 6088 for concurrent movement relative to the first frame body 6362. Here, when the second frame body 6364 is arranged in the first grip position G1 as depicted in FIG. 42A, light L can be emitted by the light source 6568 through the drive conduit 6462, along the light path LP aligned with the second axis A2 (and, thus, the trajectory T) toward the surgical site ST. With this configuration, the light source 6568 can be utilized both when tools 6042 are removed from the drive conduit 6462 and also when tools 6042 that are cannulated along the second axis A2 (e.g., to receive a guidewire GW; not shown in this embodiment) are positioned within the drive conduit 6462. Furthermore, similar to as is described above in connection with FIG. 42B, the light source 6568 could be of other types, configurations, and the like, and may comprise a variety of different optical devices (e.g., cameras, lights for general illumination, and the like). Other configurations are contemplated.

Figure 43C:
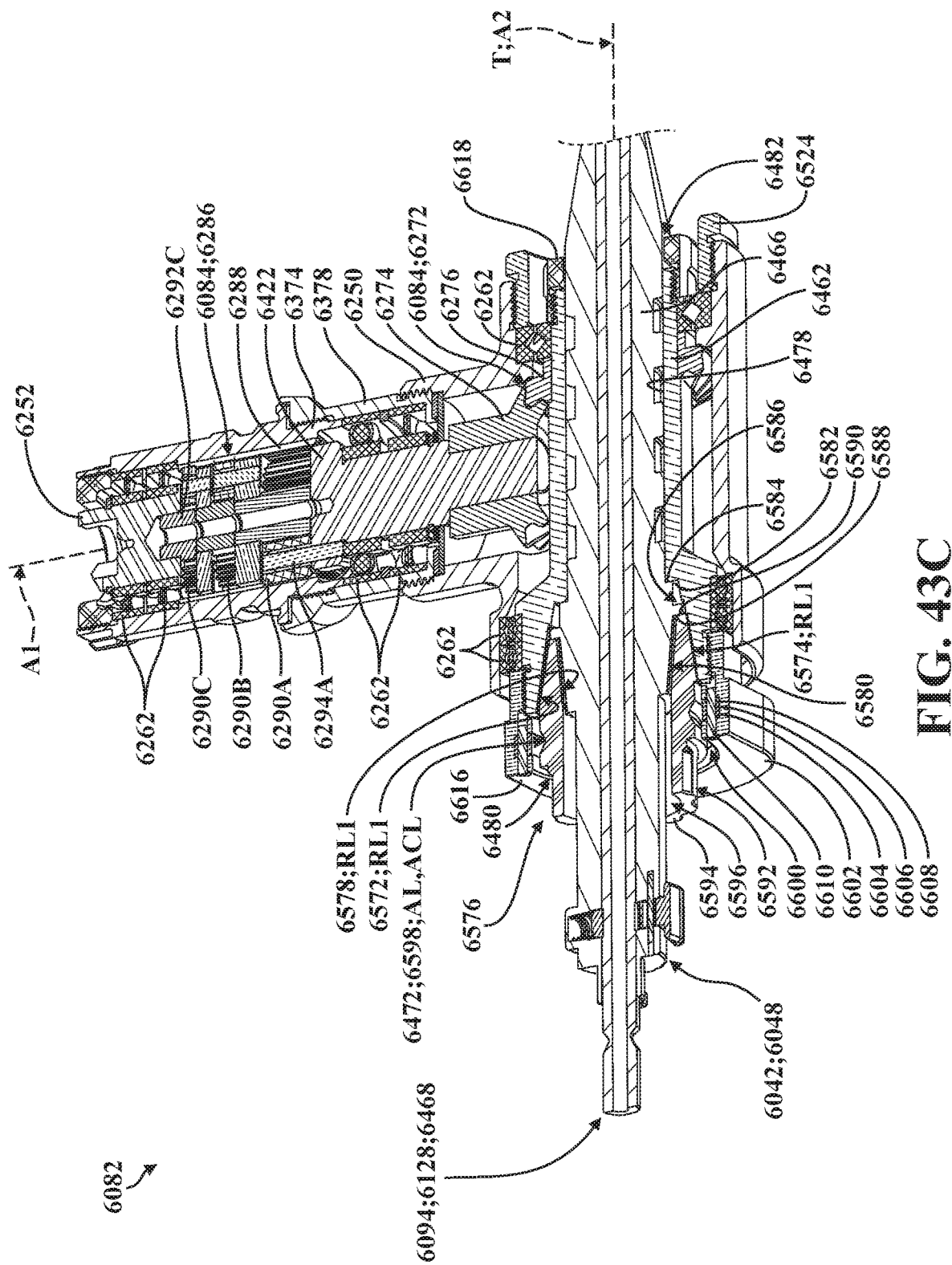
FIG. 43C is a sectional perspective view of the drive assembly of FIGS. 43A-43B, shown with the rotary driving tool of FIG. 40 secured to the drive conduit by the axial lock and by a rotational lock.

As shown in FIGS. 43A-43C, the geartrain 6084 of the drive assembly 6082 similarly employs the bevel gearset 6272 in the sixth embodiment to translate rotation about the first axis A1 into rotation about the second axis A2. To this end, the input gear 6274 is coupled to the carrier shaft 6422 for concurrent rotation about the first axis A1, and the output gear 6276 is coupled to the drive conduit 6462 for concurrent rotation about the second axis A2, with the drive conduit 6462 supported for rotation by bearings 6262 disposed in the drive body 6250. Like the fifth embodiment of the end effector 5040 described above, the bevel gearset 6272 also affords a reduction between the input gear 6274 and the output gear 6276, and utilizes a planetary type reduction gearset 6286 arranged along the first axis A1. Here, rotation of the driver input shaft 6252, which is facilitated by bearings 6262 disposed in the input body 6374, occurs concurrently with the third sun gear 6292C. The carrier shaft 6422 is supported for rotation about the first axis A1 by bearings 6262 disposed in the intermediate body 6378 and is operatively attached to the first set of pins 6294A. Each of the first, second, and third sets of planet gears 6290A, 6290B, 6290C are disposed in meshed engagement with the ring gears 6288, which is formed in the input body 6374 in this embodiment.

Referring now to FIGS. 40 and 43A-44B, in the sixth embodiment of the end effector 6040, the first rotational lock RL1 is realized as a splined bore defined by drive splines 6572 formed in the drive conduit 6462 adjacent to the proximal inlet 6480 of the drive bore 6478. The drive splines 6572 releasably engage with corresponding outer transition splines 6574 of a transition gear 6576 that are configured for releasable attachment to the axial lock AL to facilitate retention of "active" tools 6042, as described in greater detail below. The transition gear 6576 also comprises inner transition splines 6578 that releasably engage with corresponding tool splines 6580 formed in the tool body 6466 of "active" tools 6042. The drive splines 6572 formed in the drive conduit 6462, have a generally frustoconical profile that tapers inwardly relative to the second axis A2 toward the distal outlet 6482. The outer transition splines 6574 of the transition gear 6576 are shaped complimentarily to the drive splines 6572 so as to be disposed in meshed engagement therewith (see FIGS. 43C-43D). The inner transition splines 6578 also have a generally frustoconical profile, but tapers inwardly relative to the second axis A2 toward the proximal inlet 6480 rather than toward the distal outlet 6482 like the drive splines 6572. Here too, the tool splines 6580 formed in the tool body 6466 of "active" tools 6042 are shaped complimentarily to the inner transition splines 6578 of the transition gear 6576 so as to be disposed in meshed engagement therewith (see FIGS. 43C-43D).

The drive splines 6572 are arranged proximal to a drive shelf 6582 formed in the drive conduit 6462. The drive shelf 6582 has a flat, ring-shaped profile that faces away from the distal outlet 6482 and is shaped and arranged to engage against an abutment face 6584 formed on the tool body 6466 of "active" tools 6042 secured via the axial lock AL, as described in greater detail below. This configuration helps ensure that the tool body 6466 is positioned properly relative to the drive conduit 6462 along the second axis A2 when the axial lock AL is in the lock configuration ACL by limiting how far the tool body 6466 can be advanced into the drive bore 6478.

Figure 43D:
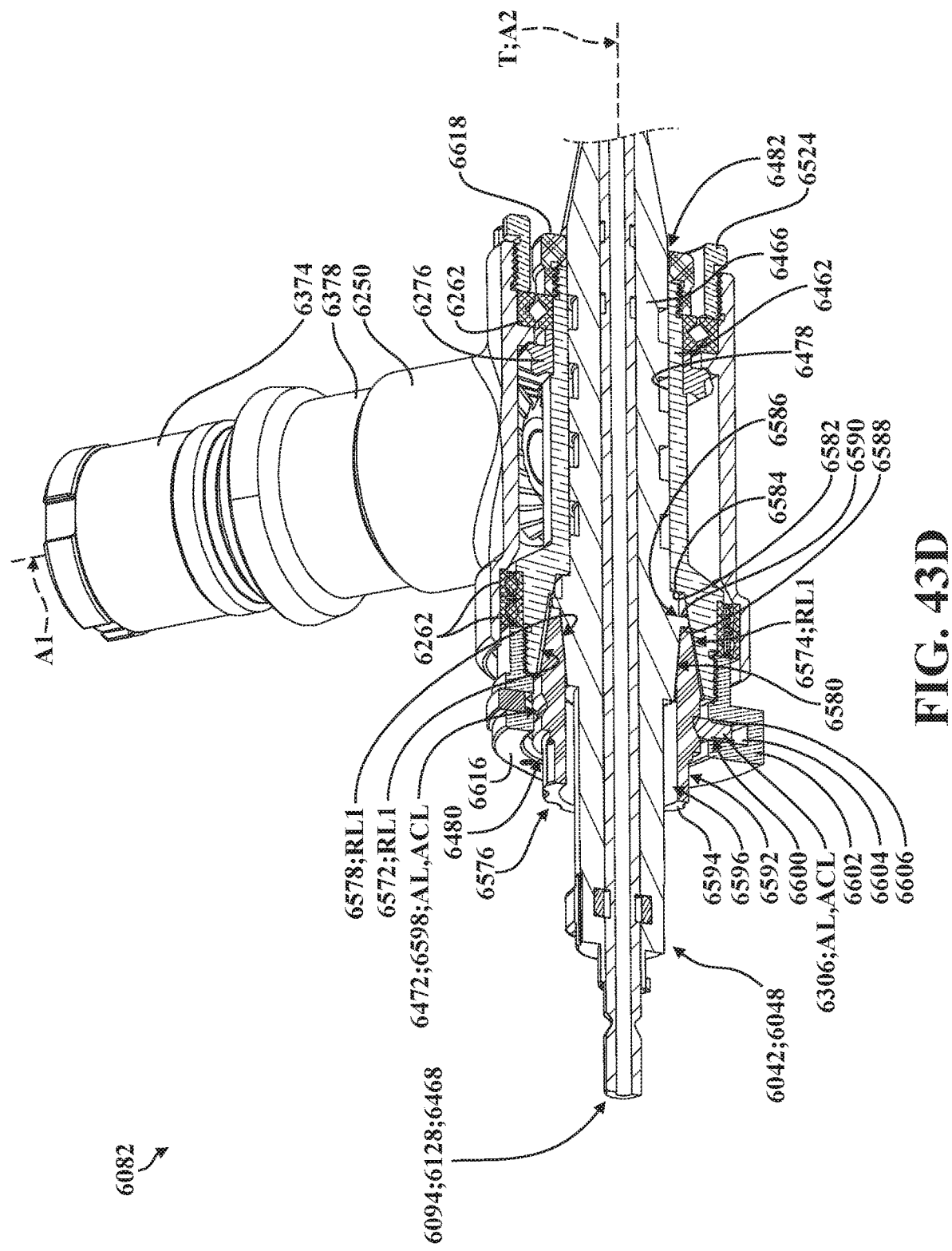
FIG. 43D is another sectional perspective view of the drive assembly, the rotary driving tool, and the rotational lock of FIG. 43C, depicted as sectioned along a plane (not shown) arranged about the second axis and disposed at acute angle relative to a longitudinal plane (not shown) arranged about the first axis.

As is best shown in FIGS. 43C-43D, the tool body 6466 of "active" tools 6042 in the sixth embodiment also comprises an engagement flange 6586 arranged between the abutment face 6584 and the tool spline 6580. The engagement flange 6586 defines a flange face 6588 facing away from the abutment face 6584. Here, the flange face 6588 is shaped and arranged to engage against a transition face 6590 of the transition gear 6576. The transition gear 6576 also comprises a handling portion 6592 that extends away from the transition face 6590 to a handling face 6594, and defines a transition bore 6596 that extends along the second axis A2 between the handling face 6594 and the transition face 6590 with the inner transition splines 6578 formed in or otherwise defined by the transition bore 6596. A transition notch 6598 arranged between the handling portion 6592 and the outer transition splines 6574 of the transition gear 6576 is provided to facilitate restricting relative movement with and between both the drive conduit 6462 and the tool body 6466 of "active" tools 6042 when the axial lock AL is in the lock configuration ACL to secure the tool 6042 for concurrent rotation with the drive conduit 6462 about the second axis A2.

While not formed as a portion of the tool 6042 in the sixth embodiment, the transition notch 6598 serves as the conduit axial retainer 6472 via engagement with a pair of axial connector elements 6306 that form part of a locking assembly, generally indicated at 6600. As is best shown in FIGS. 43A and 43D-44B, the locking assembly 6600 comprises a locking housing 6602 that is operatively attached to the drive conduit 6462 for concurrent rotation about the second axis A2. The locking housing 6602 effectively defines the proximal inlet 6480 of the drive bore 6478 and is likewise shaped to receive the working end 6470 of the tool 6042 therethrough along the second axis A2. The locking housing 6602 is provided with a slider slot 6604 in which a slider element 6606 is supported for movement in a direction substantially perpendicular to the second axis A2. The axial connector elements 6306 are operatively attached to the slider element 6606 for concurrent movement relative to the locking housing 6602, and cooperate to define the axial lock AL via engagement with the transition notch 6598.

Figure 44A:
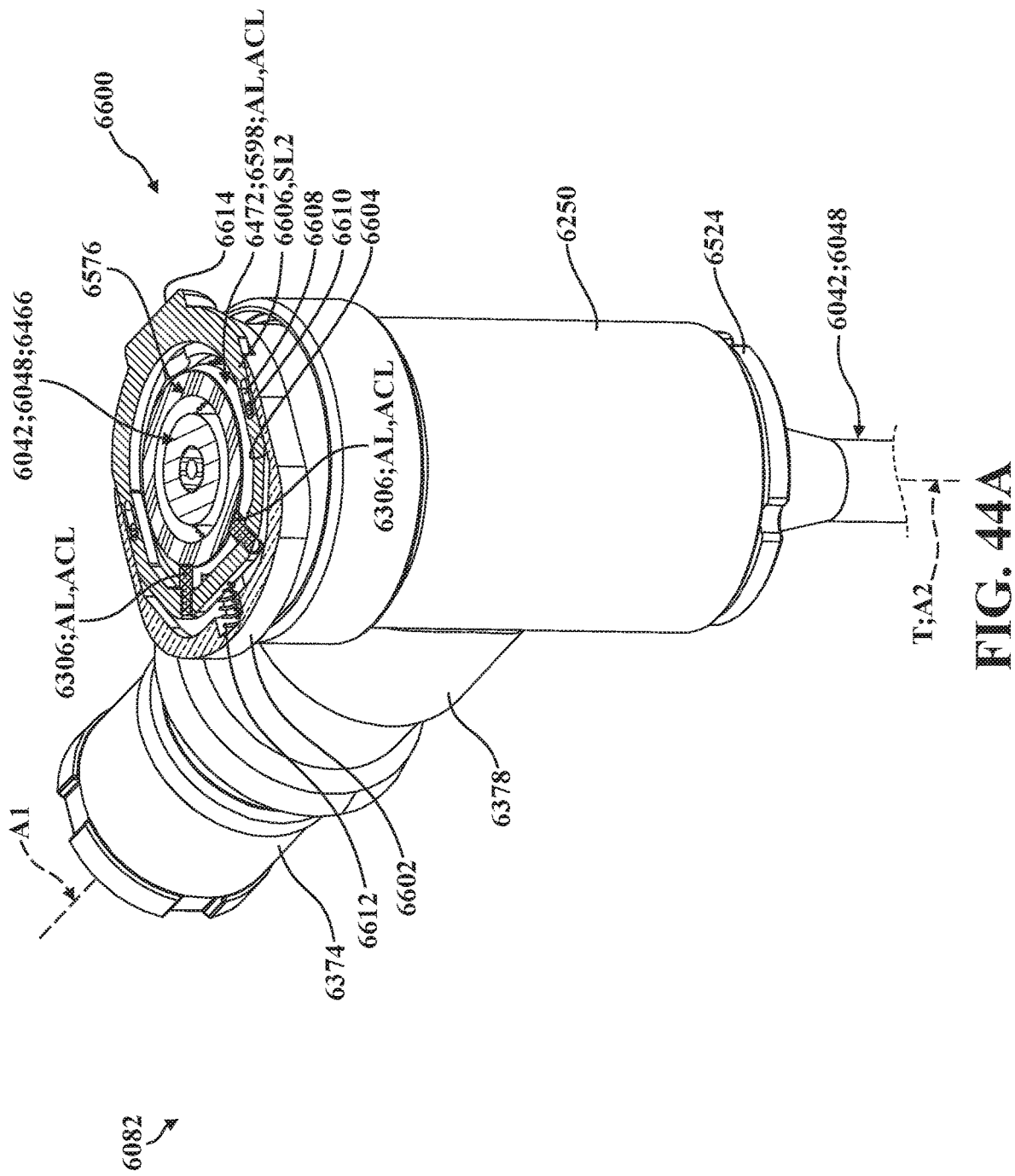
FIG. 44A is another sectional perspective view of the drive assembly, the rotary driving tool, and the rotational lock of FIGS. 43C-43D, depicted as sectioned along a plane (not shown) arranged perpendicular to the second axis and through the axial lock shown arranged in a lock configuration.
Figure 44B:
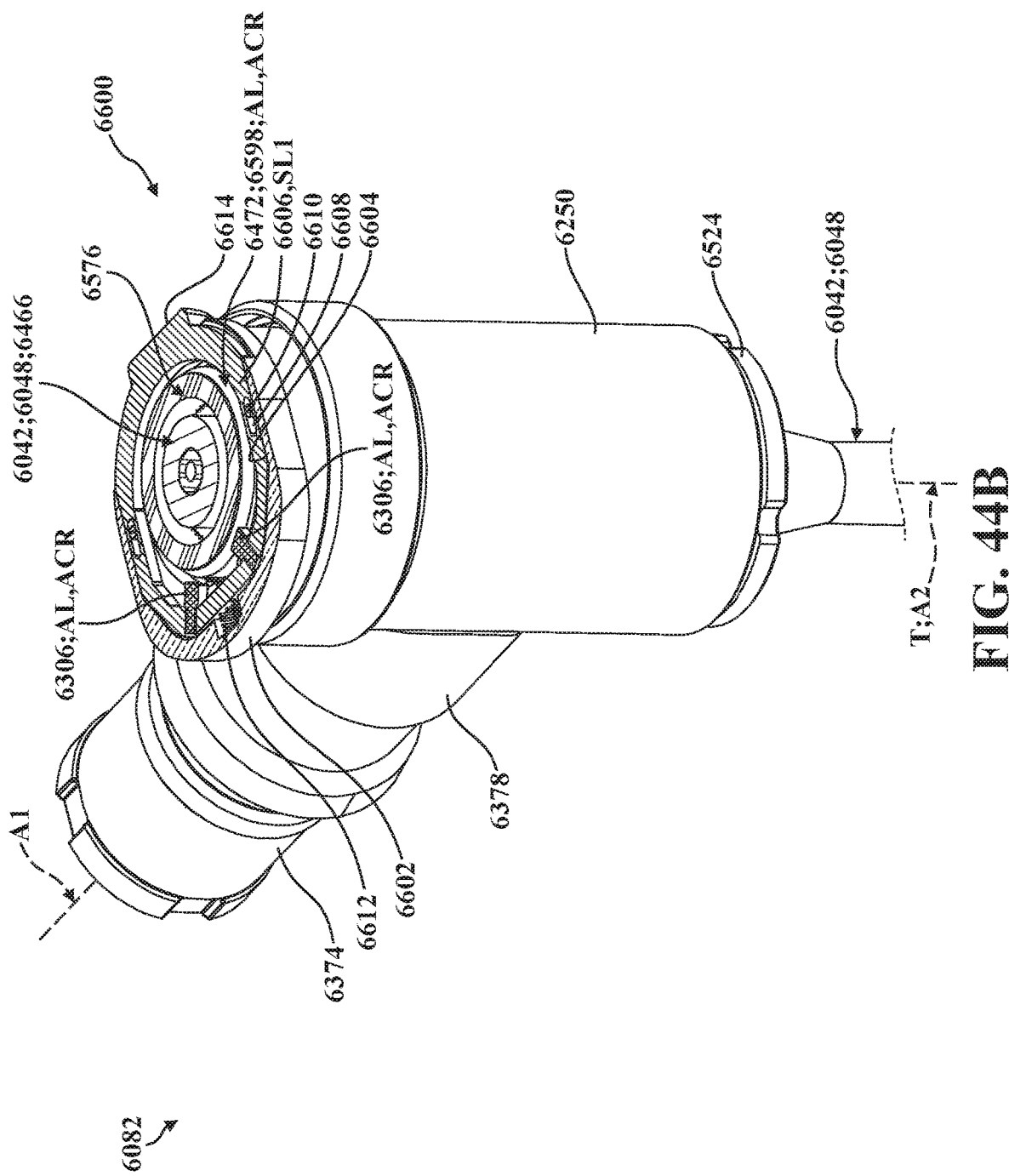
FIG. 44B is another sectional perspective view of the drive assembly, the rotary driving tool, and the rotational lock of FIG. 44A, shown with the axial lock arranged in a released configuration.
Figure 45:
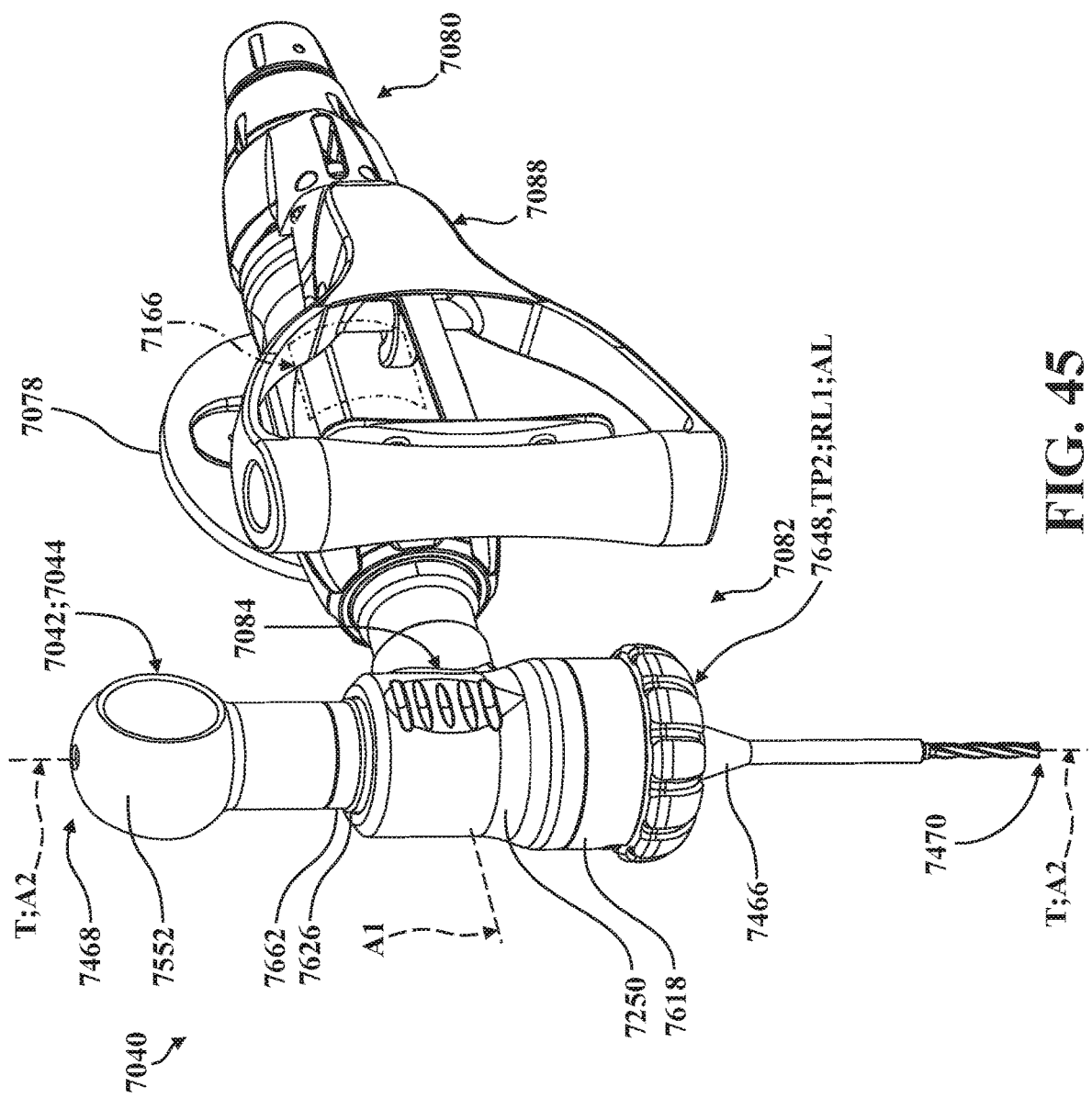
FIG. 45 is a perspective view of an end effector, according to a seventh embodiment of the present disclosure, which is likewise configured for use with the surgical system of FIG. 1, the end effector shown comprising a mount supporting a rotary instrument to generate torque about a first axis, a drive assembly with a drive conduit supporting a tool for rotation about a second axis, and a trigger assembly.

As is best shown in FIGS. 44A-44B, the slider element 6606 defines guide slots 6608 in which guide pins 6610 operatively attached to the locking housing 6602 are disposed. Here, cooperation between the guide slots 6608 and the guide pins 6610 retains the slider element 6606 within the slider slot 6604 for movement relative to the second axis A2 between a first slider element position SL1 associated with the release configuration ACR (see FIG. 44B), and a second slider element position SL2 associated with the lock configuration ACL (see FIG. 44A). The axial connector elements 6306 coupled to the slider element 6606 are disposed closer to the second axis A2 when in the second slider element position SL2 than in the first slider element position SL1. A slider biasing element 6612 disposed within the slider slot 6604 and interposed between the slider element 6606 and the locking housing 6602 urges the slider element 6606 toward the second slider element position SL2. A slider engagement button 6614 is provided integrally formed with the slider element 6606 and is arranged for engagement by the user to move from the second slider element position SL2 to the first slider element position SL1. The slider engagement button 6614 is arranged generally perpendicular to a stop face 6616 defined by the locking housing 6602, which serves as the portion of the drive assembly 6082 that abuts the stop element 6558 of "passive" tools 6042 (see FIG. 43B).

Referring now to FIGS. 43C-44B, in order to facilitate attachment of "active" tools 6042 to the drive conduit 6462 of the drive assembly 6082, the working end 6470 can be inserted into the proximal inlet 6480 of the drive bore 6478 and advance along the second axis A2 to move out of the distal outlet 6482 which, in the sixth embodiment, is defined by a lower cap 6618 that is operatively attached to the drive conduit 6462 adjacent to the lower cover 6524. Here, the tool body 6466 can be advanced into the drive bore 6478 until the abutment face 6584 of the tool 6042 comes into engagement with the drive shelf 6582 of the drive conduit 6462. Next, the user can grasp the handling portion 6592 of the transition gear 6576 to pass the interface end 6468 of the tool 6042 through the transition bore 6596 and advance the transition gear 6576 along the second axis A2 to bring the transition face 6590 toward and into abutment with the flange face 6588 of the tool body 6466. Alternatively, the user can "seat" the transition gear 6576 onto the tool 6042 to bring the inner transition splines 6578 into meshed engagement with the tool splines 6580 prior to inserting the working end 6470 into the proximal inlet 6480 of the drive bore 6478. The drive splines 6572 engage and mesh with the outer transition splines 6574, and the inner transition splines 6578 engage and mesh with the tool splines 6580, in order to define the first rotational lock RL1 such that the drive conduit 6462, the transition gear 6576, and the tool 6042 rotate concurrently about the second axis A2. Furthermore, when the transition face 6590 of the transition gear 6576 abuts the engagement flange 6586 of the tool 6042, the axial lock AL moves to the lock configuration ACL, defined by engagement between the axial connector elements 6306 carried by the slider element 6606 and the transition notch 6598 formed in the transition gear 6576, to prevent relative movement along the second axis A2 between the tool 6042, the transition gear 6576, and the drive conduit 6462.

As noted above, a seventh embodiment of the end effector of the surgical system 30 is shown in FIGS. 45-48B. In the description that follows, the structure and components of the seventh embodiment that are the same as or that otherwise correspond to the structure and components of the first embodiment of the end effector 40 are provided with the same reference numerals increased by 7000. Because many of the components and features of the seventh embodiment of the end effector 7040 are substantially similar to those of the first embodiment of the end effector 40 described above, for the purposes of clarity, consistency, and brevity, only certain specific differences between the seventh embodiment of the end effector 7040 and the first embodiment of the end effector 40 will be described below, and only some of the components and features common between the embodiments will be discussed herein and depicted in the drawings.

Thus, unless otherwise indicated below, the description of the first embodiment of the end effector 40 may be incorporated by reference with respect to the seventh embodiment of the end effector 7040 without limitation. Likewise, certain components and features of the seventh embodiment of the end effector 7040 that are similar to corresponding components and features of previously-described embodiments may be referred to or otherwise depicted in the drawings as provided with the same reference numerals increased by 1000 plus another 1000 for every intervening embodiment (e.g., for the seventh embodiment, components described in connection with the sixth embodiment would be increased by 1000, components described in connection with the fifth embodiment would be increased by 2000, components described in connection with the fourth embodiment would be increased by 3000, components described in connection with the third embodiment would be increased by 4000, and components described in connection with the second embodiment would be increased by 5000).

Referring now to FIGS. 45-48B, the seventh embodiment of the end effector 7040 is generally shown comprising the mount 7078, the rotary instrument 7080 and its actuator 7166 (depicted schematically), and the drive assembly 7082. When compared with the first embodiment described above, the seventh embodiment of the end effector 7040 generally employs the same type of trigger assembly 7088, and its drive assembly 7082 is configured to secure tools 7042 in a "top loading" manner through the drive conduit 7462 in a way that is similar to the fifth and sixth embodiments, as described in greater detail below.

Figure 46:
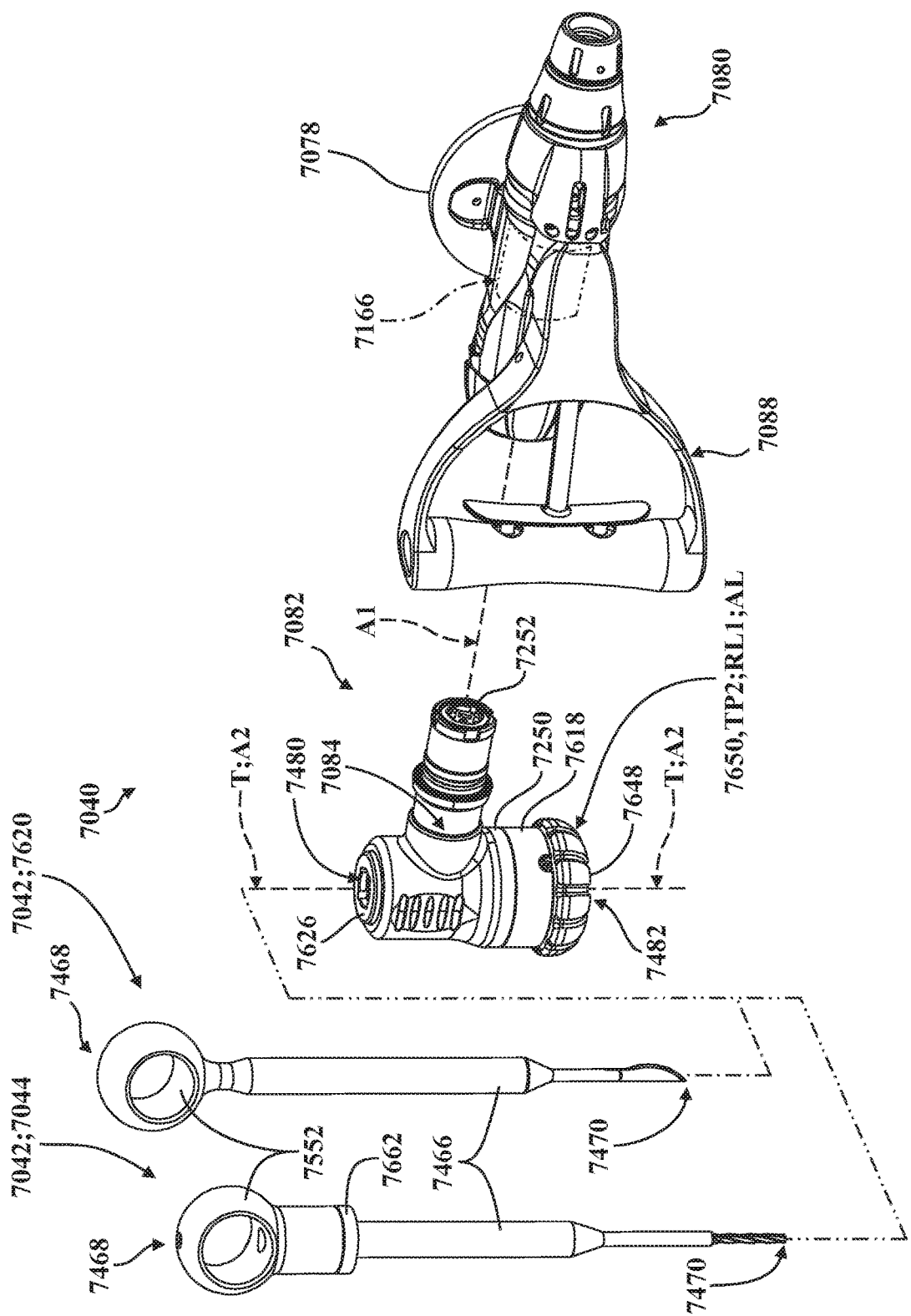
FIG. 46 is an exploded perspective view of the end effector of FIG. 45, shown with the drive assembly spaced from the rotary instrument and the trigger assembly, and shown with two tools configured for releasable attachment to the drive conduit of the drive assembly, with one of the tools shown as a rotary cutting tool with a drill bit to be driven by the rotary instrument along the trajectory maintained by the surgical robot, and with the other of the tools shown as a scalpel tool to be guided along the trajectory maintained by the surgical robot.

In the seventh embodiment, two exemplary types of tools 7042 are depicted in FIG. 46, including a differently-configured rotary cutting tool 7044 and a scalpel tool 7620. Here, the rotary cutting tool 7044 is realized as an "active" tool 7042 that is adapted for concurrent rotation with the drive conduit 7462 about the second axis A2, and the scalpel tool 7620 is realized as a "passive" tool 7042. Like the dissector tool 6544 described above in connection with the sixth embodiment of the end effector 6040, the illustrated scalpel tool 7620 and the rotary cutting tool 7044 similarly employ knobs 7552 arranged at the interface end 7468 of the tool body 7466. However, and as is illustrated in FIG. 47C, the knob 7552 of the rotary cutting tool 7044 is arranged for independent rotation relative to the tool body 7466 via a bearing 7262 operatively attached to the interface end 7468. Here in this embodiment, the illustrated rotary cutting tool 7044 does not comprise any type of manual interface, and is rotated about the second axis A2 via engagement with the drive conduit 7462 while retained by the first rotational lock RL1 and the axial lock AL of the drive assembly 7082, each of which are described in greater detail below. Put differently, the rotary cutting tool 7044 is not configured in this embodiment so as to be rotated "manually" by the user about the second axis A2 and instead utilizes the knob 7552 which, here, can be grasped by the user while the rotary instrument 7080 is utilized to rotate the working end 7470 about the second axis A2 without translating rotation back to the user's hand. However, it will be appreciated that other configurations are contemplated, and one or more tools 7042 could be provided with manual interfaces similar to those illustrated and described in connection with previous embodiments.

Referring now to FIGS. 47A-48B, in the seventh embodiment of the end effector 7040, the drive assembly 7082 likewise utilizes the drive conduit 7462 to facilitate "top loading" of tools 7042 to be driven about the second axis A2 via torque generated by the rotary instrument 7080. Here too, the geartrain 7084 comprises a planetary-type reduction gearset 7286 interposed between the driver input shaft 7252 and the carrier shaft 7422, and an addition reduction is provided by the bevel gearset 7272 in that the input gear 7274 and the 7276 have different configurations from each other. While the input gear 7274 is coupled to the carrier shaft 7422, the output gear 7276 is coupled to a taper conduit 7622 that forms part of a collet mechanism 7624 configured to facilitate axial and rotational retention of "active" tools 7042 and serving as the first rotational lock RL1 and the axial lock AL in the seventh embodiment. Here, the taper conduit 7622 is supported for rotation about the second axis A2 via bearings 7262 disposed in the drive body 7250 of the drive assembly 7082, and rotates concurrently about the second axis A2 with the lower cap 7618 and an upper cap 7626 (see FIGS. 47A-47C). The taper conduit 7622 has a taper bore 7628 with a generally frustoconical profile that increases in radius relative to the second axis A2 in a direction away from the proximal inlet 7480 and toward the distal outlet 7482. A correspondingly-shaped collet 7630 is disposed within the taper bore 7628, generally defines the drive conduit 7462 in this embodiment, and has a resilient collet body 7632 which extends from a proximal collet end 7634 to a distal collet end 7636.

Figure 47A:
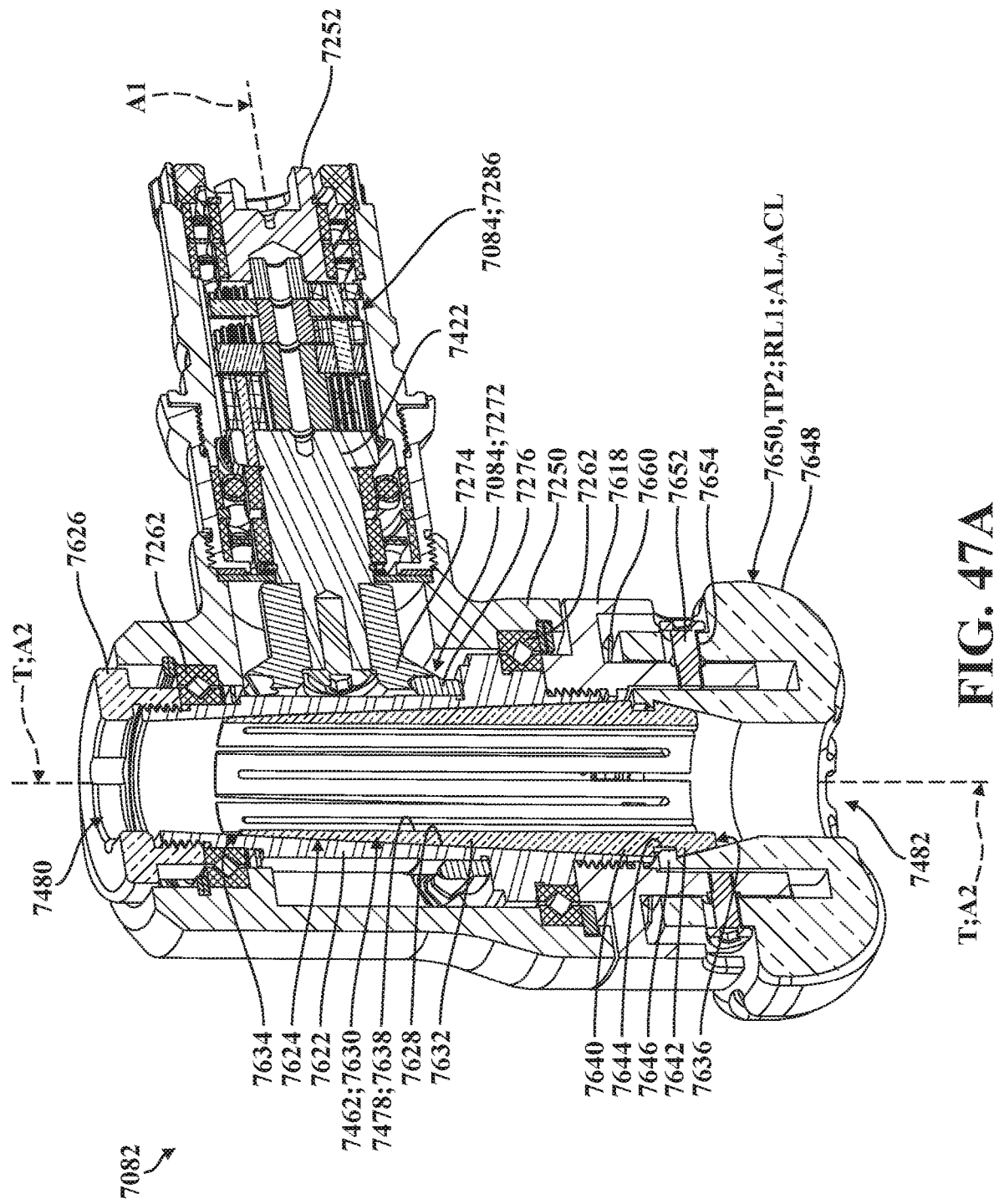
FIG. 47A is a sectional perspective view of the drive assembly of FIGS. 45-46, depicted as sectioned generally longitudinally, and show with the drive conduit comprising a collet mechanism having a collet tensioner arranged in a lock configuration.
Figure 47B:
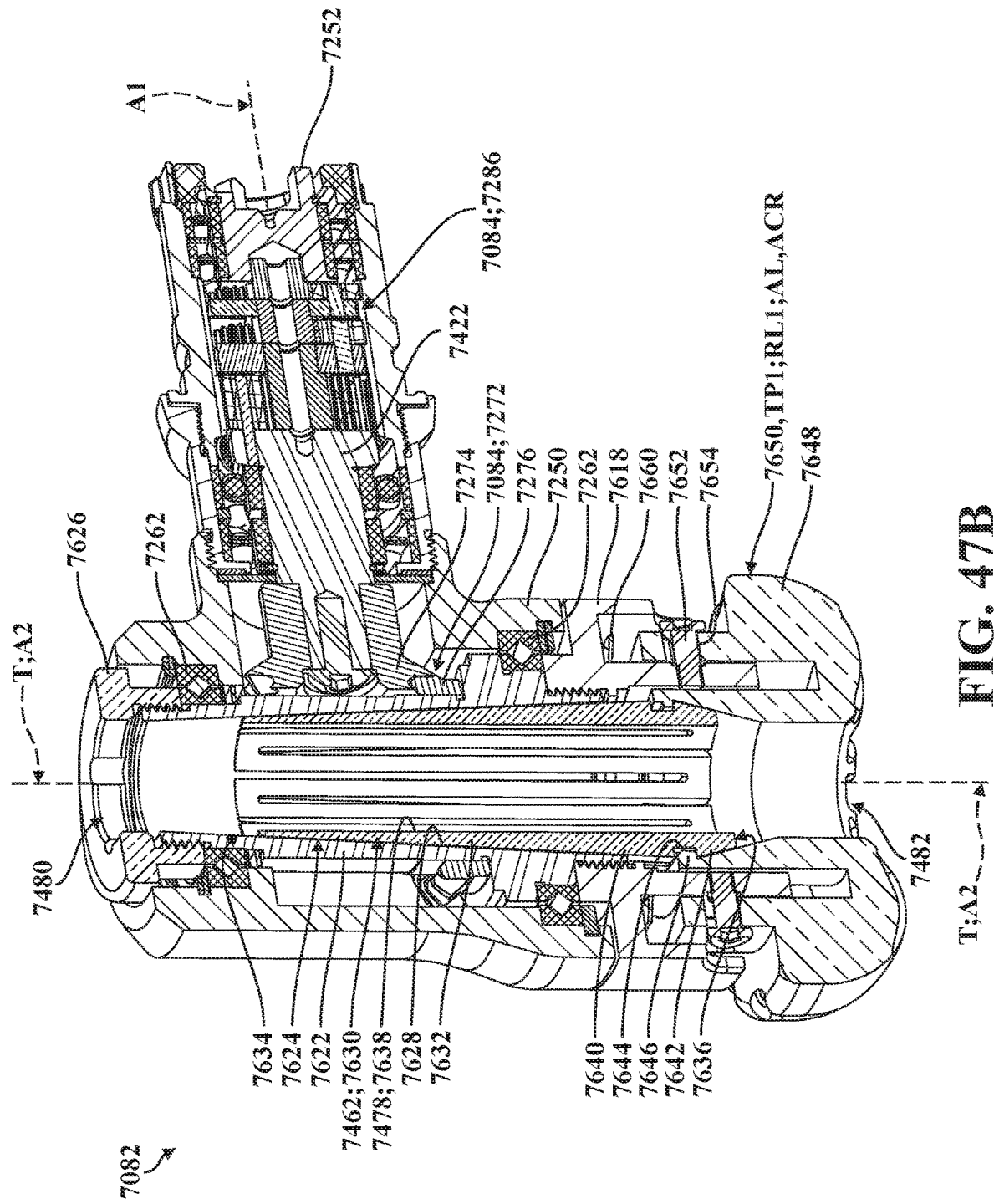
FIG. 47B is another sectional perspective view of the drive assembly of FIG. 47A, shown with the collet tensioner arranged in a release configuration.
Figure 47C:
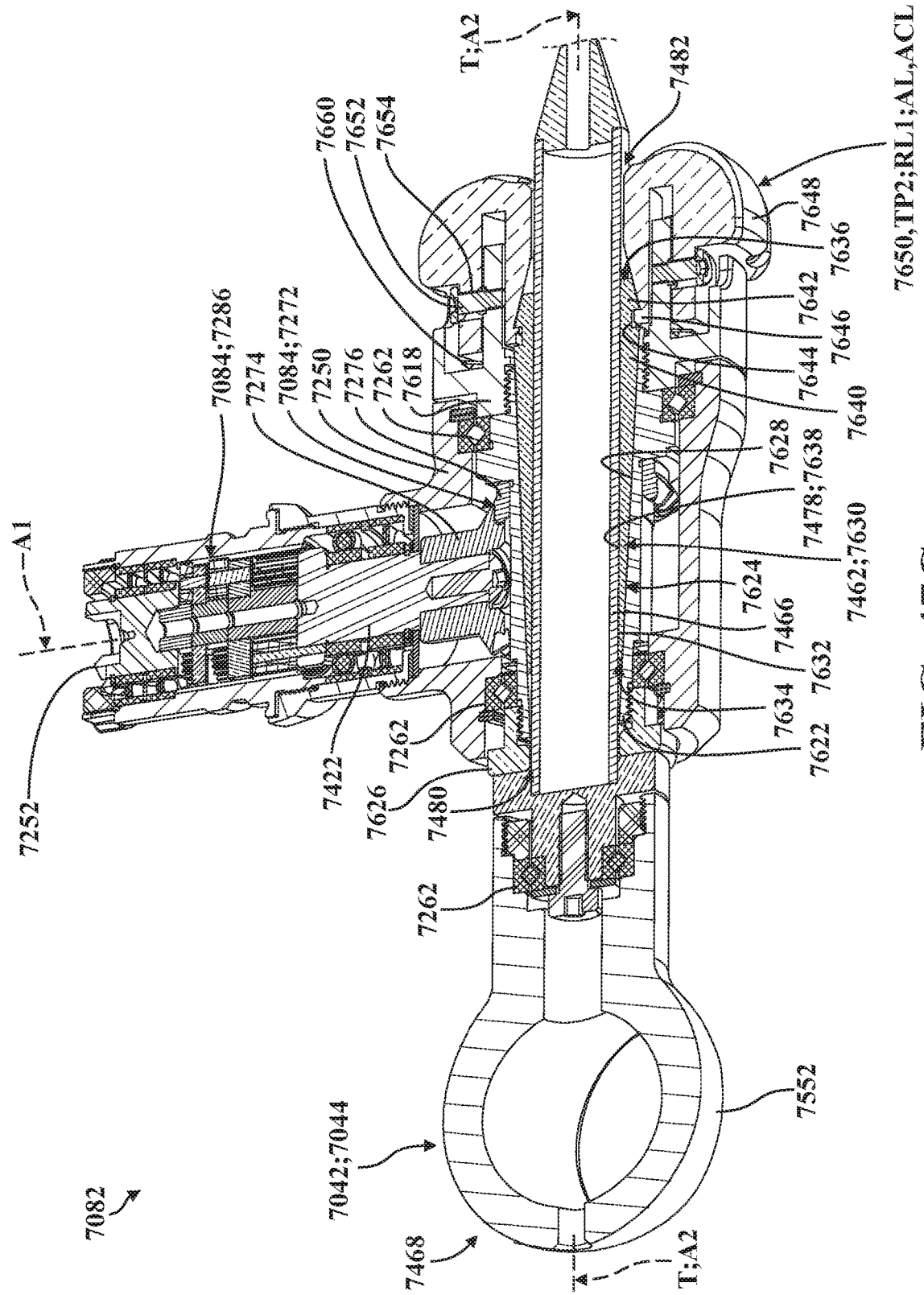
FIG. 47C is another sectional perspective view of the drive assembly of FIG. 47A, shown with the collet tensioner arranged in the lock configuration to secure a portion of the rotary cutting tool of FIG. 46 for rotation about the second axis.

As is best shown in FIG. 47A, the resilient collet body 7632 is realized as a unitary, one-piece component with an "ER collet" configuration, and defines a collet bore 7638 with a generally cylindrical profile which, in turn, defines the drive bore 7478. As is described in greater detail below, the resilient collet body 7632 is configured to deflect at least partially radially-inwardly toward the second axis A2 to facilitate retention of the tool 7042 via engagement with the tool body 7466. The collet 7630 also comprises a proximal collet portion 7640 which is shaped to be received within the taper bore 7628 of the taper conduit 7622, a distal collet portion 7642 which similarly has a generally frustoconical profile that decreases in radius relative to the second axis A2 in a direction away from the proximal inlet 7480 and toward the distal outlet 7482, and a collet notch 7644 arranged between the proximal collet portion 7640 and the distal collet portion 7642.

The collet notch 7644 receives a collet retainer 7646 of a collet knob 7648 that is arranged for engagement by the user. Here, the collet knob 7648 forms part of a collet tensioner 7650 of the collet mechanism 7624 which is coupled to the collet 7630 and is arranged for movement between a first tensioner position TP1 (see FIGS. 47B and 48B) and a second tensioner position TP2 (see FIGS. 47A and 48A). The first tensioner position TP1 is associated with the release configuration ACR of the axial lock AL where relative movement is permitted between the tool 7042 and the collet 7630, and the second tensioner position TP2 is associated with the lock configuration ACL of the axial lock AL where relative movement is restricted between the tool 7042 and the collet 7630.

Figure 48A:
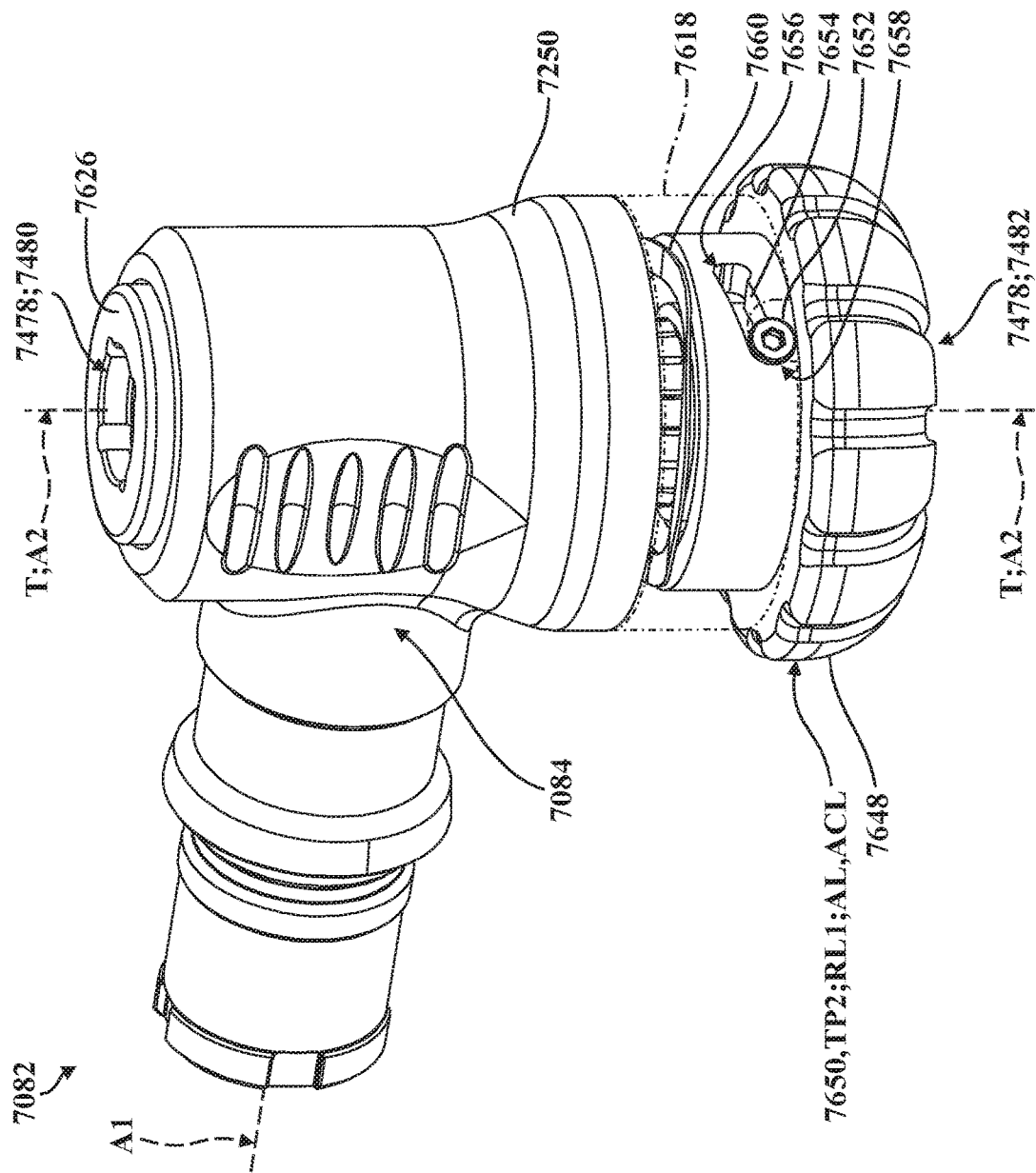
FIG. 48A is a perspective view of the drive assembly of FIGS. 45-48, shown with the collet tensioner arranged as depicted in FIG. 47A.
Figure 48B:
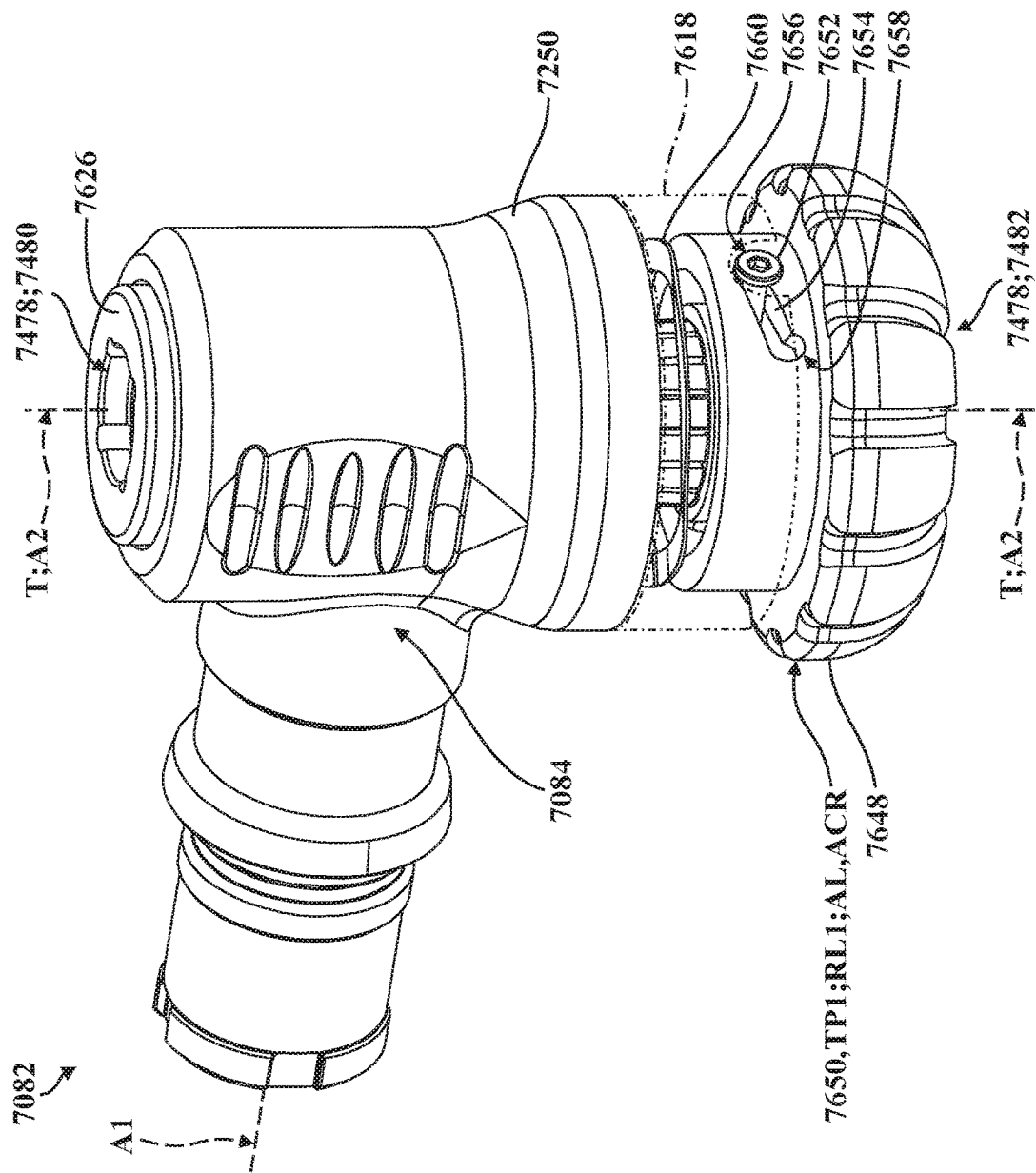
FIG. 48B is a perspective view of the drive assembly of FIGS. 45-48, shown with the collet tensioner arranged as depicted in FIG. 47B.

As is best depicted in FIGS. 47A and 48A-48B, the collet knob 7648 of the collet tensioner 7650 is operatively attached to the lower cap 7618 of the drive assembly 7082 via a pair of knob guides 7652 (e.g., fasteners) which extend through knob slots 7654 formed in the collet knob 7648. The knob slots 7654 are provided with a generally helical profile with first and second knob slot ends 7656, 7658 shaped to retain the knob guides 7652 and thereby define the first and second tensioner positions TP1, TP2, respectively, of the collet tensioner 7650. A knob biasing element 7660 interposed between the collet knob 7648 and the lower cap 7618 urges the collet tensioner 7650 toward the first tensioner position TP1 (see FIGS. 47B and 48B). This configuration allows the knob guides 7652 to "detent" into and remain seated within the first and second knob slot ends 7656, 7658 until the user rotates the collet knob 7648 relative to the lower cap 7618. Put differently, the user can rotate the collet knob 7648 to move the axial lock AL between the release configuration ACR (see FIGS. 47B and 48B) and the lock configuration ACL (see FIGS. 47A and 48A).

Because of the configuration of the knob slots 7654 described above, rotation of the collet knob 7648 via force applied by the user also results in translation of the collet knob 7648 along the second axis A2. Moreover, because of the engagement between the collet retainer 7646 of the collet knob 7648 and the collet notch 7644 of the collet 7630, rotation of the collet knob 7648 also results in translation of the collet 7630 along the second axis A2 within the taper bore 7628 of the taper conduit 7622. Here, when the user engages the collet knob 7648 to move the collet tensioner 7650 from the first tensioner position TP1 (see FIGS. 47B and 48B) to the second tensioner position TP2 (see FIGS. 47A, 47C, and 48A), the collet 7630 moves toward the proximal inlet 7480 and is compressed radially-inwardly toward the second axis A2 via engagement between the proximal collet portion 7640 and the taper bore 7628. When the tool body 7466 of the tool 7042 is disposed within the drive bore 7478 defined by the collet bore 7638, this compression urges at least a portion of the resilient collet body 7632 against the tool body 7466 to "clamp" the tool 7042 to the drive conduit 7462, thereby effecting operation of both the first rotational lock RL1 and the axial lock AL for "active" tools 7042. For "passive" tools, such as the scalpel tool 7620, the collet tensioner 7650 is utilized in the first tensioner position TP1 and is not moved to the second tensioner position TP2.

In the seventh embodiment of the end effector 7040, both "active" and "passive" tools 7042 can be inserted into and removed from the drive conduit 7462 along the second axis A2 in the "top loading" manner. To this end, when the collet tensioner 7650 is in the first tensioner position TP1 (see FIG. 47B), the working end 7470 can be placed into the proximal inlet 7480 and advanced along the second axis A2 into the collet bore 7638 (which, in this embodiment, defines the drive bore 7478) and out of the distal outlet 7482 (which, in this embodiment, is defined by the collet knob 7648). As shown in FIG. 48C, certain types of tools 7042 may comprise a stop mount 7662 at the interface end 7468 which is shaped and arranged to abut the stop face 7616 (which, in this embodiment, is defined by the upper cap 7626) and thereby prevent the tool 7042 from being advanced further into the drive bore 7478 along the second axis A2. However, it will be appreciated that other configurations are contemplated, and the position of the tool 7042 along the second axis A2 can be limited relative to the drive conduit 7462 in other ways. If the tool 7042 is of the "active" configuration, the collet tensioner 7650 can then be moved from the first tensioner position TP1 to the second tensioner position TP2 to facilitate driving the tool 7042 about the second axis A2 via the rotary instrument 7080. If, however, the tool is of the "passive" configuration, the collet tensioner 7650 can remain in the first tensioner position TP1 as noted above.

As noted above, an eighth embodiment of the end effector of the surgical system 30 is shown in FIGS. 49A-63F. In the description that follows, the structure and components of the eighth embodiment that are the same as or that otherwise correspond to the structure and components of the first embodiment of the end effector 40 are provided with the same reference numerals increased by 8000. Because many of the components and features of the eighth embodiment of the end effector 8040 are substantially similar to those of the first embodiment of the end effector 40 described above, for the purposes of clarity, consistency, and brevity, only certain specific differences between the eighth embodiment of the end effector 8040 and the first embodiment of the end effector 40 will be described below, and only some of the components and features common between the embodiments will be discussed herein and depicted in the drawings.

Thus, unless otherwise indicated below, the description of the first embodiment of the end effector 40 may be incorporated by reference with respect to the eighth embodiment of the end effector 8040 without limitation. Likewise, certain components and features of the eighth embodiment of the end effector 8040 that are similar to corresponding components and features of previously-described embodiments may be referred to or otherwise depicted in the drawings as provided with the same reference numerals increased by 1000 plus another 1000 for every intervening embodiment (e.g., for the eighth embodiment, components described in connection with the seventh embodiment would be increased by 1000, components described in connection with the sixth embodiment would be increased by 2000, components described in connection with the fifth embodiment would be increased by 3000, components described in connection with the fourth embodiment would be increased by 4000, components described in connection with the third embodiment would be increased by 5000, and components described in connection with the second embodiment would be increased by 6000).

Referring now to FIGS. 49A-63F, the eighth embodiment of the end effector 8040 is generally shown comprising the mount 8078, the rotary instrument 8080 and its actuator 8166, and the drive assembly 8082. When compared with the other embodiments described above, the eighth embodiment of the end effector 8040 is configured such that the rotary instrument 8080 and the drive assembly 8082 are formed integrally. Put differently, the drive assembly 8082 is not arranged for movement relative to the actuator 8166 in the eighth embodiment. Furthermore, and as is described in greater detail below, the eighth embodiment of the end effector 8040 is also configured such that the first axis A1 is coincident with the second axis A2, rather than being different from the second axis A2 (e.g., perpendicular) like the embodiments previously described herein. More specifically, while the eighth embodiment is similar to the previously-described embodiments in that the first axis A1 is still defined by rotational torque generated by the actuator 8166 and the second axis A2 is still defined by rotation of tools 8042 secured to the drive assembly 8082, the axes A1, A2 are the same in this embodiment. Furthermore, when compared to the other embodiments described above, the eighth embodiment of the end effector 8040 employs a differently-configured trigger assembly 8088, drive assembly 8082, first and second rotational locks RL1, RL2, and axial lock AL which cooperate to secure tools 8042 in the "top loading" manner through the drive conduit 8462 in a way that is similar to the fifth, sixth, and seventh embodiments, as described in greater detail below.

Figure 49B:
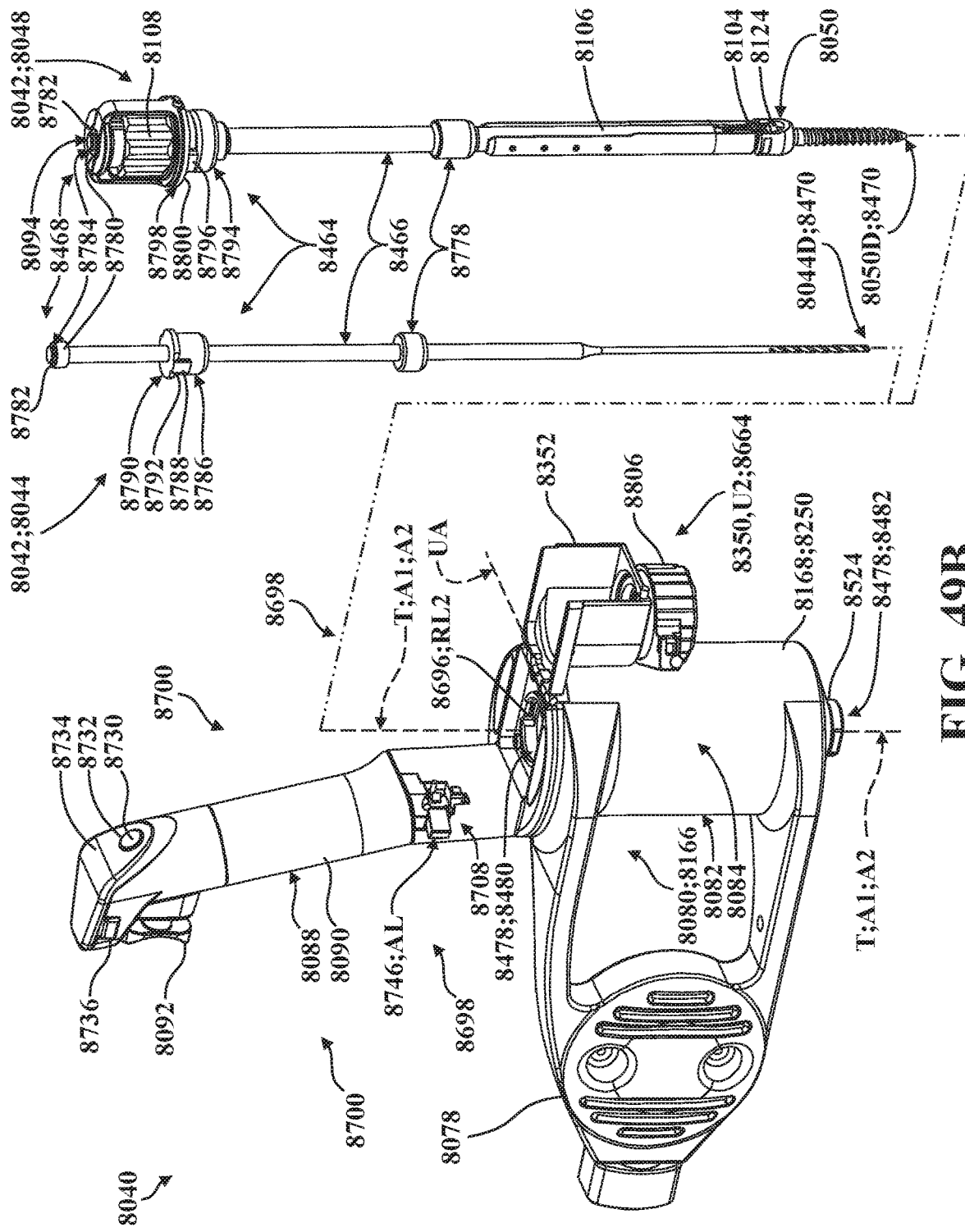
FIG. 49B is another perspective view of the end effector of FIG. 49A, shown with the guard cover arranged in a second guard position, with the end effector arranged adjacent to two tools configured for releasable attachment to the drive assembly, with one of the tools shown as a rotary cutting tool with a drill bit, and with the other of the tools shown as an rotary driving tool supporting an anchor.

Referring now to FIGS. 49A-49B, because the drive assembly 8082 and the actuator 8166 of the rotary instrument 8080 are formed integrally in the eighth embodiment of the end effector 8040 as noted above, the instrument housing 8168 and the drive body 8250 are realized by the same component (hereinafter referred to as the drive body 8250). The mount 8078 is operatively attached to or otherwise formed as a part of the drive body 8250 and is similarly adapted for releasable attachment to the coupler 38 of the robotic arm 36 of the surgical robot 32 (see FIG. 1). In addition to the mount 8078, the trigger assembly 8088 and a retention mechanism 8664 are also operatively attached to the drive body 8250. Furthermore, the drive body 8250 accommodates an actuator subassembly 8666 therein (see FIG. 50) which serves as or otherwise defines the rotary instrument 8080 and its actuator 8166, the reduction gearset 8286, and the drive conduit 8462 in the eighth embodiment of the end effector 8040. As is described in greater detail below in connection with FIGS. 56A-59B, the retention mechanism 8664 comprises the guard cover 8350 and is configured to facilitate retention of tools 8042 to the drive conduit 8462 along the second axis A2.

Figure 50:
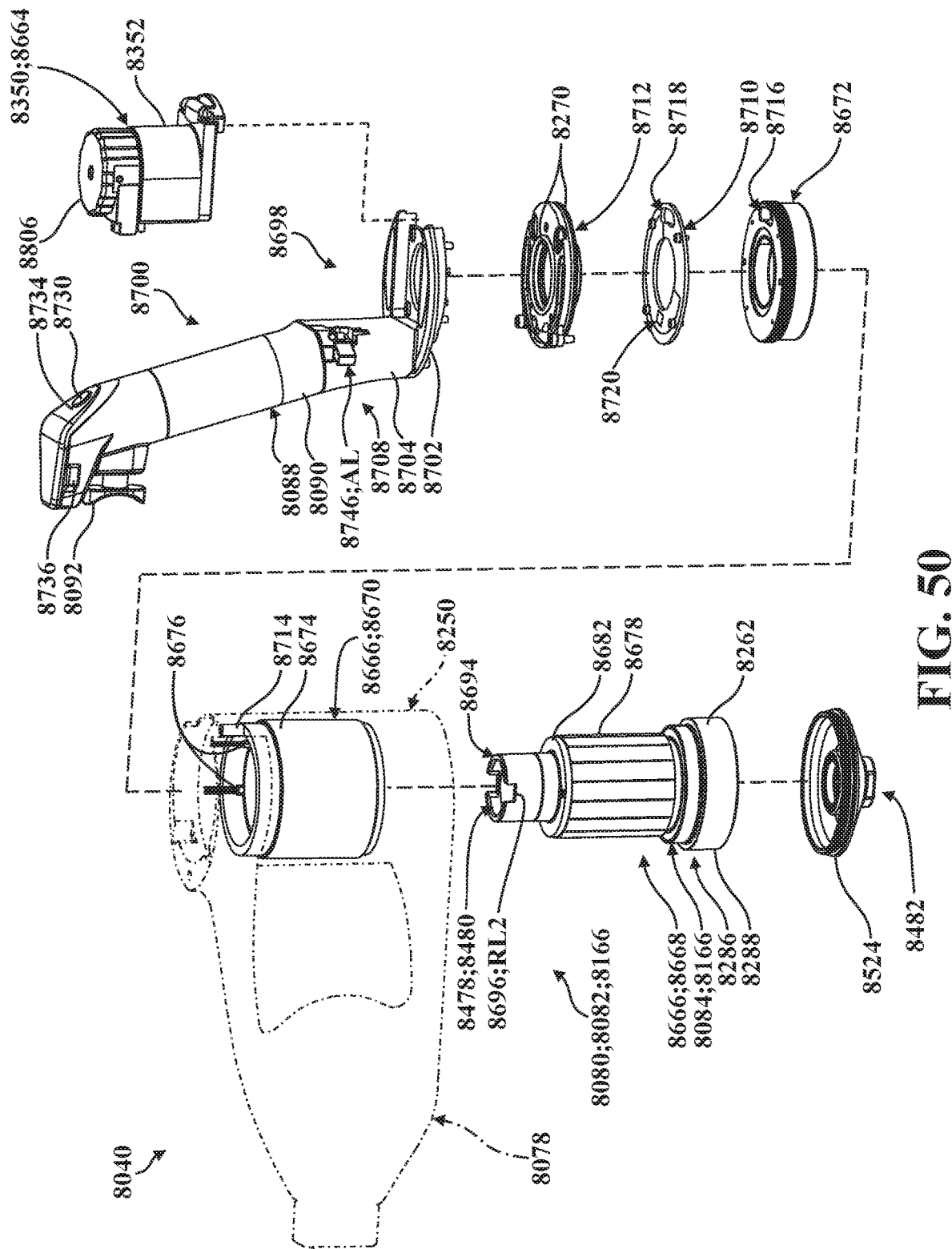
FIG. 50 is an exploded perspective view of the end effector of FIGS. 49A-49B, shown with portions of the retention mechanism and the trigger assembly spaced from the mount and from an actuator subassembly.

As is best shown in FIG. 50, the actuator subassembly 8666 generally comprises a rotor subassembly 8668 and a stator subassembly 8670. The rotor subassembly 8668 is configured to be received distally into the stator subassembly 8670 and is retained in the drive body 8250 via the lower cover 8524. The stator subassembly 8670 is received proximally into the drive body 8250 and is retained via an actuator end plate 8672 which, in turn, is disposed in threaded engagement with the drive body 8250 (see also FIG. 57). The stator subassembly 8670 comprises a stator 8674 (depicted generically) and motor sensors 8676 used to, among other things, effect commutation of the actuator 8166 which, in the representative embodiment illustrated herein, is realized as an inrunner brushless direct current electric motor with a rotor 8678 formed as a part of the rotor assembly 8668.

Figure 51:
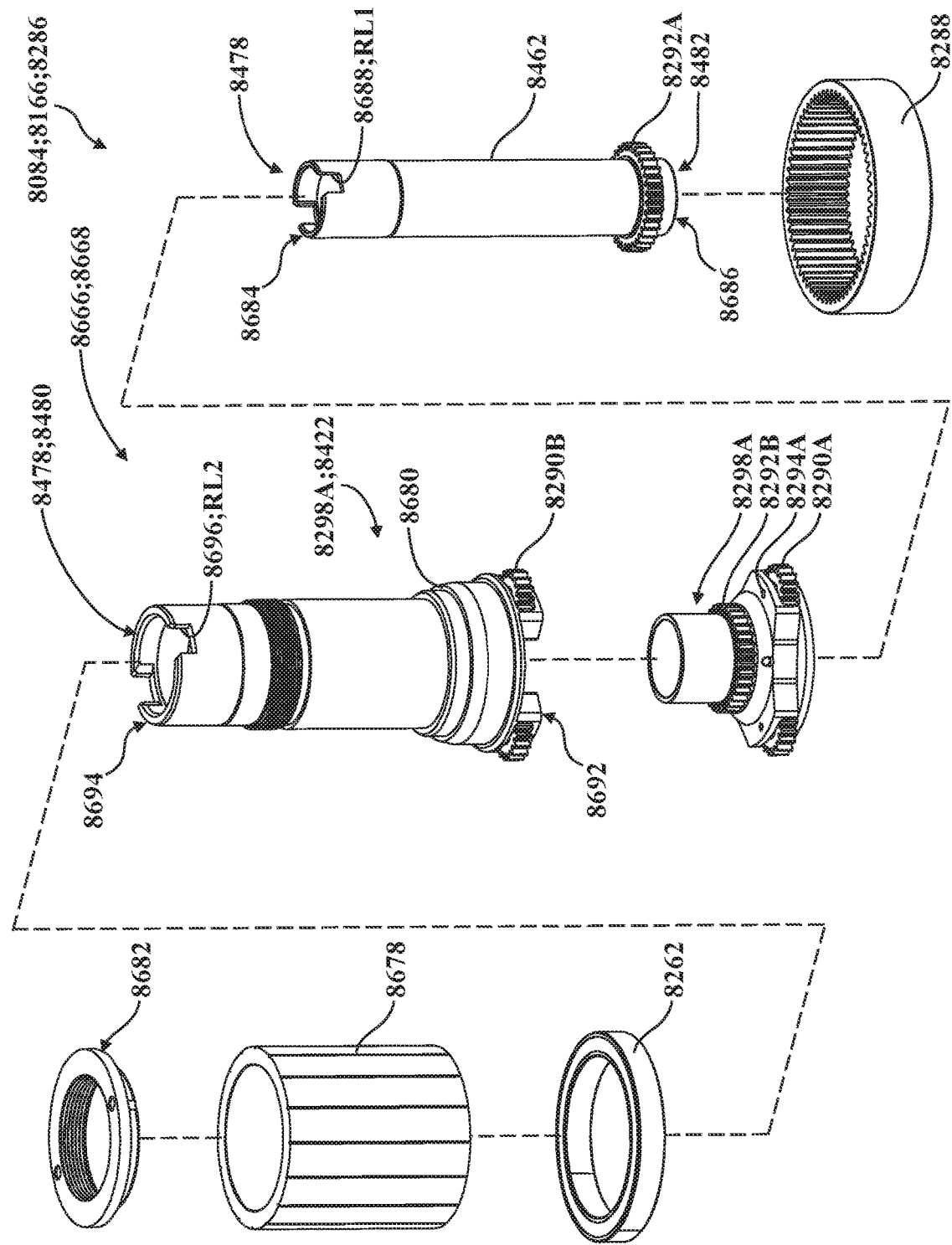
FIG. 51 is an exploded perspective view of a portion of the actuator subassembly of FIG. 50.

More specifically, and as is best depicted in FIG. 51, the rotor assembly 8668 comprises the rotor 8678, the reduction gearset 8286, and the drive conduit 8462. Here, the rotor 8678 has a generally tube-shaped profile and is seated on a perch 8680 formed in the carrier shaft 8422 such that the carrier shaft 8422, which also has a generally tube-shaped profile in this embodiment, extends through the rotor 8678. An actuator ring clamp 8682 secures the rotor 8678 to the carrier shaft 8422 via threaded engagement, and the carrier shaft 8422 is supported by a bearing 8262 disposed in the drive body 8250 such that the rotor 8678 and the carrier shaft 8422 of the reduction gearset 8286 rotate concurrently about the second axis A2 (and also, in this embodiment, the first axis A1). In the eighth embodiment, the carrier shaft 8422 also defines the second carrier 8298B of the reduction gearset 8286 and, as is described in greater detail below, both the second rotational lock RL2 and the proximal inlet 8480 of the drive bore 8478 of the drive assembly 8082.

Figure 57:
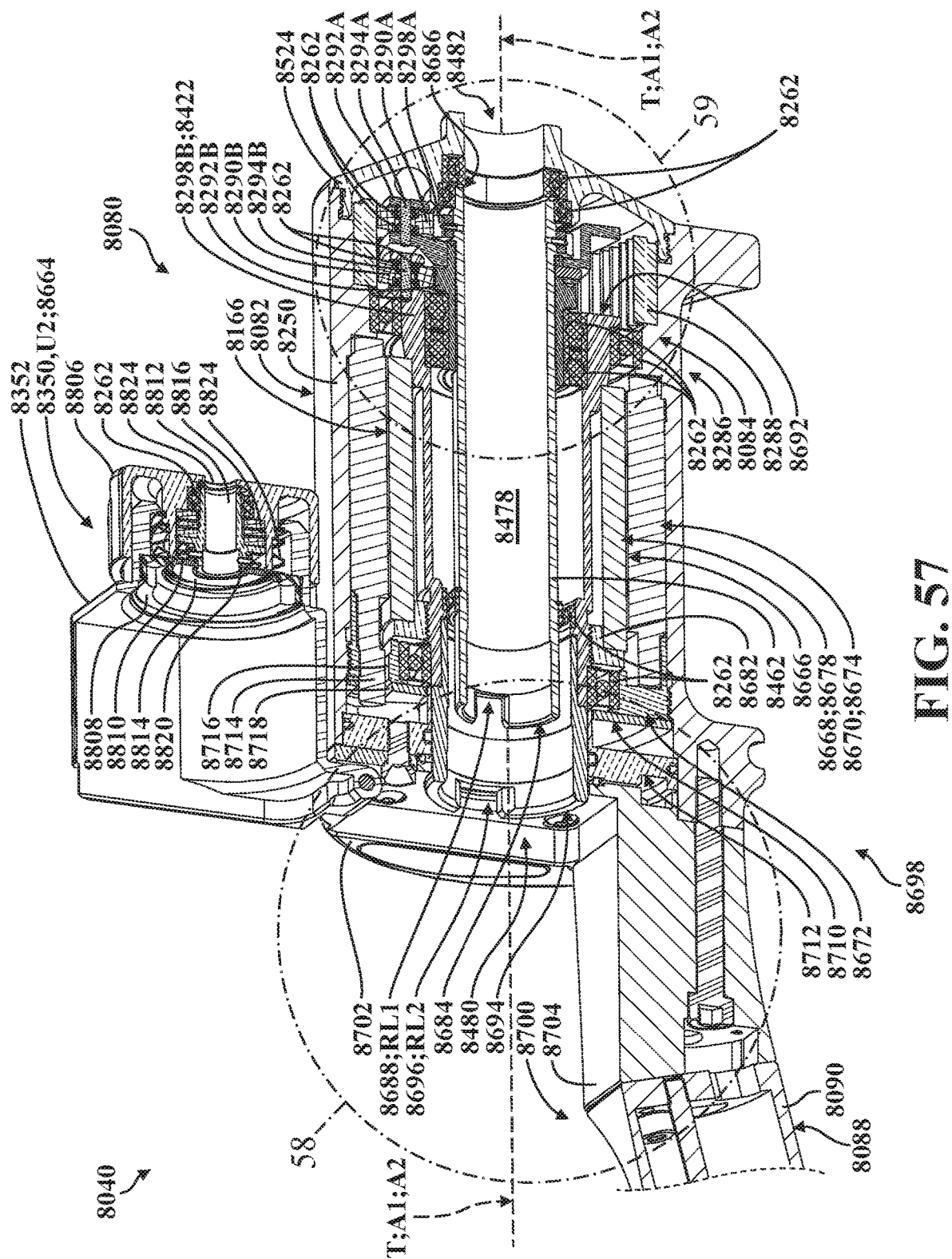
FIG. 57 is a partial, sectional perspective view of the end effector of FIGS. 49A-50, depicted as sectioned generally longitudinally, shown with the guard cover of the retention mechanism arranged in the second guard position as depicted in FIG. 49B.

Referring now to FIGS. 51 and 57, the drive conduit 8462 extends along the second axis A2 between a proximal conduit end 8684 and a distal conduit end 8686, forming part of the drive bore 8478 of the drive assembly 8082 therebetween. The first rotational lock RL1 is realized as a first notch 8688 formed at the proximal conduit end 8684 of the drive conduit 8462, and is configured to rotatably secure certain tools 8042 for rotation about the second axis A2 as described in greater detail below. The first sun gear 8292A of the reduction gearset 8286 is secured at the distal conduit end 8686 via one or more retention pins 8690 (see FIGS. 59A-59B) for concurrent rotation with the drive conduit 8462. The first sun gear 8292A is disposed in meshed engagement with the first set of planet gears 8290A which, in turn, are also disposed in meshed engagement with the ring gear 8288. The first set of planet gears 8290A are supported by the first carrier 8298A which, like the second carrier 8298B defined by the carrier shaft 8422, has a generally tube-shaped profile when coupled to the second sun gear 8292B through which the drive conduit 8462 extends. Here, the first set of planet gears 8290A are supported by bearings 8262 which, in turn, are supported by the first set of pins 8294A which are coupled to the first carrier 8298A.

The second sun gear 8292B is secured to the first carrier 8298A via one or more retention pins 8690 (see FIG. 57) and is disposed in meshed engagement with the second set of planet gears 8290B which, in turn, are also disposed in meshed engagement with the ring gear 8288 and are supported by the second carrier 8298B defined by the carrier shaft 8422. More specifically, in this embodiment, the carrier shaft 8422 extends between a distal carrier end 8692 and a proximal carrier end 8694, and the second carrier 8298B of the reduction gearset 8286 is arranged adjacent to the distal carrier end 8692. Here, the second set of planet gears 8290B are supported by bearings 8262 which, in turn, are supported by the second set of pins 8294B which are coupled to the second carrier 8298B. The second rotational lock RL2 is different from the first rotational lock RL1, is realized as a second notch 8696 formed at the proximal carrier end 8694 of the carrier shaft 8422, and is configured to rotatably secure certain tools 8042 for rotation about the second axis A2 independent of rotation of the first rotational lock RL1, as described in greater detail below.

In the eighth embodiment of the end effector 8040, the reduction gearset 8286 employs a two-stage planetary configuration that affords a torque reduction (and a speed increase) between the second rotational lock RL2 defined by the second notch 8696 formed in the carrier shaft 8422 (which rotates concurrently with the rotor 8678 of the actuator 8166 as noted above), and the first rotational lock RL1 defined by the first notch 8688 formed in the drive conduit 8462 of the drive assembly 8082. Put differently, the drive conduit 8462 (and the first rotational lock RL1) rotates at higher speed than the actuator 8166 (and the second rotational lock RL2) in the eighth embodiment. Furthermore, in the eighth embodiment, rotation of the second rotational lock RL2 about the second axis A2 occurs at a ratio of 1:1 with respect to rotation of the actuator 8166 about the first axis A1 (coincident with the second axis A2 in this embodiment). Relative rotation between the drive conduit 8462 and the carrier shaft 8422 is facilitated via bearings 8262 supported on the first carrier 8298A and in the carrier shaft 8422 (see FIG. 57). As is described in greater detail below, irrespective of whether the tool 8042 engages the first rotational lock RL1 to rotate concurrently with the drive conduit 8462 or the second rotational lock RL2 to rotate concurrently with the actuator 8166, at least a portion of the tool body 8466 extends through the drive conduit 8462 along the second axis A2 when the tool 8042 is secured to the end effector 8040.

As noted above, the eighth embodiment of the end effector 8040 is provided with a differently-configured trigger assembly 8088 and input trigger 8092 arranged for engagement by the user to facilitate driving tools 8042 via rotational torque generated by the actuator 8166. As is best shown in FIG. 50, the trigger assembly 8088 generally comprises a first trigger subassembly 8698 and a second trigger subassembly 8700 that is operatively attached to the first trigger subassembly 8698 such as via one or more fasteners (see FIG. 57). More specifically, the first trigger subassembly 8698 comprises an upper mount plate 8702, and a grip mount 8704 to which the second trigger subassembly 8698 is attached. As is described in greater detail below, the retention mechanism 8664 is operatively attached adjacent to the upper mount plate 8702, and the upper mount plate 8702 also supports a pair of indicator housings, generally indicated at 8706. Moreover, the grip mount 8704 comprises a guard locking subassembly 8708 configured to releasably secure the guard cover 8350 of the retention mechanism 8664, as described in greater detail below.

In addition to the actuator end plate 8672, a circuit board 8710 and a mid mount plate 8712 are also interposed between the stator subassembly 8670 and the upper mount plate 8702 of the first trigger subassembly 8698. Here, the actuator end plate 8672 is secured to the drive body 8250 via threaded engagement, and the circuit board 8710 is secured to the actuator end plate 8672 via one or more fasteners. Similarly, the mid mount plate 8712 is secured to the drive body 8250 via one or more fasteners, and the upper mount plate 8702 is secured to the mid mount plate 8712 via one or more fasteners. The mid mount plate 8712 supports various seals 8270 and fasteners (e.g., bolts, circlips, and the like), and generally promotes ease of assembly of the end effector 8040.

In the illustrated embodiment, the stator subassembly 8670 comprises an indexing tab 8714 which extends away from the lower cover 8524 and through both a plate aperture 8716 formed in the actuator end plate 8672 and through a board aperture 8718 formed in the circuit board 8710. This configuration helps facilitate alignment of the stator assembly 8670 relative to the drive body 8250 and the motor sensors 8676 supported therein which, in the illustrated embodiment, are disposed in electrical communication with a board controller 8720 (depicted schematically; electrical connections not shown) mounted to the circuit board 8710. Here, the board controller 8720 may be utilized to, among other things, communicate with other components of the surgical system 30, facilitate commutation and/or operation of the actuator 8166, and control various inputs (e.g., additional sensors) and/or outputs (e.g., indicators) of the end effector 8040, as described in greater detail below.

Figure 52:
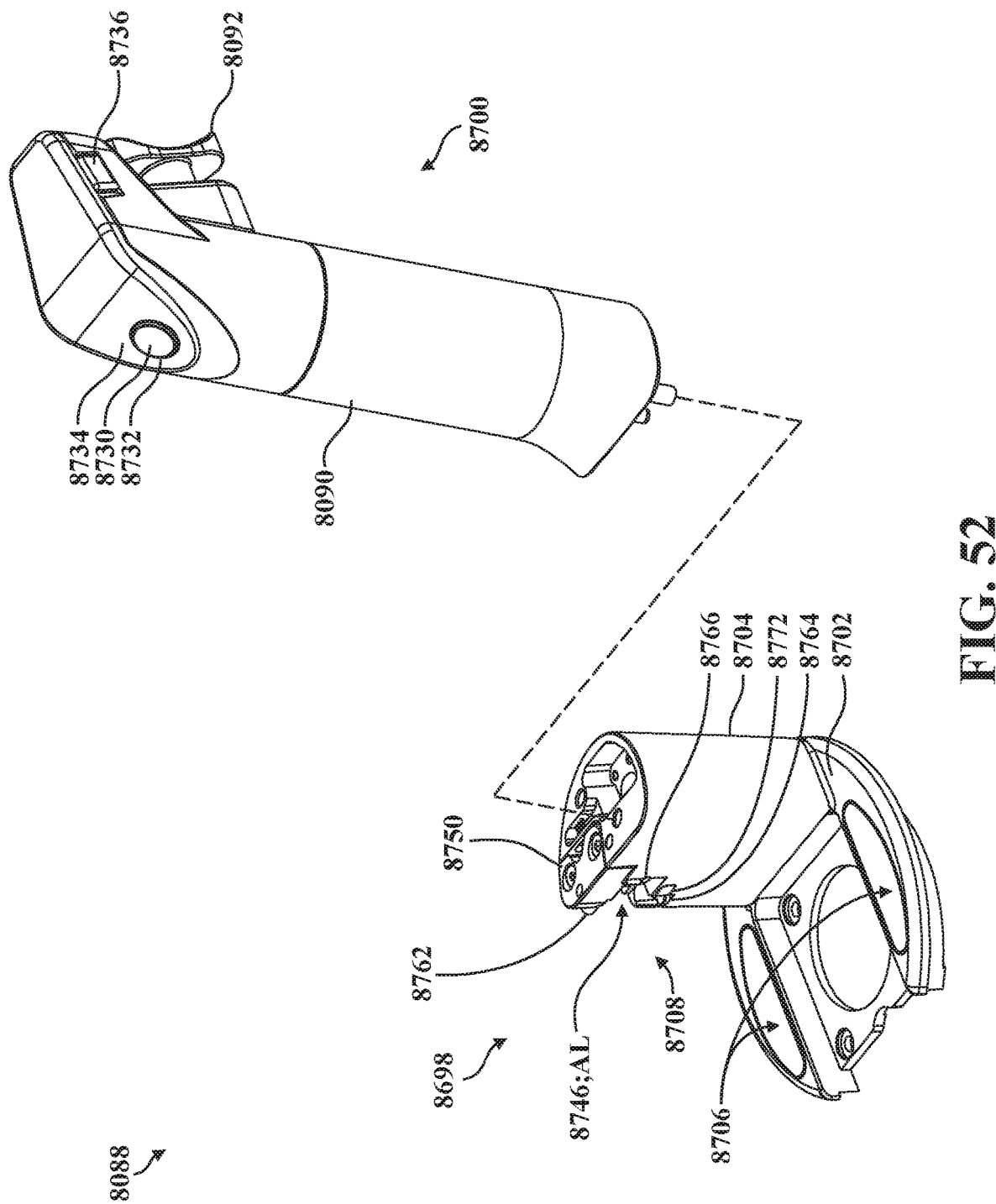
FIG. 52 is an exploded perspective view of the trigger assembly of FIG. 50, shown having a first trigger subassembly spaced from a second trigger subassembly.
Figure 53A:
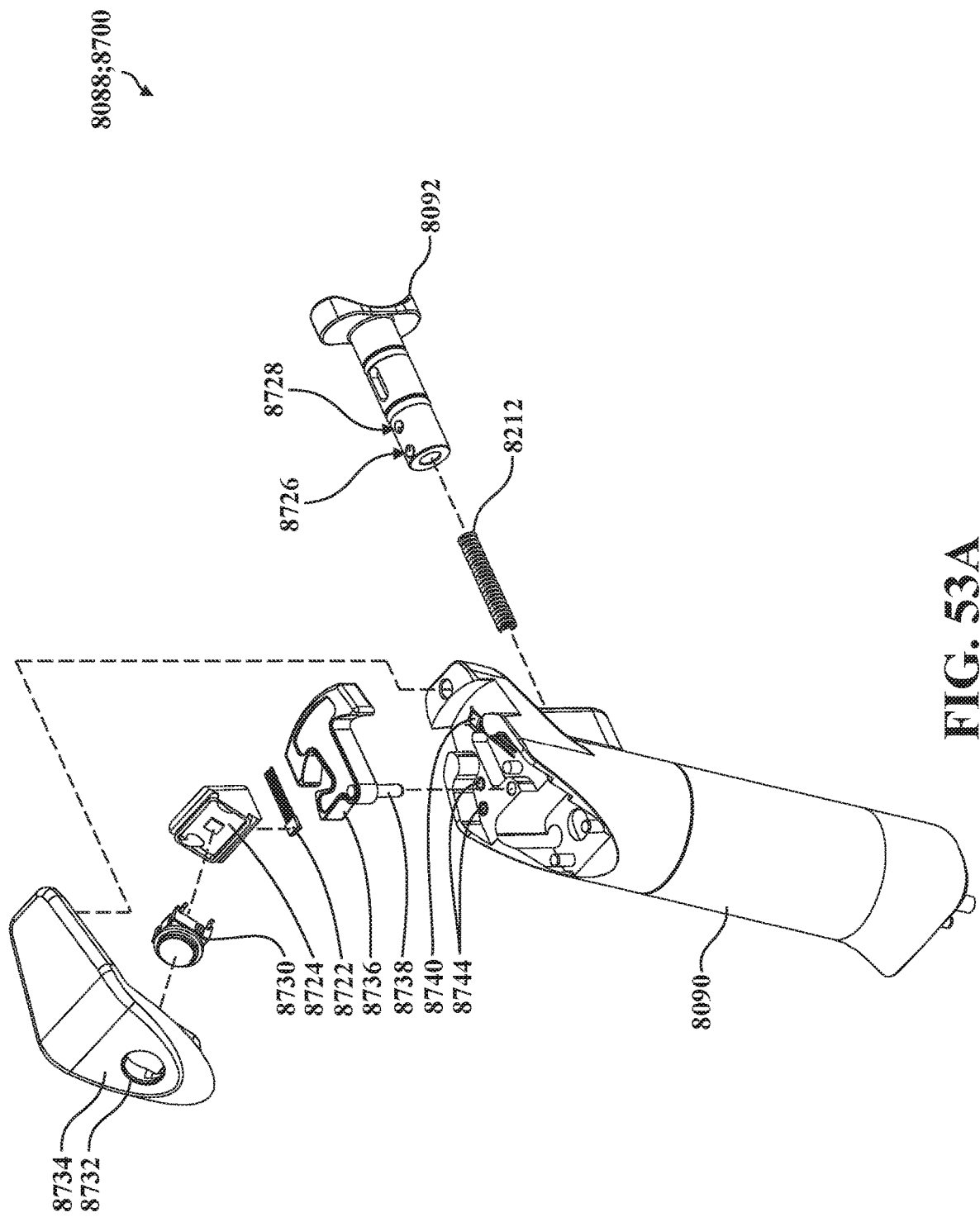
FIG. 53A is an exploded perspective view of the second trigger subassembly of FIG. 52.
Figure 53B:
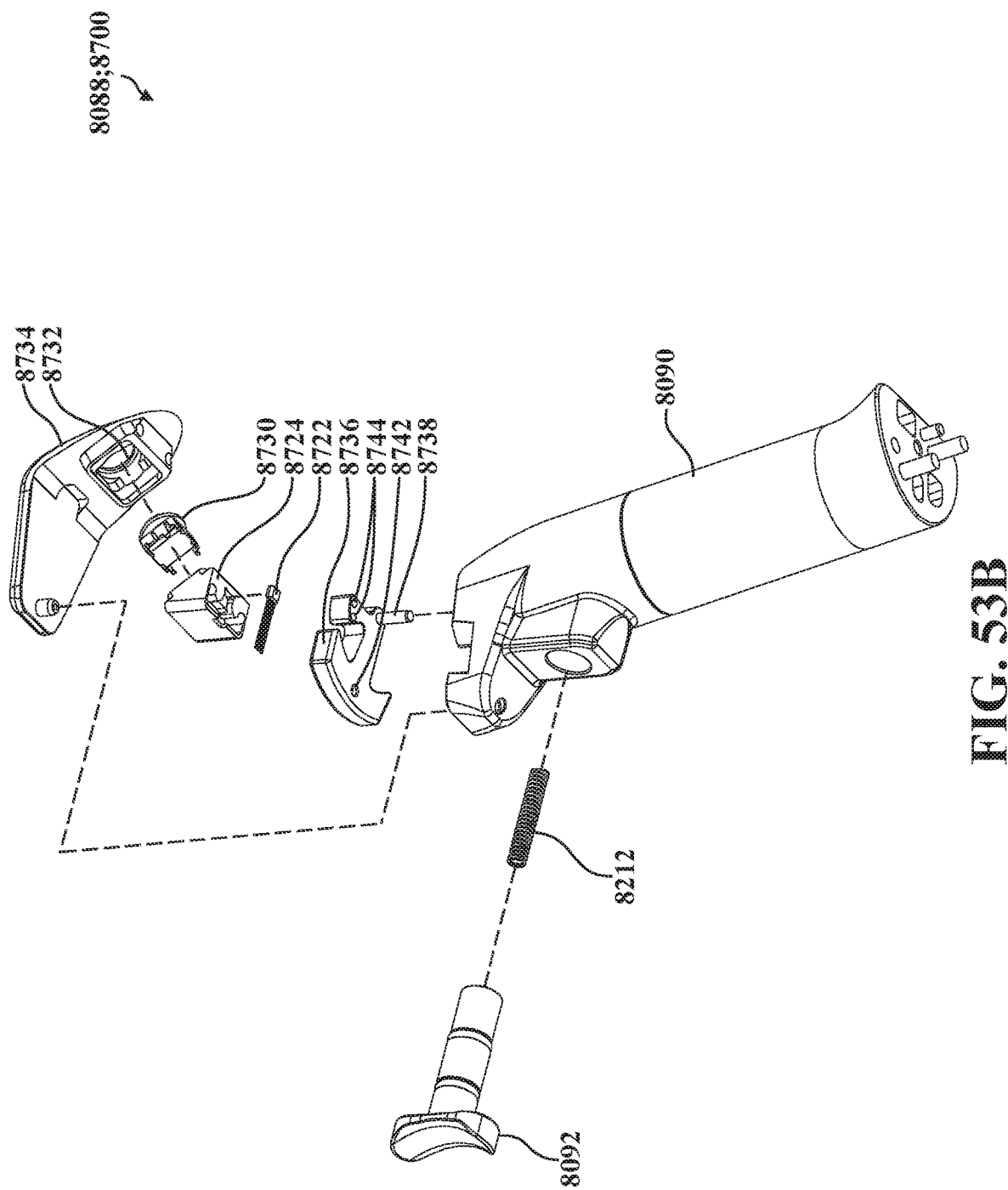
FIG. 53B is another exploded perspective view of the second trigger subassembly of FIG. 53A.
Figure 54:
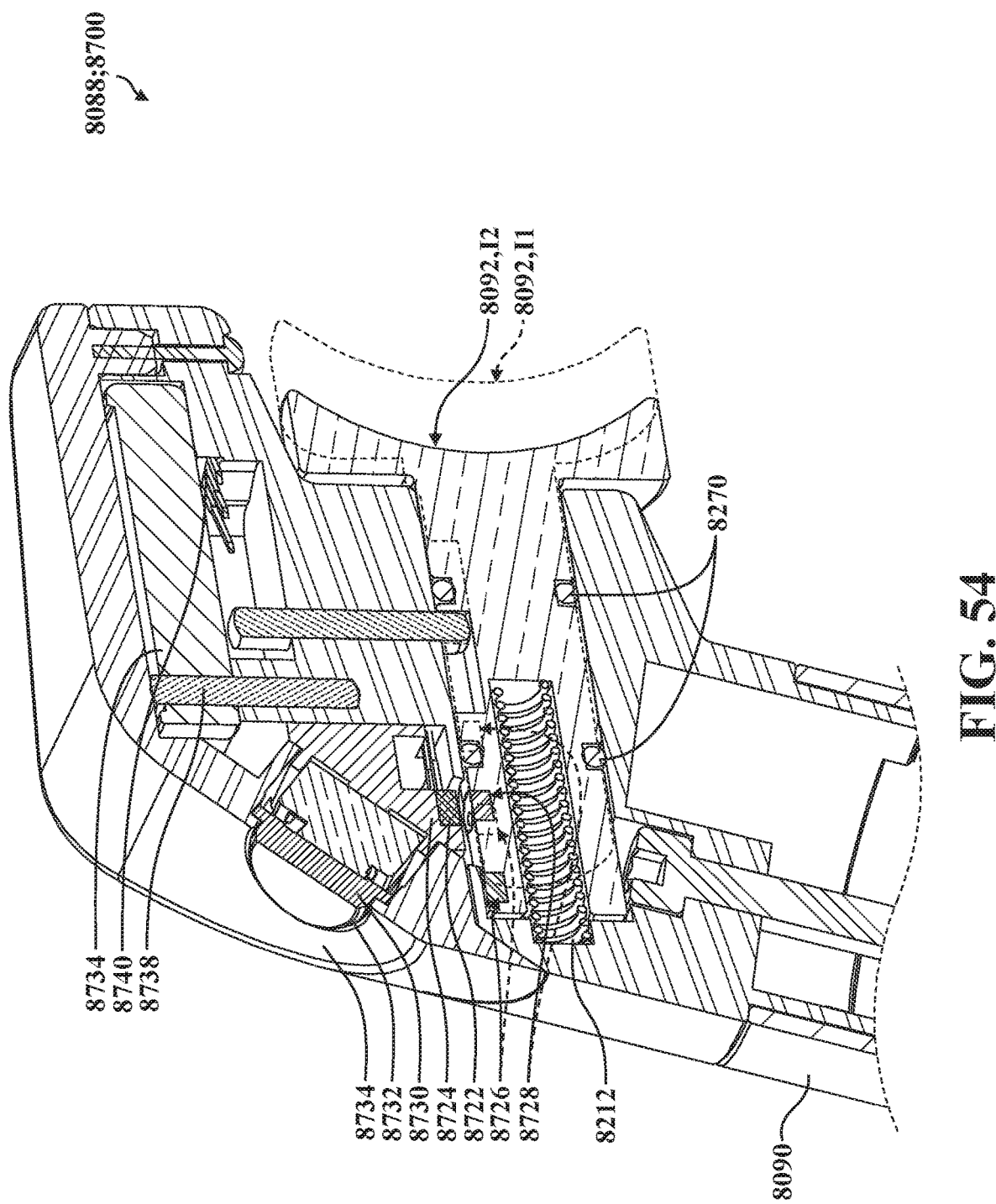
FIG. 54 is a partial, sectional perspective view of the second trigger subassembly of FIGS. 53A-53B, depicted as sectioned generally longitudinally.

Referring now to FIGS. 52-54, the second trigger subassembly 8700 is operatively attached to the grip mount 8704 of the first trigger subassembly 8698, such as by one or more fasteners. The second trigger subassembly 8700 generally comprises the grip 8090, the input trigger 8092, and the trigger biasing element 8212 which is seated in the input trigger 8092 (see FIG. 54). Here in the eighth embodiment of the end effector 8040, movement of the input trigger 8092 between the first and second input positions I1, I2 is determined via a trigger sensor 8722 supported in a trigger sensor keeper 8724 secured to the grip 8090 (see FIGS. 53A-53B), and the input trigger 8092 is retained relative to the grip 8090 via a pin and slot arrangement (not shown in detail).

The trigger sensor 8722 is disposed in electrical communication with board controller 8720 mounted on the circuit board 8710 (see FIG. 50; electrical connection not shown) and is responsive to movement of first and second trigger emitters 8726, 8728 coupled to the input trigger 8092 for concurrent movement between the first and second input positions I1, I2 (see FIG. 54). To this end, the input trigger 8092 is configured such that the first trigger emitter 8726 is arranged adjacent to the trigger sensor 8722 when in the first input position I1 and the second trigger 8728 is arranged adjacent to the trigger sensor 8722 when in the second input position I2. The trigger sensor keeper 8724 also supports an input button 8730, which is likewise disposed in electrical communication with the board controller 8720 (see FIG. 50; electrical connection not shown) and is arranged for engagement by the user. The input button 8730 is seated within a cover aperture 8732 formed in a grip cover 8734 secured to the grip 8090 via a fastener, and is arranged for engagement by the user to facilitate additional control of the surgical system 30. It will be appreciated that the input button 8730 could be configured to facilitate control over a number of different aspects of the end effector 8040 (e.g., switching into haptic mode). Other configurations are contemplated.

In addition to the input trigger 8092 and the input button 8730, the second trigger subassembly 8700 also comprises an input switch 8736 which is supported by a switch shaft 8738 for pivoting movement relative to the grip 8090 between left and right switch positions (not shown in detail) via engagement by the user. Here, a switch sensor 8740 disposed in electrical communication with the board controller 8720 is seated in the grip 8090 (see FIG. 50; electrical connection not shown). The switch sensor 8740 is responsive to movement of a switch emitter 8742 coupled to the input switch 8736 for concurrent movement relative to the grip 8090. In the illustrated embodiment, a switch detent arrangement, generally indicated at 8744, is provided to keep the input switch 8736 in one of the left and right switch positions during an absence of engagement from the user. While not illustrated in detail, the switch emitter 8742 is disposed adjacent to the switch sensor 8740 in one of the left and right switch positions maintained by the switch detent arrangement 8744 and is spaced from the switch sensor 8740 in the other of the left and right switch positions such that the board controller 8720 can differentiate therebetween. Like the input button 8730 described above, movement of the input switch 8736 can be utilized to facilitate additional control of the surgical system 30. By way of non-limiting example, movement of the input switch 8736 between the left and right switch positions described above could correspond to operation of the actuator 8166 in respective "forward" and "reverse" directions to, for example, rotate the tool 8042 about the second axis A2 in clockwise and counterclockwise directions. Other configurations are contemplated.

Figure 55:
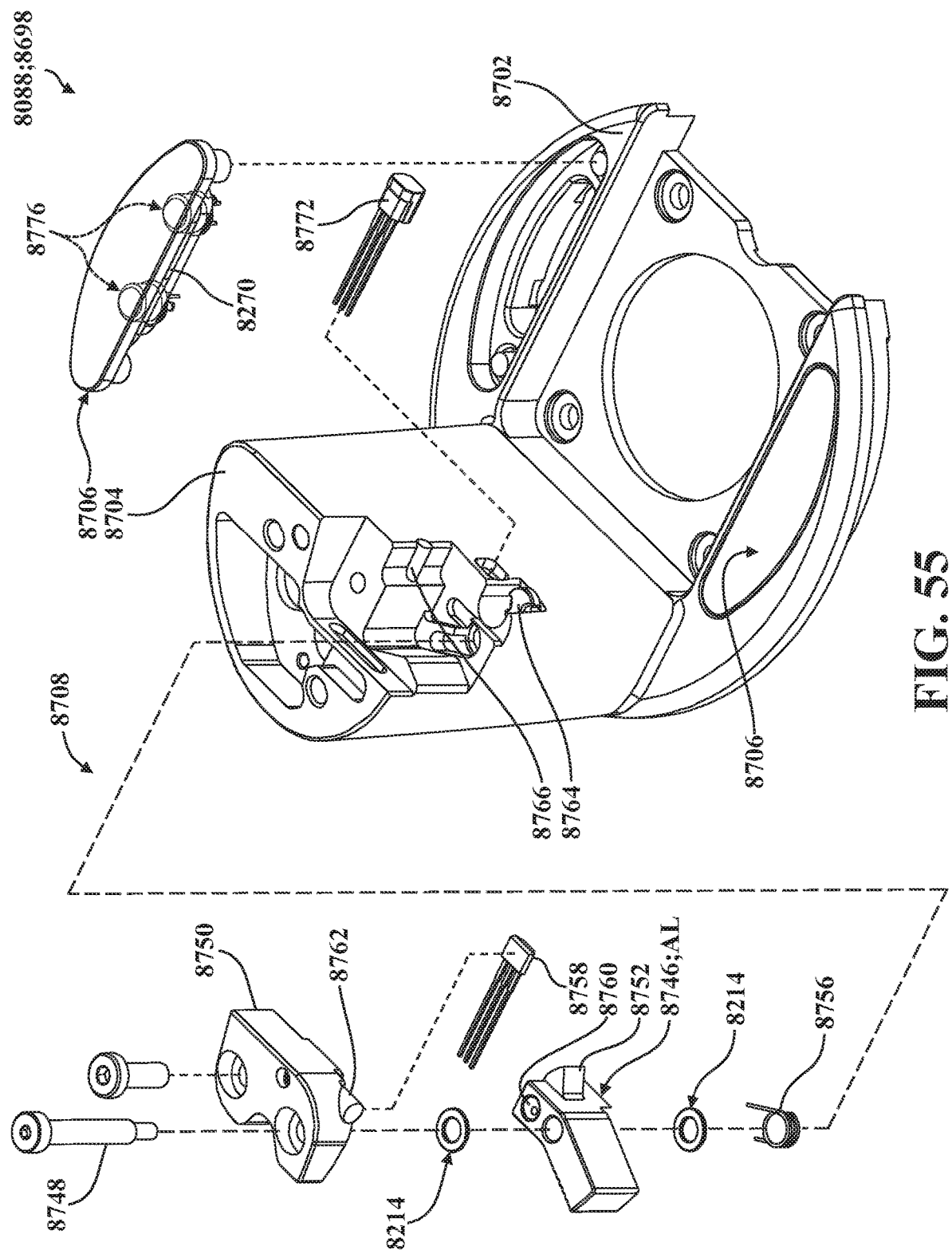
FIG. 55 is an exploded perspective view of the first trigger subassembly of FIG. 52, shown having a guard locking subassembly to secure the retention mechanism of FIGS. 49A-50.

Referring now to FIGS. 55-57, the first trigger subassembly 8698 is configured to facilitate releasably securing the guard cover 8350 of the retention mechanism 8664 in the first guard position U1 which, in the eighth embodiment, ensures that the tool 8042 is retained both rotatably by one of the first and second rotational locks RL1, RL2 and also axially by the axial lock AL. Here, and as will be appreciated from the subsequent description of the retention mechanism 8664 below, the first guard position U1 also defines operation of the axial lock AL in the lock configuration ACL and, unlike the second embodiment of the end effector 2040 described above, promotes access to the manual interface 8094.

In order to maintain operation axial lock AL in the lock configuration ACL, the guard locking subassembly 8708 of the first trigger subassembly 8698 selectively inhibits movement of the guard cover 8350 of the retention mechanism 8664 relative to the grip mount 8704. To this end, and as is best depicted in FIG. 55, the guard locking subassembly 8708 comprises a guard lever 8746 supported for pivoting movement relative to the grip mount 8704 via a lever fastener shank 8748 defined by a fastener securing a keeper mount 8750 to the grip mount 8704. The guard lever 8746 is arranged between a pair of washers 8214 supported on the lever fastener shank 8748, and comprises a lever pawl 8752 which is disposed in engagement with a pawl stop member 8754 of the retention mechanism 8664 via a lever biasing element 8756, as described in greater detail below. The keeper mount 8750 also supports a lever sensor 8758 which is responsive to movement of a lever emitter 8760 coupled to the guard lever 8746 for concurrent movement between the lock configuration ACL and the release configuration ACR. The guard locking subassembly 8708 also comprises an upper vertical stop 8762 coupled to the keeper mount 8750, and a lower vertical stop 8764 and a lateral stop 8766 each coupled to the grip mount 8704. As is described in greater detail below, in the lock configuration ACL, the pawl stop member 8754 is disposed in engagement between the lever pawl 8752 and the lateral stop 8766, and the upper vertical stop 8762 and the lower vertical stop 8764 respectively engage an upper vertical member 8768 and a lower vertical member 8770 each coupled to the retention mechanism 8664 (see FIG. 56C).

With continued reference to FIG. 55, the guard locking subassembly 8708 of the first trigger subassembly 8698 also comprises a guard sensor 8772 supported in the grip mount 8704 adjacent to the lower vertical stop 8764. The guard sensor 8772 is responsive to changes in the position of a guard emitter 8774 (see FIGS. 56B and 56D) coupled to the retention mechanism 8664. Both the guard sensor 8772 and the lever sensor 8758 are disposed in electrical communication with the board controller 8720 (see FIG. 50; electrical connection not shown), and cooperate to determine operation of the axial lock AL between the lock configuration ACL and the release configuration ACR, as described in greater detail below. Furthermore, the indicator housings 8706 coupled to the upper mount plate 8702 of the first trigger subassembly 8698 each comprise a pair of indicator modules 8776 (e.g., light emitting diodes) that are similarly disposed in electrical communication with the board controller 8720 (see FIG. 50; electrical connection not shown), and may be employed to provide the user with visual feedback by changing color, state, brightness, and the like, in response to various corresponding or otherwise predetermined configurations or operational parameters of and/or associated with the end effector 8040. By way of non-limiting example, the indicator modules 8776 could emit red-colored light when the axial lock AL is in the release configuration ACR, and could emit green-colored light when the axial lock AL is in the lock configuration ACL. Other configurations are contemplated.

It will be appreciated that electrical communication between the various electrical components operatively attached to the first and second trigger subassemblies 8698, 8700 and the board controller 8720 and/or other components mounted on the circuit board 8710 can be facilitated in a number of different ways, including without limitation wired connections, wireless communication, and the like. Furthermore, while the trigger assembly 8088 is not generally arranged for movement relative to the drive body 8250 in the eighth embodiment of the end effector 8040, it will be appreciated that all or a portion of the trigger assembly 8088 could be configured to move or to otherwise be selectively positioned by the user in some embodiments. By way of non-limiting example, all or a portion of the grip 8090 may be movable (e.g., rotatable) such that one or more sensors, buttons, and the like move concurrently with the grip 8090 relative to the circuit board 8710 and/or the drive body 8250. In such embodiments, electrical communication may be facilitated such as is described in U.S. Provisional Patent Application No. 62/678,838, filed on May 31, 2018, entitled "Rotating Switch Sensor for a Robotic System," the disclosure of which is hereby incorporated by reference in its entirety. Other configurations are contemplated.

Referring now to FIG. 49B, two types of tools 8042 are shown configured for "top loading" attachment to the drive conduit 8462 of the end effector 8040: the rotary cutting tool 8044 and the rotary driving tool 8048 with the anchor 8050. Here, the tools 8042 each comprise a bearing element 8778 formed on the tool body 8466 between the interface end 8468 and the working end 8470. The bearing element 8778 is shaped and arranged to engage a bearing 8262 that defines a portion of the drive bore 8478 defined adjacent to the distal outlet 8482 (see FIG. 59B). This configuration helps promote alignment of the tool 8042 for rotation about the second axis A2. Each of the tools 8042 also comprises a proximal key body 8780 arranged at the interface end 8468 of the tool body 8466. The proximal key body 8780 for each of the representative tools 8042 illustrated in FIG. 49B are different from one another, but each defines a proximal key face 8782 that is substantially perpendicular to the second axis A2. A proximal key element 8784, which has a cylindrical outer profile, extends from the proximal key face 8782 in a direction facing away from the working end 8470 of the tool body 8466. The proximal key face 8782 and the proximal key element 8784 cooperate with the retention mechanism 8664 to facilitate operation of the axial lock AL, as described in greater detail below.

In the eight embodiment, each of the illustrated types of tools 8042 has a differently-configured conduit rotational retainer 8464 interposed between the proximal key element 8784 and the bearing element 8778. More specifically, the rotary cutting tool 8044 comprises a first seat element 8786 with a first notch element 8788 and a first seat flange 8790 that defines a first seat face 8792, and the rotary driving tool 8048 comprises a second seat element 8794 with a second notch element 8796 and a second seat flange 8798 that defines a second seat face 8800. The first seat element 8786 is shaped and arranged so as to be disposed within the drive conduit 8462, with the first notch element 8788 disposed in the first notch 8688 and with the first seat face 8792 abutting the proximal conduit end 8684 of the drive conduit 8462 to define the first rotational lock RL1 (see FIGS. 58A-58D). The second seat element 8794, in turn, is shaped and arranged so as to be disposed within the carrier shaft 8422, with the second notch element 8796 disposed in the second notch 8696 and with the second seat face 8800 abutting the proximal carrier end 8694 of the carrier shaft 8422 to define the second rotational lock RL2 (see FIGS. 63A-63E; not shown in detail).

Figure 56A:
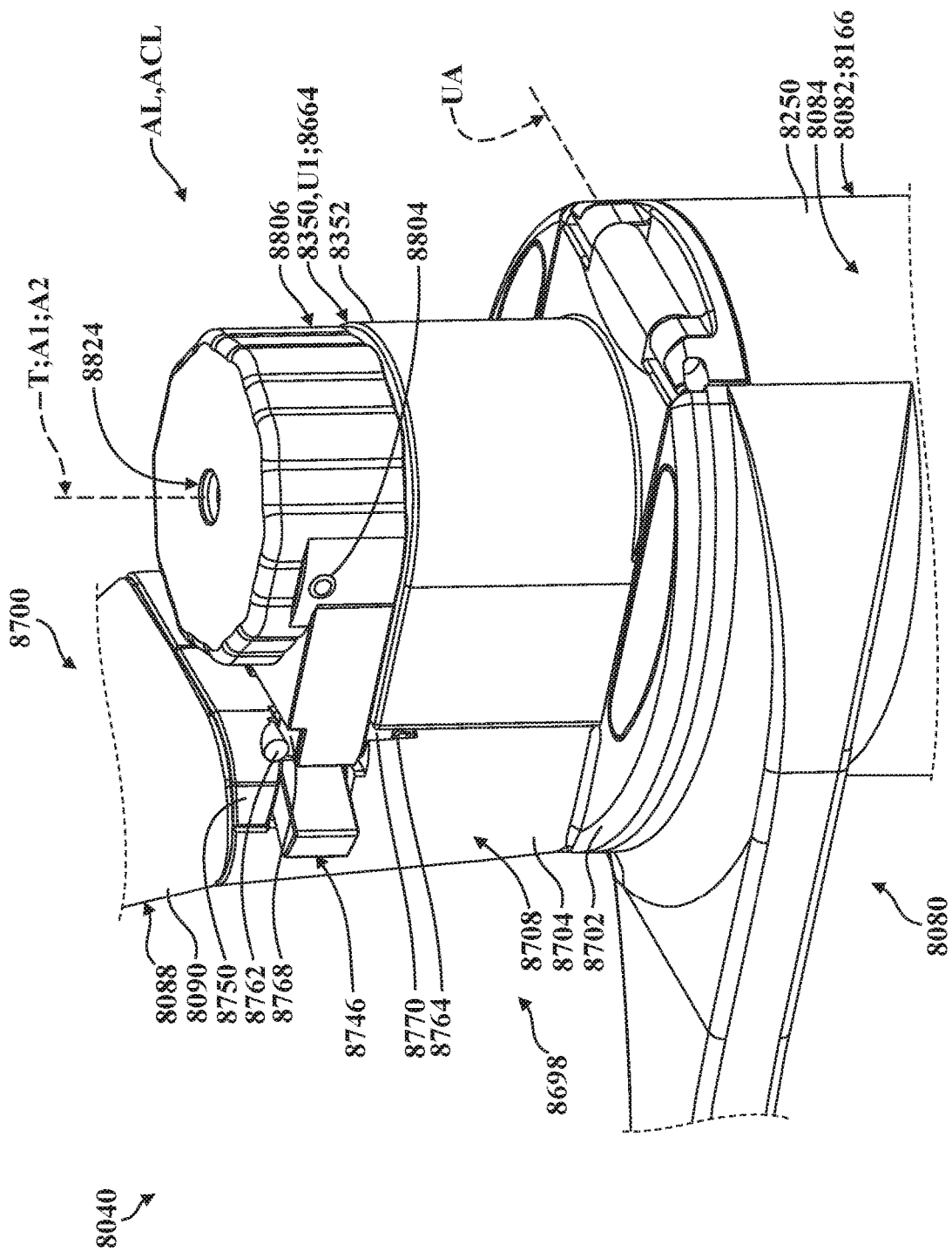
FIG. 56A is a partial perspective view of the end effector of FIGS. 49A-50, shown with the guard cover of the retention mechanism secured in the first guard position by the guard locking subassembly of FIG. 55.
Figure 56B:
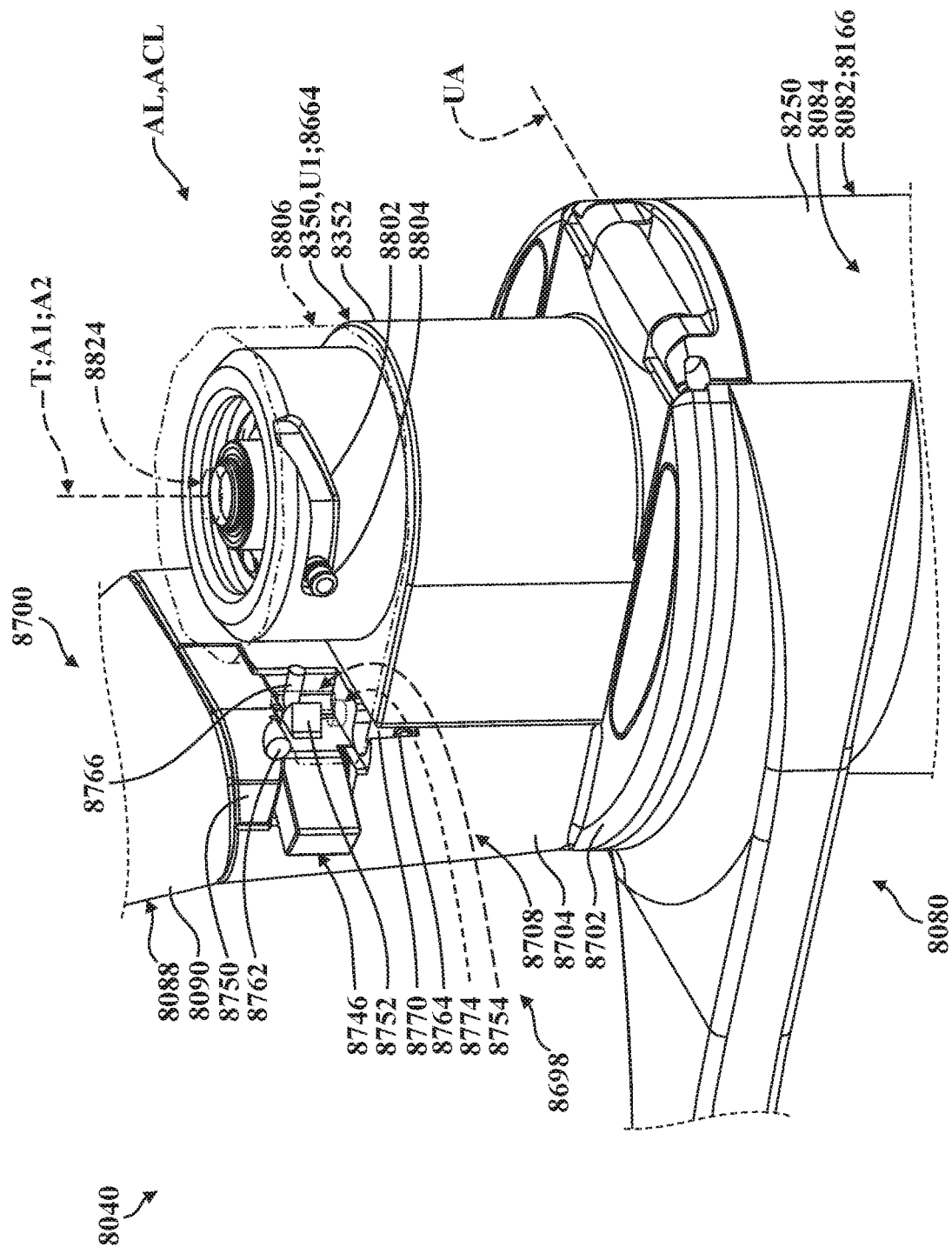
FIG. 56B is another partial perspective view of the end effector of FIG. 56A, shown with portions of the retention mechanism engaging portions of the guard locking subassembly.

Referring now to FIGS. 56A-57, the retention mechanism 8664 defines the axial lock AL and comprises the guard cover 8350 in the eighth embodiment of the end effector 8040, as noted above. Here, the guard cover 8350 is similarly movable from the first guard position U1 (see FIGS. 56A-56D) to the second guard position U2 (see FIG. 57) to facilitate "top loading" insertion and removal of tools 8042 from the drive conduit 8462. Furthermore, the axial lock AL can be moved into and out of engagement with the guard locking subassembly 8708 between the lock configuration ACL (see FIGS. 56A-56B) and the release configuration ACR (see FIGS. 56C-56D). Here in the eighth embodiment of the end effector 8040, the guard cover 8350 needs to be arranged in the first guard position U1 before the axial lock AL can be moved to the lock configuration ACL, which simultaneously restricts relative movement between the secured tool 8042 and the drive conduit 8462 via the retention mechanism 8664, and also between the guard cover 8350 and the drive body 8250 via the guard locking subassembly 8708. To this end, and as is best depicted in FIGS. 56B and 57, the guard body 8352 of the guard cover 8350 comprises knob guideslots 8802 along which knob retainers 8804 coupled to a guard knob 8806 ride. The knob retainers 8804 support bearings 8262 thereon, and travel along the knob guideslots 8802 as the guard knob 8806 is rotated to facilitate operation of the axial lock AL, as described in greater detail below.

The guard knob 8806 is prevented from detaching from the guard body 8352 via one or more fasteners (e.g., rings, circlips, and the like) and a knob keeper 8808 that supports a guard knob biasing element 8810 disposed in engagement with the guard knob 8806 to urge the guard knob 8806 away from the guard body 8352. This configuration provides the user with haptic feedback when engaging the guard knob 8806 to move the axial lock AL from the lock configuration ACL (see FIGS. 56A-56B and 58D) to the release configuration ACR (see FIGS. 56C-56D and 58C), and also results in compressing the guard knob biasing element 8810 when the user rotates the guard knob 8806 to move from the release configuration ACR to the lock configuration ACL as the knob retainers 8804 ride along the knob guideslots 8802.

Figure 58A:
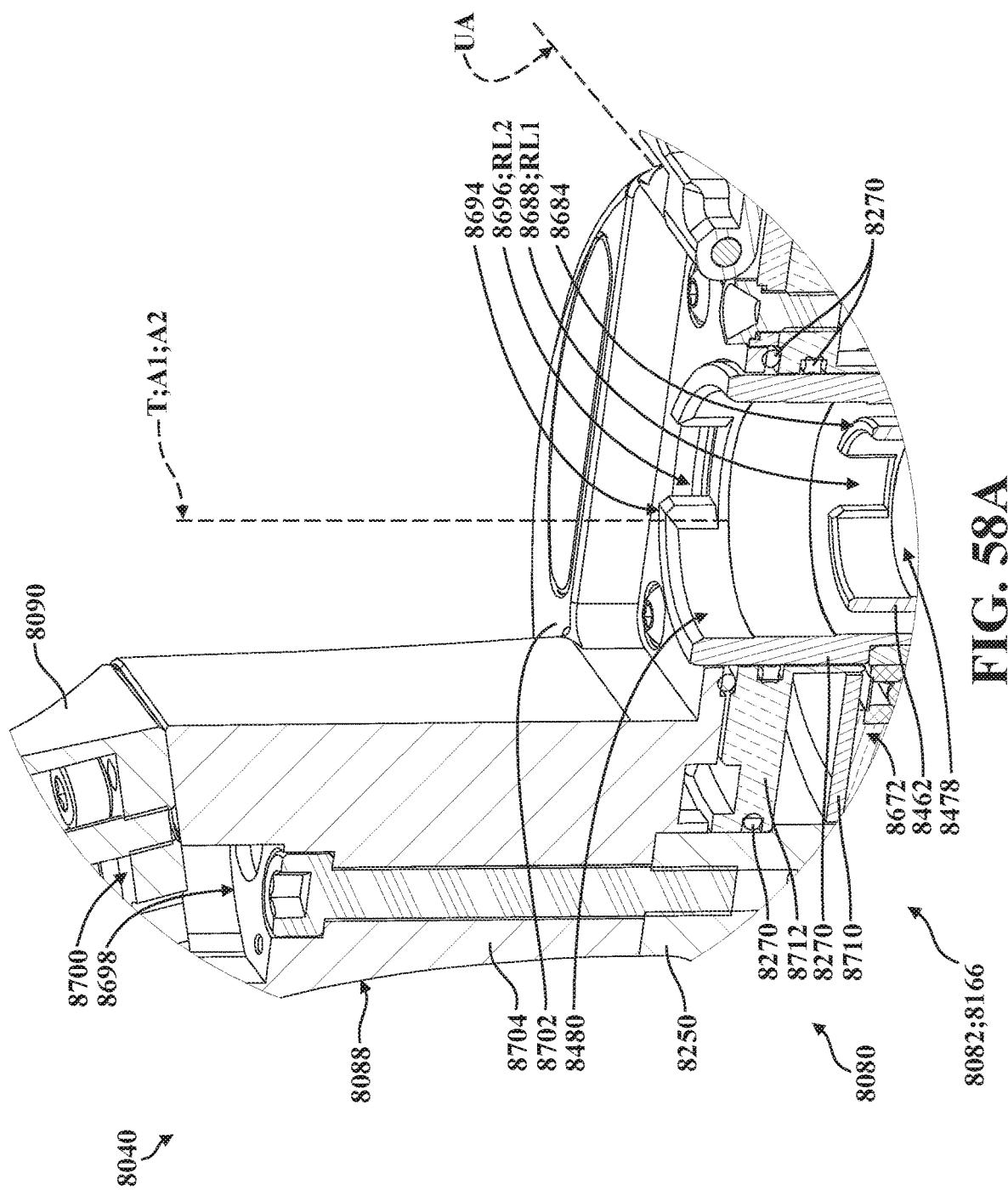
FIG. 58A is an enlarged, partial sectional perspective view taken along indicia 58 of FIG. 57.
Figure 58C:
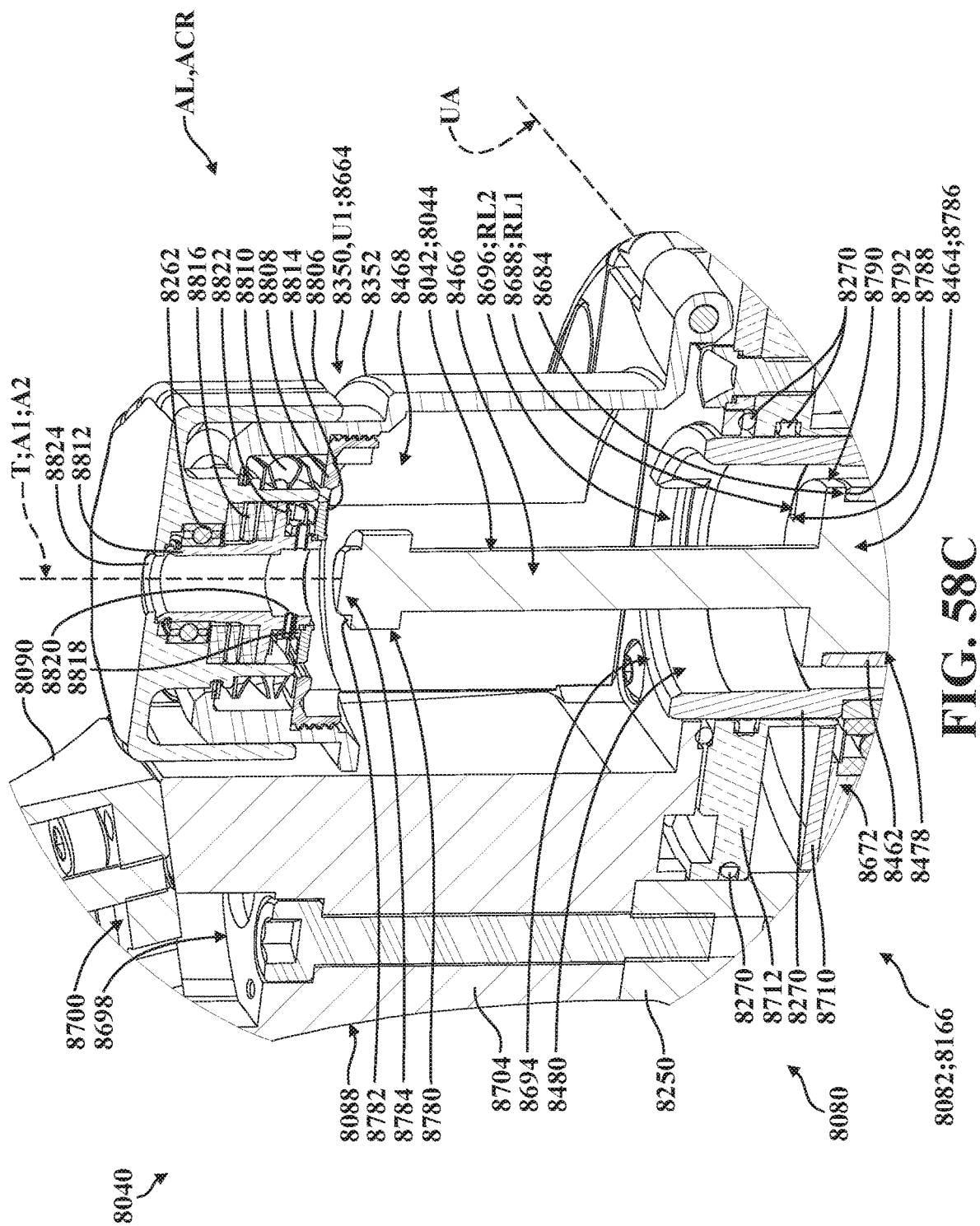
FIG. 58C is another enlarged, partial sectional perspective view of the end effector and the rotary driving tool of FIG. 58B, shown with the guard cover of the retention mechanism arranged as depicted in FIGS. 56C-56D.
Figure 58D:
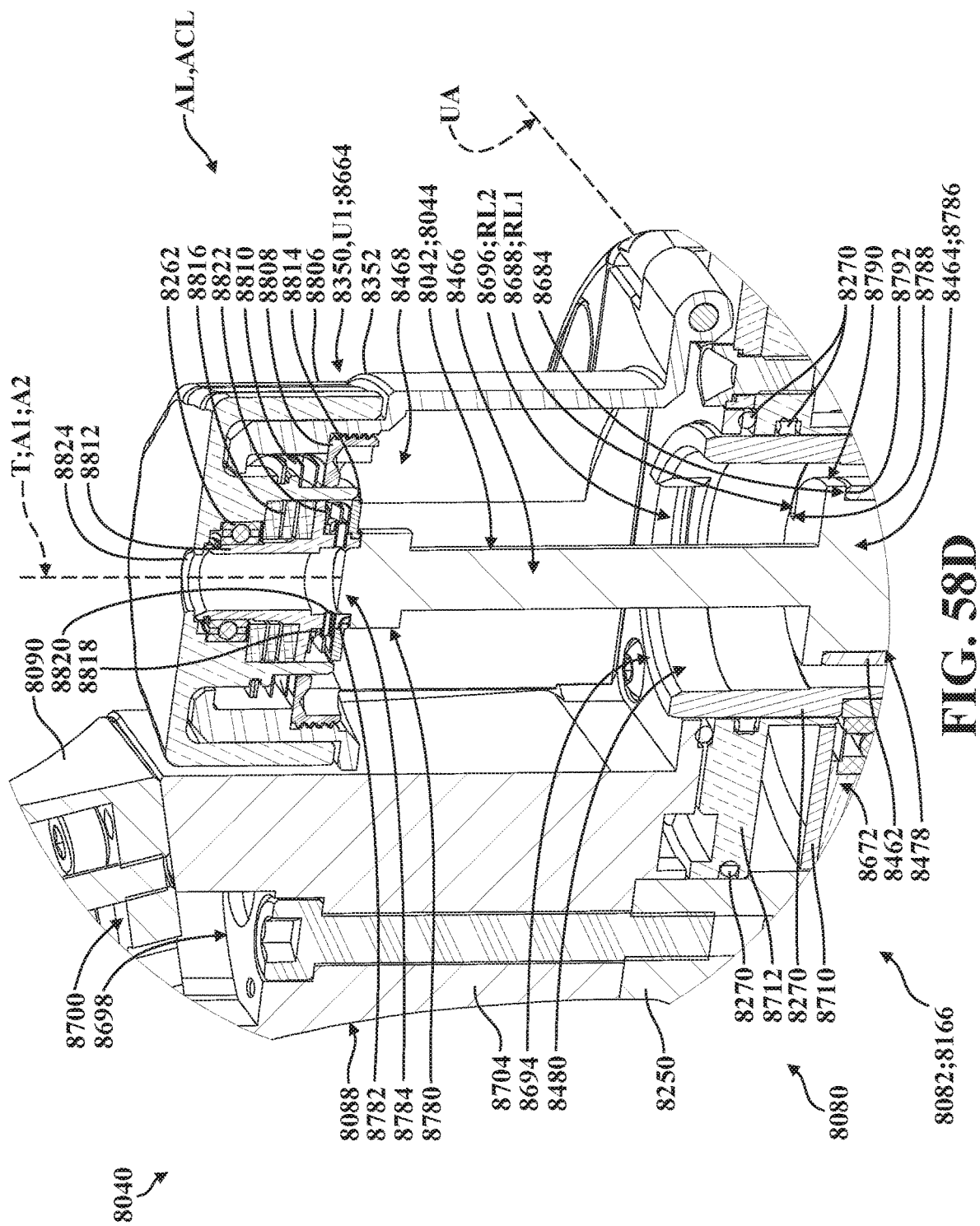
FIG. 58D is another enlarged, partial sectional perspective view of the end effector and the rotary driving tool of FIG. 58C, shown with the guard cover of the retention mechanism arranged in the first guard position as depicted in FIGS. 56A-56B.
Figure 59A:
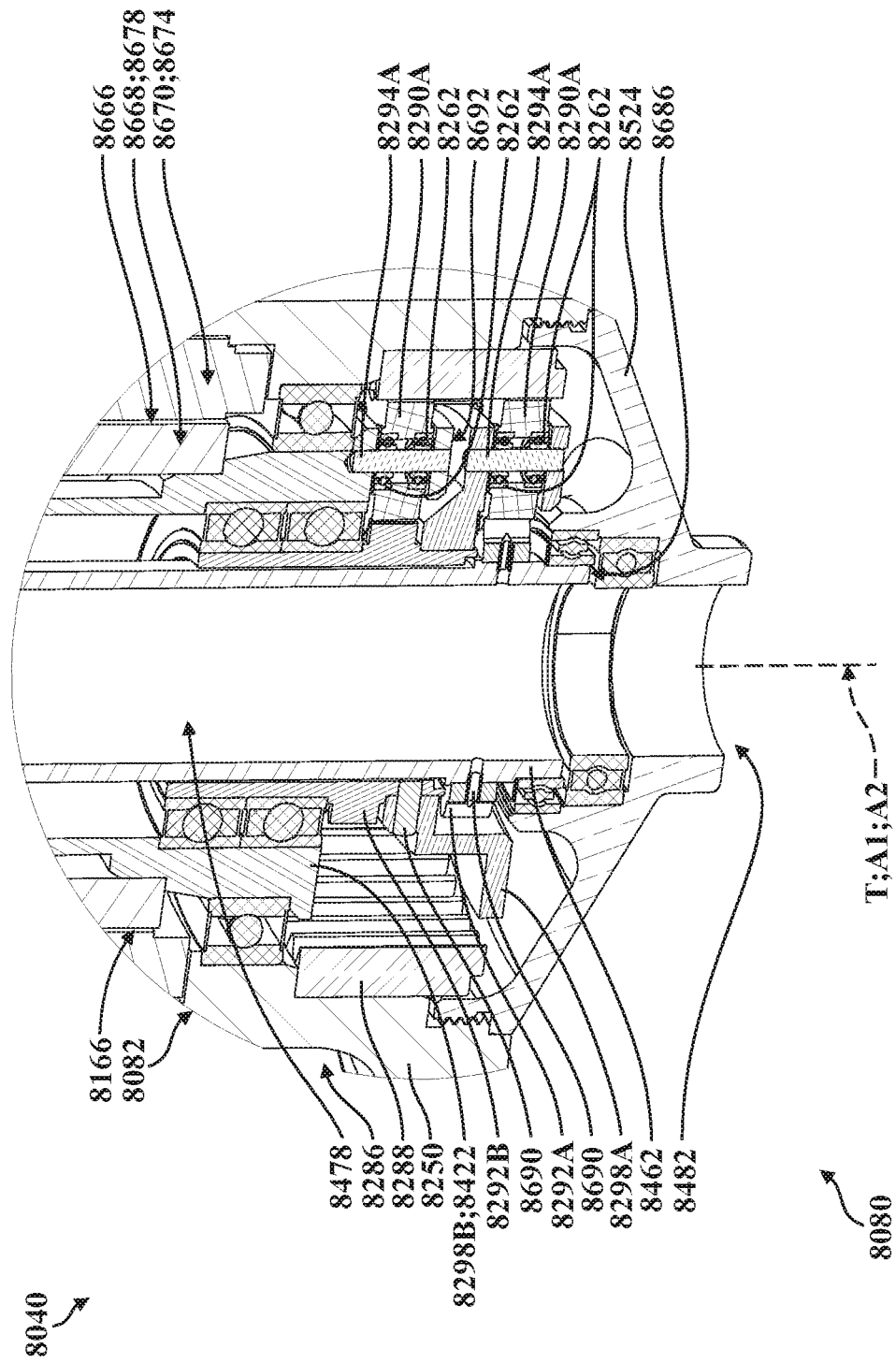
FIG. 59A is an enlarged, partial sectional perspective view taken along indicia 59 of FIG. 57.
Figure 59B:
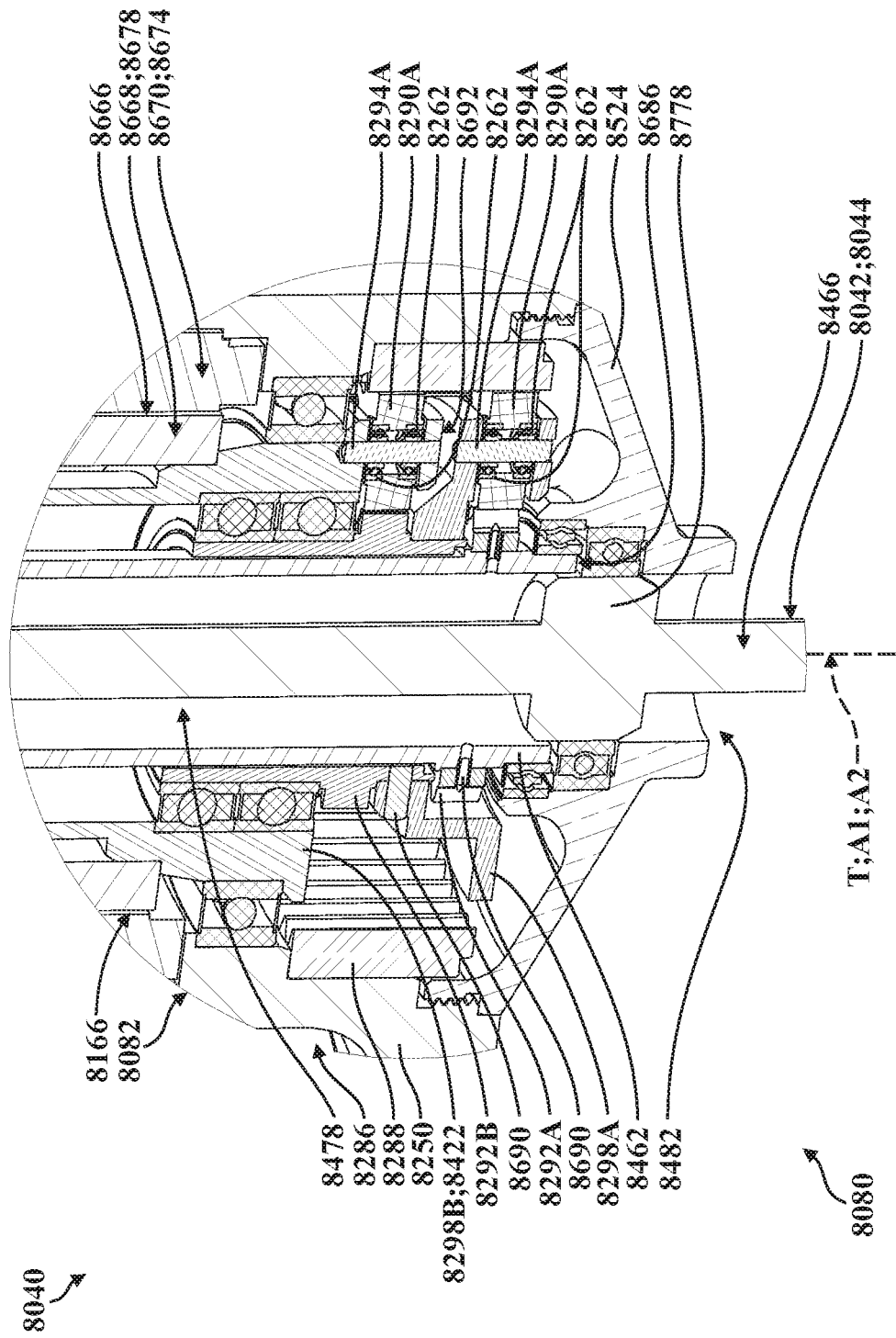
FIG. 59B is another enlarged, partial sectional perspective view of the end effector of FIG. 59A, shown with portions of the rotary driving tool of FIG. 49B supported in the drive conduit of the drive assembly.

Referring now to FIGS. 56A-58D, the retention mechanism 8664 also comprises a key hub 8812 and a key collar 8814 that are operatively attached to the guard knob 8806. A bearing 8262 rotatably supports the key hub 8812 for rotation relative to the guard knob 8806, and a key thrust bearing 8816 helps prevent binding between the key hub 8812 and the guard knob 8806 as the axial lock AL moves between the release configuration ACR and the lock configuration ACL. The key collar 8814 comprises key collar slots 8818 in which key pins 8820 coupled to the key hub 8812 are arranged for movement. This configuration facilitates limited movement of the key collar 8814 relative to the key hub 8812 while also retaining the key collar 8814. A key collar biasing element 8822 interposed between the key hub 8812 and the key collar 8814 urges the key collar 8814 generally away from the key hub 8812. When one of the tools 8042 has been inserted through the drive conduit 8462 and when the guard cover 8350 has been moved to the first guard position U1 as depicted in FIG. 58C, both the key hub 8812 and the key collar 8814 are spaced away from the proximal key element 8784 of the tool 8042. Here, the key collar 8814 is disposed closer to the proximal key element 8784 than the key hub 8812 until rotation of the guard knob 8806 brings the key collar 8814 into abutment with the proximal key face 8782 of the tool body 8466 as the axial lock AL moves toward the lock configuration ACL which, in turn, compresses the key collar biasing element 8822. As shown in FIG. 58D, the key hub 8812 is shaped to receive the proximal key element 8784 of the tool 8042 therein when in the lock configuration ACL, with portions of both the key hub 8812 and the key collar 8814 disposed in abutment with the proximal key face 8782. This configuration helps guide the proximal key element 8784 into the key hub 8812 which, in turn, helps facilitate alignment of the tool 8042 about the second axis A2.

The key collar 8814 and the key hub 8812 each have a generally cylindrical inner profile which are disposed in communication with the drive bore 8478 adjacent to the proximal inlet 8480 when the guard cover 8350 is in the first guard position U1. Furthermore, the guard cover 8350 is provided with a generally cylindrical knob aperture 8824 that is disposed in communication with the inner profiles of the key collar 8814 and the key hub 8812. This configuration provides the user with the ability to access the manual interface 8094 through the knob aperture 8824 which, in the eighth embodiment of the end effector 8040, is realized as a part of the rotary driving tool 8048 described in greater detail below in connection with FIGS. 60-62B.

Figure 56C:
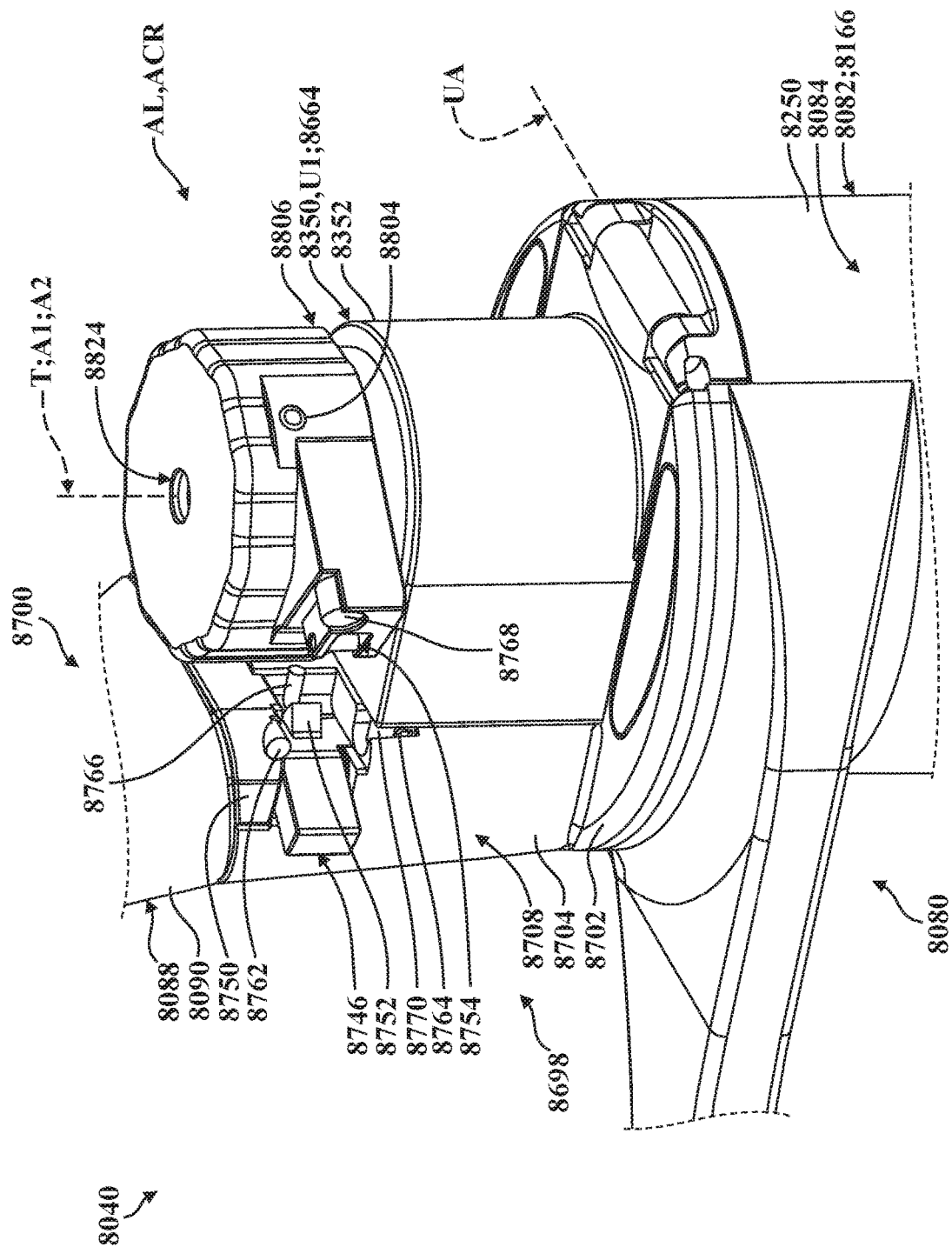
FIG. 56C is a partial perspective view of the end effector of FIGS. 49A-50, shown with the guard cover of the retention mechanism arranged in the first guard position but disengaged from the guard locking subassembly of FIG. 55.
Figure 56D:
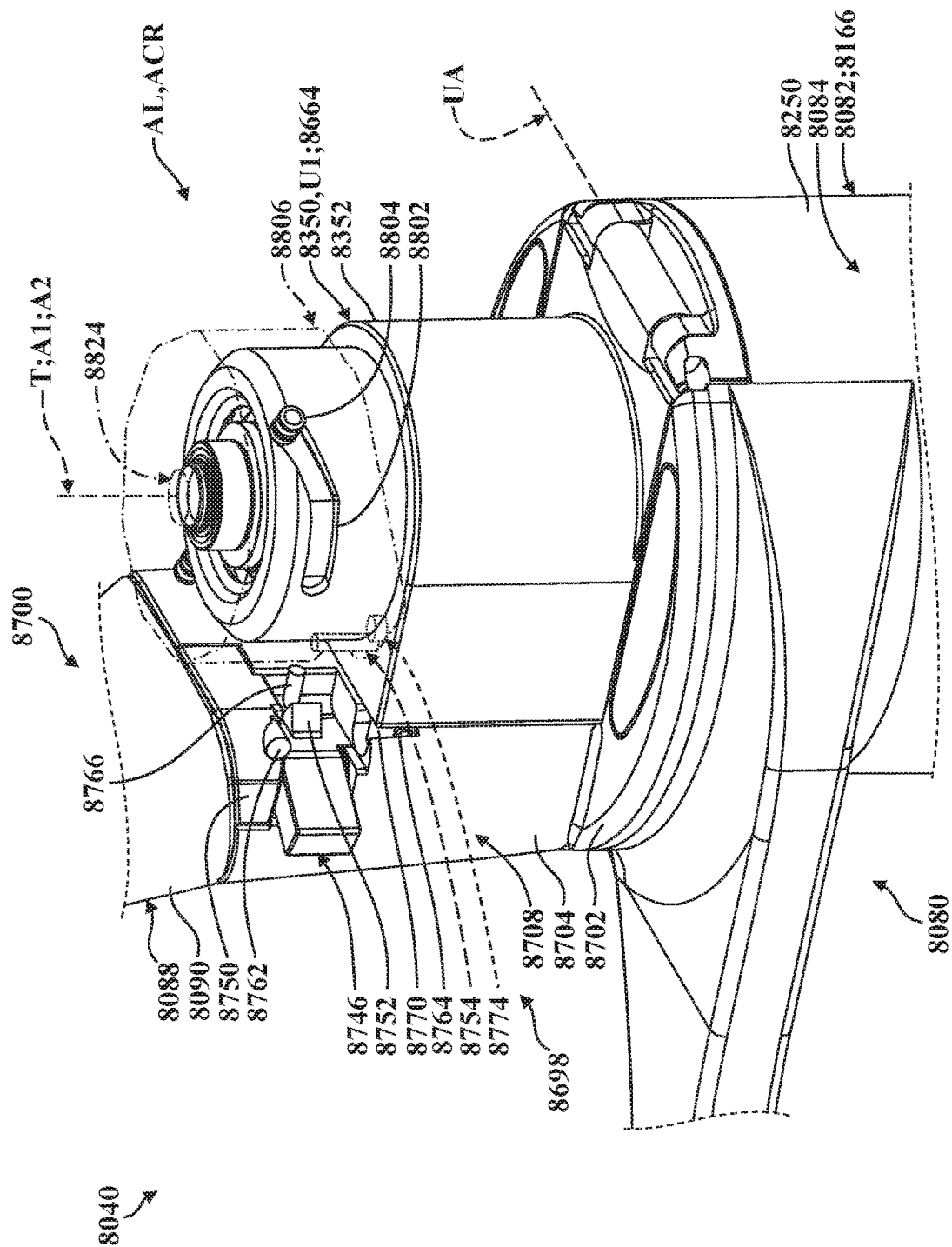
FIG. 56D is another partial perspective view of the end effector of FIG. 56C, shown with portions of the retention mechanism disengaged from but adjacent to portions of the guard locking subassembly.

As is best depicted in FIG. 56C, the lower vertical member 8770 is coupled to the guard body 8352 and abuts the lower vertical stop 8764 coupled to the grip mount 8704 when the guard cover 8350 is in the first guard position U1. The upper vertical member 8768, the pawl stop member 8754, and the guard emitter 8774 (see FIG. 56D) are each coupled to the guard knob 8806 for concurrent movement relative to the guard body 8352. When the guard knob 8806 is rotated to bring the axial lock AL from the release configuration ACR depicted in FIGS. 56C-56D to the lock configuration ACL depicted in FIGS. 56A-56B, the pawl stop member 8754 first comes into contact with the lever pawl 8752 of the guard lever 8746 which pivots the guard lever 8746 until continued rotation of the guard knob 8806 brings the pawl stop member 8754 into abutment with the lateral stop 8766. Here in the lock configuration ACL depicted in FIGS. 56A-56B, the lever biasing element 8756 urges the guard lever 8746 against the pawl stop member 8754 which, in turn, is also disposed in abutment with the lateral stop 8766. Here too, the upper vertical member 8768 comes into abutment with the upper vertical stop 8762. As such, in the lock configuration ACL, movement of the guard knob 8806 relative to the guard body 8352 and the grip mount 8704 is inhibited until the user engages the guard lever 8746 to release the pawl stop member 8754. As noted above, the guard sensor 8772 coupled to the grip mount 8704 is responsive to movement of the guard emitter 8774 coupled to the guard knob 8806 such that the board controller 8720 can determine movement of the axial lock AL between the lock configuration ACL and the release configuration ACR. Similarly, the lever sensor 8758 coupled to the grip mount 8704 is responsive to movement of the lever emitter 8760 coupled to the guard lever 8746 such that the board controller 8720 can determine movement of the guard lever 8746.

Figure 60:
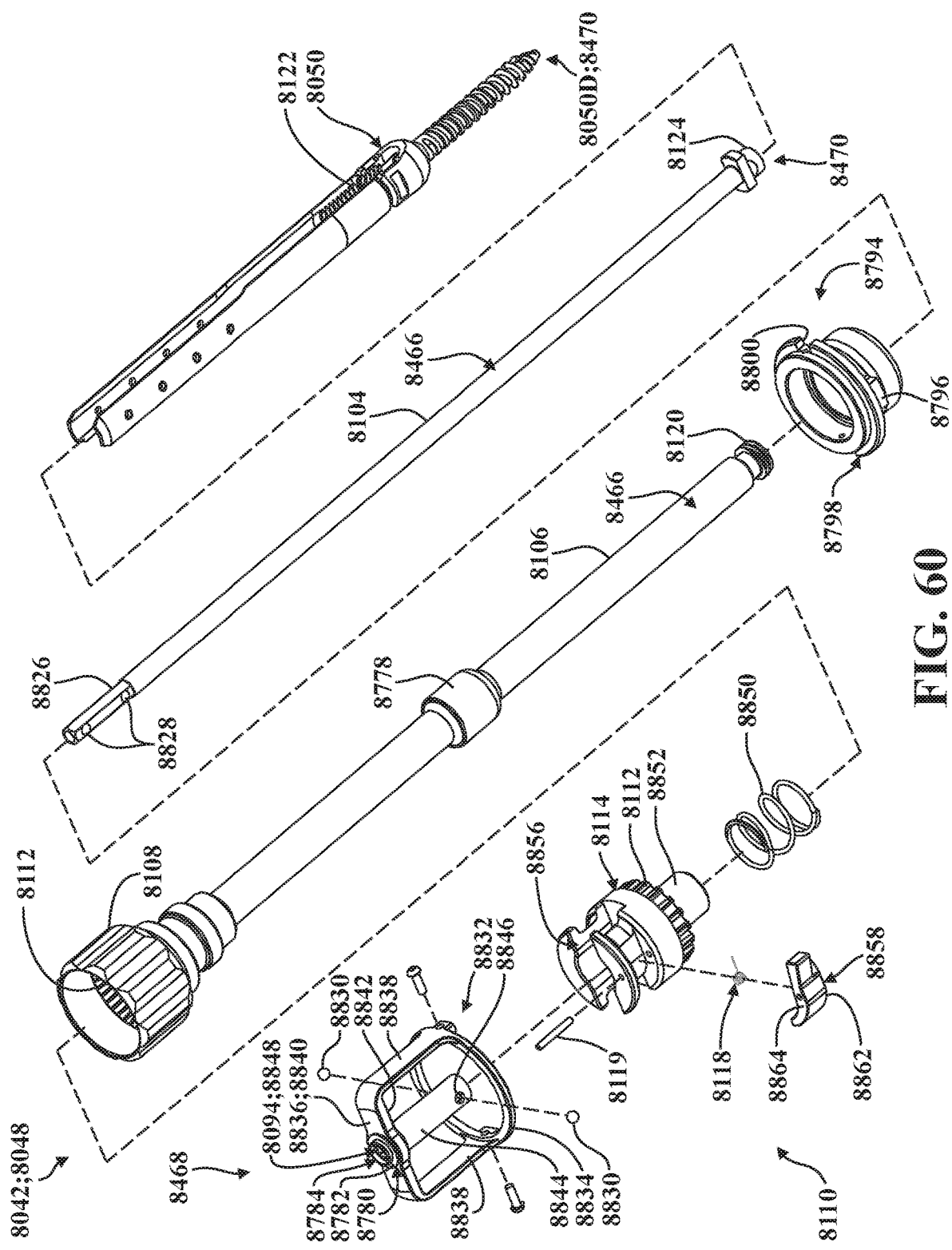
FIG. 60 is an exploded perspective view of the rotary driving tool and anchor of FIG. 49B, the rotary driving tool shown having a locking subassembly.

Referring now to FIGS. 60-62B, as noted above, the illustrated rotary driving tool 8048 is adapted for releasable attachment to the eighth embodiment of the end effector 8040 in the "top loading" manner and, in turn, is configured to releasably attach to the anchor 8050 using a differently-configured locking subassembly 8810 when compared to the rotary driving tool 48 described above in connection with the first embodiment of the end effector 40. Here in the eighth embodiment, and as is best depicted in FIG. 60, the support tube 8106 generally defines the tool body 8466 and extends between the external threads 8120 adjacent to the working end 8470 and the contoured body 8108 adjacent to the interface end 8468, with the bearing element 8778 arranged therebetween. The driveshaft 8104, which is similarly arranged so as to be rotatably supported within the support tube 8106, extends between the driver key 8124 adjacent to the working end 8470 and a hex portion 8826 adjacent to the interface end 8468. Lock element detents 8828 formed in the hex portion 8826 are shaped to receive driveshaft lock elements 8830 in order to facilitate concurrent rotation of the driveshaft 8104 and the support tube 8106 under certain conditions described in greater detail below.

The second seat element 8794 is formed as a separate component from the support tube 8106 and is disposed adjacent to the contoured body 8108. Here, a pair of fasteners secure the second seat element 8794 to a carriage 8832 for concurrent translation and rotation about the second axis A2. The carriage 8832 generally comprises a carriage ring 8834 which generally secures to the second seat element 8794, a carriage bridge 8836, and a pair of carriage arms 8838 which extend between and merge with the carriage ring 8834 and the carriage bridge 8836. The carriage bridge 8836 defines a first carriage face 8840 and an opposing second carriage face 8842. Here, the proximal key body 8780 and the proximal key element 8784 extend from the first carriage face 8840 such that the proximal key face

8782 is spaced from and substantially parallel to the first carriage face 8840. A carriage pilot 8844 extends from the second carriage face 8842 toward the carriage ring 8834, and comprises a pair of lock element pockets 8846 which are shaped to support the driveshaft lock elements 8830 therein. The carriage pilot 8844 also comprises a hex bore 8848 extending therethrough (and out of the proximal key element 8784) which is shaped to receive the hex portion 8826 of the driveshaft 8104. Here too in the eighth embodiment, the hex bore 8848 also serves as the manual interface 8094 and is accessible along the second axis A2 through the knob aperture 8824 (see FIG. 58D). While not illustrated in this embodiment, it will be appreciated that the manual interface 8094 could be engaged via a correspondingly-shaped handle assembly to rotate the carriage 8832 about the second axis A2.

Figure 61A:
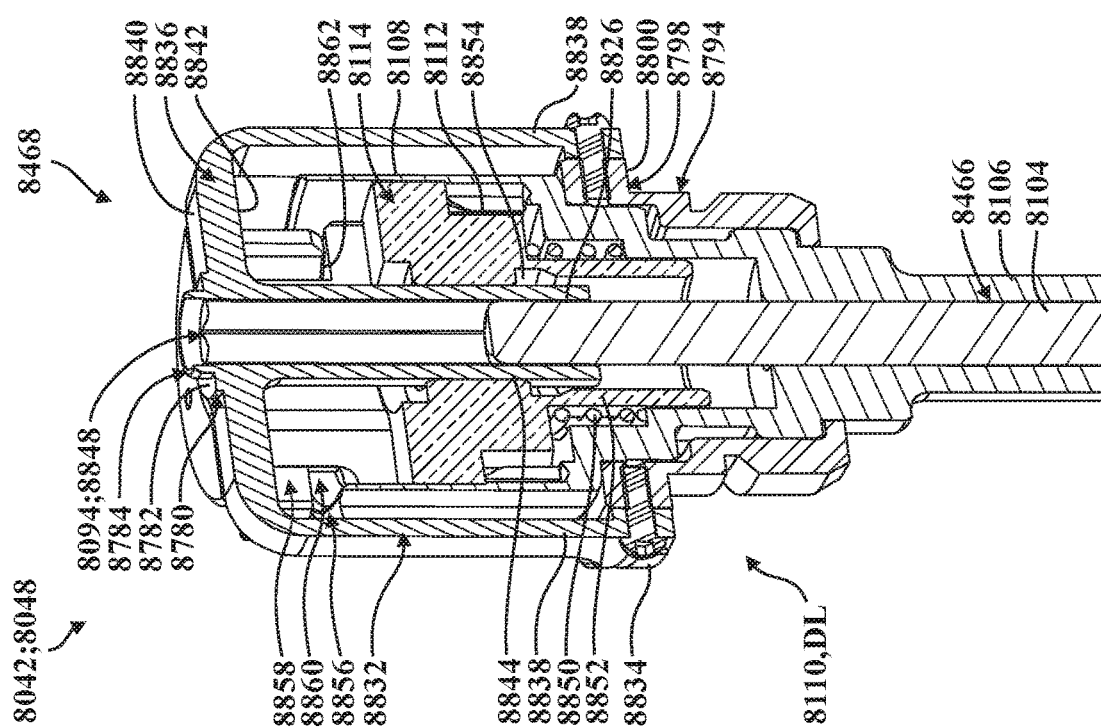
FIG. 61A is a partial, sectional perspective view of the rotary driving tool of FIG. 60, depicted as sectioned generally longitudinally, shown with the locking subassembly arranged in a driver locked configuration.
Figure 61B:
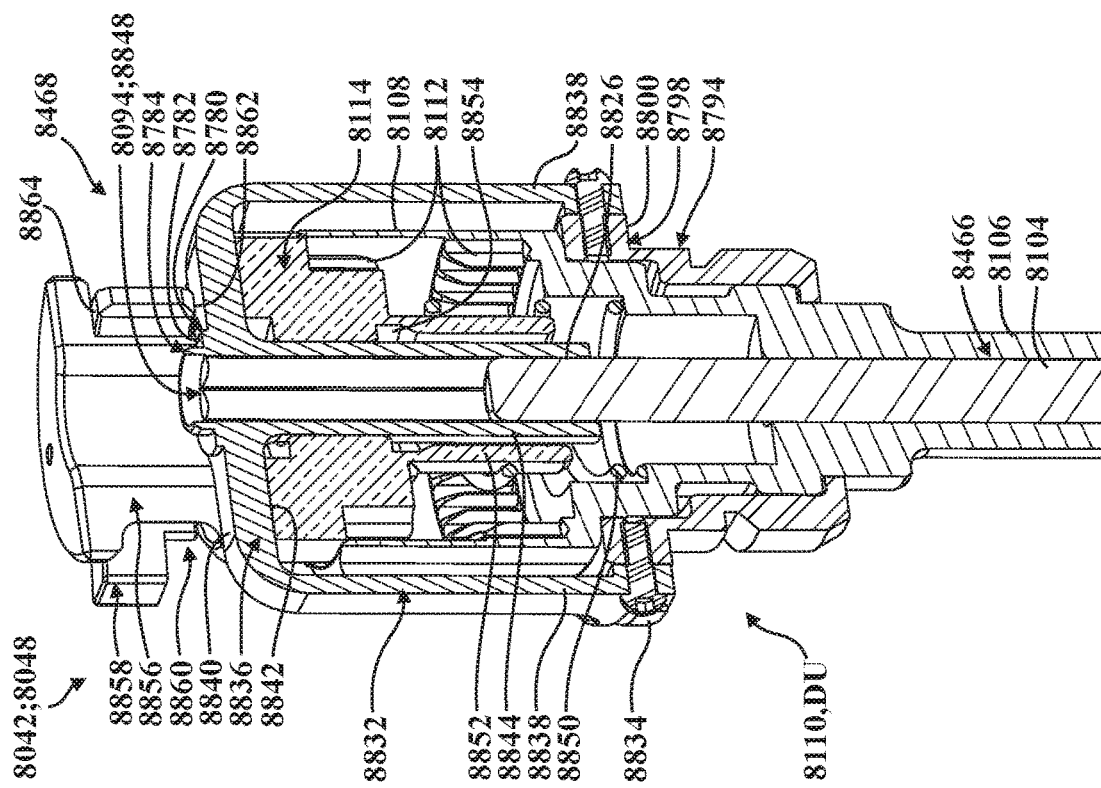
FIG. 61B is another partial, sectional perspective view of the rotary driving tool of FIG. 61A, shown with the locking subassembly arranged in a driver unlocked configuration.
Figure 62B:
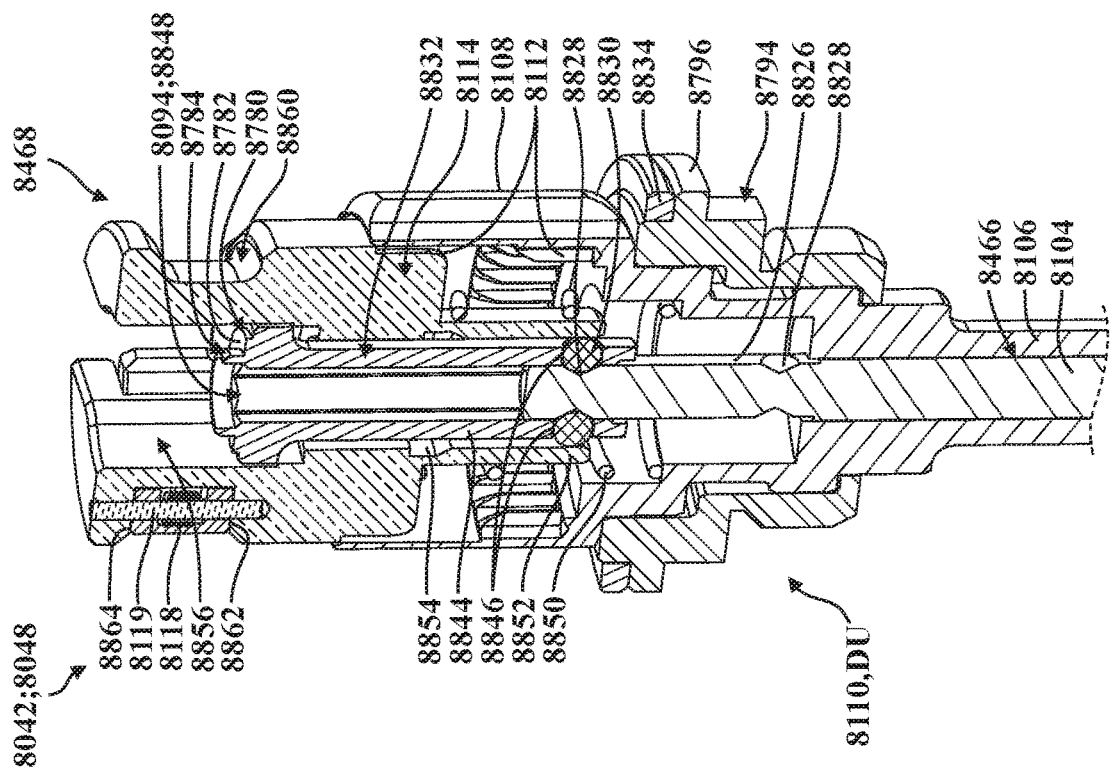
FIG. 62B is another partial, sectional perspective view of the rotary driving tool of FIG. 61B, shown with the locking subassembly arranged in a driver unlocked configuration.

With continued reference to FIGS. 60-62B, the locking subassembly 8810 of the rotary driving tool 8048 also comprises the locking body 8114, which is arranged between the contoured body 8108 and the carriage 8832 and can rotate concurrently with the support tube 8106 via the splined engagement 8112 with the contoured body 8108 when the locking subassembly 8810 operates in a driver locked configuration DL (see FIGS. 61A and 62A). However, the support tube 8106 can be rotated independently of the driveshaft 8104 when the locking subassembly 8810 operates in a driver unlocked configuration DU where the splined engagement 8112 is interrupted between the contoured body 8108 and the locking body 8114 (see FIGS. 61B and 62B). Here, a locking body biasing element 8850 supported by a locking seat 8852 formed on the locking body 8114 is disposed within the contoured body 8108 and urges the locking subassembly 8810 toward the driver unlocked configuration DU.

The locking body 8114 also comprises a relief pocket 8854 disposed in the locking seat 8852 axially-adjacent to the splined engagement 8112 (see FIGS. 61A-62B), and a bridge notch 8856 which is shaped to receive the carriage bridge 8836 of the carriage 8832 therein such that relative rotation between the carriage 8832 and the locking body 8114 is inhibited in both the driver locked configuration DL and the driver unlocked configuration DU. The relief pocket 8854 is formed inside in the locking body 8114 and is arranged to accommodate the driveshaft lock elements 8830 when the locking subassembly 8810 is in the driver locked configuration DL (see FIG. 62A). This configuration permits the driveshaft 8104 to be advanced along the second axis A2 relative to the carriage 8832, such as to facilitate attachment of the anchor 8050 prior to loading the tool 8042 into the drive conduit 8462. Conversely, when in the driver unlocked configuration DU (see FIG. 62B), the driveshaft lock elements 8830 are spaced from the relief pocket 8854 and are disposed generally within the locking seat 8852 to inhibit axial movement of the driveshaft 8104 relative to the carriage 8832. This configuration also permits the support tube 8106 to be rotated relative to the driveshaft 8104, such as to facilitate removal of the anchor 8050 by disengaging the external threads 8120 of the support tube 8106 from the internal threads 8122 of the anchor 8050.

In order to selectively maintain the locking subassembly 8110 in either the driver locked configuration DL or the driver unlocked configuration DU, the locking subassembly 8810 also comprises a carriage lock lever 8858 that is seated within a stepped region 8860 of the locking body 8114. The carriage lock lever 8858 is supported for pivoting movement relative to the locking body 8114 via the pin 8119, is biased via the spring 8118, and defines a first lever face 8862 and an opposing second lever face 8864. Here, the first lever face 8862 abuts the first carriage face 8840 in the driver unlocked configuration DU (see FIG. 61B), and the second lever face 8864 abuts the second carriage face 8842 in the driver locked configuration DL (see FIG. 61A; not shown in detail). Here, the user can engage the carriage lock lever 8858 and pivot it about the pin 8119 into the stepped region 8860 of the locking body 8114 to permit the locking body 8114 to move along the second axis A2 relative to the carriage 8832 in an absence of abutment between the first lever face 8862 and the first carriage face 8840 or between the second lever face 8864 and the second carriage face 8842.

Referring now to FIGS. 63A-63F, certain exemplary steps of utilizing the rotary driving tool 8048 to secure the anchor 8050 at the surgical site ST with the eighth embodiment of the end effector 8040 are shown sequentially. Beginning with FIG. 63A, the schematically-depicted surgical site ST is shown with the pilot hole 8046 already formed along the trajectory T. The rotary driving tool 8048 is shown secured to the anchor 8050 and spaced from the end effector 8040. Here, the guard cover 8350 of the retention mechanism 8664 is positioned in the second guard position U2 to expose the proximal inlet 8480 of the drive bore 8478 of the drive assembly 8082.

Figure 63A:
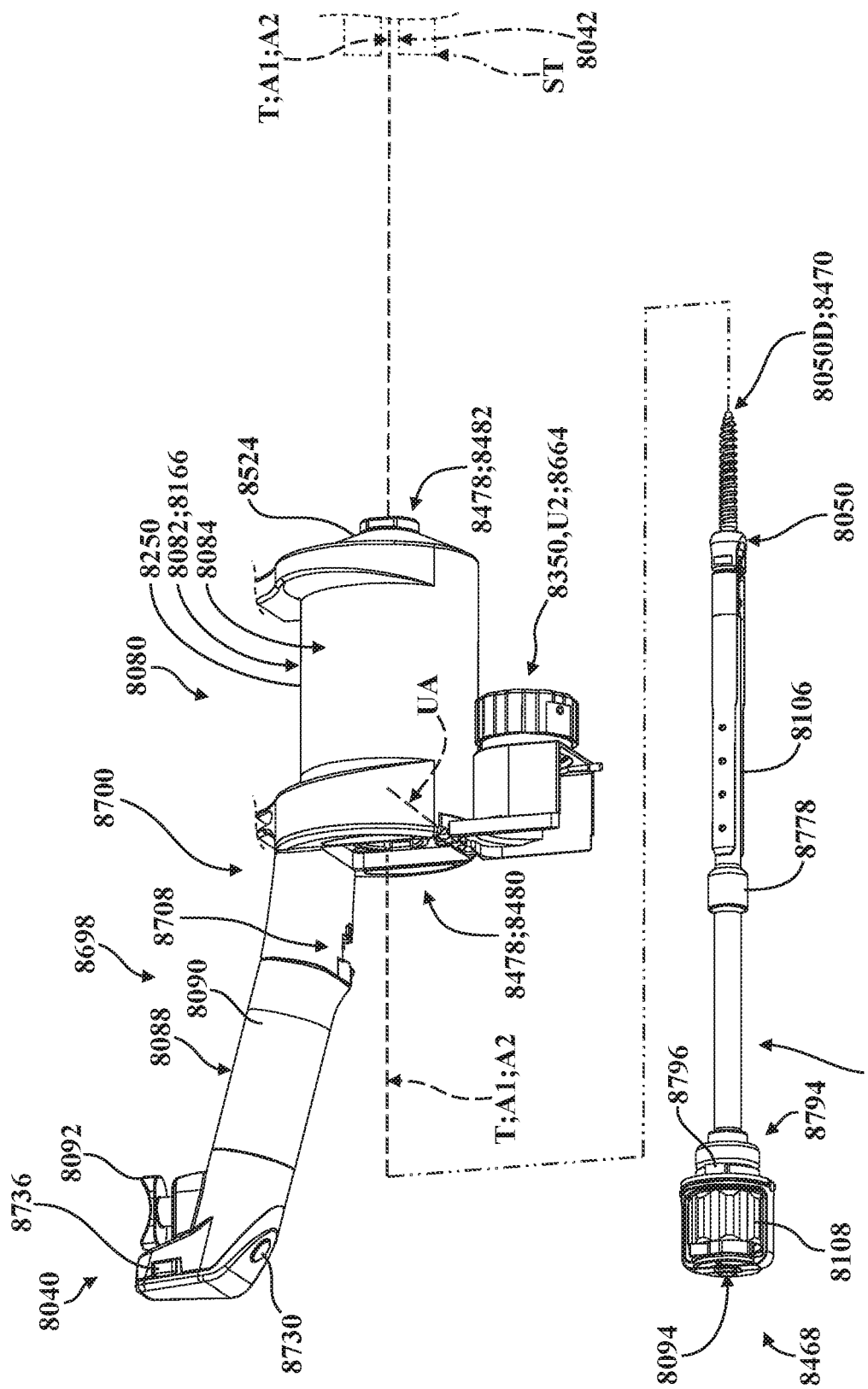
FIG. 63A is a partial perspective view of the end effector of FIGS. 49A-50, shown with the guard cover of the retention mechanism arranged in the first guard position, shown arranged adjacent to the rotary driving tool of FIGS. 61A-62B, with the locking subassembly arranged in the driver locked configuration to drive an anchor.
Figure 63B:
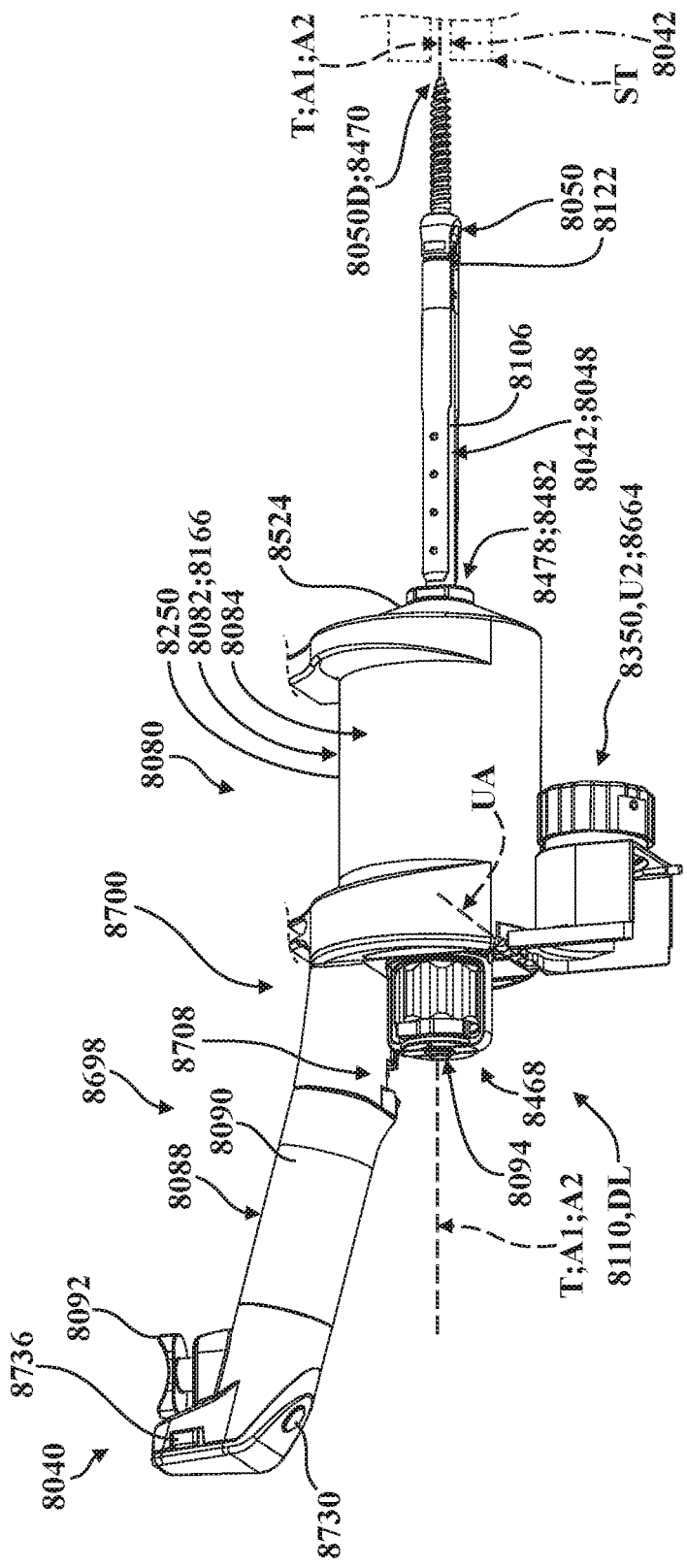
FIG. 63B is another partial perspective view of the end effector, the rotary driving tool, and the anchor of FIG. 63A, shown with the rotary driving tool supported in the drive conduit of the drive assembly as depicted in FIG. 58B, and shown with the anchor arranged along the trajectory.

In FIG. 63B, the user has loaded the tool 8042 into the drive conduit 8462 in the "top loading" manner by inserting the working end 8470 of the tool 8042 (defined here by the distal tip 8050D of the anchor 8050) into the proximal inlet 8480 of the drive bore 8478 and advanced along the second axis A2 through the drive conduit 8462 and out of the distal outlet 8482 of the drive bore 8478 toward the surgical site ST. The axial lock AL defined by the retention mechanism 8664 remains in the release configuration ACR while the guard cover 8350 is arranged in the second guard position U2, which permits the tool 8042 to be freely removed from the drive conduit 8462 along the second axis A2 in a direction facing away from the surgical site ST. However, further movement along the second axis A2 relative to the drive conduit 8462 toward the surgical site ST is inhibited by the engagement between second seat element 8794 of the tool body 8466 and the proximal carrier end 8694 of the carrier shaft 8422. Here too, engagement of the second notch element 8796 of the rotary driving tool 8048 with the second notch 8696 of the carrier shaft 8422 (see FIGS. 51 and 57) defines the second rotational lock RL2 such that the rotary driving tool 8048 and the carrier shaft 8422 rotate concurrently about the second axis A2.

Figure 63C:
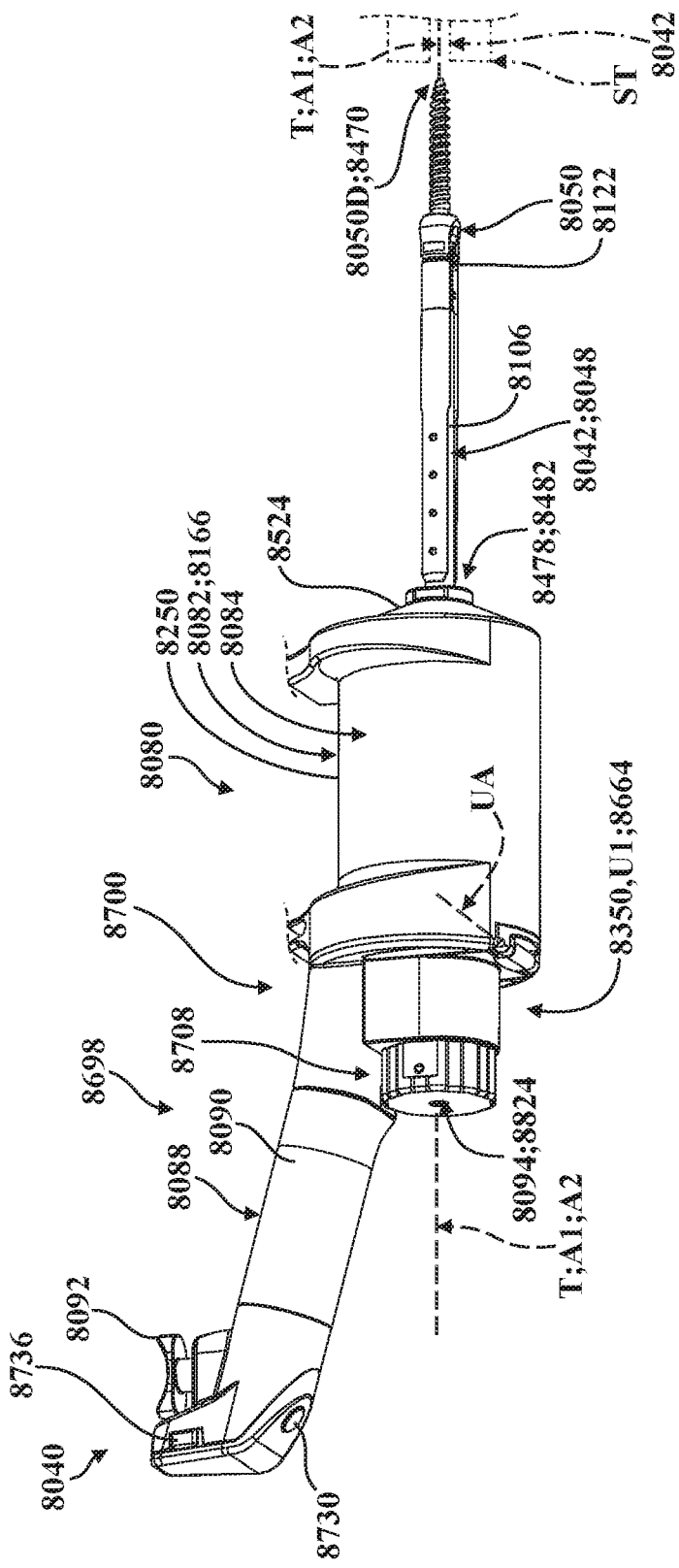
FIG. 63C is another partial perspective view of the end effector, the rotary driving tool, and the anchor of FIG. 63B, shown with the guard cover of the retention mechanism arranged in the second guard position as depicted in FIG. 58D.

In FIG. 63C, the guard cover 8350 of the retention mechanism 8664 has been pivoted to the first guard position U1, and the guard knob 8806 has been rotated to move the axial lock AL from the release configuration ACR (see FIG. 58C) to the lock configuration ACL (see FIG. 58D). Here, relative movement between the drive assembly 8082 and the rotary driving tool 8048 is restricted along the second axis A2, and the user can drive the tool 8042 via the trigger assembly 8088 to advance the anchor 8050 along the trajectory T into the pilot hole 8046 of the surgical site ST using the actuator 8166 of the rotary instrument 8080. Here too, the user can also apply force to the manual interface 8094 to drive the tool 8042 along the trajectory T without the actuator 8166, such as with a handle assembly inserted through the knob aperture 8824 and into the hex bore 8848 of the rotary driving tool 8048 (see FIGS. 61A-62B).

Figure 63D:
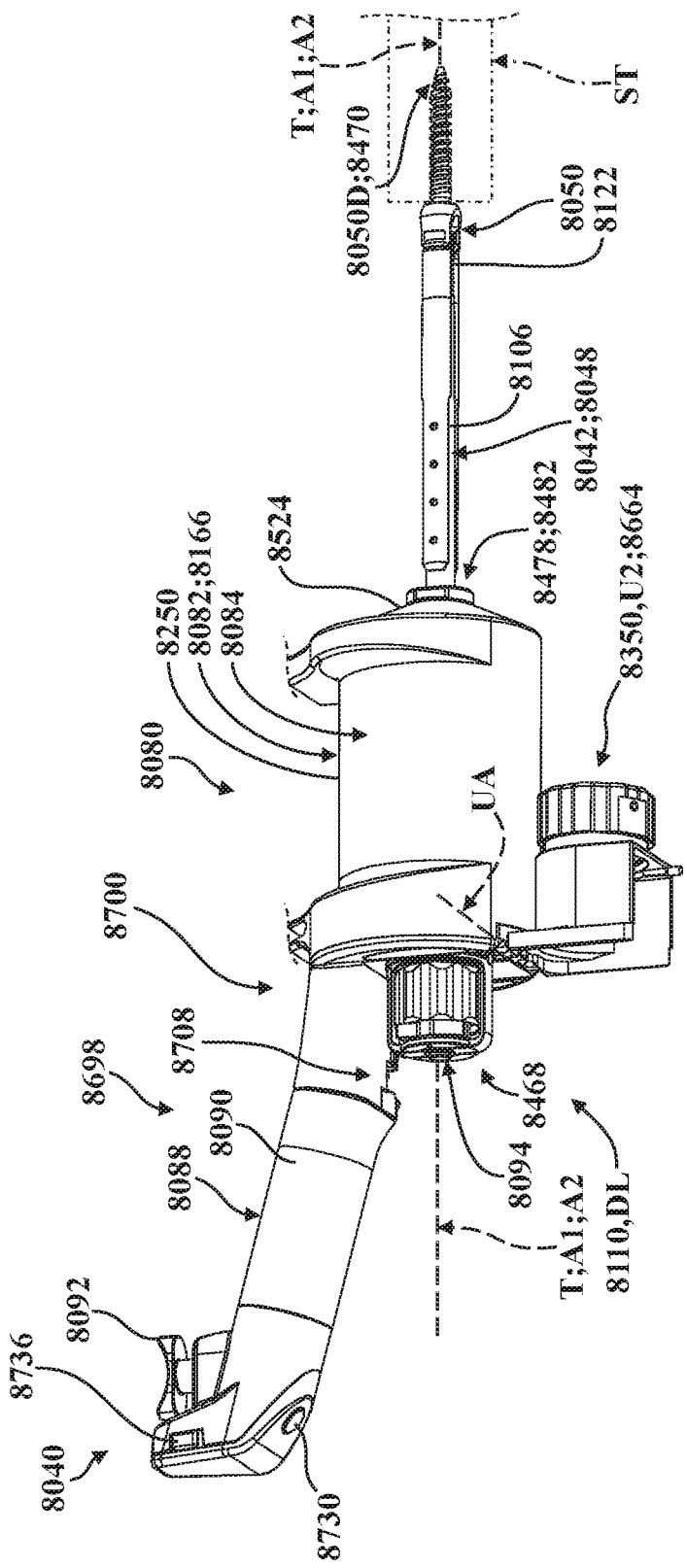
FIG. 63D is another partial perspective view of the end effector, the rotary driving tool, and the anchor of FIG. 63C, shown with the guard cover of the retention mechanism arranged in the first guard position, shown with the locking subassembly of the rotary driving tool arranged in the driver locked configuration, and shown with the anchor advanced along the trajectory.

In FIG. 63D, the user has completed installation of the anchor 8050 at the surgical site ST along the trajectory T. Here, the guard cover 8350 of the retention mechanism 8664 has been moved back to the second guard position U2 and the axial lock AL is in the release configuration ACR. Moreover, the locking subassembly 8810 of the rotary driving tool 8048 is arranged in the driver locked configuration DL. However, in FIG. 63E, the locking subassembly 8810 has been moved to the driver unlocked configuration DU such that the rotary driving tool 8048 can be released from the anchor 8050 and subsequently removed from the drive conduit 8462 of the end effector 8040, as shown in FIG. 63F.

Figure 63E:
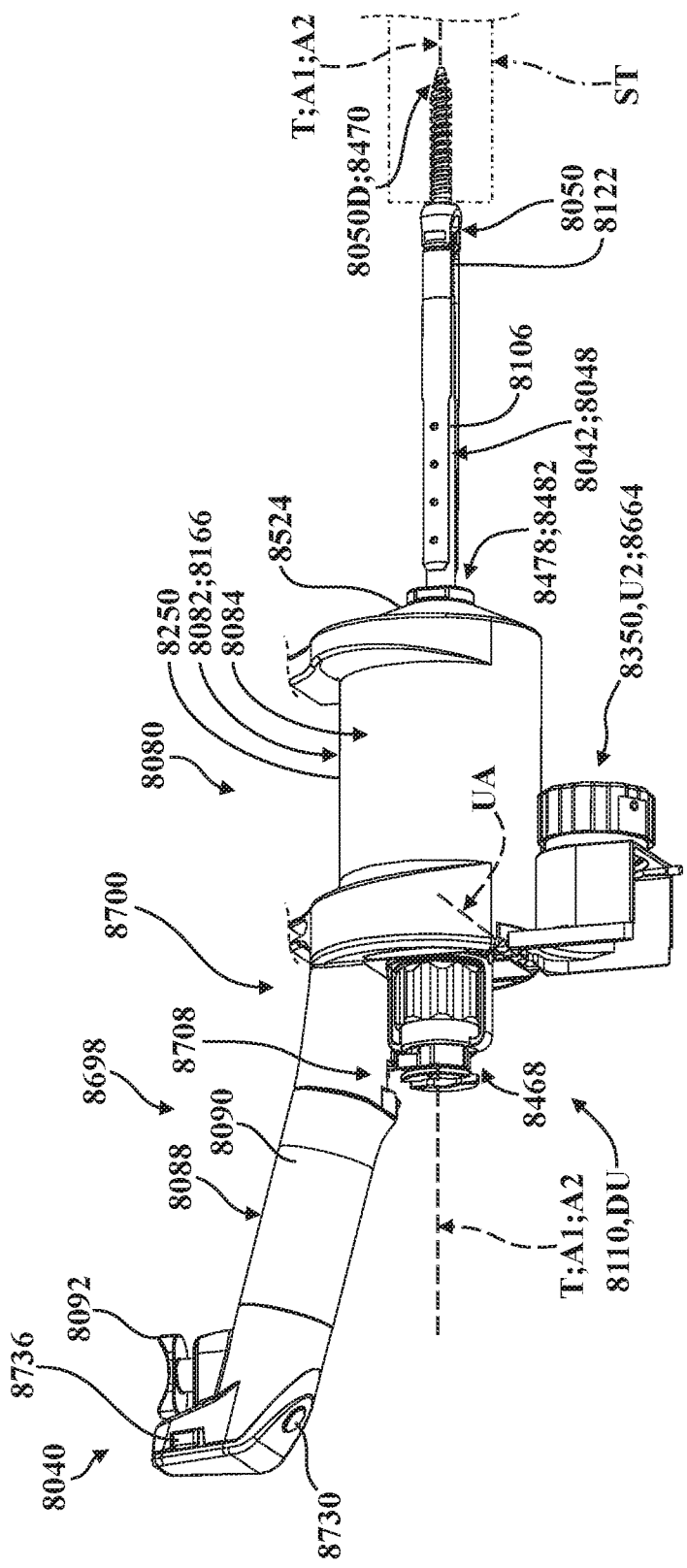
FIG. 63E is another partial perspective view of the end effector, the rotary driving tool, and the anchor of FIG. 63D, shown with the locking subassembly of the rotary driving tool arranged in the driver locked configuration.

Referring again to FIG. 63D, in order to release the anchor 8050 from the rotary driving tool 8084 after the user has completed installation of the anchor 8050 at the surgical site ST along the trajectory T, the actuator 8166 (or another component of the end effector 8050) may be placed into a mode which restricts or otherwise prevents rotation of the drive conduit 8462 in both directions (e.g., by driving the actuator 8166 to maintain a position without rotating) or in a single direction (e.g., by driving the actuator 8166 to prevent rotation in a direction that is opposite to the rotational direction used to install the anchor 8050). To this end, it will be appreciated that the actuator 8166 itself could be driven in various ways, and that additional components and/or locking features could be employed to, for example, inhibit or otherwise limit rotation of the drive conduit 8462 relative to the drive body 8250 or another portion of the end effector 8040. Here, inhibiting rotation of the drive conduit 8462 also inhibits rotation of the second seat element 8794 via the second rotational lock RL2. Thus, when the locking subassembly 8810 is in the driver unlocked configuration DU as depicted in FIG. 63E, the support tube 8106 can be rotated (and translated axially) relative to the driveshaft 8104 (and, thus, to the anchor 8050) in order to disengage the external threads 8120 of the support tube 8106 from the internal threads 8122 of the anchor 8050 (see FIG. 60) and thereby facilitate removal of the anchor 8050 as shown in FIG. 63F.

The embodiments of the surgical systems 30, end effectors, and methods described herein afford advantages in connection with a broad number of medical and/or surgical procedures including, for example, where surgical robots 32 are utilized in minimally-invasive surgical procedures such as spinal fusions. Specifically, it will be appreciated that the embodiments of the end effector described and illustrated herein are configured to facilitate rotation of different types of tools along the second axis A2 via rotation from the actuator of the rotary instrument about the first axis A1, which may be the same as the second axis A2 or may be different from the second axis A2 as noted above. Moreover, it will be appreciated that the manual interface affords surgeons with the ability to rotate tools about the second axis A2 via torque generated by the actuator of the rotary instrument and/or via manual application of force to the handle assembly. Furthermore, the arrangement of the trigger assembly allows the surgeon to apply force to the end effector to advance the tool along the trajectory T in-line with the second axis A2 while simultaneously engaging the input trigger to drive the rotary instrument, while also affording the surgeon with unobstructed access to the manual interface after moving to the second trigger assembly position P2 or otherwise presenting the manual interface.

Those having ordinary skill in the art will appreciate that aspects of the embodiments described and illustrated herein can be interchanged or otherwise combined.

It will be further appreciated that the terms "include," "includes," and "including" have the same meaning as the terms "comprise," "comprises," and "comprising." Moreover, it will be appreciated that terms such as "first," "second," "third," and the like are used herein to differentiate certain structural features and components for the non-limiting, illustrative purposes of clarity and consistency.

Several configurations have been discussed in the foregoing description. However, the configurations discussed herein are not intended to be exhaustive or limit the invention to any particular form. The terminology which has been used is intended to be in the nature of words of description rather than of limitation. Many modifications and variations are possible in light of the above teachings and the invention may be practiced otherwise than as specifically described.

What is claimed is:

1. An end effector for driving a tool at a surgical site along a trajectory maintained by a surgical robot, the tool having an interface end and a working end, said end effector comprising:
   a mount adapted to attach to the surgical robot;
   an actuator coupled to said mount and configured to generate rotational torque about a first axis; and
   a drive assembly comprising:
      a geartrain to translate rotation from said actuator about said first axis into rotation about a second axis,
      a drive conduit supported for rotation about said second axis, said drive conduit defining a drive bore shaped for receiving the working end of the tool along said second axis,
      a first rotational lock operatively attached to said drive conduit to releasably secure the tool for concurrent rotation about said second axis, and
      an axial lock to releasably secure the tool for concurrent translation with said drive conduit along the trajectory maintained by the surgical robot, said axial lock being operable between:
         a release configuration wherein relative movement between said drive assembly and the tool is permitted along said second axis, and
         a lock configuration wherein relative movement between said drive assembly and the tool is restricted along said second axis
      wherein said drive assembly defines a proximal inlet and an opposing distal outlet, with said drive conduit interposed in communication between said proximal inlet and said distal outlet for permitting the working end of the tool to be inserted along said second axis into said proximal inlet and advanced through said drive bore and out of said distal outlet toward the surgical site when said axial lock is in said release configuration.

2. The end effector as set forth in claim 1, wherein at least a portion of said drive bore of said drive conduit defines said first rotational lock.

3. The end effector as set forth in claim 2, wherein said first rotational lock of said drive assembly is shaped to engage at least a portion of the tool between the interface end and the working end when said axial lock is in said lock configuration such that the interface end of the tool is arranged proximal to said drive bore and the working end of the tool is arranged distal to said drive bore.

4. The end effector as set forth in claim 1, wherein said geartrain of said drive assembly comprises at least one reduction gearset interposed in rotational communication between said actuator and said drive conduit such that rotation of said actuator about said first axis occurs at a different speed than rotation of said first rotational lock about said second axis.

5. The end effector as set forth in claim 4, wherein said drive assembly further comprises a second rotational lock, different from said first rotational lock, operatively attached to said drive conduit to releasably secure a second tool for concurrent rotation about said second axis, with said second rotational lock disposed in rotational communication with said geartrain such that rotation of said second rotational lock about said second axis occurs at a different speed than rotation of said first rotational lock about said second axis.

6. The end effector as set forth in claim 5, wherein rotation of said second rotational lock about said second axis occurs at a ratio of 1:1 with respect to rotation of said actuator about said first axis.

7. The end effector as set forth in claim 1, wherein said geartrain of said drive assembly comprises a transmission interposed in rotational communication between said actuator and said drive conduit, said transmission comprising a first gearset, a second gearset, and a shift collar arranged for movement between:
  a first collar position where said shift collar engages said first gearset to translate rotation between said actuator and said drive conduit at a first drive ratio, and
a second collar position where said shift collar engages said second gearset to translate rotation between said actuator and said drive conduit at a second drive ratio different from said first drive ratio.

8. The end effector as set forth in claim 7, wherein said transmission further comprises a transmission linkage operatively attached to said shift collar for concurrent movement between said first collar position and said second collar position, said transmission linkage defining a selector arranged to engage at least a portion of the tool to move said shift collar to said second collar position when said axial lock is in said lock configuration.

9. The end effector as set forth in claim 1, wherein said first rotational lock comprises one or more of a keyed bore, a splined bore, and a notch.

10. The end effector as set forth in claim 1, wherein said axial lock comprises a slider element arranged for movement relative to said second axis between:
  a first slider element position associated with said release configuration; and
  a second slider element position associated with said lock configuration.

11. The end effector as set forth in claim 1, wherein said axial lock comprises a collet mechanism comprising:
  a collet arranged to receive the tool therethrough along said second axis; and
  a collet tensioner coupled to said collet and arranged for movement between a first tensioner position associated with said release configuration where relative movement is permitted between the tool and said collet, and a second tensioner position associated with said lock configuration where relative movement is restricted between the tool and said collet.

12. The end effector as set forth in claim 1, further comprising a light source operatively attached to said mount and configured to emit light toward the surgical site.

13. The end effector as set forth in claim 12, wherein the light source is configured for removable attachment to said drive conduit of said drive assembly.

14. An end effector for guiding tools relative to a surgical site along a trajectory maintained by a surgical robot, the tools including a first tool and a second tool different from the first tool, said end effector comprising:
  a mount adapted to attach to the surgical robot;
  a rotary instrument coupled to said mount and comprising an actuator configured to generate rotational torque about a first axis; and
  a drive assembly comprising a geartrain to translate rotation from said rotary instrument about said first axis into rotation about a second axis, a first rotational lock disposed in rotational communication with said geartrain to releasably secure the first tool for concurrent rotation about said second axis at a first drive ratio, a second rotational lock disposed in communication with said geartrain to releasably secure the second tool for concurrent rotation about said second axis at a second drive ratio different from said first drive ratio, and an axial lock to releasably secure one of the first tool and the second tool for concurrent translation with said drive assembly along the trajectory maintained by the surgical robot, said axial lock being operable between:
    a release configuration wherein relative movement between said drive assembly and the secured tool is permitted along said second axis, and
    a lock configuration wherein relative movement between said drive assembly and the secured tool is restricted along said second axis.

15. An end effector for driving tools at a surgical site along a trajectory maintained by a surgical robot, the tools including a first tool and a second tool different from the first tool, said end effector comprising:
  a mount adapted to attach to the surgical robot;
  a rotary instrument coupled to said mount and comprising an actuator configured to generate rotational torque about a first axis; and
  a drive assembly comprising a geartrain to translate rotation from said rotary instrument into rotation about a second axis different from said first axis, a connector configured to releasably secure one of the first tool and the second tool for rotation about said second axis, and a transmission interposed in rotational communication between said rotary instrument and said connector, said transmission comprising a first gearset, a second gearset, and a shift collar arranged for movement between:
    a first collar position where said shift collar engages said first gearset to translate rotation between said rotary instrument and said connector at a first drive ratio, and
    a second collar position where said shift collar engages at said second gearset to translate rotation between said rotary instrument and said connector at a second drive ratio different from said first drive ratio.

16. An end effector for driving a tool at a surgical site along a trajectory maintained by a surgical robot, said end effector comprising:
  a mount adapted to attach to the surgical robot;
  a rotary instrument coupled to said mount and comprising an actuator configured to generate rotational torque about a first axis;
  a drive assembly comprising a geartrain to translate rotation from said rotary instrument into rotation about a second axis different from said first axis, and a connector configured to releasably secure the tool for rotation about said second axis;
  a trigger assembly comprising a grip to support a user's hand, and an input trigger in communication with said rotary instrument and arranged for engagement by the user to drive said rotary instrument and rotate the tool about said second axis; and a manual interface to communicate with said drive assembly and arranged to receive and translate applied force from the user into rotational torque to rotate the tool about said second axis.

17. The end effector as set forth in claim 16, wherein said trigger assembly comprises a frame supporting said grip and said input trigger for movement relative to said rotary instrument between a plurality of trigger assembly positions, said frame comprising:
   a first frame body arranged for movement relative to said rotary instrument between said plurality of trigger assembly positions; and
   a second frame body supporting said grip and said input trigger for movement relative to said first frame body between a plurality of grip positions.

18. The end effector as set forth in claim 17, wherein said plurality of grip positions include:
   a first grip position where at least a portion of said second frame body limits access to said manual interface, and where said input trigger is arranged for engagement by the user to drive said rotary instrument to rotate the tool about said second axis; and
   a second grip position where said second frame body is disposed in spaced relation to said manual interface to facilitate receiving applied force from the user to rotate the tool about said second axis.

19. The end effector as set forth in claim 17, wherein said plurality of trigger assembly positions include:
   a first trigger assembly position where said trigger assembly is arranged for engagement by the user to drive said rotary instrument to rotate the tool about said second axis; and
   a second trigger assembly position where said manual interface is arranged to receive applied force from the user to rotate the tool about said second axis.

20. The end effector as set forth in claim 19, wherein said grip of said trigger assembly is substantially parallel to said second axis when said trigger assembly is in one of said first and second trigger assembly positions.

21. The end effector as set forth in claim 19, wherein said grip of said trigger assembly is substantially perpendicular to said second axis when said trigger assembly is in one of said first and second trigger assembly positions.

22. The end effector as set forth in claim 21, wherein said grip of said trigger assembly is substantially parallel to said second axis when said trigger assembly is in the other of said first and second trigger assembly positions.

23. The end effector as set forth in claim 16, wherein said manual interface comprises a head arranged for rotation about said second axis to received applied rotational force from the user; and
   further comprising a guard cover operatively attached to said drive assembly and arranged for movement relative to said second axis between:
   a first guard position wherein said second axis intersects at least a portion of said guard cover to limit access to said manual interface; and
   a second guard position wherein said guard cover is spaced from said second axis to promote access to said manual interface.

24. The end effector as set forth in claim 16, further comprising a handle assembly to attach to said manual interface such that force applied to said handle assembly rotates the tool about said second axis.

25. The end effector as set forth in claim 24, wherein said manual interface comprises a head arranged for rotation about said second axis; and wherein said handle assembly comprises a driver shaped to receive said head of said manual interface for concurrent rotation in response to force applied to said handle assembly by the user.

26. The end effector as set forth in claim 25, further comprising a differential assembly interposed between said rotary instrument, said connector, and said manual interface, said differential assembly being operable between:
   a haptic mode where rotational torque generated by said rotary instrument translates through said differential assembly to said connector to rotate the tool about said second axis and also translates to said head of said manual interface to provide tactile torque feedback at said manual interface;
   a first interrupt mode where rotational torque generated by said rotary instrument translates through said differential assembly to said connector to rotate the tool about said second axis without translating rotational torque to said head of said manual interface; and
   a second interrupt mode where rotational torque applied to said head of said manual interface translates through said differential assembly to said connector to rotate the tool about said second axis without translating rotational torque to said rotary instrument.

27. The end effector as set forth in claim 16, wherein said geartrain of said drive assembly comprises at least one reduction gearset interposed in rotational communication between said rotary instrument and said connector such that rotation of said rotary instrument occurs at a different speed than rotation of the tool.

28. The end effector as set forth in claim 16, wherein said geartrain of said drive assembly comprises at least one bevel gearset interposed in rotational communication between said rotary instrument and said connector to translate rotation about said first axis into rotation about said second axis.

29. The end effector as set forth in claim 28, wherein said bevel gearset comprises a reduction gearset configured such that rotation of said rotary instrument occurs at a different speed than rotation of the tool.

30. An end effector for driving a tool at a surgical site along different trajectories selectively maintained by a surgical robot, said end effector comprising:
   a mount adapted to attach to the surgical robot;
   a rotary instrument coupled to said mount and comprising an actuator configured to generate rotational torque about a first axis;
   a drive assembly comprising a geartrain to translate rotation from said rotary instrument into rotation about a second axis different from said first axis, and a connector configured to releasably secure the tool for rotation about said second axis; and
   a coupling operatively attached to said rotary instrument and configured to releasably secure said drive assembly to said rotary instrument in a plurality of orientations to selectively position said second axis relative to said rotary instrument along different trajectories selectively maintained by the surgical robot.

31. The end effector as set forth in claim 30, wherein said geartrain of said drive assembly comprises at least one reduction gearset interposed in rotational communication between said rotary instrument and said connector such that rotation of said rotary instrument occurs at a different speed than rotation of the tool.

32. The end effector as set forth in claim 31, wherein said at least one reduction gearset comprises a planetary gearset.

33. The end effector as set forth in claim 30, wherein said geartrain of said drive assembly comprises at least one bevel gearset interposed in rotational communication between said rotary instrument and said connector to translate rotation about said first axis into rotation about said second axis.

34. The end effector as set forth in claim 33, wherein said bevel gearset comprises a reduction gearset configured such that rotation of said rotary instrument occurs at a different speed than rotation of the tool.

35. The end effector as set forth in claim 33, wherein said geartrain of said drive assembly further comprises at least one reduction gearset interposed in rotational communication between said rotary instrument and said bevel gearset such that rotation of said rotary instrument occurs at a different speed than rotation of the tool.

36. The end effector as set forth in claim 33, wherein said geartrain of said drive assembly further comprises at least one reduction gearset interposed in rotational communication between said bevel gearset and said connector such that rotation of said rotary instrument occurs at a different speed than rotation of the tool.

37. The end effector as set forth in claim 36, wherein said geartrain of said drive assembly further comprises at least one auxiliary gearset interposed in rotational communication between said rotary instrument and said bevel gearset.

38. An end effector for guiding tools relative to a surgical site along a trajectory maintained by a surgical robot, the tools including a first tool and a second tool different from the first tool, said end effector comprising:
 a mount adapted to attach to the surgical robot;
 an actuator coupled to said mount and configured to generate rotational torque about a first axis; and
 a drive assembly comprising:
  a geartrain to translate rotation from said actuator about said first axis into rotation about a second axis,
  a drive conduit supported for rotation about said second axis,
  a first rotational lock operatively attached to said drive conduit to releasably secure the first tool for concurrent rotation about said second axis,
  said geartrain of said drive assembly comprises at least one reduction gearset interposed in rotational communication between said actuator and said drive conduit such that rotation of said actuator about said first axis occurs at a different speed than rotation of said first rotational lock about said second axis,
  a second rotational lock, different from said first rotational lock, operatively attached to said drive conduit to releasably secure the second tool for concurrent rotation about said second axis, with said second rotational lock disposed in rotational communication with said geartrain such that rotation of said second rotational lock about said second axis occurs at a different speed than rotation of said first rotational lock about said second axis, and
  an axial lock to releasably secure one of the first tool and the second tool for concurrent translation with said drive conduit along the trajectory maintained by the surgical robot, said axial lock being operable between:

a release configuration wherein relative movement between said drive assembly and the secured tool is permitted along said second axis, and
   a lock configuration wherein relative movement between said drive assembly and the secured tool is restricted along said second axis.

39. The end effector as set forth in claim 38, wherein rotation of said second rotational lock about said second axis occurs at a ratio of 1:1 with respect to rotation of said actuator about said first axis.

40. An end effector for driving a tool at a surgical site along a trajectory maintained by a surgical robot, the tool having an interface end and a working end, said end effector comprising:
 a mount adapted to attach to the surgical robot;
 an actuator coupled to said mount and configured to generate rotational torque about a first axis; and
 a drive assembly comprising:
  a geartrain to translate rotation from said actuator about said first axis into rotation about a second axis,
  a drive conduit supported for rotation about said second axis,
  said geartrain of said drive assembly comprises a transmission interposed in rotational communication between said actuator and said drive conduit, said transmission comprising a first gearset, a second gearset, and a shift collar arranged for movement between:
   a first collar position where said shift collar engages said first gearset to translate rotation between said actuator and said drive conduit at a first drive ratio; and
   a second collar position where said shift collar engages said second gearset to translate rotation between said actuator and said drive conduit at a second drive ratio different from said first drive ratio,
  a first rotational lock operatively attached to said drive conduit to releasably secure the tool for concurrent rotation about said second axis, and
  an axial lock to releasably secure the tool for concurrent translation with said drive conduit along the trajectory maintained by the surgical robot, said axial lock being operable between:
   a release configuration wherein relative movement between said drive assembly and the tool is permitted along said second axis, and
   a lock configuration wherein relative movement between said drive assembly and the tool is restricted along said second axis.

41. The end effector as set forth in claim 40, wherein said transmission further comprises a transmission linkage operatively attached to said shift collar for concurrent movement between said first collar position and said second collar position, said transmission linkage defining a selector arranged to engage at least a portion of the tool to move said shift collar to said second collar position when said axial lock is in said lock configuration.

* * * * *

UNITED STATES PATENT AND TRADEMARK OFFICE
CERTIFICATE OF CORRECTION

| | | |
|---|---|---|
| PATENT NO. | : 11,160,620 B2 | Page 1 of 1 |
| APPLICATION NO. | : 16/257605 | |
| DATED | : November 2, 2021 | |
| INVENTOR(S) | : Peter L. Ebbitt et al. | |

It is certified that error appears in the above-identified patent and that said Letters Patent is hereby corrected as shown below:

On the Title Page

Item [72], "Oscar Williams, Foster CIty, CA" should be deleted and changed to:
--Oscar Williams, Foster City, CA--

Signed and Sealed this
Third Day of September, 2024

Katherine Kelly Vidal
*Director of the United States Patent and Trademark Office*